(12) United States Patent
Kanamoto et al.

(10) Patent No.: US 10,230,055 B2
(45) Date of Patent: Mar. 12, 2019

(54) COMPOUND, LIGHT-EMITTING ELEMENT, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Miki Kanamoto, Kanagawa (JP); Takeyoshi Watabe, Kanagawa (JP); Hideko Inoue, Kanagawa (JP); Satoshi Seo, Kanagawa (JP); Satomi Mitsumori, Kanagawa (JP); Tatsuyoshi Takahashi, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 110 days.

(21) Appl. No.: 15/256,000

(22) Filed: Sep. 2, 2016

(65) Prior Publication Data

US 2017/0069852 A1    Mar. 9, 2017

(30) Foreign Application Priority Data

Sep. 4, 2015 (JP) .................................. 2015-174830
Apr. 21, 2016 (JP) .................................. 2016-084974

(51) Int. Cl.
*H01L 51/50* (2006.01)
*H01L 51/00* (2006.01)
(Continued)

(52) U.S. Cl.
CPC ...... *H01L 51/0072* (2013.01); *C07D 491/048* (2013.01); *C07F 15/0033* (2013.01); *C09K 11/06* (2013.01); *H01L 51/0071* (2013.01); *H01L 51/0085* (2013.01); *C09K 2211/1007* (2013.01); *C09K 2211/1044* (2013.01); *C09K 2211/1048* (2013.01); *C09K 2211/1059* (2013.01); *C09K 2211/185* (2013.01); *H01L 27/322* (2013.01); *H01L 27/323* (2013.01);
(Continued)

(58) Field of Classification Search
None
See application file for complete search history.

(56) References Cited

U.S. PATENT DOCUMENTS 6,602,618 B2 * 8/2003 Watanabe ........... H01L 51/0081
313/504
9,276,228 B2   3/2016 Seo et al.
(Continued)

FOREIGN PATENT DOCUMENTS

CN    104292241 A    1/2015
EP    2 826 781 A1   1/2015
(Continued)

OTHER PUBLICATIONS

International Search Report re Application No. PCT/IB2016/055036, dated Nov. 8, 2016.
(Continued)

*Primary Examiner* — Gregory D Clark
(74) *Attorney, Agent, or Firm* — Husch Blackwell LLP

(57) ABSTRACT

Provided is a novel compound or a light-emitting element with high emission efficiency. The provided novel compound includes a bicarbazole skeleton and a benzofuropyrimidine skeleton or a benzothienopyrimidine skeleton. The provided light-emitting element includes the compound.

19 Claims, 74 Drawing Sheets

(51) Int. Cl.
  *C07D 491/048*  (2006.01)
  *C07F 15/00*  (2006.01)
  *C09K 11/06*  (2006.01)
  *H01L 27/32*  (2006.01)

(52) U.S. Cl.
  CPC ...... *H01L 51/5012* (2013.01); *H01L 51/5016* (2013.01); *H01L 51/5056* (2013.01); *H01L 51/5072* (2013.01)

(56) References Cited

U.S. PATENT DOCUMENTS

| | | |
|---|---|---|
| 2007/0159083 A1 | 7/2007 | Matsuura et al. |
| 2009/0163545 A1 | 6/2009 | Goldfarb |
| 2011/0121277 A1 | 5/2011 | Matsuura et al. |
| 2012/0153267 A1 | 6/2012 | Matsuura et al. |
| 2012/0187381 A1 | 7/2012 | Xia et al. |
| 2013/0324721 A1 | 12/2013 | Inoue et al. |
| 2014/0291645 A1 | 10/2014 | Inoue et al. |
| 2015/0021555 A1 | 1/2015 | Kwong et al. |
| 2015/0021556 A1* | 1/2015 | Xia .................. H01L 51/0071 257/40 |
| 2015/0243893 A1 | 8/2015 | Joseph et al. |
| 2015/0318495 A1 | 11/2015 | Kawakami et al. |
| 2016/0072078 A1 | 3/2016 | Lee et al. |
| 2016/0322585 A1 | 11/2016 | Kim et al. |

FOREIGN PATENT DOCUMENTS

| | | |
|---|---|---|
| EP | 2 991 128 A1 | 3/2016 |
| JP | 2004-241374 A | 8/2004 |
| JP | 2006-024830 A | 1/2006 |
| JP | 2010-182699 A | 8/2010 |
| JP | 2011-084531 A | 4/2011 |
| JP | 2014-045179 A | 3/2014 |
| JP | 2015-021007 A | 2/2015 |
| JP | 2015-021008 A | 2/2015 |
| JP | 2015-134745 A | 7/2015 |
| JP | 2016-051901 A | 4/2016 |
| KR | 2015-0009461 A | 1/2015 |
| KR | 2015-0009462 A | 1/2015 |
| KR | 2015-0105906 A | 9/2015 |
| KR | 2015-0133998 A | 12/2015 |
| KR | 2016-0026744 A | 3/2016 |
| WO | WO 2015/037675 A1 | 3/2015 |
| WO | WO 2015/108301 A1 | 7/2015 |
| WO | WO 2015/137630 A1 | 9/2015 |
| WO | WO 2016/153283 A1 | 9/2016 |

OTHER PUBLICATIONS

Written Opinion re Application No. PCT/IB2016/055036, dated Nov. 8, 2016.

* cited by examiner

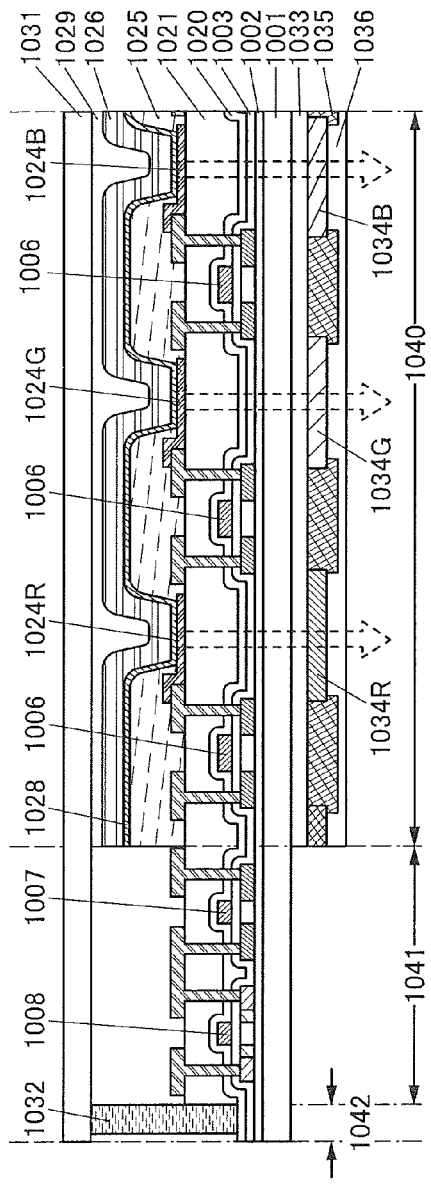

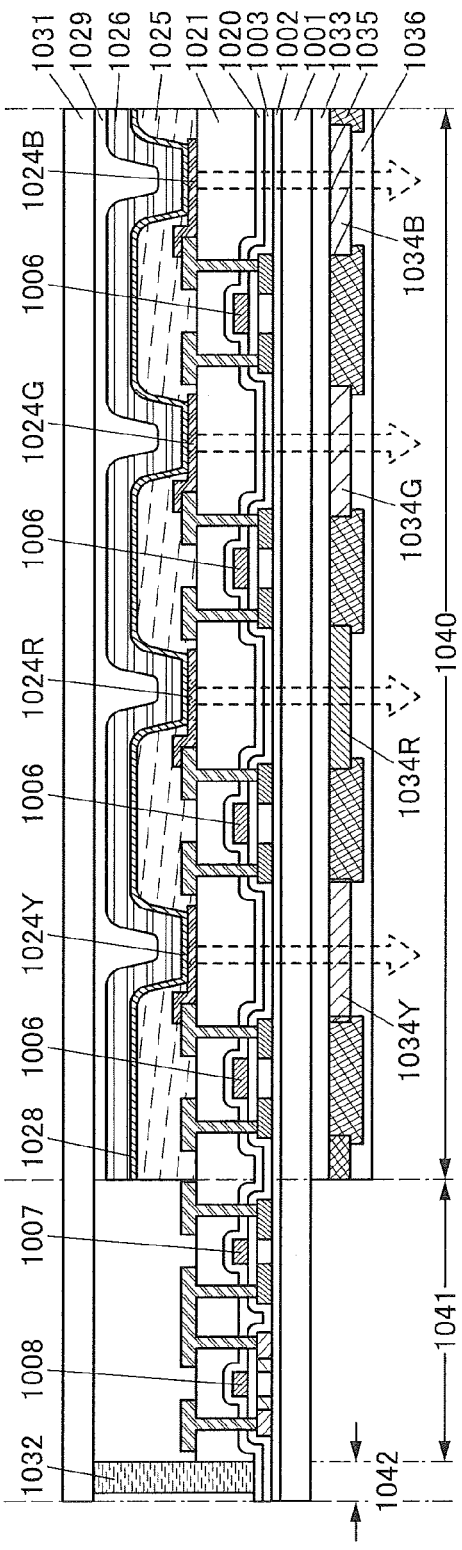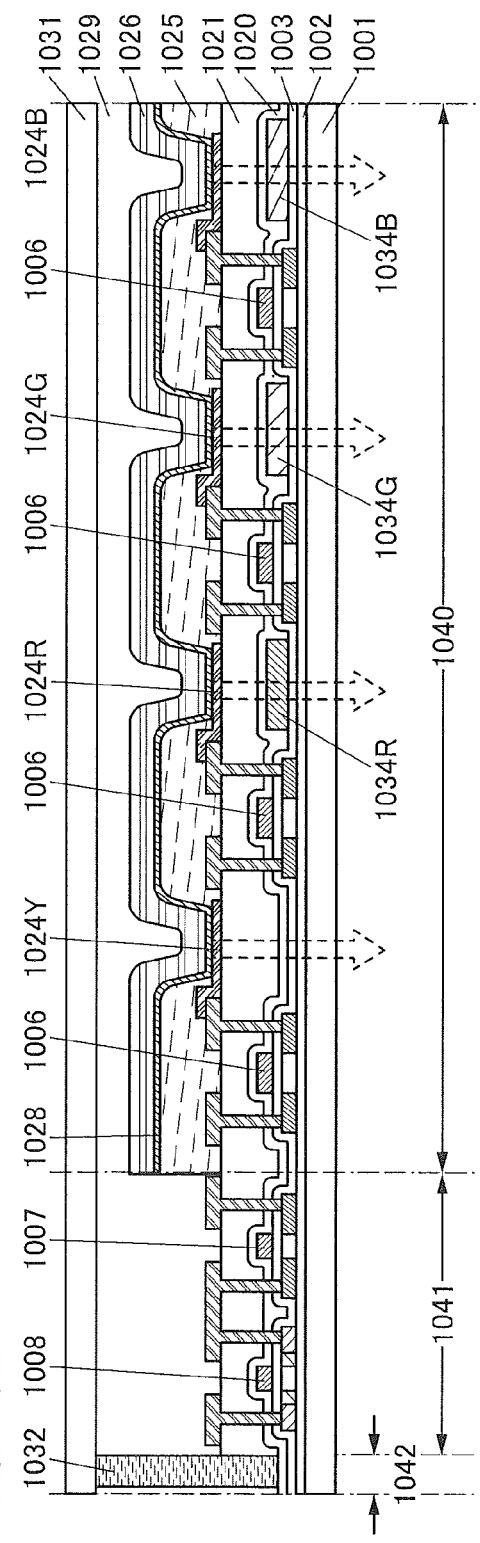

COMPOUND, LIGHT-EMITTING ELEMENT, DISPLAY DEVICE, ELECTRONIC DEVICE, AND LIGHTING DEVICE

TECHNICAL FIELD

One embodiment of the present invention relates to a compound including a bicarbazole skeleton and a benzofuropyrimidine skeleton or a benzothienopyrimidine skeleton. One embodiment of the present invention relates to a light-emitting element including the compound, a display device including the light-emitting element, an electronic device including the light-emitting element, and a lighting device including the light-emitting element.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, a method for driving any of them, and a method for manufacturing any of them.

BACKGROUND ART

In recent years, research and development have been extensively conducted on light-emitting elements using electroluminescence (EL). In a basic structure of such a light-emitting element, a layer containing a light-emitting material (an EL layer) is interposed between a pair of electrodes. By applying a voltage between the pair of electrodes of this element, light emission from the light-emitting material can be obtained.

Since the above light-emitting element is of a self-luminous type, a display device using this light-emitting element has advantages such as high visibility, no necessity of a backlight, low power consumption, and the like. Further, the display device also has advantages in that it can be formed to be thin and lightweight, and has high response speed.

In a light-emitting element (e.g., an organic EL element) whose EL layer contains an organic material as a light-emitting material and is provided between a pair of electrodes, application of a voltage between the pair of electrodes causes injection of electrons from a cathode and holes from an anode into the EL layer having a light-emitting property and thus a current flows. By recombination of the injected electrons and holes, the organic material having a light-emitting property is brought into an excited state to provide light emission.

Note that an excited state formed by an organic material can be a singlet excited state (S*) or a triplet excited state (T*). Light emission from the singlet excited state is referred to as fluorescence, and light emission from the triplet excited state is referred to as phosphorescence. The formation ratio of S* to T* in the light-emitting element is 1:3. In other words, a light-emitting element including a compound emitting phosphorescence (phosphorescent compound) has higher light emission efficiency than a light-emitting element including a compound emitting fluorescence (fluorescent compound). Therefore, light-emitting elements containing phosphorescent materials capable of converting energy of the triplet excited state into light emission have been actively developed in recent years (e.g., see Patent Document 1).

Among light-emitting elements including phosphorescent materials, a light-emitting element that emits blue light has not been put into practical use yet because it is difficult to develop a stable material having a high triplet excitation energy level. For this reason, the development of a more stable fluorescent material for a light-emitting element that emits blue light has been conducted and a technique for increasing the emission efficiency of a light-emitting element including a fluorescent material has been searched.

As a material capable of converting part of energy of the triplet excited state into light emission, a thermally activated delayed fluorescence (TADF) material is known. In the thermally activated delayed fluorescence material, a singlet excited state is formed from a triplet excited state by reverse intersystem crossing, and conversion from the singlet excited state into light emission is caused. Patent Documents 2 and 3 each disclose a material emitting activated delayed fluorescence.

Patent Document 4 discloses a method: in a light-emitting element including a thermally activated delayed fluorescence material and a fluorescent material, singlet excitation energy of the thermally activated delayed fluorescence material is transferred to the fluorescent material and light emission is obtained from the fluorescent material.

REFERENCE

Patent Document

[Patent Document 1] Japanese Published Patent Application No. 2010-182699
[Patent Document 2] Japanese Published Patent Application No. 2004-241374
[Patent Document 3] Japanese Published Patent Application No. 2006-24830
[Patent Document 4] Japanese Published Patent Application No. 2014-45179

DISCLOSURE OF INVENTION

In order to increase emission efficiency of a light-emitting element including a thermally activated delayed fluorescence material, not only efficient generation of a singlet excited state from a triplet excited state but also efficient emission from a singlet excited state, that is, high fluorescence quantum yield is important in a thermally activated delayed fluorescence material. A thermally activated delayed fluorescence material that emits light with high energy and a short emission wavelength, such as blue light, is required to have a high singlet excitation energy level and a high triplet excitation energy level.

In a light-emitting element including a thermally activated delayed fluorescence material and a fluorescent material, it is necessary that carriers be efficiently recombined in the thermally activated delayed fluorescence material to increase emission efficiency or to reduce the drive voltage. In addition, it is important to efficiently transfer excitation energy generated in the thermally activated delayed fluorescence material to a singlet excited state of the fluorescent material.

Therefore, an object of one embodiment of the present invention is to provide a novel compound. Another object of one embodiment of the present invention is to provide a novel compound that emits blue fluorescence. Another object of one embodiment of the present invention is to provide a novel compound with a high triplet excitation energy level. Another object of one embodiment of the present invention is to provide a novel compound having a high carrier-transport property. Another object of one embodiment of the present invention is to provide a light-emitting element including a novel compound. Another object of one embodiment of the present invention is to provide a light-emitting element with high emission efficiency. Another object of one embodiment of the present invention is to provide a light-emitting element emitting fluorescence with high emission efficiency. Another object of one embodiment of the present invention is to provide a light-emitting element emitting blue fluorescence with high emission efficiency. Another object of one embodiment of the present invention is to provide a light-emitting element with low drive voltage. Another object of one embodiment of the present invention is to provide a novel light-emitting device with high emission efficiency and low power consumption. Another object of one embodiment of the present invention is to provide a novel display device.

Note that the description of these objects does not disturb the existence of other objects. In one embodiment of the present invention, there is no need to achieve all the objects. Other objects will be apparent from and can be derived from the description of the specification and the like.

One embodiment of the present invention is a compound including a bicarbazole skeleton and a benzofuropyrimidine skeleton or a benzothienopyrimidine skeleton. Another embodiment of the present invention is a light-emitting element including the compound including a bicarbazole skeleton and a benzofuropyrimidine skeleton or a benzothienopyrimidine skeleton.

Therefore, one embodiment of the present invention is a compound represented by General Formula (G0) below.

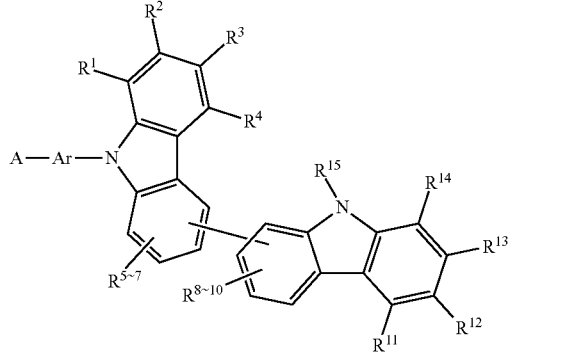

(G0)

In General Formula (G0), A represents a substituted or unsubstituted benzofuropyrimidine skeleton or a substituted or unsubstituted benzothienopyrimidine skeleton; each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms or a single bond.

In the above structure, the benzofuropyrimidine skeleton is preferably a benzofuro[3,2-d]pyrimidine skeleton. In addition, the benzothienopyrimidine skeleton is preferably a benzothieno[3,2-d]pyrimidine skeleton.

Another embodiment of the present invention is a compound represented by General Formula (G1) below.

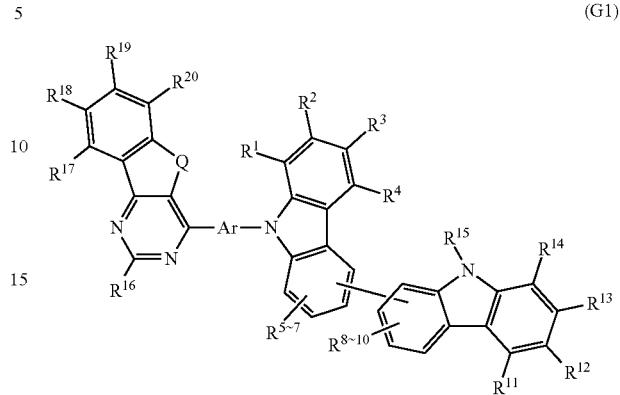

(G1)

In General Formula (G1), Q represents oxygen or sulfur; each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms; and Ar represents a substituted or unsubstituted arylene group having 6 to 25 carbon atoms or a single bond.

Another embodiment of the present invention is a compound represented by General Formula (G2) below.

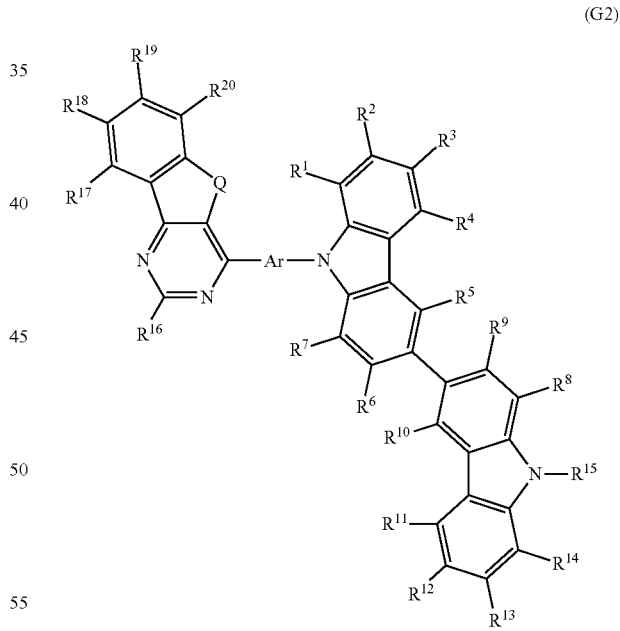

(G2)

In General Formula (G2), Q represents oxygen or sulfur; each of $R^1$ to $R^{20}$ independently represents hydrogen, a substituted or unsubstituted alkyl group having 1 to 6 carbon atoms, a substituted or unsubstituted cycloalkyl group having 3 to 7 carbon atoms, or a substituted or unsubstituted aryl group having 6 to 13 carbon atoms; and Ar represents a substituted or unsubstituted arylene group having 6 to 25 carbon atoms or a single bond.

Another embodiment of the present invention is a compound represented by General Formula (G3) below.

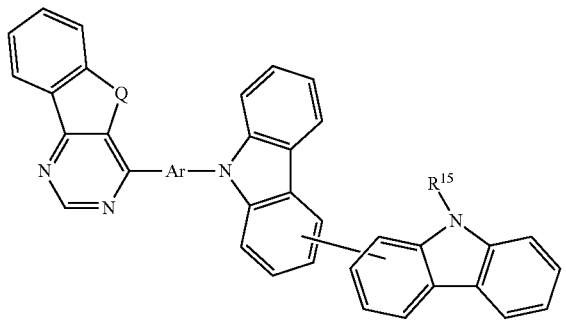

(G3)

In General Formula (G3), Q represents oxygen or sulfur; $R^{15}$ represents hydrogen, a substituted or unsubstituted alkyl group having 1 to 6 carbon atoms, a substituted or unsubstituted cycloalkyl group having 3 to 7 carbon atoms, or a substituted or unsubstituted aryl group having 6 to 13 carbon atoms; and Ar represents a substituted or unsubstituted arylene group having 6 to 25 carbon atoms or a single bond.

Another embodiment of the present invention is a compound represented by General Formula (G4) below.

(G4)

In General Formula (G4), Q represents oxygen or sulfur; $R^{15}$ represents hydrogen, a substituted or unsubstituted alkyl group having 1 to 6 carbon atoms, a substituted or unsubstituted cycloalkyl group having 3 to 7 carbon atoms, or a substituted or unsubstituted aryl group having 6 to 13 carbon atoms; and Ar represents a substituted or unsubstituted arylene group having 6 to 25 carbon atoms or a single bond.

Another embodiment of the present invention is a light-emitting element including the compound with any of the above-described structures.

In any of the above structures, the light-emitting element preferably has a function of emitting light including delayed fluorescence. The light-emitting element preferably further includes a phosphorescent material. The light-emitting element preferably has a function of emitting blue light.

Another embodiment of the present invention is a display device including the light-emitting element having any of the above-described structures, and at least one of a color filter and a transistor. Another embodiment of the present invention is an electronic device including the above-described display device and at least one of a housing and a touch sensor. Another embodiment of the present invention is a lighting device including the light-emitting element having any of the above-described structures, and at least one of a housing and a touch sensor. The category of one embodiment of the present invention includes not only a light-emitting device including a light-emitting element but also an electronic device including a light-emitting device. The light-emitting device in this specification refers to an image display device and a light source (e.g., a lighting device). The light-emitting device may be included in a module in which a connector such as a flexible printed circuit (FPC) or a tape carrier package (TCP) is connected to a light-emitting device, a module in which a printed wiring board is provided on the tip of a TCP, or a module in which an integrated circuit (IC) is directly mounted on a light-emitting element by a chip on glass (COG) method.

One embodiment of the present invention can provide a novel a novel compound. One embodiment of the present invention can provide a novel compound that emits blue fluorescence. One embodiment of the present invention can provide a novel compound with a high triplet excitation energy level. One embodiment of the present invention can provide a novel compound having a high carrier-transport property. One embodiment of the present invention can provide a light-emitting element including a novel compound. One embodiment of the present invention can provide a light-emitting element with high emission efficiency. One embodiment of the present invention can provide a light-emitting element emitting fluorescence with high emission efficiency. One embodiment of the present invention can provide a light-emitting element emitting blue fluorescence with high emission efficiency. One embodiment of the present invention can provide a light-emitting element with low drive voltage. One embodiment of the present invention can provide a novel light-emitting device with high emission efficiency and low power consumption. One embodiment of the present invention can provide a novel display device.

Note that the description of these effects does not disturb the existence of other effects. One embodiment of the present invention does not necessarily have all the effects described above. Other effects will be apparent from and can be derived from the description of the specification, the drawings, the claims, and the like.

BRIEF DESCRIPTION OF DRAWINGS

FIGS. 14A and 14B are schematic cross-sectional views each illustrating a display device of one embodiment of the present invention.

FIGS. 17A and 17B are schematic cross-sectional views each illustrating a display device of one embodiment of the present invention.

BEST MODE FOR CARRYING OUT THE INVENTION

Figure 1A:
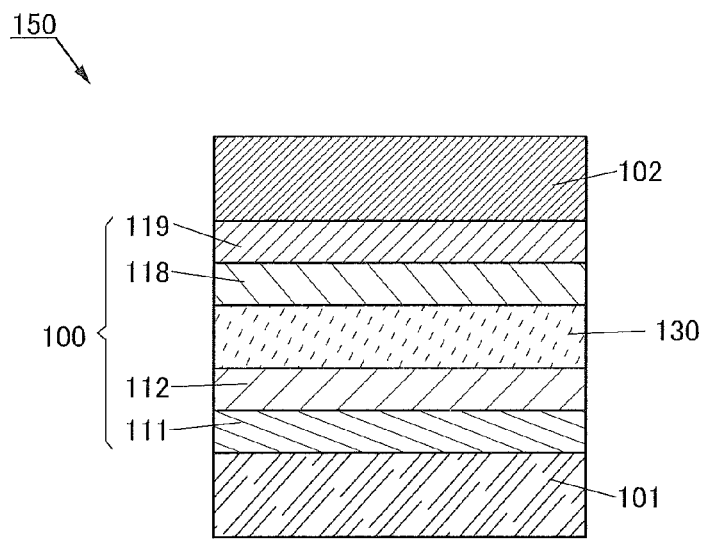
FIGS. 1A and 1B are schematic cross-sectional views illustrating a light-emitting element of one embodiment of the present invention and FIG. 1C is a schematic diagram illustrating the correlation of energy levels in a light-emitting layer.

Embodiments of the present invention will be described below with reference to the drawings. However, the present invention is not limited to description to be given below, and it is to be easily understood that modes and details thereof can be variously modified without departing from the purpose and the scope of the present invention. Accordingly, the present invention should not be interpreted as being limited to the content of the embodiments below.

Note that the position, the size, the range, or the like of each structure illustrated in drawings and the like is not accurately represented in some cases for simplification. Therefore, the disclosed invention is not necessarily limited to the position, the size, the range, or the like disclosed in the drawings and the like.

Note that the ordinal numbers such as "first", "second", and the like in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the description of modes of the present invention in this specification and the like with reference to the drawings, the same components in different diagrams are commonly denoted by the same reference numeral in some cases.

In this specification and the like, the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

In this specification and the like, a singlet excited state (S*) refers to a singlet state having excitation energy. An S1 level means the lowest level of the singlet excitation energy, that is, the excitation energy level of the lowest singlet excited state. A triplet excited state (T*) refers to a triplet state having excitation energy. A T1 level means the lowest level of the triplet excitation energy, that is, the excitation energy level of the lowest triplet excited state. Note that in this specification and the like, simple expressions "singlet excited state" and "singlet excitation energy level" mean the lowest singlet excited state and the S1 level, respectively, in some cases. In addition, simple expressions "triplet excited state" and "triplet excitation energy level" mean the lowest triplet excited state and the T1 level, respectively, in some cases.

In this specification and the like, a fluorescent material refers to a material that emits light in the visible light region when the relaxation from the singlet excited state to the ground state occurs. A phosphorescent material refers to a material that emits light in the visible light region at room temperature when the relaxation from the triplet excited state to the ground state occurs. That is, a phosphorescent material refers to a material that can convert triplet excitation energy into visible light.

Phosphorescence emission energy or a triplet excitation energy can be obtained from a wavelength of a phosphorescence emission peak (including a shoulder) or a rising portion on the shortest wavelength side of phosphorescence emission. Note that the phosphorescence emission can be observed by time-resolved photoluminescence in a low-temperature (e.g., 10 K) environment. A thermally activated delayed fluorescence emission energy can be obtained from a wavelength of an emission peak (including a shoulder) or a rising portion on the shortest wavelength side of thermally activated delayed fluorescence.

Note that in this specification and the like, "room temperature" refers to a temperature higher than or equal to 0° C. and lower than or equal to 40° C.

In this specification and the like, a wavelength range of blue refers to a wavelength range of greater than or equal to 400 nm and less than 500 nm, and blue light has at least one peak in that range in an emission spectrum. A wavelength range of green refers to a wavelength range of greater than or equal to 500 nm and less than 580 nm, and green light has at least one peak in that range in an emission spectrum. A wavelength range of red refers to a wavelength range of greater than or equal to 580 nm and less than or equal to 740 nm, and red light has at least one peak in that range in an emission spectrum.

Embodiment 1

In this embodiment, for example, a compound that can be suitably used in a light-emitting element of one embodiment of the present invention is described below.

A compound of one embodiment of the present invention is a compound including at least a bicarbazole skeleton and a benzofuropyrimidine skeleton or a benzothienopyrimidine skeleton. The compound has a wide band gap; thus, a light-emitting element including the compound can have high emission efficiency. In addition, the compound has a high carrier-transport property; thus, a light-emitting element including the compound can have low drive voltage. The compound is highly resistant to repetition of oxidation and reduction; thus, a light-emitting element including the compound can have high reliability. Therefore, a light-emitting element including the compound is a high-performance light-emitting element having excellent emission characteristics.

The compound includes a π-electron rich heteroaromatic ring (a bicarbazole skeleton) and a π-electron deficient heteroaromatic ring (a benzofuropyrimidine skeleton or a benzothienopyrimidine skeleton). Accordingly, a donor-acceptor excited state is easily formed in a molecule. Furthermore, the π-electron rich heteroaromatic ring (the bicarbazole skeleton) and the π-electron deficient heteroaromatic ring (the benzofuropyrimidine skeleton or the benzothienopyrimidine skeleton) are bonded directly or through an arylene group, which can improve both the donor property and the acceptor property. By increasing both the donor property and the acceptor property in the molecule, an overlap between a region where the highest occupied molecular orbital (HOMO) is distributed and a region where the lowest unoccupied molecular orbital (LUMO) is distributed can be small, and the energy difference between the singlet excitation energy level and the triplet excitation energy level of the compound can be small. Moreover, the triplet excitation energy level of the compound can be kept high. Note that the molecular orbital refers to spatial distribution of electrons in a molecule, and can show the probability of finding of electrons. In addition, with the molecular orbital, electron configuration of the molecule (spatial distribution and energy of electrons) can be described in detail.

When a difference between the singlet excitation energy level and the triplet excitation energy level is small, with low thermal energy at 100° C. or lower, preferably at approximately room temperature, the triplet excitation energy can be upconverted to the singlet excitation energy by reverse intersystem crossing. Therefore, the compound of one embodiment of the present invention is suitably used as a compound that has a function of converting the triplet excitation energy into the singlet excitation energy or a compound that has a function of converting the triplet excitation energy into the singlet excitation energy and converting it into light emission. For efficient reverse intersystem crossing, the difference between the singlet excitation energy level and the triplet excitation energy level is preferably greater than 0 eV and less than or equal to 0.3 eV, more preferably greater than 0 eV and less than or equal to 0.2 eV, still more preferably greater than 0 eV and less than or equal to 0.1 eV.

Note that when the region where the HOMO is distributed and the region where the LUMO is distributed overlap each other and transition dipole moment between the HOMO level and the LUMO level is larger than 0, light emission can be obtained from an excited state related to the HOMO level and the LUMO level (e.g., the lowest singlet excited state). Therefore, the compound of one embodiment of the present invention is suitable as a light-emitting material that has a function of converting the triplet excitation energy into the singlet excitation energy; in other words, the compound is suitable as a thermally activated delayed fluorescence material.

The compound of one embodiment of the present invention has high excitation energy and a high carrier-transport property; thus, the compound is suitable as a host material of a light-emitting material. In addition, since the compound of one embodiment of the present invention can have a high singlet excitation energy level (S1 level) and a high triplet excitation energy level (T1 level) as described above, the compound can be suitably used for a light-emitting element including a fluorescent material or a phosphorescent material as a light-emitting material.

As a skeleton including a π-electron deficient heteroaromatic ring, a diazine skeleton is preferred because of its high excitation energy. Among diazine skeletons, a condensed heterocyclic skeleton including a diazine skeleton is further preferred because of its stability and high reliability, and a benzofuropyrimidine skeleton and a benzothienopyrimidine skeleton are preferred because of their high acceptor property. As an example of the benzofuropyrimidine skeleton, a benzofuro[3,2-d]pyrimidine skeleton is given. As an example of the benzothienopyrimidine skeleton, benzothieno[3,2-d]pyrimidine skeleton is given.

Among skeletons having the π-electron rich heteroaromatic ring, a pyrrole skeleton is preferable because of its high excitation energy. Among pyrrole skeletons, a carbazole skeleton is preferred because of its stability and high reliability. Specifically, a bicarbazole skeleton, in particular, a bicarbazole skeleton in which any of the 2- to 4-positions of a carbazolyl group is bonded to any of the 2- to 4-positions of another carbazolyl group is preferable because of its high donor property. As such a bicarbazole skeleton, for example, 2,2'-bi-9H-carbazole skeleton, 3,3'-bi-9H-carbazole skeleton, 4,4'-bi-9H-carbazole skeleton, 2,3'-bi-9H-carbazole skeleton, 2,4'-bi-9H-carbazole skeleton, 3,4'-bi-9H-carbazole skeleton, and the like are given.

In the case where the bicarbazole skeleton is directly bonded to the benzofuropyrimidine skeleton or the benzothienopyrimidine skeleton, a relatively low molecular compound is formed, and therefore, a structure that is suitable for vacuum evaporation (a structure that can be formed by vacuum evaporation at a relatively low temperature) is obtained, which is preferable. In general, a lower molecular weight tends to reduce heat resistance after film formation. However, because of high rigidity of the benzofuropyrimidine skeleton, the benzothienopyrimidine skeleton, and the bicarbazole skeleton, a compound including the skeleton can have sufficient heat resistance even with a relatively low molecular weight. The structure is preferable because a band gap and an excitation energy level are increased.

In the case where the bicarbazole skeleton is bonded to the benzofuropyrimidine skeleton or the benzothienopyrimidine skeleton through an arylene group having 6 to 25 carbon atoms, preferably 6 to 13 carbon atoms, a relatively low molecular compound is forming, and therefore, a structure that is suitable for vacuum evaporation (a structure that can be formed by vacuum evaporation at a relatively low temperature) is obtained.

In the case where a bicarbazole skeleton is bonded, directly or through an arylene group, to a benzofuro[3,2-d]pyrimidine skeleton or a benzothieno[3,2-d]pyrimidine skeleton, preferably the 4-position of the benzofuro[3,2-d]pyrimidine skeleton or the benzothieno[3,2-d]pyrimidine skeleton in a compound, the compound has a high carrier-transport property. Accordingly, a light-emitting element using the compound can be driven at a low voltage.

In other words, the above compound is a benzofuropyrimidine compound or a benzothienopyrimidine compound in which a bicarbazole skeleton is bonded to a benzofuropyrimidine skeleton or a benzothienopyrimidine skeleton. The compound can be easily synthesized with high purity, so that deterioration due to impurities can be suppressed. In terms of stability and reliability of element characteristics of a light-emitting element, the number of carbon atoms of an aryl group bonded to the benzofuropyrimidine skeleton, the benzothienopyrimidine skeleton, or the bicarbazole skeleton is preferably 6 to 13. In that case, the compound can be vacuum-evaporated at a relatively low temperature, and accordingly deterioration such as pyrolysis is unlikely to occur at evaporation. A structure in which the bicarbazole skeleton is bonded to the 4-position of the benzofuro[3,2-d]pyrimidine skeleton or the benzothieno[3,2-d]pyrimidine skeleton directly or through an arylene group is preferable because the structure has high electrochemical stability and a high carrier-transport property.

A compound in which the 9-position of one of two carbazolyl groups of the bicarbazole skeleton is bonded to the benzofuropyrimidine skeleton or the benzothienopyrimidine skeleton directly or through an arylene group has a wide band gap, and thus can be suitably used in a light-emitting element emitting high-energy light such as blue light. For a wider band gap and higher triplet excitation energy, it is preferable that the 9-position of one of two carbazolyl groups of the bicarbazole skeleton be directly bonded to the benzofuropyrimidine skeleton or the benzothienopyrimidine skeleton. Note that in the case where the bicarbazole skeleton is bonded to the benzofuropyrimidine skeleton or the benzothienopyrimidine skeleton through an arylene group, for both a wide band gap and high triplet excitation energy, the arylene group is preferably a phenylene group, a biphenyldiyl group, or the like.

For the above reasons, a compound in which the 9-position of one of two carbazolyl groups, which are bonded to each other at any of the 2- to 4-positions, of the bicarbazole skeleton is bonded to the 4-position of the benzofuro[3,2-d]pyrimidine skeleton or the benzothieno[3,2-d]pyrimidine skeleton difectly or through an arylene group is particularly preferred. In terms of stability of a compound and a light-emitting element, the number of carbon atoms of the arylene group that is bonded to the benzofuro[3,2-d]pyrimidine skeleton or the benzothieno[3,2-d]pyrimidine skeleton and the bicarbazole skeleton is preferably 6 to 25, more preferably 6 to 13. The compound has features of a wide band gap and a high triplet excitation energy level owing to the influence of the bicarbazole skeleton and the benzofuropyrimidine skeleton or the benzothienopyrimidine skeleton, in addition to the above-described features such as the ease of evaporation and high electrochemical stability, and a carrier-transport property. Therefore, the compound is suitable as a light-emitting material or a host material in a light-emitting layer of a light-emitting element. In particular, the compound is suitably used in a blue light-emitting element.

Example 1 of Compound

The above-described compound of one embodiment of the present invention is a compound represented by General Formula (G0) below.

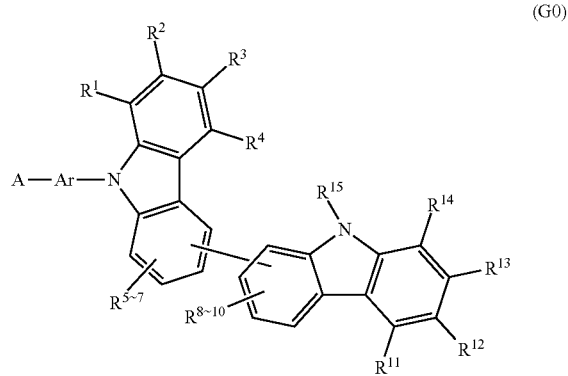

(G0)

In General Formula (G0), A represents a substituted or unsubstituted benzofuropyrimidine skeleton or a substituted or unsubstituted benzothienopyrimidine skeleton. In the case where the benzofuropyrimidine skeleton or the benzothienopyrimidine skeleton has a substituent, as the substituent, an alkyl group having 1 to 6 carbon atoms, a cycloalkyl group having 3 to 7 carbon atoms, or a substituted or unsubstituted aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Further, each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, Ar represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

In the compound in this embodiment, the benzofuropyrimidine skeleton is preferably a benzofuro[3,2-d]pyrimidine skeleton.

In the compound in this embodiment, the benzothienopyrimidine skeleton is preferably a benzothieno[3,2-d]pyrimidine skeleton.

Example 2 of Compound

The compound in this embodiment in which the 9-position of one of the carbazolyl groups in the bicarbazole skeleton is bonded, directly or through the arylene group, to the 4-position of the benzofuro[3,2-d]pyrimidine skeleton or the benzothieno[3,2-d]pyrimidine skeleton has a high donor property, a high acceptor property, and a wide band gap, and therefore can suitably be used in a light-emitting element that emits light with high energy such as blue light, which is preferable. The above-described compound is a compound represented by General Formula (G1).

(G1)

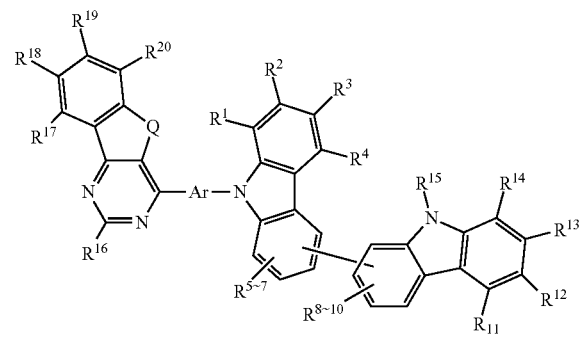

In General Formula (G1), Q represents oxygen or sulfur.

Further, each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atom. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, Ar represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Example 3 of Compound

In a compound of this embodiment, the bicarbazole skeleton is a 3,3'-bi-9H-carbazole skeleton, and the 9-position of one of two carbazolyl groups of the bicarbazole skeleton is bonded to the 4-position of the benzofuro[3,2-d]pyrimidine skeleton or the benzothieno[3,2-d]pyrimidine skeleton directly or through an arylene group. This compound has a high carrier-transport property, and a light-emitting element including the compound can be driven at a low voltage; therefore, the structure of the compound is preferred. The compound is represented by General Formula (G2).

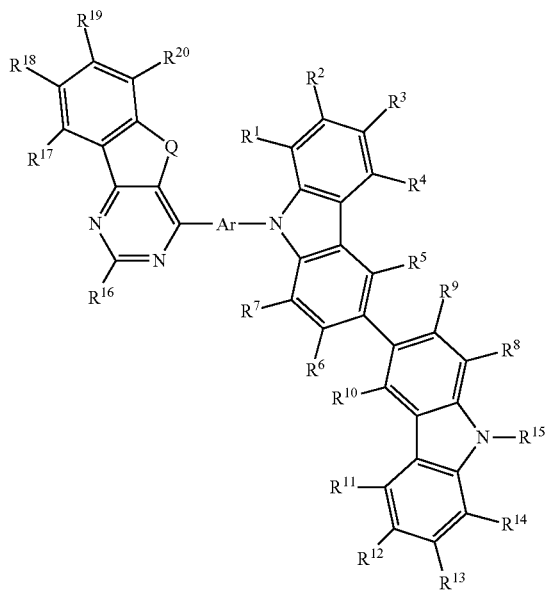

(G2)

In General Formula (G2), Q represents oxygen or sulfur.

Further, each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atom. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, Ar represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

In the case where the bicarbazole skeleton is directly bonded to the benzofuropyrimidine skeleton or the benzothienopyrimidine skeleton in the compound in this embodiment, the compound has a wider band gap and can be synthesized with higher purity, which is preferable. Because the compound has an excellent carrier-transport property, a light-emitting element including the compound can be driven at a low voltage, which is preferable.

Example 4 of Compound

In the case where each of $R^1$ to $R^{14}$ and $R^{16}$ to $R^{20}$ represents hydrogen in General Formula (G1) or (G2), the compound is advantageous in terms of easiness of synthesis and material cost and has a relatively low molecular weight to be suitable for vacuum evaporation, which is particularly preferable. The compound is a compound represented by General Formula (G3) or (G4).

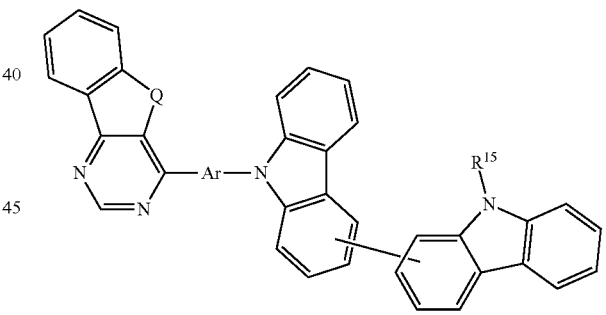

(G3)

In General Formula (G3), Q represents oxygen or sulfur.

Further, $R^{15}$ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, Ar represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

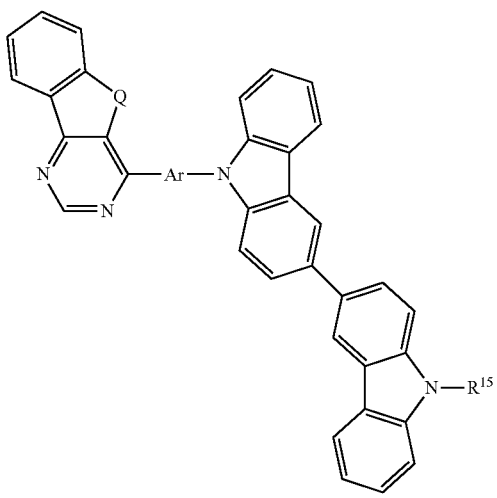

(G4)

In General Formula (G4), Q represents oxygen or sulfur.

Further, $R^{15}$ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Furthermore, Ar represents an arylene group having 6 to 25 carbon atoms or a single bond. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 25 carbon atoms include a phenylene group, a naphthylene group, a biphenyldiyl group, a fluorenediyl group, and the like. In the case where the arylene group has a substituent, as the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

Examples of Substituents

As the benzofuropyrimidine skeleton or the benzothienopyrimidine skeleton represented by A in General Formula (G0), any of structures represented by Structural Formulae (Ht-1) to (Ht-24) can be used, for example. Note that a structure that can be used as A is not limited to these.

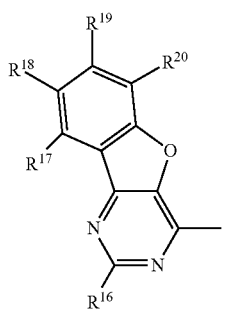

(Ht-1)

(Ht-2)
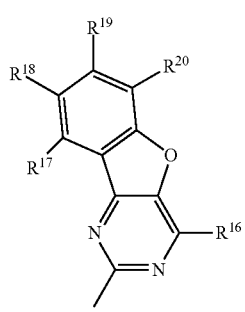
(Ht-3)
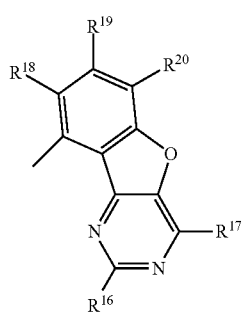
(Ht-4)
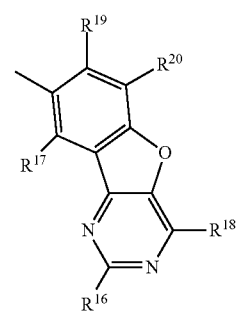
(Ht-5)
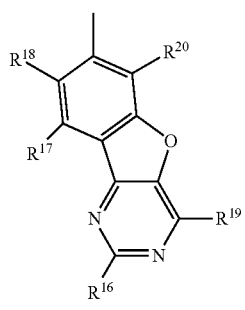
(Ht-6)
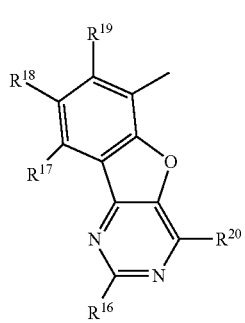
(Ht-7)
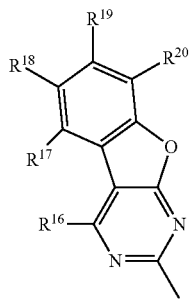
(Ht-8)
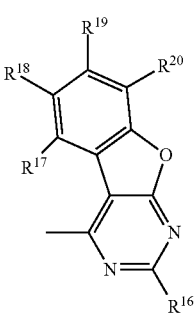
(Ht-9)
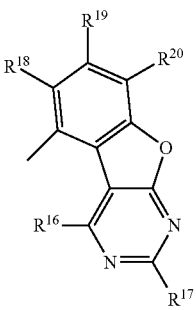
(Ht-10)
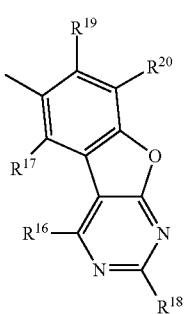
(Ht-11)
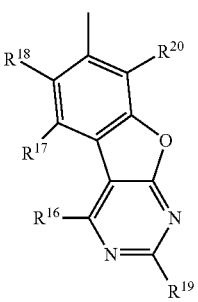

(Ht-12) 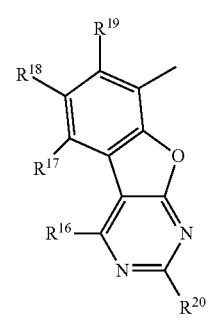
(Ht-13) 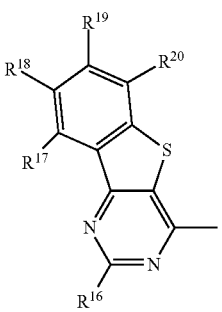
(Ht-14) 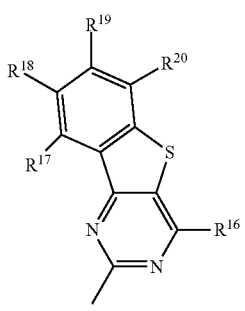
(Ht-15) 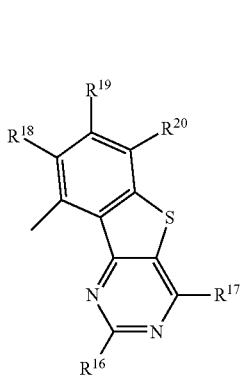
(Ht-16) 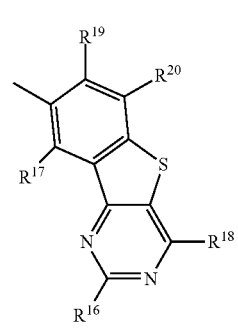
(Ht-17) 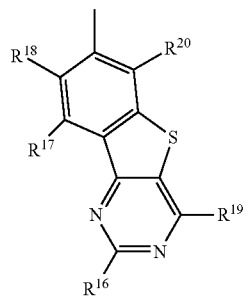
(Ht-18) 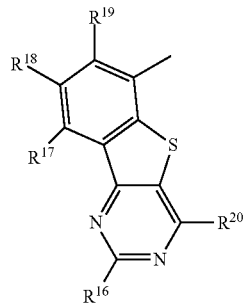
(Ht-19) 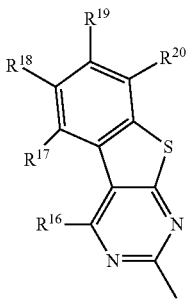
(Ht-20) 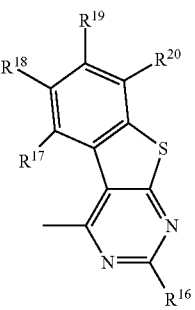
(Ht-21) 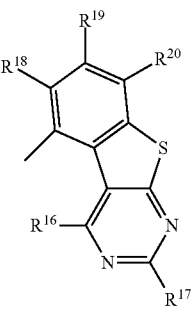

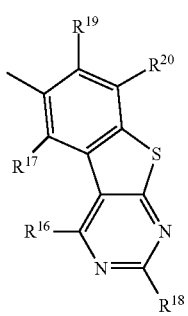
(Ht-22)

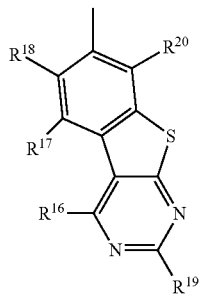
(Ht-23)

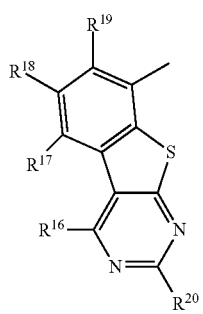
(Ht-24)

In Structural Formulae (Ht-1) to (Ht-24), each of $R^{16}$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

For example, structures represented by Structural Formulae (Cz-1) to (Cz-9) shown below can be used as the structure of the bicarbazole skeleton in General Formulae (G0) and (G1). Note that the structures of the bicarbazole skeleton are not limited to these.

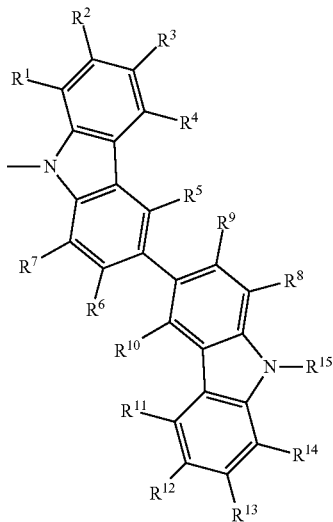
(Cz-1)

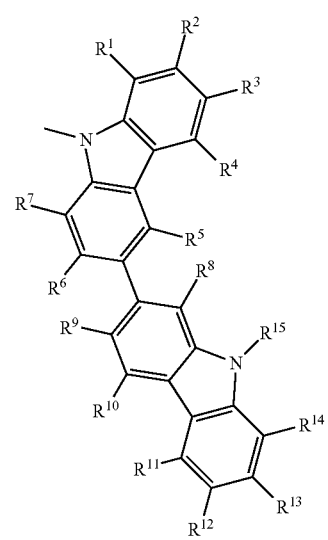
(Cz-2)

-continued
(Cz-3)
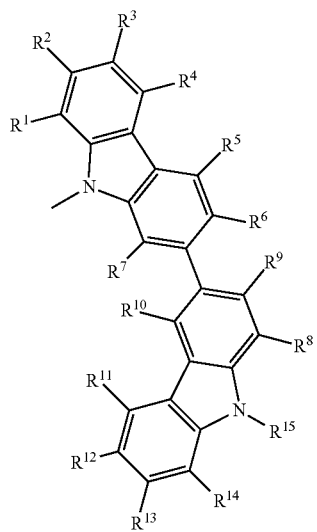
(Cz-4)
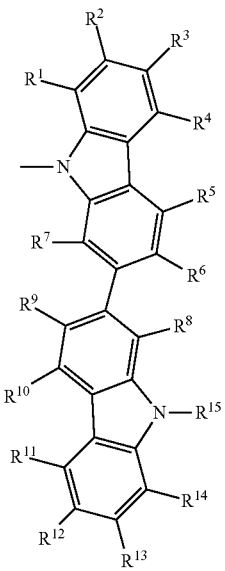
(Cz-5)
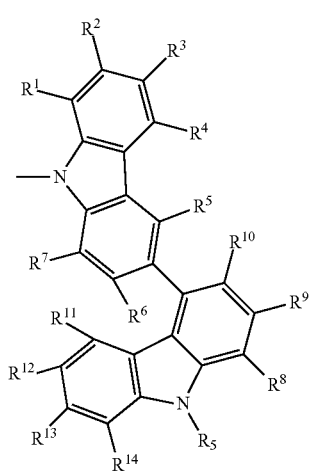
(Cz-6)
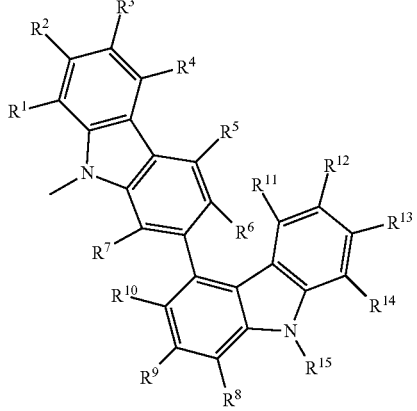
(Cz-7)
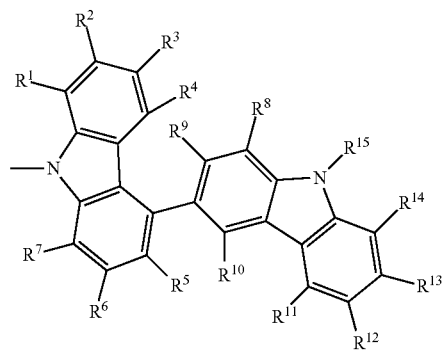
(Cz-8)
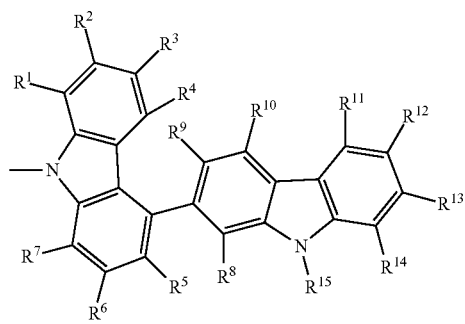
(Cz-9)
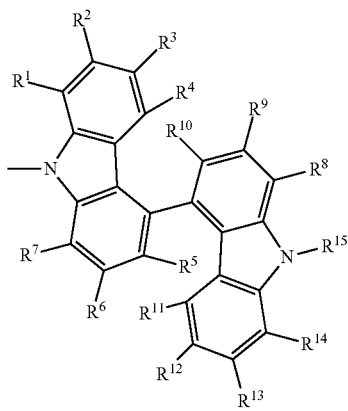
In Structural Formulae (Cz-1) to (Cz-9), each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like. The above alkyl group, cycloalkyl group, and aryl group may include one or more substituents, and the substituents may be bonded to each other to form a ring. As the substituent, an alkyl group having 1 to 6 carbon atoms, a cycloalkyl group having 3 to 7 carbon atoms, or an aryl group having 6 to 13 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 7 carbon atoms include a cyclopropyl group, a cyclobutyl group, a cyclopentyl group, a cyclohexyl group, and the like. Specific examples of the aryl group having 6 to 13 carbon atoms include a phenyl group, a naphthyl group, a biphenyl group, a fluorenyl group, and the like.

As the arylene group represented by Ar in General Formulae (G0) to (G4), any of groups represented by Structure Formulae (Ar-1) to (Ar-27) can be used, for example. Note that the group that can be used for Ar is not limited to these and may include a substituent.

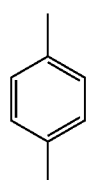
(Ar-1)

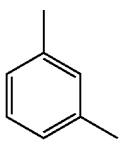
(Ar-2)

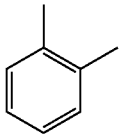
(Ar-3)

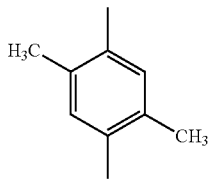
(Ar-4)

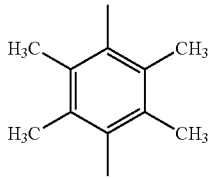
(Ar-5)

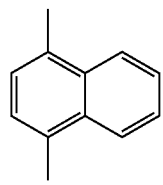
(Ar-6)

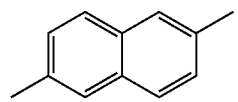
(Ar-7)

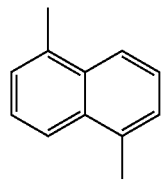
(Ar-8)

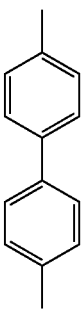
(Ar-9)

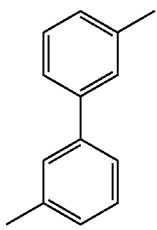
(Ar-10)

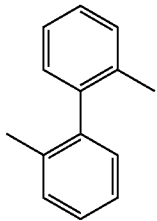
(Ar-11)

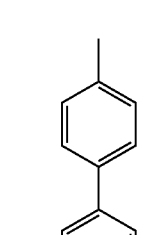
(Ar-12)

(Ar-13) 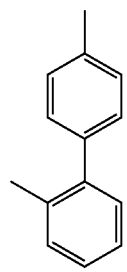
(Ar-14) 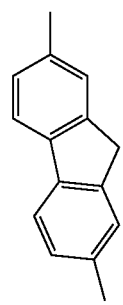
(Ar-15) 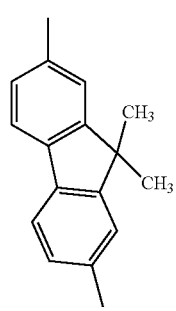
(Ar-16) 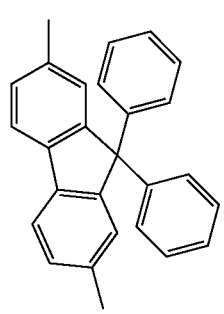
(Ar-17) 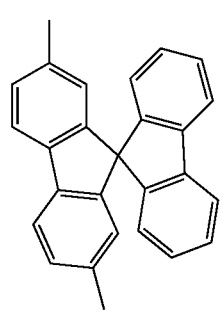
(Ar-18) 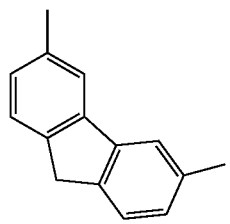
(Ar-19) 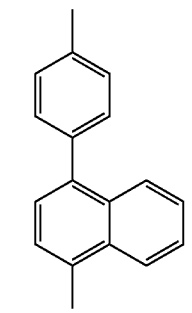
(Ar-20) 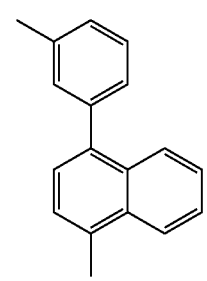
(Ar-21) 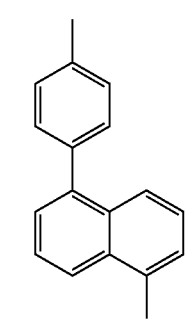
(Ar-22) 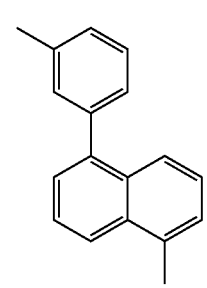

(Ar-23)

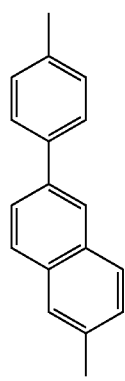

(Ar-24)

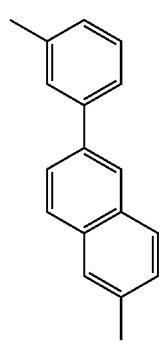

(Ar-25)

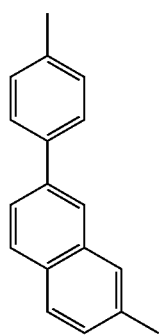

(Ar-26)

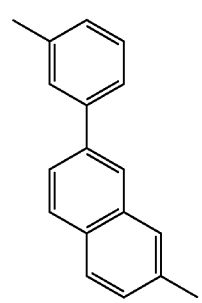

(Ar-27)

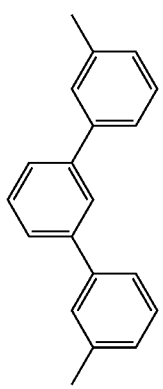

For example, any of groups represented by Structural Formulae (R-1) to (R-29) can be used for the alkyl group, the cycloalkyl group, or the aryl group represented by $R^1$ to $R^{20}$ in General Formulae (G1) and (G2), $R^1$ to $R^{15}$ in General Formula (G0), and $R^{15}$ represented by General Formulae (G3) and (G4). Note that group that can be used as the alkyl group, the cycloalkyl group, or the aryl group is not limited to these and may include a substituent.

(R-1)

H—

(R-2)

CH₃—

(R-3)

H₃C—CH₂—

(R-4)

CH₃
|
H₂C—CH₂—

(R-5)

H₃C    CH₃
   \\  /
    CH—

(R-6)

H₃C—CH₂
         \\
          H₂C—CH₂—

(R-7)

CH₃
|
H₃C—CH—CH₂—

(R-8)

H₂
H₃C—C—CH—CH₃
          |

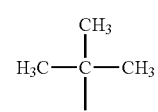 (R-9)
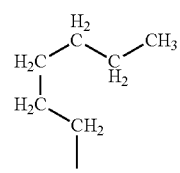 (R-10)
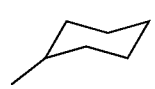 (R-11)
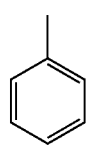 (R-12)
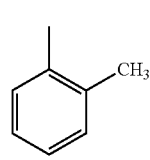 (R-13)
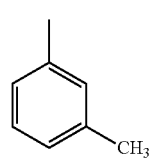 (R-14)
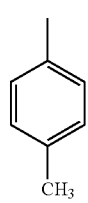 (R-15)
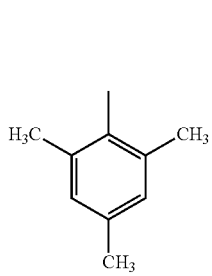 (R-16)
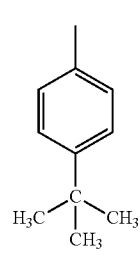 (R-17)
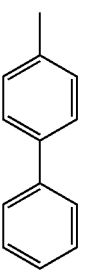 (R-18)
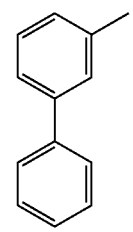 (R-19)
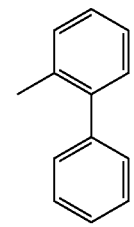 (R-20)
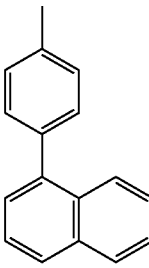 (R-21)
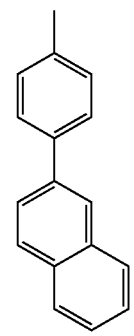 (R-22)
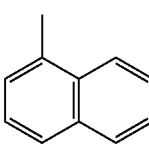 (R-23)

-continued
(R-24) 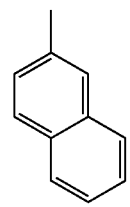
(R-25) 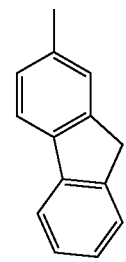
(R-26) 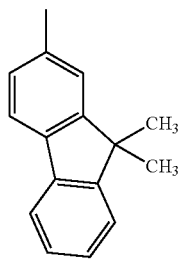
(R-27) 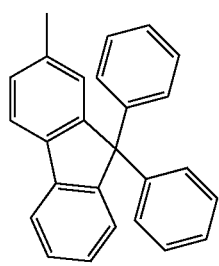
(R-28) 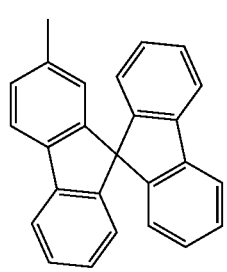
(R-29) 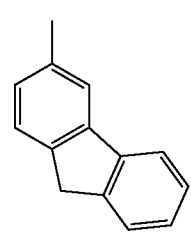
Specific Examples of Compounds
Specific examples of structures of the compounds represented by General Formulae (G0) to (G4) include compounds represented by Structural Formulae (100) to (147). Note that the compounds represented by General Formulae (G0) to (G4) are not limited to the following examples.
(100) 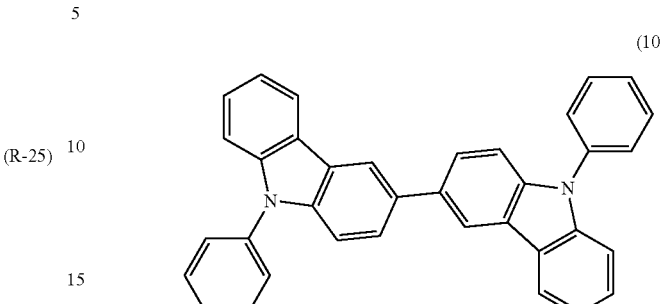
(101) 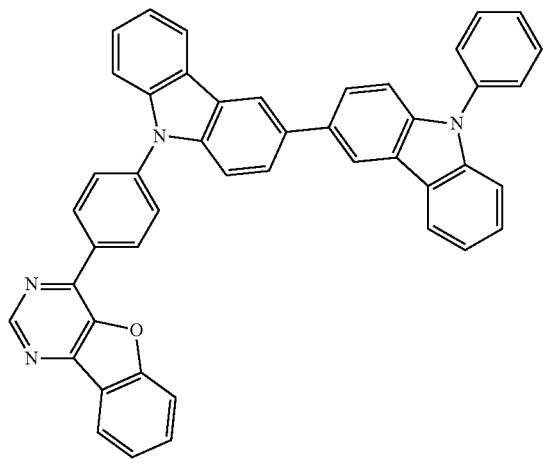
(102) 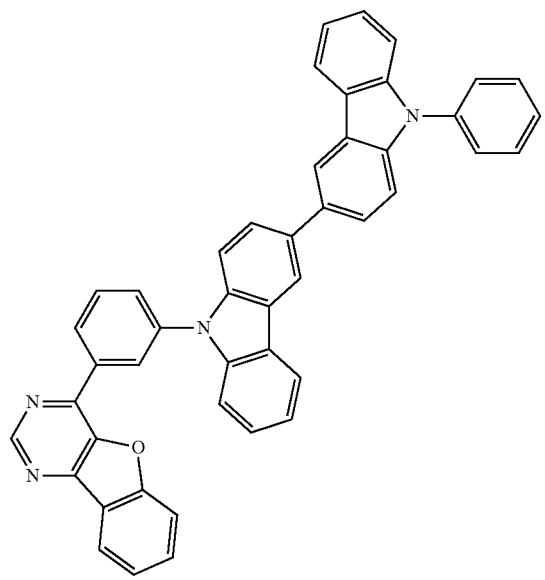

(103)
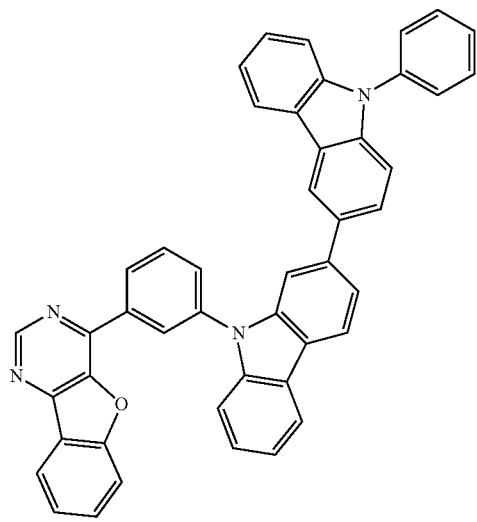
(104)
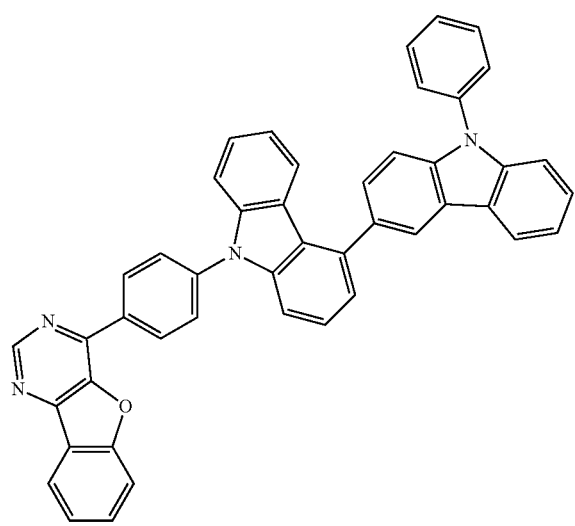
(105)
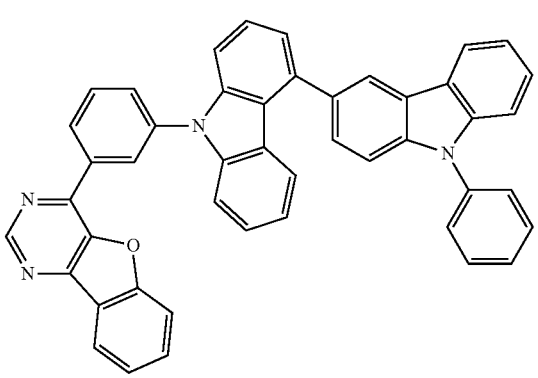
(106)
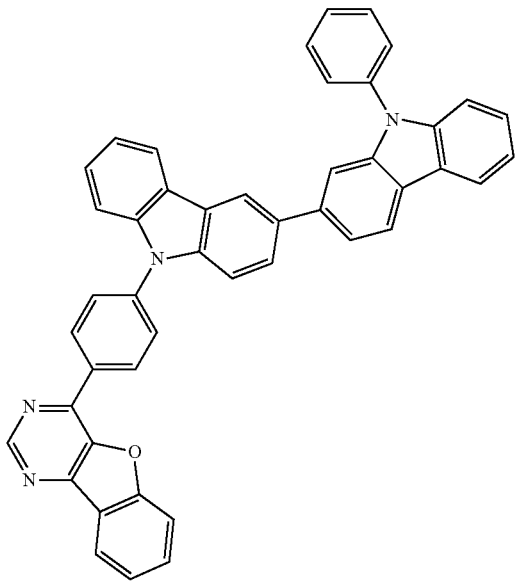
(107)
(108)
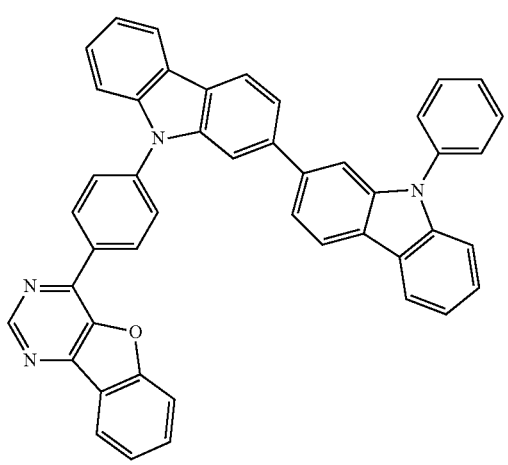

(109)
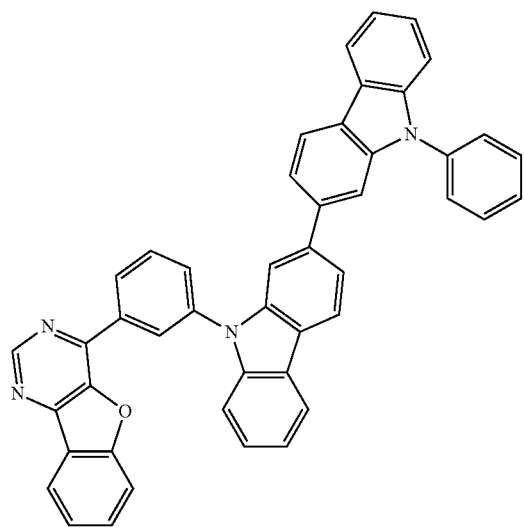
(110)
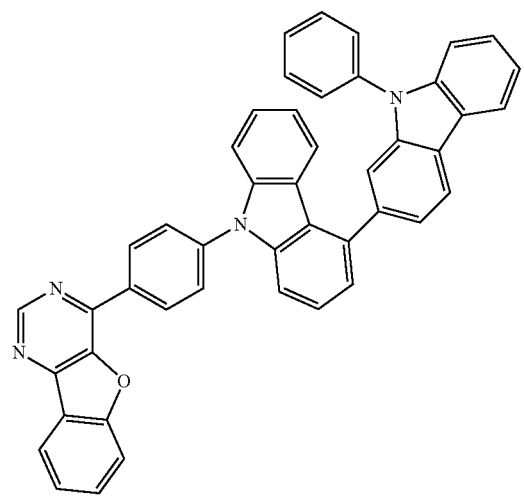
(111)
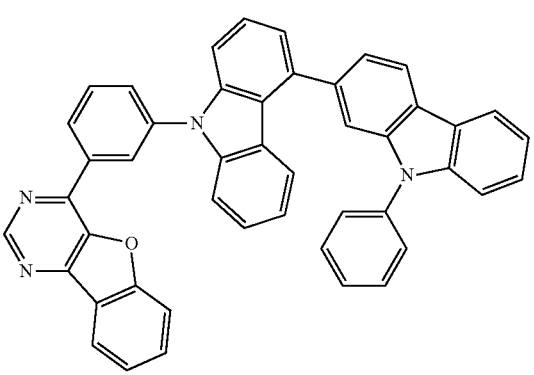
(112)
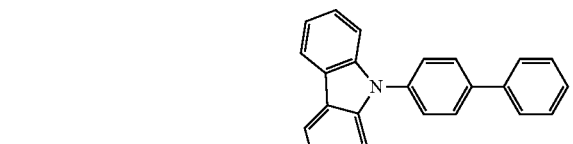
(113)
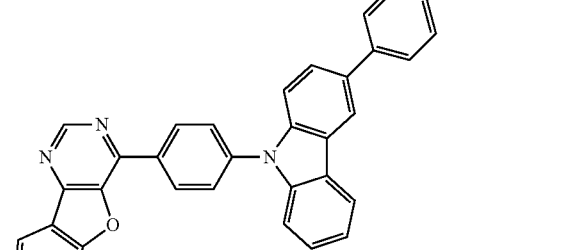
(114)
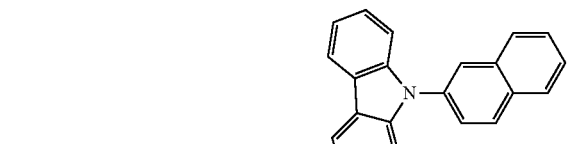
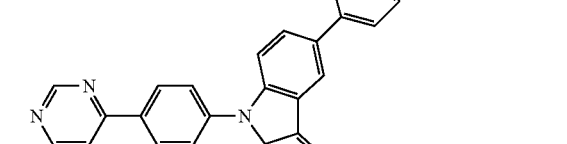
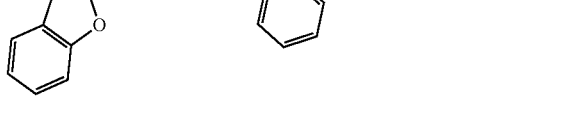

(115)
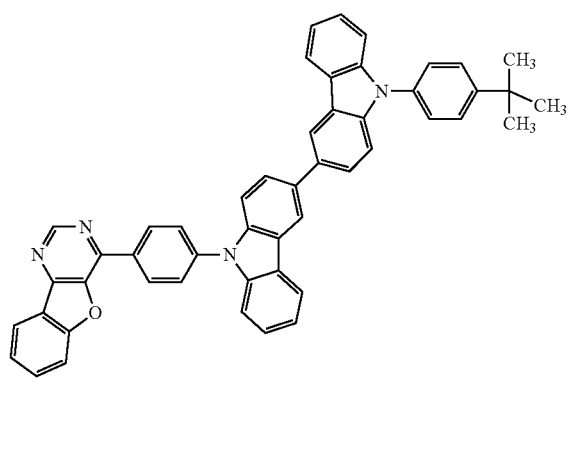
(116)
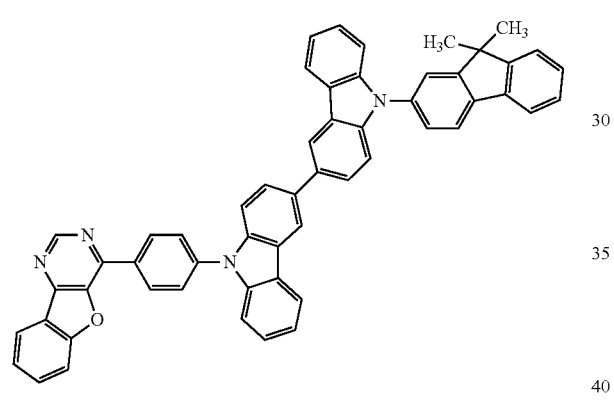
(117)
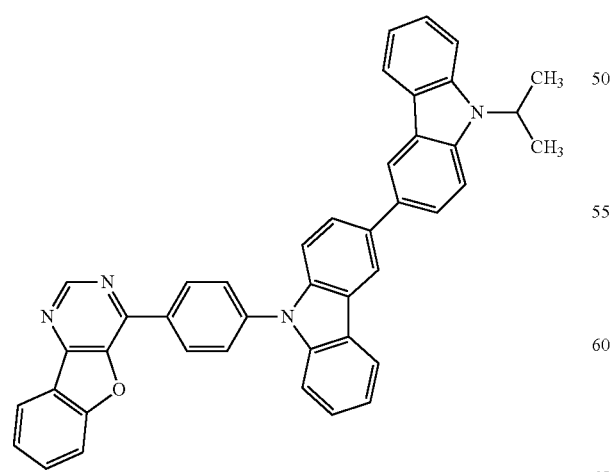
(118)
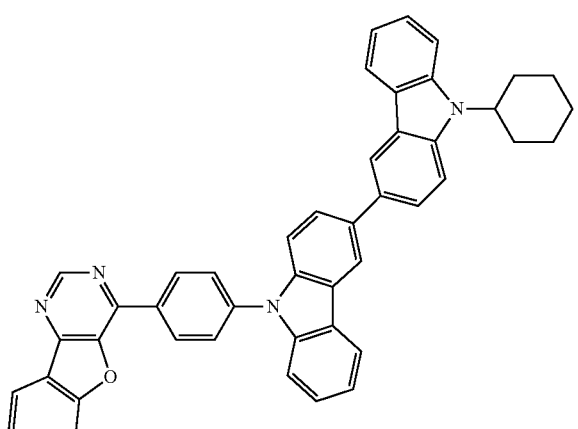
(119)
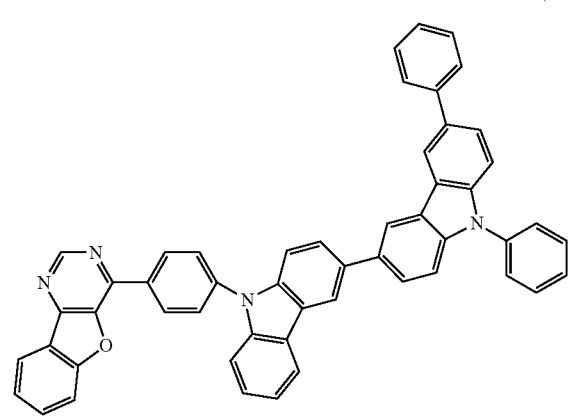
(120)
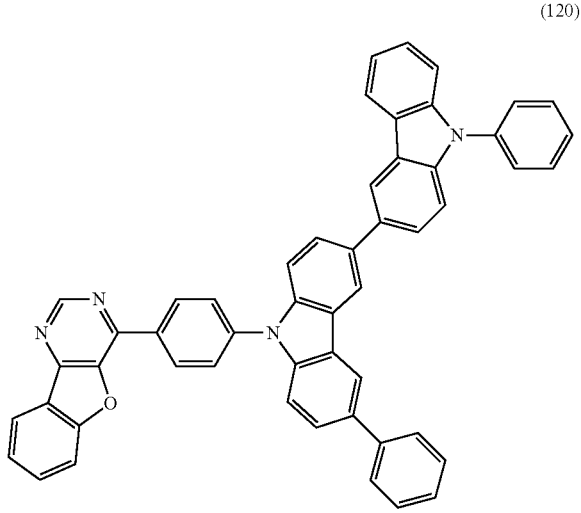

(121)
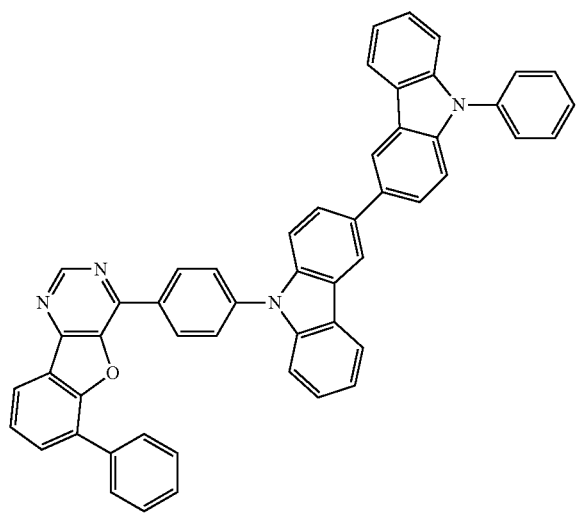
(122)
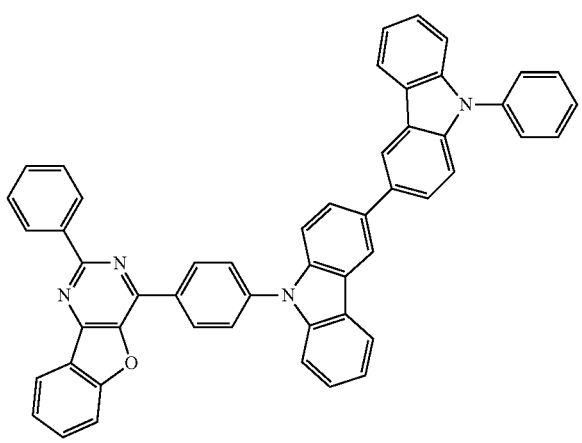
(123)
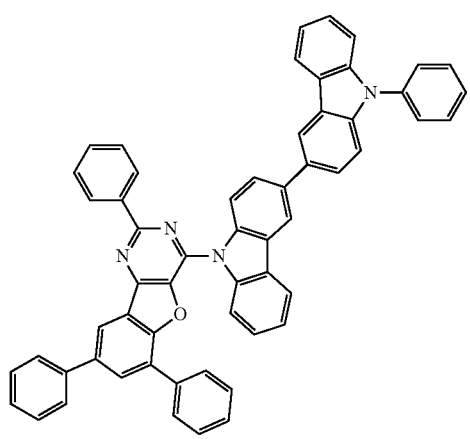
(124)
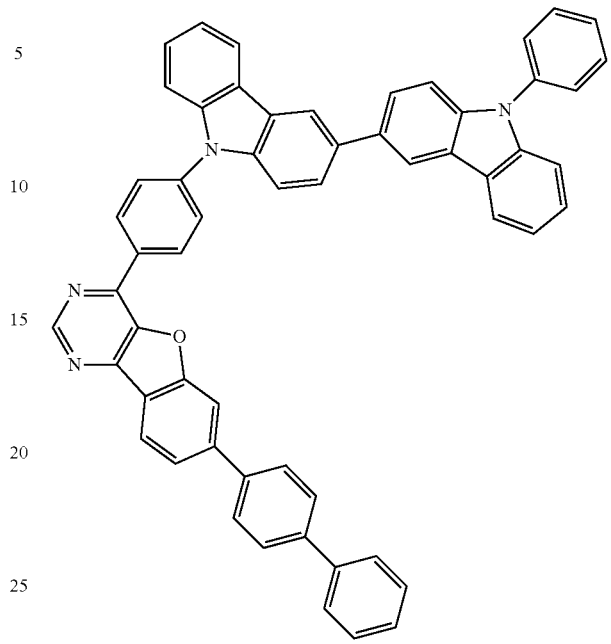
(125)
(126)
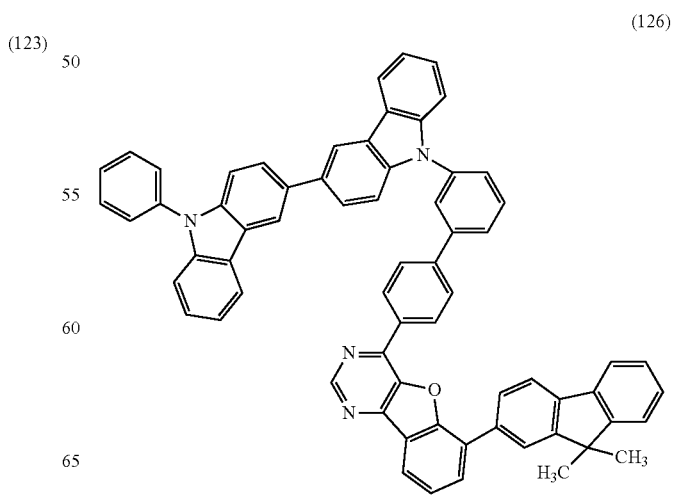

(127)
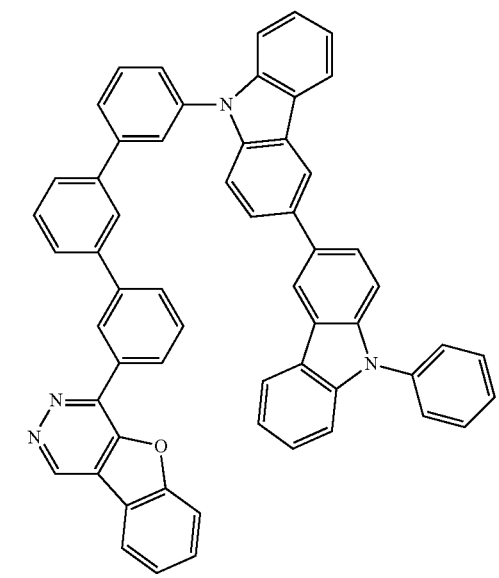
(128)
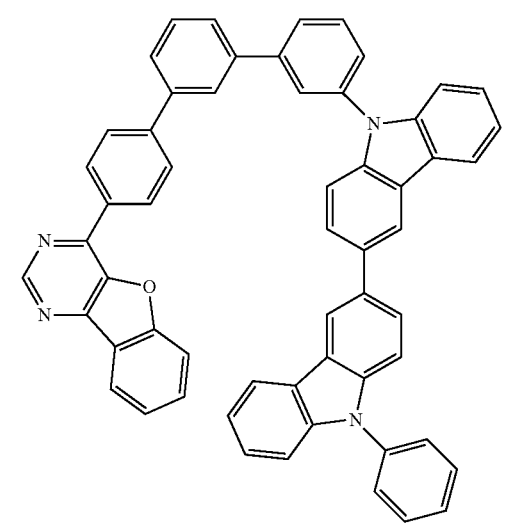
(129)
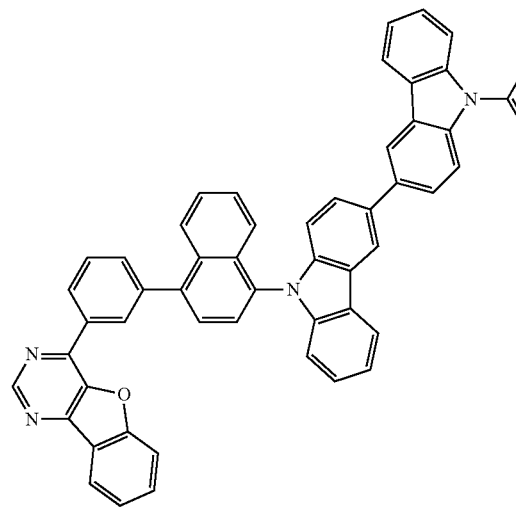
(130)
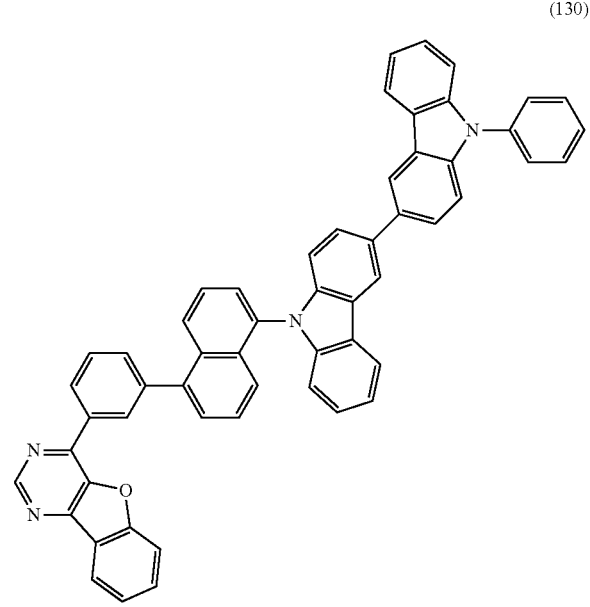
(131)
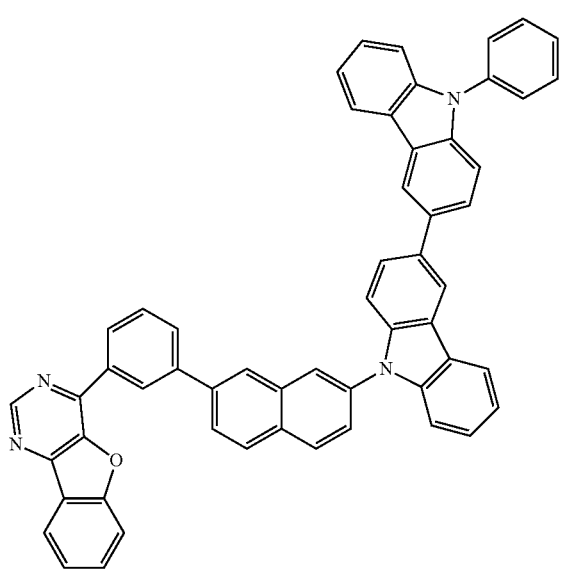

(132)
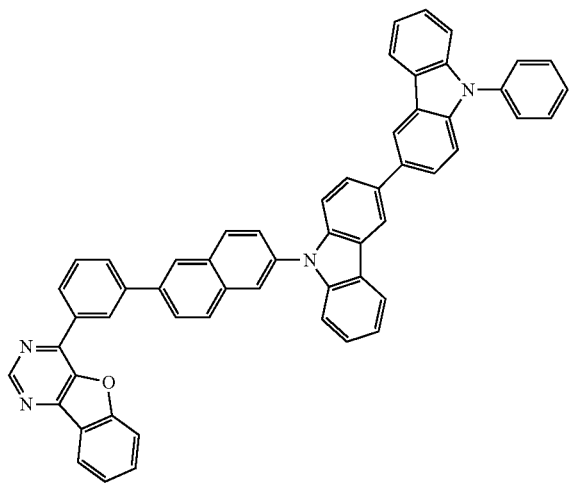
(133)
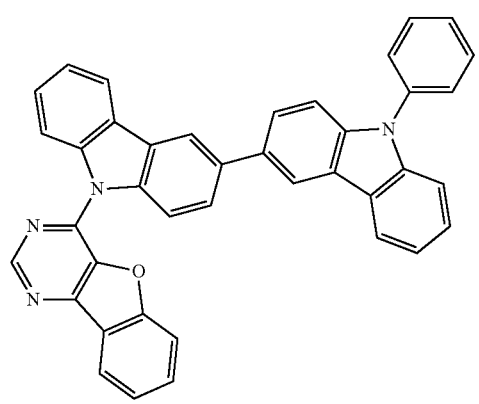
(134)
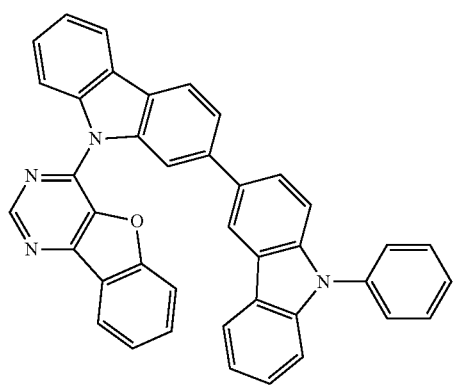
(135)
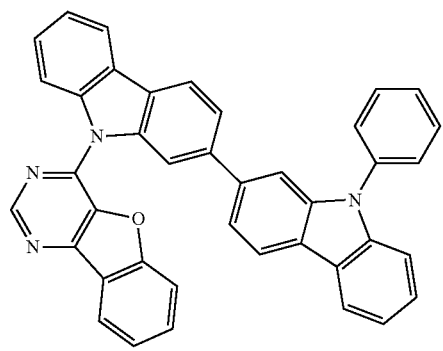
(136)
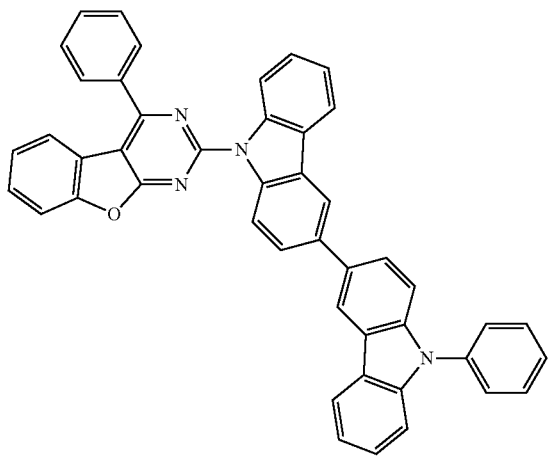
(137)
(138)
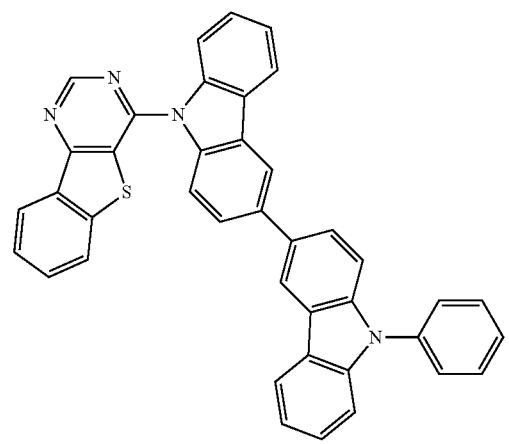

(139)
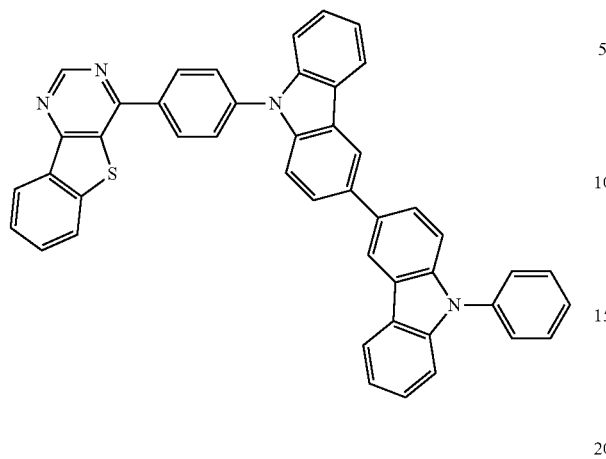
(140)
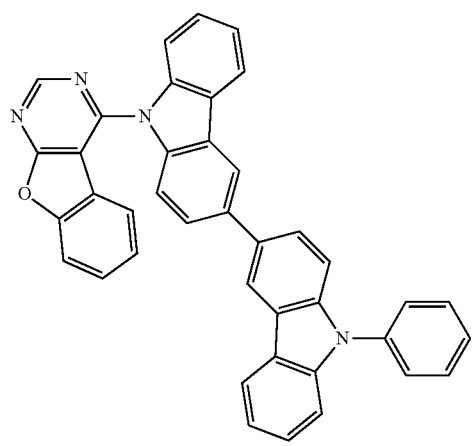
(141)
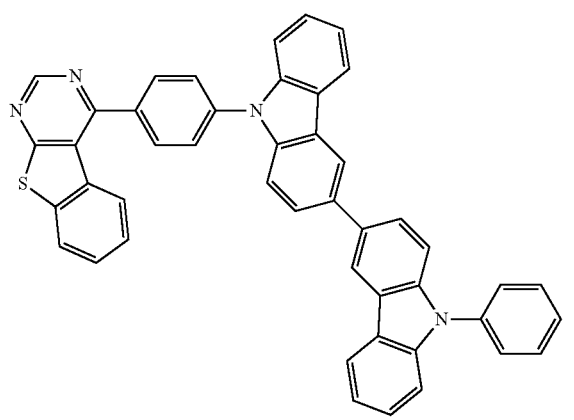
(142)
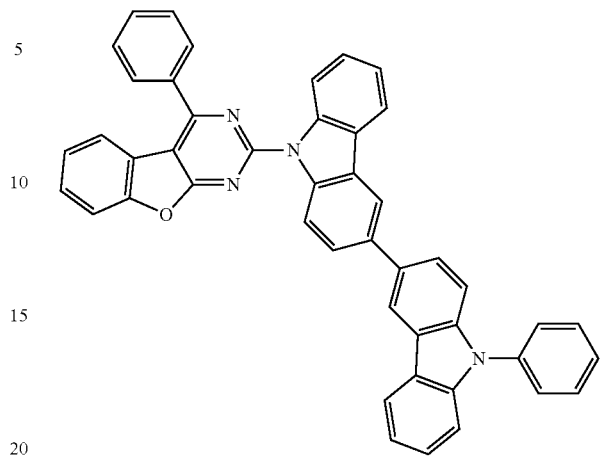
(143)
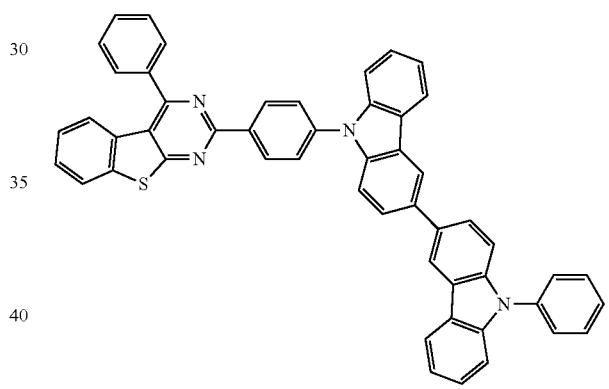
(144)
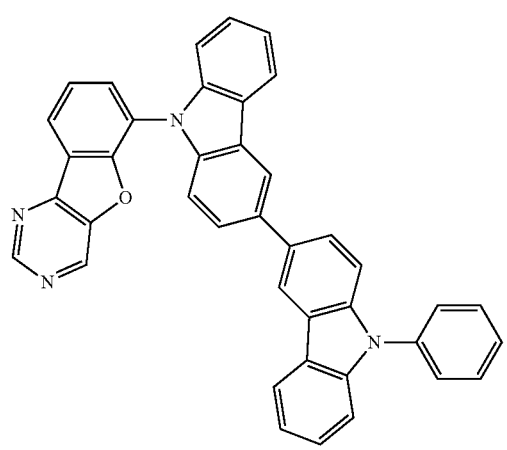

(145)

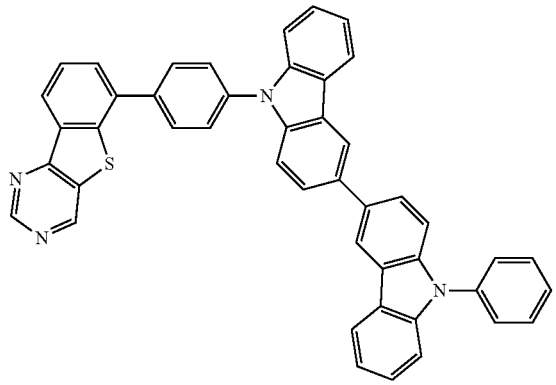

(146)

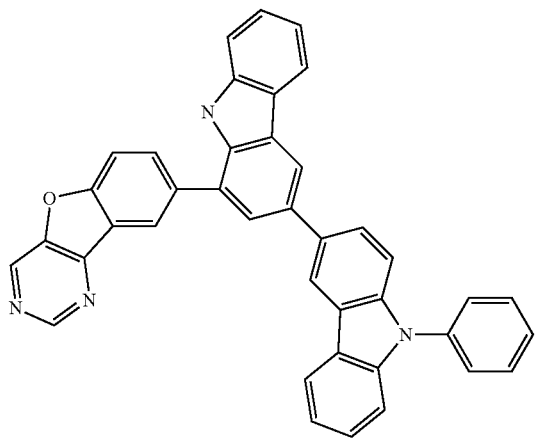

(147)

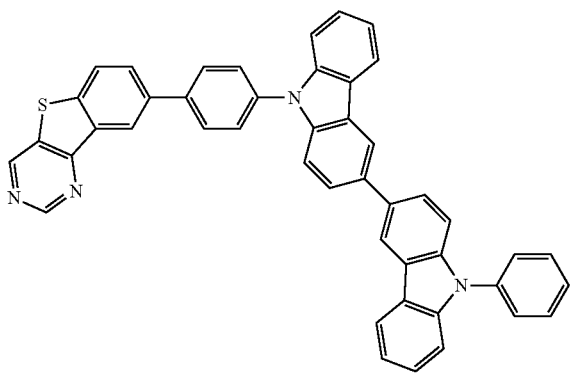

As described above, the compound of this embodiment has both a high donor property and a high acceptor property, and thus is suitable as a thermally activated delayed fluorescence material. With the use of this, a light-emitting element with high emission efficiency can be manufactured. In particular, the compound of this embodiment is suitable as a light-emitting material, a host material, and a carrier-transport material of a blue light-emitting element because of its wide band gap. With the use of this, a blue light-emitting element with high emission efficiency can be manufactured. In addition, the compound of this embodiment is suitable as a host material or a carrier-transport material of a light-emitting element because of its high carrier-transport property. Accordingly, a light-emitting element with low drive voltage can be manufactured. In addition, since the compound of this embodiment is highly resistant to repetition of oxidation and reduction, a light-emitting element including the compound can have a long driving lifetime. Therefore, the compound of this embodiment is a material suitably used for a light-emitting element.

A film of the compound of this embodiment can be formed by an evaporation method (including a vacuum evaporation method), an inkjet method, a coating method, gravure printing, or the like.

The compound described in this embodiment can be used in combination with any of the structures described in the other embodiments as appropriate.

Embodiment 2

In this embodiment, a method for synthesizing the compound represented by General Formula (G0) is described. A variety of reactions can be applied to the method for synthesizing the compound. For example, synthesis reactions described below enable the synthesis of the compound represented by General Formula (G0). Note that the method for synthesizing the compound of one embodiment of the present invention is not limited to the synthesis method described below.

The compound represented by General Formula (G0) can be synthesized by a simple synthesis scheme as follows. For example, as shown below in a synthesis scheme (a), a halogen compound of a substituted or unsubstituted benzofuropyrimidine or a halogen compound of a substituted or unsubstituted benzothienopyrimidine (A1) reacts with an arylboronic acid compound of a bicarbazole derivative (A2) or a bicarbazole derivative (A2') to form the compound represented by General Formula (G0).

The compound represented by General Formula (G0) may be obtained in such a manner that an intermediate (B2) is obtained through a reaction with a halogen-substituted aryl boronic acid compound (B1) and then made to react with a boronic acid compound (B3) of a bicarbazole derivative, as shown a synthesis scheme (b) below.

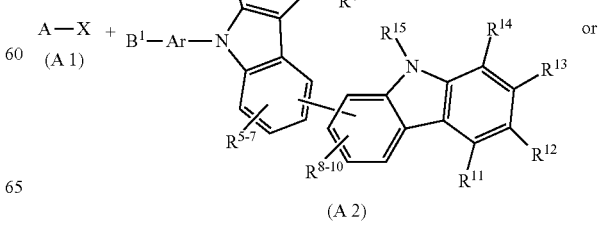

(a)

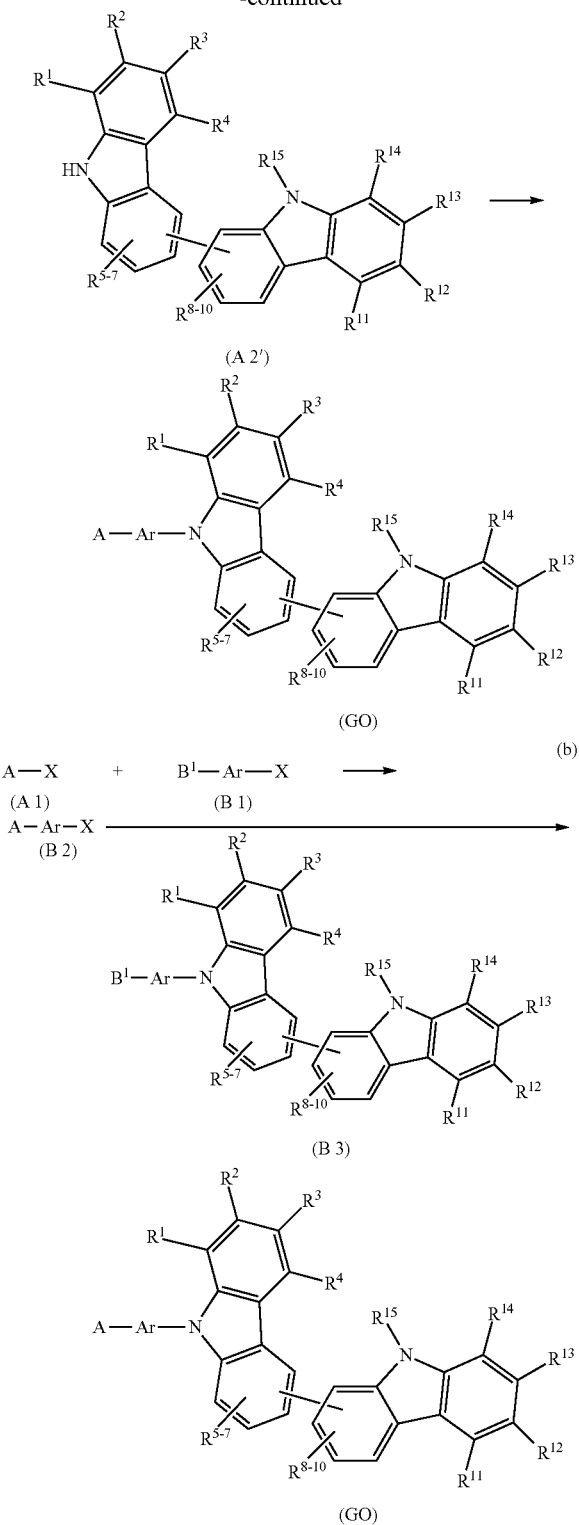

tuted or unsubstituted aryl group having 6 to 13 carbon atoms; and Ar represents a substituted or unsubstituted arylene group having 6 to 25 carbon atoms or a single bond.

Furthermore, X represents a halogen element; and $B^1$ represents a boronic acid, a boronic ester, a cyclic-triolborate salt, or the like. As the cyclic-triolborate salt, a lithium salt, a potassium salt, or a sodium salt may be used.

Note that a boronic acid compound of a substituted or unsubstituted benzofuropyrimidine or a boronic acid compound of a substituted or unsubstituted benzothienopyrimidine may be reacted with a halogen compound of the bicarbazole derivative, and the reaction may be performed via the reaction with the halogen-substituted arylboronic acid compound (B1).

A variety of the above compounds (A1), (A2), (A2'), (B1), (B2), and (B3) are commercially available or can be obtained by synthesis, which means that various types of the compound represented by General Formula (G0) can be synthesized. Thus, a feature of the compound of one embodiment of the present invention is the abundance of variations.

The above is the description of the example of a method for synthesizing the compound of one embodiment of the present invention; however, the present invention is not limited thereto and any other synthesis method may be employed.

Note that the compound described in this embodiment can be used in combination with any of the structures described in the other embodiments as appropriate.

Embodiment 3

In this embodiment, a structure example of a light-emitting element including the compound which includes a bicarbazole skeleton and a benzofuropyrimidine skeleton or a benzothienopyrimidine skeleton and is described in Embodiment 1 is described below with reference to FIGS. 1A to 1C, FIGS. 2A and 2B, and FIGS. 3A and 3B.

First, a structure example of the light-emitting element of one embodiment of the present invention will be described with reference to FIGS. 1A to 1C.

FIG. 1A is a schematic cross-sectional view of a light-emitting element 150 of one embodiment of the present invention.

The light-emitting element 150 includes a pair of electrodes (an electrode 101 and an electrode 102) and an EL layer 100 between the pair of electrodes. The EL layer 100 includes at least a light-emitting layer 130.

The EL layer 100 illustrated in FIG. 1A includes functional layers such as a hole-injection layer 111, a hole-transport layer 112, an electron-transport layer 118, and an electron-injection layer 119, in addition to the light-emitting layer 130.

In this embodiment, although description is given assuming that the electrode 101 and the electrode 102 of the pair of electrodes serve as an anode and a cathode, respectively, they are not limited thereto for the structure of the light-emitting element 150. That is, the electrode 101 may be a cathode, the electrode 102 may be an anode, and the stacking order of the layers between the electrodes may be reversed. In other words, the hole-injection layer 111, the hole-transport layer 112, the light-emitting layer 130, the electron-transport layer 118, and the electron-injection layer 119 may be stacked in this order from the anode side.

The structure of the EL layer 100 is not limited to the structure illustrated in FIG. 1A, and a structure including at least one layer selected from the hole-injection layer 111, the In the synthesis schemes (a) and (b), A represents a substituted or unsubstituted benzofuropyrimidine skeleton or a substituted or unsubstituted benzothienopyrimidine skeleton; each of $R^1$ to $R^{15}$ independently represents any of hydrogen, a substituted or unsubstituted alkyl group having 1 to 6 carbon atoms, a substituted or unsubstituted cycloalkyl group having 3 to 7 carbon atoms, and a substihole-transport layer 112, the electron-transport layer 118, and the electron-injection layer 119 may be employed in addition to the light-emitting layer 130. Alternatively, the EL layer 100 may include a functional layer which is capable of lowering a hole- or electron-injection barrier, improving a hole- or electron-transport property, inhibiting a hole- or electron-transport property, or suppressing a quenching phenomenon by an electrode, for example. Note that the functional layers may each be a single layer or stacked layers.

In the light-emitting element 150 in FIG. 1A, the compound described in Embodiment 1 is used in any layer in the EL layer 100.

Since including the bicarbazole skeleton and the benzofuropyrimidine skeleton or the benzothienopyrimidine skeleton, the compound described in Embodiment 1 can have a high donor property and a high acceptor property. Thus, an energy difference between the singlet excitation energy level and the triplet excitation energy level can be small, so that the compound described in Embodiment 1 can have a function of converting triplet excitation energy into singlet excitation energy by reverse intersystem crossing and a function of converting the singlet excitation energy into light emission. Therefore, the compound described in Embodiment 1 is suitable as a thermally activated delayed fluorescence material. Accordingly, with use of the compound as a light-emitting material in the light-emitting layer 130 of the light-emitting element 150, the light-emitting element 150 can have high emission efficiency.

The compound having a wide band gap is suitable for a host material or a carrier-transport material particularly in a blue light-emitting element. Thus, the structure of this embodiment can provide a light-emitting element emitting blue light and having high emission efficiency.

The compound having an excellent carrier-transport property is suitable for a host material or a carrier-transport material in a light-emitting element. Thus, the structure of this embodiment can provide a light-emitting element that can be driven at a low voltage.

Since the compound is highly resistant to repetition of oxidation and reduction, the structure of this embodiment can provide a light-emitting element having a long driving lifetime.

Structure Example 1 of Light-Emitting Element

Figure 1B:
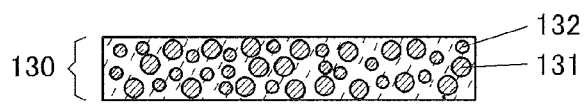

FIG. 1B is a schematic cross-sectional view illustrating an example of the light-emitting layer 130 in FIG. 1A. The light-emitting layer 130 in FIG. 1B includes a material 131 and a host material 132.

The material 131 may be a light-emitting organic material, and the light-emitting organic material is preferably a material capable of emitting fluorescence (hereinafter also referred to as a fluorescent material).

In the light-emitting element 150 of one embodiment of the present invention, voltage application between a pair of electrodes (the electrodes 101 and 102) causes electrons and holes to be injected from the cathode and the anode, respectively, into the EL layer 100 and thus current flows. By recombination of the injected electrons and holes, excitons are formed. The ratio of singlet excitons to triplet excitons (hereinafter referred to as exciton generation probability) which are generated by carrier (electrons and holes) recombination is approximately 1:3 according to the statistically obtained probability. Accordingly, in a light-emitting element that uses a fluorescent material, the probability of generation of singlet excitons, which contribute to light emission, is 25% and the probability of generation of triplet excitons, which do not contribute to light emission, is 75%. Therefore, converting the triplet excitons, which do not contribute to light emission, into singlet excitons, which contribute to light emission, is important for increasing the emission efficiency of the light-emitting element.

For this reason, the material 131 preferably has a function of converting a triplet exciton into a singlet exciton by reverse intersystem crossing. Accordingly, the material 131 preferably has a function of emitting thermally activated delayed fluorescence at room temperature. Alternatively, the material 131 is preferably a thermally activated delayed fluorescence material. That is, the compound of one embodiment of the present invention which includes a bicarbazole skeleton and a benzofuropyrimidine skeleton or a benzothienopyrimidine skeleton and is described in Embodiment 1 is preferably used as the material 131.

Note that the term "exciton" refers to a carrier (electron and hole) pair. Since excitons have energy, a material where excitons are generated is brought into an excited state.

A difference between the singlet excitation energy level and the triplet excitation energy level of the material 131 is preferably greater than 0 eV and less than or equal to 0.3 eV, more preferably greater than 0 eV and less than or equal to 0.2 eV, further more preferably greater than 0 eV and less than or equal to 0.1 eV.

Figure 1C:
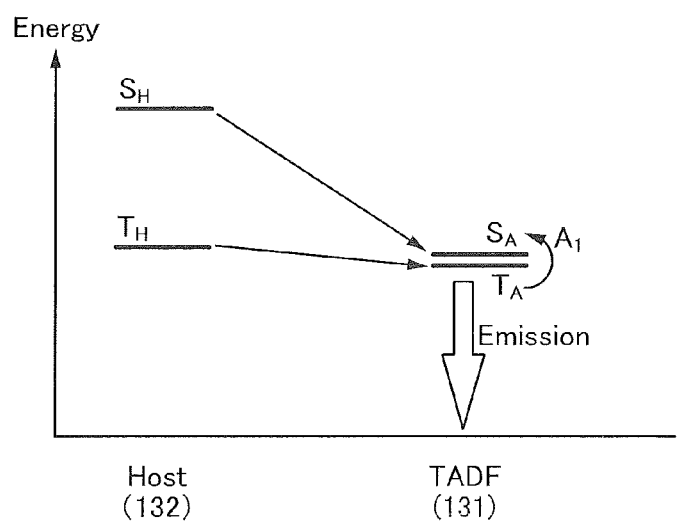

FIG. 1C shows the correlation of energy levels of the material 131 and the host material 132 in the light-emitting layer 130. The following explains what the terms and signs in FIG. 1C represent:

TADF (131): the material 131;
Host (132): the host material 132;
$S_A$: the S1 level of the material 131;
$T_A$: the T1 level of the material 131;
$S_H$: the S1 level of the host material 132; and
$T_H$: the T1 level of the host material 132.

In the case where carriers are recombined in the light-emitting layer 130 and the singlet excited state and the triplet excited state of the host material 132 are formed, energy of the singlet excited state transfers from the S1 level ($S_H$) of the host material 132 to the S1 level ($S_A$) of the material 131, and energy of the triplet excited state transfers from the T1 level ($T_H$) of the host material 132 to the T1 level ($T_A$) of the material 131; thus, the singlet excited state and the triplet excited state of the material 131 are formed.

Alternatively, carriers are recombined in the material 131, and the singlet excited state having excitation energy that corresponds to the S1 level ($S_A$) and the triplet excited state having excitation energy that corresponds to the T1 level ($T_A$) are formed.

In either case, the singlet excited state and the triplet excited state of the material 131 can be formed by the carrier recombination.

In the light-emitting element 150 of one embodiment of the present invention, the S1 level ($S_A$) and the T1 level ($T_A$) of the material 131 included in the light-emitting layer 130 are energy levels adjacent to each other.

Since the S1 level ($S_A$) and the T1 level ($T_A$) of the material 131 are adjacent energy levels, the material 131 has a function of converting triplet excitation energy into singlet excitation energy by reverse intersystem crossing (see Route $A_1$ in FIG. 1C). Thus, the triplet excitation energy generated in the light-emitting layer 130 is partly converted into singlet excitation energy by the material 131. For this conversion, the energy difference between the S1 level ($S_A$) and the T1 level ($T_A$) of the material 131 is preferably greater than 0 eV and less than or equal to 0.3 eV. Fluorescence is obtained from the material 131 in the singlet excited state.

In fluorescence exhibited by the material 131, light emission from the singlet excited state directly formed by carrier recombination (including a prompt emission component) and light emission from the singlet excited state formed through reverse intersystem crossing from the triplet excited state (including a delayed fluorescence component) have different fluorescence lifetimes. Accordingly, the material 131 has a function of emitting light including at least two emission lifetime components: the prompt emission component and the delayed fluorescence component. In other words, the material 131 has a function of emitting delayed fluorescence. The delayed fluorescence is also called thermally activated delayed fluorescence because it is based on reverse intersystem crossing promoted by thermal energy at room temperature or the like. Thus, the material 131 has a function of emitting thermally activated delayed fluorescence.

To obtain efficient light emission from the singlet excited state of the material 131, the fluorescence quantum yield of the material 131 is preferably high, and specifically, 50% or higher, further preferably 70% or higher, still further preferably 90% or higher.

In order to make reverse intersystem crossing occur efficiently, the T1 level ($T_A$) of the material 131 is preferably lower than the T1 level ($T_H$) of the host material 132. Thus, quenching of the triplet excitation energy of the material 131 caused by the host material 132 is less likely to occur, which causes efficient reverse intersystem crossing in the material 131. In order to obtain efficient light emission in the material 131, the S1 level ($S_A$) of the material 131 is preferably lower than the S1 level ($S_H$) of the host material 132. Thus, transfer of singlet excitation energy from the material 131 to the host material 132 can be suppressed.

The material 131 preferably includes the bicarbazole skeleton that has a strong donor property, in which case a hole that has been injected to the light-emitting layer 130 is easily injected to the material 131 and easily transported. In addition, the material 131 preferably includes the benzofuropyrimidine skeleton or the benzothienopyrimidine skeleton that has a strong acceptor property, in which case an electron that has been injected to the light-emitting layer 130 is easily injected to the material 131 and easily transported. In that case, the host material 132 preferably includes a donor skeleton whose donor property is weaker than that of the donor skeleton included in the material 131 and an acceptor skeleton whose acceptor property is weaker than that of the acceptor skeleton included in the material 131. With this structure, reaction for forming an exciplex by the material 131 and the host material 132 can be suppressed.

For example, when the HOMO level of the material 131 is higher than that of the host material 132 and the LUMO level of the material 131 is lower than that of the host material 132, both the electron and the hole which are carriers injected to the light-emitting layer 130 are easily injected to the material 131 and easily transported. Thus, the carrier recombination easily occurs in the material 131, which is preferable.

In the case where the combination of the material 131 and the host material 132 is a combination of a compound having a hole-transport property and a compound having an electron-transport property, the carrier balance can be easily controlled depending on the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Note that the light-emitting layer 130 does not necessarily includes the host material 132 as long as the carrier balance in the light-emitting layer 130 can be controlled by only the material 131. Alternatively, the light-emitting layer 130 may include a material in addition to the material 131 and the host material 132 in order to control the carrier balance.

As described above, when the reverse intersystem crossing process of Route $A_1$ efficiently occurs, triplet excitation energy of the material 131 is efficiently converted into singlet excitation energy; thus, the light-emitting element 150 can emit light with high emission efficiency.

When the light-emitting layer 130 has the above-described structure, light emission from the material 131 of the light-emitting layer 130 can be obtained efficiently.

Structure Example 2 of Light-Emitting Element

Next, a light-emitting element with a structure different from the above structure is described below with reference to FIGS. 2A and 2B.

Figure 2A:
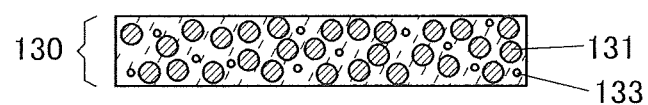
FIG. 2A is a schematic cross-sectional view of a light-emitting layer of a light-emitting element of one embodiment of the present invention and FIG. 2B is a schematic diagram illustrating the correlation of energy levels.

FIG. 2A is a schematic cross-sectional view illustrating an example of the light-emitting layer 130 in FIG. 1A. The light-emitting layer 130 in FIG. 2A includes at least the material 131 and a guest material 133.

The guest material 133 may be a light-emitting organic material, and the light-emitting organic material is preferably a fluorescent material. An example in which a fluorescent material is used as the guest material 133 is described below. Note that the guest material 133 may be rephrased as the fluorescent material.

The material 131 is preferably a material that can form the singlet excited state from the triplet excited state by reverse intersystem crossing. Alternatively, the material 131 preferably has a function of exhibiting thermally activated delayed fluorescence at room temperature. That is, it is preferable to use a thermally activated delayed fluorescence material as the material 131. The compound of one embodiment of the present invention which includes a bicarbazole skeleton and a benzofuropyrimidine skeleton or a benzothienopyrimidine skeleton and is described in Embodiment 1 is preferably used as the material 131.

A difference between the singlet excitation energy level and the triplet excitation energy level of the material 131 is preferably greater than 0 eV and less than or equal to 0.3 eV, more preferably greater than 0 eV and less than or equal to 0.2 eV, further more preferably greater than 0 eV and less than or equal to 0.1 eV. Note that the material 131 does not necessarily emit a thermally activated delayed fluorescence as long as it has a function of converting triplet excitation energy into singlet excitation energy.

Figure 2B:
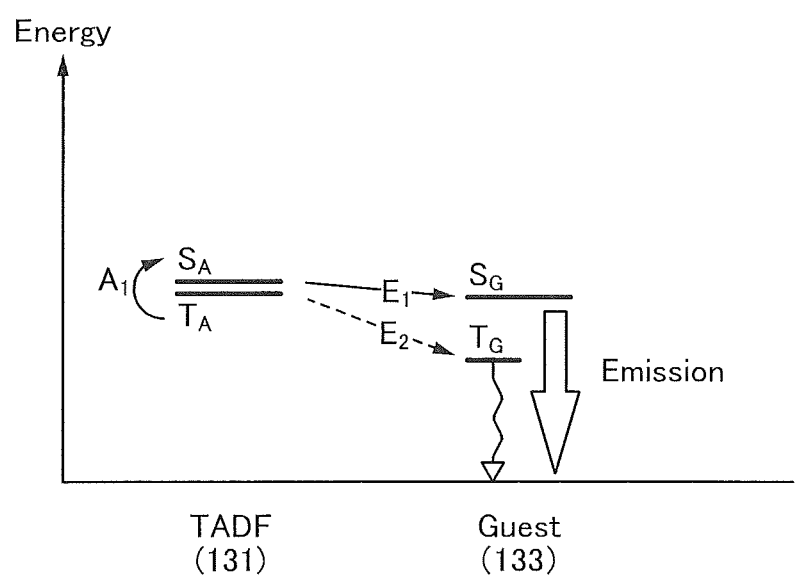

FIG. 2B shows the correlation of energy levels of the material 131 and the guest material 133 in the light-emitting layer 130. The following explains what the terms and signs in FIG. 2B represent:

TADF (131): the material 131;
Guest (133): the guest material 133 (fluorescent material)
$S_A$: the S1 level of the material 131;
$T_A$: the T1 level of the material 131;
$S_G$: the S1 level of the guest material 133 (fluorescent material); and
$T_G$: the T1 level of the guest material 133 (fluorescent material).

In the case where carriers are recombined in the light-emitting layer 130 and the singlet excited state and the triplet excited state of the material 131 are formed, energy of the singlet excited state can transfer from the S1 level ($S_A$) of the material 131 to the S1 level ($S_G$) of the guest material 133.

In the light-emitting element 150 of one embodiment of the present invention, the S1 level ($S_A$) and the T1 level ($T_A$) of the material 131 are energy levels adjacent to each other.

Since the S1 level ($S_A$) and the T1 level ($T_A$) of the material 131 are adjacent energy levels, the material 131 has a function of converting triplet excitation energy into singlet excitation energy by reverse intersystem crossing (see Route $A_1$ in FIG. 2B). Thus, the triplet excitation energy generated in the light-emitting layer 130 is partly converted into singlet excitation energy by the material 131. For this conversion, the energy difference between the S1 level ($S_A$) and the T1 level ($T_A$) of the material 131 is preferably greater than 0 eV and less than or equal to 0.3 eV. Fluorescence is obtained from the material 131 in the singlet excited state.

The S1 level ($S_A$) of the material 131 is preferably higher than the S1 level ($S_G$) of the guest material 133. With such a relation between the S1 levels, the singlet excitation energy of the material 131 can transfer from the S1 level ($S_A$) of the material 131 to the S1 level ($S_G$) of the guest material 133. As a result, the guest material 133 is brought into the singlet excited state and emits fluorescence (see Route $E_1$ in FIG. 2B).

To obtain efficient light emission from the singlet excited state of the guest material 133, the fluorescence quantum yield of the guest material 133 is preferably high, and specifically, 50% or higher, further preferably 70% or higher, still further preferably 90% or higher. In the light-emitting element in this structure example, the guest material 133 does not need to have a function of converting triplet excitation energy into singlet excitation energy by reverse intersystem crossing. For this reason, this structure example has an advantage that design for a high fluorescence quantum yield of the guest material is facilitated.

In order to make reverse intersystem crossing occur efficiently, the T1 level ($T_A$) of the material 131 is preferably higher than the T1 level ($T_G$) of the guest material 133. Thus, quenching of the triplet excitation energy of the material 131 caused by the guest material 133 is less likely to occur, which causes efficient reverse intersystem crossing.

In the case where the material 131 includes the bicarbazole skeleton that has a strong donor property, a hole that has been injected to the light-emitting layer 130 is easily injected to the material 131 and easily transported. In addition, in the case where the material 131 includes the benzofuropyrimidine skeleton or the benzothienopyrimidine skeleton that has a strong acceptor property, an electron that has been injected to the light-emitting layer 130 is easily injected to the material 131 and easily transported. In that case, the guest material 133 preferably includes a donor skeleton whose donor property is weaker than that of the donor skeleton included in the material 131. Alternatively, the guest material 133 preferably includes an acceptor skeleton whose acceptor property is weaker than that of the acceptor skeleton included in the material 131.

Note that since direct transition from the singlet ground state to the triplet excited state in the guest material 133 is forbidden, energy transfer from the S1 level ($S_A$) of the material 131 to the T1 level ($T_G$) of the guest material 133 is unlikely to be a main energy transfer process.

When transfer of the triplet excitation energy from the T1 level ($T_A$) of the material 131 to the T1 level ($T_G$) of the guest material 133 occurs, the triplet excitation energy is deactivated (see Route $E_2$ in FIG. 2B). Thus, it is preferable that the energy transfer of Route $E_2$ be less likely to occur because the efficiency of generating the triplet excitons in the guest material 133 can be decreased and thermal deactivation of triplet excitation energy can be reduced. In order to make this condition, the weight ratio of the guest material 133 to the material 131 is preferably low, specifically, preferably greater than or equal to 0.001 and less than or equal to 0.05, further preferably greater than or equal to 0.001 and less than or equal to 0.03, further preferably greater than or equal to 0.001 and less than or equal to 0.01.

Note that when the direct carrier recombination process in the guest material 133 is dominant, a large number of triplet excitons are generated in the guest material 133, resulting in decreased emission efficiency of the light-emitting element due to thermal deactivation of the triplet excitation energy of the triplet excitons. Thus, it is preferable that the probability of the excitation energy transfer process through carrier recombination in the material 131 (Routes $A_1$ and $E_1$ in FIG. 2B) be higher than the probability of the direct carrier recombination process in the guest material 133 because the efficiency of generating the triplet excitons in the guest material 133 can be decreased and thermal deactivation of the triplet excitation energy can be reduced. Therefore, as described above, the weight ratio of the guest material 133 to the material 131 is preferably low, specifically, preferably greater than or equal to 0.001 and less than or equal to 0.05, further preferably greater than or equal to 0.001 and less than or equal to 0.03, further preferably greater than or equal to 0.001 and less than or equal to 0.01.

By making all the energy transfer processes of Routes $A_1$ and $E_1$ efficiently occur in the above-described manner, both the singlet excitation energy and the triplet excitation energy of the material 131 can be efficiently converted into the singlet excitation energy of the guest material 133, whereby light emission from the guest material 133 can be efficiently obtained. Therefore, the light-emitting element 150 can emit light with high emission efficiency.

<Energy Transfer Mechanism>

Next, factors controlling the processes of intermolecular energy transfer between the material 131 and the guest material 133 will be described. As mechanisms of the intermolecular energy transfer, two mechanisms, i.e., Förster mechanism (dipole-dipole interaction) and Dexter mechanism (electron exchange interaction), have been proposed. Although the intermolecular energy transfer process between the material 131 and the guest material 133 is described here.

<<Förster Mechanism>>

In Förster mechanism, energy transfer does not require direct contact between molecules and energy is transferred through a resonant phenomenon of dipolar oscillation between the material 131 and the guest material 133. By the resonant phenomenon of dipolar oscillation, the material 131 provides energy to the guest material 133, and thus, the material 131 in an excited state is brought to a ground state and the guest material 133 in a ground state is brought to an excited state. Note that the rate constant $k_{h^* \to g}$ of Förster mechanism is expressed by Formula (1).

[Formula 1]

$$k_{h^* \to g} = \frac{9000c^4 K^2 \phi \ln 10}{128\pi^5 n^4 N \tau R^6} \int \frac{f'_h(v)\varepsilon_g(v)}{v^4} dv \qquad (1)$$

In Formula (1), v denotes a frequency, $f'_h(v)$ denotes a normalized emission spectrum of the host material 131 (a fluorescent spectrum in energy transfer from a singlet excited state, and a phosphorescent spectrum in energy transfer from a triplet excited state), $\varepsilon_g(v)$ denotes a molar absorption coefficient of the guest material 133, N denotes Avogadro's number, n denotes a refractive index of a medium, R denotes an intermolecular distance between the material 131 and the guest material 133, τ denotes a measured lifetime of an excited state (fluorescence lifetime or phosphorescence lifetime), c denotes the speed of light, φ denotes an emission quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the material 131 and the guest material 133. Note that $K^2$ is ⅔ in random orientation.

<<Dexter Mechanism>>

In Dexter mechanism, the material 131 and the guest material 133 are close to a contact effective range where their orbitals overlap, and the material 131 in an excited state and the guest material 133 in a ground state exchange their electrons, which leads to energy transfer. Note that the rate constant $k_{h^* \to g}$ of Dexter mechanism is expressed by Formula (2).

[Formula 2]

$$k_{h^* \to g} = \left(\frac{2\pi}{h}\right) K^2 \exp\left(-\frac{2R}{L}\right) \int f'_h(v) \varepsilon'_g(v) dv \quad (2)$$

In Formula (2), h denotes a Planck constant, K denotes a constant having an energy dimension, v denotes a frequency, $f'_h(v)$ denotes a normalized emission spectrum of the host material 131 (a fluorescent spectrum in energy transfer from a singlet excited state, and a phosphorescent spectrum in energy transfer from a triplet excited state), $\varepsilon'_g(v)$ denotes a normalized absorption spectrum of the guest material 133, L denotes an effective molecular radius, and R denotes an intermolecular distance between the host material 131 and the guest material 133.

Here, the efficiency of energy transfer from the material 131 to the guest material 133 (energy transfer efficiency $\phi_{ET}$) is expressed by Formula (3). In the formula, $k_r$ denotes a rate constant of a light-emission process (fluorescence in energy transfer from a singlet excited state, and phosphorescence in energy transfer from a triplet excited state) of the material 131, $k_n$ denotes a rate constant of a non-light-emission process (thermal deactivation or intersystem crossing) of the material 131, and τ denotes a measured lifetime of an excited state of the material 131.

[Formula 3]

$$\phi_{ET} = \frac{k_{h^* \to g}}{k_r + k_n + k_{h^* \to g}} = \frac{k_{h^* \to g}}{\left(\frac{1}{\tau}\right) + k_{h^* \to g}} \quad (3)$$

According to Formula (3), it is found that the energy transfer efficiency $\phi_{ET}$ can be increased by increasing the rate constant $k_{h^* \to g}$ of energy transfer so that another competing rate constant $k_r + k_n (= 1/\tau)$ becomes relatively small.

<<Concept for Promoting Energy Transfer>>

First, energy transfer by Förster mechanism is considered. When Formula (1) is substituted into Formula (3), τ can be eliminated. Thus, in Förster mechanism, the energy transfer efficiency $\phi_{ET}$ does not depend on the lifetime τ of the excited state of the material 131. In addition, it can be said that the energy transfer efficiency $\phi_{ET}$ is higher when the emission quantum yield φ (here, the fluorescence quantum yield because energy transfer from a singlet excited state is discussed) is higher. In general, the emission quantum yield of an organic compound in a triplet excited state is extremely low at room temperature. Thus, in the case where the material 131 is in a triplet excited state, a process of energy transfer by Förster mechanism can be ignored, and a process of energy transfer by Förster mechanism is considered only in the case where the material 131 is in a singlet excited state.

Furthermore, it is preferable that the emission spectrum (the fluorescent spectrum in the case where energy transfer from a singlet excited state is discussed) of the material 131 largely overlap with the absorption spectrum (absorption corresponding to the transition from the singlet ground state to the singlet excited state) of the guest material 133. Moreover, it is preferable that the molar absorption coefficient of the guest material 133 be also high. This means that the emission spectrum of the material 131 overlaps with the absorption band of the guest material 133 which is on the longest wavelength side. Since direct transition from the singlet ground state to the triplet excited state of the guest material 133 is forbidden, the molar absorption coefficient of the guest material 133 in the triplet excited state can be ignored. Thus, a process of energy transfer to a triplet excited state of the guest material 133 by Förster mechanism can be ignored, and only a process of energy transfer to a singlet excited state of the guest material 133 is considered. That is, in Förster mechanism, a process of energy transfer from the singlet excited state of the material 131 to the singlet excited state of the guest material 133 is considered.

Next, energy transfer by Dexter mechanism is considered. According to Formula (2), in order to increase the rate constant $k_{h^* \to g}$, it is preferable that an emission spectrum of the material 131 (a fluorescent spectrum in the case where energy transfer from a singlet excited state is discussed) largely overlap with an absorption spectrum of the guest material 133 (absorption corresponding to transition from a singlet ground state to a singlet excited state). Therefore, the energy transfer efficiency can be optimized by making the emission spectrum of the material 131 overlap with the absorption band of the guest material 133 which is on the longest wavelength side.

When Formula (2) is substituted into Formula (3), it is found that the energy transfer efficiency $\phi_{ET}$ in Dexter mechanism depends on τ. In Dexter mechanism, which is a process of energy transfer based on the electron exchange, as well as the energy transfer from the singlet excited state of the material 131 to the singlet excited state of the guest material 133, energy transfer from the triplet excited state of the material 131 to the triplet excited state of the guest material 133 occurs.

In the case where the guest material 133 is a fluorescent material, the efficiency of energy transfer to the triplet excited state of the guest material 133 is preferably low. That is, the energy transfer efficiency based on Dexter mechanism from the material 131 to the guest material 133 is preferably low and the energy transfer efficiency based on Förster mechanism from the material 131 to the guest material 133 is preferably high.

As described above, the energy transfer efficiency in Förster mechanism does not depend on the lifetime of the excited state of the material 131. In contrast, the energy transfer efficiency in Dexter mechanism depends on the excitation lifetime of the material 131. Thus, to reduce the energy transfer efficiency in Dexter mechanism, the excitation lifetime τ of the material 131 is preferably short.

In addition, fluorescence lifetime of a thermally activated delayed fluorescence component in light emitted from the material 131 is preferably short, and specifically, preferably 10 ns or longer and 50 μs or shorter, further preferably 10 ns or longer and 30 μs or shorter.

The proportion of a thermally activated delayed fluorescence component in the light emitted from the material 131 is preferably high. Specifically, the proportion of a thermally activated delayed fluorescence component in the light emitted from the material 131 is preferably higher than or equal to 5%, further preferably higher than or equal to 10%.

Structure Example 3 of Light-Emitting Element

Next, a light-emitting element with a structure different from the above structure is described below with reference to FIGS. 3A and 3B. For details of components in this structure example similar to those in the above-described structures, the above structure examples can be referred to.

Figure 3A:
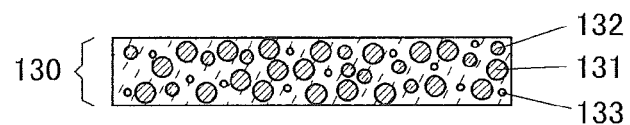
FIG. 3A is a schematic cross-sectional view of a light-emitting layer of a light-emitting element of one embodiment of the present invention and FIG. 3B is a schematic diagram illustrating the correlation of energy levels.

FIG. 3A is a schematic cross-sectional view illustrating an example of the light-emitting layer 130 in FIG. 1A. The light-emitting layer 130 in FIG. 3A includes at least the material 131, the host material 132, and the guest material 133.

In the light-emitting layer 130, the material 131 or the host material 132 is present in the highest proportion by weight, and the guest material 133 is dispersed in the material 131 and the host material 132. Here, the structure in which a fluorescent material is used as the guest material 133 is described.

Figure 3B:
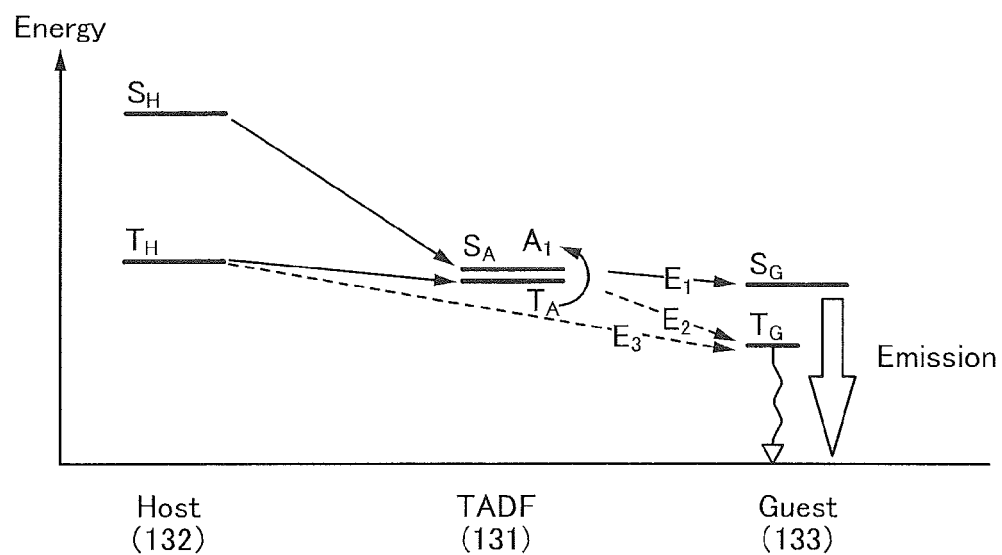

In order to describe the energy transfer process of the material 131, the host material 132, and the guest material 133, a schematic diagram illustrating the correlation of energy levels is shown in FIG. 3B. The following explains what terms and signs in FIG. 3B represent. The other terms and signs in FIG. 3B are similar to those in FIG. 2B.

Host (132): the host material 132
$S_H$: the S1 level of the host material 132
$T_H$: the T1 level of the host material 132

In the case where carriers are recombined in the light-emitting layer 130 and the singlet excited state and the triplet excited state of the host material 132 are formed, energy of the singlet excited state can transfer from the S1 level ($S_H$) of the host material 132 to the S1 level ($S_A$) of the material 131, and energy of the triplet excited state can transfer from the T1 level ($T_H$) of the host material 132 to the T1 level ($T_A$) of the material 131.

When the singlet excited state and the triplet excited state of the material 131 are formed by energy transfer from the host material 132 or carrier recombination in the material 131, both the singlet excitation energy and the triplet excitation energy of the material 131 transfer to the S1 level ($S_G$) of the guest material 133 through Route $A_1$ and Route $E_1$ in FIG. 3B as in the description of FIG. 2B, so that the guest material 133 is brought into the singlet excited state. Fluorescence is obtained from the guest material 133 in the singlet excited state.

In order to efficiently transfer triplet excitation energy from the T1 level ($T_A$) of the material 131 to the S1 level ($S_G$) of the guest material 133, the S1 level ($S_A$) and the T1 level ($T_A$) of the material 131 are preferably adjacent energy levels, and the material 131 is preferably a material having a function of converting triplet excitation energy into singlet excitation energy by reverse intersystem crossing. That is, it is preferable to use a thermally activated delayed fluorescence material as the material 131. The compound of one embodiment of the present invention which includes a bicarbazole skeleton and a benzofuropyrimidine skeleton or a benzothienopyrimidine skeleton and is described in Embodiment 1 is preferably used as the material 131.

A difference between the S1 level and the T1 level of the material 131 is preferably greater than 0 eV and less than or equal to 0.3 eV, more preferably greater than 0 eV and less than or equal to 0.2 eV, further more preferably greater than 0 eV and less than or equal to 0.1 eV. Note that the material 131 does not necessarily emit a thermally activated delayed fluorescence as long as it has a function of converting triplet excitation energy into singlet excitation energy.

The S1 level ($S_H$) of the host material 132 is preferably greater than or equal to the S1 level ($S_A$) of the material 131, and the T1 level ($T_H$) of the host material 132 is preferably greater than or equal to the T1 level ($T_A$) of the material 131. Thus, quenching of the singlet excitation energy and the triplet excitation energy of the material 131 by the host material 132 is less likely to occur; accordingly, energy transfers from the material 131 to the guest material 133 efficiently.

The T1 level ($T_A$) of the material 131 is preferably higher than the T1 level ($T_G$) of the guest material 133. Thus, quenching of the triplet excitation energy of the material 131 caused by the guest material 133 is less likely to occur, which causes efficient reverse intersystem crossing.

Note that since direct transition from the singlet ground state to the triplet excited state in the guest material 133 is forbidden, energy transfer from the S1 level ($S_H$) of the host material 132 to the T1 level ($T_G$) of the guest material 133 is unlikely to be a main energy transfer process.

When transfer of the triplet excitation energy from the T1 level ($T_H$) of the host material 132 to the T1 level ($T_G$) of the guest material 133 occurs, the triplet excitation energy is deactivated (see Route $E_3$ in FIG. 3B). Thus, it is preferable that the energy transfer of Route $E_3$ be less likely to occur because the efficiency of generating the triplet excitons in the guest material 133 can be decreased and thermal deactivation can be reduced. In order to make this condition, the weight ratio of the guest material 133 to (the material 131 and the host material 132) is preferably the lowest, specifically, preferably greater than or equal to 0.001 and less than or equal to 0.05, further preferably greater than or equal to 0.001 and less than or equal to 0.03, further preferably greater than or equal to 0.001 and less than or equal to 0.01.

In the case where the combination of the host material 132 and the material 131 is a combination of a material having a function of transporting a hole and a material having a function of transporting an electron, the carrier balance can be easily controlled depending on the mixture ratio. Specifically, the weight ratio of the material having a function of transporting a hole to the material having a function of transporting an electron is preferably within a range of 1:9 to 9:1. Since the carrier balance can be easily controlled with the structure, a carrier recombination region can also be controlled easily.

When the light-emitting layer 130 has the above-described structure, light emission from the guest material 133 of the light-emitting layer 130 can be obtained efficiently.

<Material>

Next, components of a light-emitting element of one embodiment of the present invention are described in detail below.

<<Light-Emitting Layer>>

Materials that can be used for the light-emitting layer 130 are described below.

<<Material 131>>

An energy difference between the S1 level and the T1 level of the material 131 is preferably small. Specifically, the energy difference between the S1 level and the T1 level is preferably greater than 0 eV and less than or equal to 0.3 eV, more preferably greater than 0 eV and less than or equal to 0.2 eV, more preferably greater than 0 eV and less than or equal to 0.1 eV. Such a material is, for example, a thermally activated delayed fluorescence material. As the thermally activated delayed fluorescence material, the compound described in Embodiment 1 is favorably used.

Note that the material 131 does not necessarily have a function of emitting thermally activated delayed fluorescence as long as the energy difference between the S1 level and the T1 level is small.

<<Guest Material 133>>

The guest material 133 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N'-diphenyl-N,N'-bis[4-(9-pheny-9H-fluoren-9-yl)phenyl]-3,8-dicyclohexylpyrene-1,6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phen ylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N''',N''''-octaphenyldibenzo[g,p]chrysene-2,7,10,15-tetraamine (abbreviation: DBC 1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N''-tetrakis(4-methylphenyl)tetracene-5,11-diamine (abbreviation: p-mPhTD), 7,14-diphenyl-N,N,N',N''-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[i/]quinolizin-9-yl)ethenyl]-4H-pyran-4-ylidene}propanedinitrile (abbreviation: BisDCJTM), and 5,10,15,20-tetraphenylbisbenzo[5,6]indeno[1,2,3-cd: 1',2',3'-lm]perylene.

As described above, the energy transfer efficiency based on Dexter mechanism from the material 131 to the guest material 133 (fluorescent material) is preferably low. The rate constant of Dexter mechanism is inversely proportional to the exponential function of the distance between the two molecules. In general, when the distance between the two molecules is approximately 1 nm or less, Dexter mechanism is dominant, and when the distance is approximately 1 nm or more, FBrster mechanism is dominant. To reduce the energy transfer efficiency in Dexter mechanism, the distance between the material 131 and the guest material 133 (fluorescent material) is preferably large, and specifically, 0.7 nm or more, further preferably 0.9 nm or more, still further preferably 1 nm or more. In view of the above, the guest material 133 (fluorescent material) preferably has a substituent that prevents the proximity to the host material 131. The substituent is preferably aliphatic hydrocarbon, further preferably an alkyl group, still further preferably a branched alkyl group. Specifically, the guest material 133 preferably includes at least two alkyl groups each having 2 or more carbon atoms. Alternatively, the guest material 133 preferably includes at least two branched alkyl groups each having 3 to 10 carbon atoms. Alternatively, the guest material 133 (fluorescent material) preferably includes at least two cycloalkyl groups each having 3 to 10 carbon atoms.

It is preferable that the material 131 and the guest material 133 (fluorescent material) be selected such that the emission peak of the material 131 overlaps with an absorption band on the longest wavelength side (low energy side) of the guest material 133. This makes it possible to provide a light-emitting element with drastically improved emission efficiency.

<<Host Material 132>>

Examples of the compound that can be used as the host material 132 are, but not particularly limited to, a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples are an aromatic amine and a carbazole derivative.

Alternatively, as the host material 132, any of the following hole-transport materials and electron-transport materials can be used.

A material having a property of transporting more holes than electrons can be used as the hole-transport material, and a material having a hole mobility of $1\times10^{-6}$ cm$^2$/Vs or higher is preferable. Specifically, an aromatic amine, a carbazole derivative, an aromatic hydrocarbon, a stilbene derivative, or the like can be used. Furthermore, the hole-transport material may be a high molecular compound.

Examples of the material having a high hole-transport property are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-dia mine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminopenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1\times10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacryla mide] (abbreviation: PTPDMA), and poly[N,N'-bis(4-butylphenyl)-N,N'-bis(phenyl)benzidine] (abbreviation: poly-TPD).

Examples of the material having a high hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluor en-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are amine compounds, carbazole compounds, thiophene compounds, furan compounds, fluorene compounds; triphenylene compounds; phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di(9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviated as DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylene-2-yl)phenyl]dibenzothiophene (abbreviation: mDBTPTp-II). The substances described here are mainly substances having a hole mobility of $1\times10^{-6}$ cm$^2$/Vs or higher. Note that other than these substances, any substance that has a property of transporting more holes than electrons may be used.

As the electron-transport material, a material having a property of transporting more electrons than holes can be used, and a material having an electron mobility of $1\times10^{-6}$ cm$^2$/Vs or higher is preferable. A π-electron deficient heteroaromatic compound such as a nitrogen-containing heteroaromatic compound, a metal complex, or the like can be used as the material that easily accepts electrons (the material having an electron-transport property). Specific examples include a metal complex having a quinoline ligand, a benzoquinoline ligand, an oxazole ligand, or a thiazole ligand, an oxadiazole derivative, a triazole derivative, a phenanthroline derivative, a pyridine derivative, a bipyridine derivative, a pyrimidine derivative, and the like.

Examples include metal complexes having a quinoline or benzoquinoline skeleton, such as tris(8-quinolinolato)aluminum(III) (abbreviation: Alq), tris(4-methyl-8-quinolinolato)aluminum(II) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq) and bis(8-quinolinolato)zinc(II) (abbreviation: Znq), and the like. Alternatively, a metal complex having an oxazole-based or thiazole-based ligand, such as bis[2-(2-benzoxazolyl)phenolate]zinc(II) (abbreviation: ZnPBO) or bis[2-(2-benzothiazolyl)phenolato]zinc(II) (abbreviation: ZnBTZ) can be used. Other than such metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(biphenyl-4-yl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[fh]quinoxaline (abbreviation: 2mDBTBPDBq-II), 2-[3'-(9H-carbazol-9-yl)biphenyl-3-yl]dibenzo[fh]quinoxaline (abbreviation: 2mCzBPDBq), 2-[4-(3,6-diphenyl-9H-carbazol-9-yl)phenyl]dibenzo[fh]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[fh]quinoxaline (abbreviation: 2mCzC-zPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as PCCzPTzn; heterocyclic compounds having a pyridine skeleton such as 3,5-bis[3-(9H-carbazol-9-yl)phenyl]pyridine (abbreviation: 35DCzPPy); and heteroaromatic compounds such as 4,4'-bis(5-methylbenzoxazol-2-yl)stilbene (abbreviation: BzOs). Among the heterocyclic compounds, the heterocyclic compounds having diazine skeletons (pyrimidine, pyrazine, pyridazine) or having a pyridine skeleton are highly reliable and stable and is thus preferably used. In addition, the heterocyclic compounds having the skeletons have a high electron-transport property to contribute to a reduction in drive voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1\times10^{-6}$ cm$^2$/Vs or higher. Note that other substances may also be used as long as their electron-transport properties are higher than their hole-transport properties.

The light-emitting layer 130 can have a structure in which two or more layers are stacked. For example, in the case where the light-emitting layer 130 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

The light-emitting layer 130 may contain a material other than the material 131, the host material 132, and the guest material 133.

Note that the light-emitting layer 130 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide (CdSe); cadmium sulfide (CdS); cadmium telluride (CdTe); zinc selenide (ZnSe); zinc oxide (ZnO); zinc sulfide (ZnS); zinc telluride (ZnTe); mercury sulfide (HgS); mercury selenide (HgSe); mercury telluride (HgTe); indium arsenide (InAs); indium phosphide (InP); gallium arsenide (GaAs); gallium phosphide (GaP); indium nitride (InN); gallium nitride (GaN); indium antimonide (InSb); gallium antimonide (GaSb); aluminum phosphide (AlP); aluminum arsenide (AlAs); aluminum antimonide (AlSb); lead(II) selenide (PbSe); lead(II) telluride (PbTe); lead(II) sulfide (PbS); indium selenide (In$_2$Se$_3$); indium telluride (In$_2$Te$_3$); indium sulfide (In$_2$S$_3$); gallium selenide (Ga$_2$Se$_3$); arsenic(III) sulfide (As$_2$S$_3$); arsenic(III) selenide (As$_2$Se$_3$); arsenic(III) telluride (As$_2$Te$_3$); antimony(III) sulfide (Sb$_2$S$_3$); antimony(III) selenide (Sb$_2$Se$_3$); antimony(III) telluride (Sb$_2$Te$_3$); bismuth(III) sulfide (Bi$_2$S$_3$); bismuth(III) selenide (Bi$_2$Se$_3$); bismuth(III) telluride (Bi$_2$Te$_3$); silicon (Si); silicon carbide (SiC); germanium (Ge); tin (Sn); selenium (Se); tellurium (Te); boron (B); carbon (C); phosphorus (P); boron nitride (BN); boron phosphide (BP); boron arsenide (BAs); aluminum nitride (AlN); aluminum sulfide ($Al_2S_3$); barium sulfide (BaS); barium selenide (BaSe); barium telluride (BaTe); calcium sulfide (CaS); calcium selenide (CaSe); calcium telluride (CaTe); beryllium sulfide (BeS); beryllium selenide (BeSe); beryllium telluride (BeTe); magnesium sulfide (MgS); magnesium selenide (MgSe); germanium sulfide (GeS); germanium selenide (GeSe); germanium telluride (GeTe); tin(IV) sulfide ($SnS_2$); tin(II) sulfide (SnS); tin(II) selenide (SnSe); tin(II) telluride (SnTe); lead(II) oxide (PbO); copper(I) fluoride (CuF); copper(I) chloride (CuCl); copper(I) bromide (CuBr); copper(I) iodide (CuI); copper(I) oxide ($Cu_2O$); copper(I) selenide ($Cu_2Se$); nickel(II) oxide (NiO); cobalt(II) oxide (CoO); cobalt(II) sulfide (CoS); triiron tetraoxide ($Fe_3O_4$); iron(II) sulfide (FeS); manganese(II) oxide (MnO); molybdenum(IV) sulfide ($MoS_2$); vanadium(II) oxide (VO); vanadium(IV) oxide ($VO_2$); tungsten(IV) oxide ($WO_2$); tantalum (V) oxide ($Ta_2O_5$); titanium oxide (e.g., $TiO_2$, $Ti_2O_5$, $Ti_2O_3$, or $Ti_5O_9$); zirconium oxide ($ZrO_2$); silicon nitride ($Si_3N_4$); germanium nitride ($Ge_3N_4$); aluminum oxide ($Al_2O_3$); barium titanate ($BaTiO_3$); a compound of selenium, zinc, and cadmium (CdZnSe); a compound of indium, arsenic, and phosphorus (InAsP); a compound of cadmium, selenium, and sulfur (CdSeS); a compound of cadmium, selenium, and tellurium (CdSeTe); a compound of indium, gallium, and arsenic (InGaAs); a compound of indium, gallium, and selenium (InGaSe); a compound of indium, selenium, and sulfur (InSeS); a compound of copper, indium, and sulfur (e.g., $CuInS_2$); and combinations thereof. What is called an alloyed quantum dot, whose composition is represented by a given ratio, may be used. For example, an alloyed quantum dot represented by $CdS_xSe_{1-x}$ (where x is any number between 0 and 1 inclusive) is a means effective in obtaining blue light because the emission wavelength can be changed by changing x.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide (ZnS) and zinc oxide (ZnO).

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxylethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolones; animoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

The quantum dots may be quantum rods, which are rod-like shape quantum dots. A quantum rod emits directional light polarized in the c-axis direction; thus, quantum rods can be used as a light-emitting material to obtain a light-emitting element with higher external quantum efficiency.

In the case of using quantum dots as the light-emitting material in the light-emitting layer, the thickness of the light-emitting layer is set to 3 nm to 100 nm, preferably 10 nm to 100 nm, and the light-emitting layer is made to contain 1 volume % to 100 volume % of the quantum dots. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, blade coating method, a roll coating method, an ink jet method, a printing method, a spray coating method, a curtain coating method, or a Langmuir-Blodgett method) may be employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1\times10^{-6}$ cm$^2$/Vs or higher is preferable. Specifically, any of the aromatic amine, carbazole derivative, aromatic hydrocarbon, stilbene derivative, and the like described as examples of the hole-transport material that can be used in the light-emitting layer 130 can be used. Furthermore, the hole-transport material may be a high molecular compound.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 has a function of transporting holes injected into the hole-injection layer 111 to the light-emitting layer 130, the HOMO level of the hole-transport layer 112 is preferably equal or close to the HOMO level of the hole-injection layer 111.

As the hole-transport material, a substance having a hole mobility of $1\times10^{-6}$ cm$^2$/Vs or higher is preferably used. Note that any substance other than the above substances may be used as long as the hole-transport property is higher than the electron-transport property. The layer including a substance having a high hole-transport property is not limited to a single layer, and two or more layers containing the aforementioned substances may be stacked.

<<Electron-Transport Layer>>

The electron-transport layer 118 has a function of transporting, to the light-emitting layer 130, electrons injected from the other of the pair of electrodes (the electrode 101 or the electrode 102) through the electron-injection layer 119. A material having a property of transporting more electrons than holes can be used as the electron-transport material, and a material having an electron mobility of $1\times10^{-6}$ cm$^2$/Vs or higher is preferable. As the compound which easily accepts electrons (the material having an electron-transport property), a π-electron deficient heteroaromatic compound such as a nitrogen-containing heteroaromatic compound, a metal complex, or the like can be used, for example. Specifically, a metal complex having a quinoline ligand, a benzoquinoline ligand, an oxazole ligand, or a thiazole ligand, which is described as the electron-transport material that can be used in the light-emitting layer 130, can be given. In addition, an oxadiazole derivative, a triazole derivative, a phenanthroline derivative, a pyridine derivative, a bipyridine derivative, a pyrimidine derivative, and the like can be given. A substance having an electron mobility of $1\times10^{-6}$ cm$^2$/Vs or higher is preferable. Note that other than these substances, any substance that has a property of transporting more electrons than holes may be used for the electron-transport layer. The electron-transport layer 118 is not limited to a single layer, and may include stacked two or more layers containing the aforementioned substances.

Between the electron-transport layer 118 and the light-emitting layer 130, a layer that controls transfer of electron carriers may be provided. The layer that controls transfer of electron carriers is a layer formed by addition of a small amount of a substance having a high electron-trapping property to a material having a high electron-transport property described above, and the layer is capable of adjusting carrier balance by suppressing transfer of electron carriers. Such a structure is very effective in preventing a problem (such as a reduction in element lifetime) caused when electrons pass through the light-emitting layer.

An n-type compound semiconductor may also be used, and an oxide such as titanium oxide ($TiO_2$), zinc oxide (ZnO), silicon oxide ($SiO_2$), tin oxide ($SnO_2$), tungsten oxide ($WO_3$), tantalum oxide ($Ta_2O_3$), barium titanate ($BaTiO_3$), barium zirconate ($BaZrO_3$), zirconium oxide ($ZrO_2$), hafnium oxide ($HfO_2$), aluminum oxide ($Al_2O_3$), yttrium oxide ($Y_2O_3$), or zirconium silicate ($ZrSiO_4$); a nitride such as silicon nitride ($Si_3N_4$); cadmium sulfide (CdS); zinc selenide (ZnSe); or zinc sulfide (ZnS) can be used, for example.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given. Specifically, an alkali metal, an alkaline earth metal, or a compound thereof, such as lithium fluoride (LiF), sodium fluoride (NaF), cesium fluoride (CsF), calcium fluoride ($CaF_2$), or lithium oxide ($LiO_x$), can be used. Alternatively, a rare earth metal compound like erbium fluoride ($ErF_3$) can be used. Electride may also be used for the electron-injection layer 119. Examples of the electride include a substance in which electrons are added at high concentration to calcium oxide-aluminum oxide. The electron-injection layer 119 can be formed using the substance that can be used for the electron-transport layer 118.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons. Specifically, the above-listed substances for forming the electron-transport layer 118 (e.g., the metal complexes and heteroaromatic compounds) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, and ytterbium are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

<<Pair of Electrodes>>

The electrodes 101 and 102 function as an anode and a cathode of each light-emitting element. The electrodes 101 and 102 can be foimed using a metal, an alloy, or a conductive compound, a mixture or a stack thereof, or the like.

One of the electrode 101 and the electrode 102 is preferably formed using a conductive material having a function of reflecting light. Examples of the conductive material include aluminum (Al), an alloy containing Al, and the like. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for manufacturing a light-emitting element with aluminum. Alternatively, Ag, an alloy of silver (Ag) and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), or gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, an alloy containing silver and ytterbium, and the like. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrode 101 and the electrode 102 is preferably formed using a conductive material having a function of transmitting light. As the conductive material, a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm can be used.

The electrodes 101 and 102 may each be formed using a conductive material having functions of transmitting light and reflecting light. As the conductive material, a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm can be used. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and ytterbium (Yb), or the like can be used.

In this specification and the like, as the material transmitting light, a material that transmits visible light and has conductivity is used. Examples of the material include, in addition to the above-described oxide conductor typified by an ITO, an oxide semiconductor and an organic conductor containing an organic substance. Examples of the organic conductive containing an organic substance include a composite material in which an organic compound and an electron donor (donor material) are mixed and a composite material in which an organic compound and an electron acceptor (acceptor material) are mixed. Alternatively, an inorganic carbon-based material such as graphene may be used. The resistivity of the material is preferably lower than or equal to $1 \times 10^5$ Ω·cm, further preferably lower than or equal to $1 \times 10^4$ Ω·cm.

Alternatively, the electrode 101 and/or the electrode 102 may be formed by stacking two or more of these materials.

Furthermore, to increase light extraction efficiency, a material having a higher refractive index than an electrode that has a function of transmitting light may be formed in contact with the electrode. Such a material may be a conductive material or a non-conductive material as long as having a function of transmitting visible light. For example, in addition to the above-described oxide conductor, an oxide semiconductor and an organic material are given as examples. As examples of the organic material, materials of the light-emitting layer, the hole-injection layer, the hole-transport layer, the electron-transport layer, and the electron-injection layer are given. Alternatively, an inorganic carbon-based material or a metal thin film that allows transmission of light can be used. A plurality of layers each of which is formed using the material having a high refractive index and has a thickness of several nanometers to several tens of nanometers may be stacked.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, an alloy containing aluminum and silver, and the like.

In the case where the electrode 101 or the electrode 102 is used as an anode, a material having a high work function (higher than or equal to 4.0 eV) is preferably used.

Alternatively, the electrodes 101 and 102 may each be a stack of a conductive material having a function of reflecting light and a conductive material having a function of transmitting light. In that case, the electrodes 101 and 102 can each have a function of adjusting the optical path length so that desired light emitted from each light-emitting layer resonates and is intensified; thus, such a structure is preferable.

As the method for forming the electrode 101 and the electrode 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element in one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or an optical element or as long as it has a function of protecting the light-emitting element or an optical element.

In this specification and the like, a light-emitting element can be formed using any of a variety of substrates, for example. There is no particular limitation on the type of substrate. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper which include a fibrous material, a base material film, and the like. As an example of a glass substrate, a barium borosilicate glass substrate, an aluminoborosilicate glass substrate, a soda lime glass substrate, and the like can be given. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, paper, and the like.

Alternatively, a flexible substrate may be used as the substrate such that the light-emitting element is provided directly on the flexible substrate. Further alternatively, a separation layer may be provided between the substrate and the light-emitting element. The separation layer can be used when part or the whole of a light-emitting element formed over the separation layer is separated from the substrate and transferred onto another substrate. In such a case, the light-emitting element can be transferred to a substrate having low heat resistance or a flexible substrate as well. For the above separation layer, a stack including inorganic films, which are a tungsten film and a silicon oxide film, and a structure in which a resin film of polyimide or the like is formed over a substrate can be used, for example.

In other words, after the light-emitting element is formed using a substrate, the light-emitting element may be transferred to another substrate. Example of the substrate to which the light-emitting element is transferred are, in addition to the above substrates, a cellophane substrate, a stone substrate, a wood substrate, a cloth substrate (including a natural fiber (e.g., silk, cotton, and hemp), a synthetic fiber (e.g., nylon, polyurethane, and polyester), a regenerated fiber (e.g., acetate, cupra, rayon, and regenerated polyester), and the like), a leather substrate, a rubber substrate, and the like. When such a substrate is used, a light-emitting element with high durability, high heat resistance, reduced weight, or reduced thickness can be formed.

The light-emitting element 150 may be formed over an electrode electrically connected to a field-effect transistor (FET), for example, which is formed over any of the above-described substrates. Accordingly, an active matrix display device in which the FET controls the driving of the light-emitting element 150 can be manufactured.

In Embodiment 3, one embodiment of the present invention has been described. Other embodiments of the present invention are described in Embodiments 1, 2, and 4 to 13. Note that one embodiment of the present invention is not limited thereto. That is, since various embodiments of the present invention are disclosed in Embodiments 1 to 13, one embodiment of the present invention is not limited to a specific embodiment. An example in which one embodiment of the present invention is used in a light-emitting element is described; however, one embodiment of the present invention is not limited thereto. Depending on circumstances or conditions, one embodiment of the present invention is not necessarily used in a light-emitting element, for example. In one embodiment of the present invention, an example in which the compound including a bicarbazole skeleton and a benzofuropyrimidine skeleton or a benzothienopyrimidine skeleton is a thermally activated delayed fluorescence material is described; however, one embodiment of the present invention is not limited to this example. Depending on circumstances or conditions, in one embodiment of the present invention, for example, the compound is not necessarily a thermally activated delayed fluorescence material. In one embodiment of the present invention, an example in which the energy difference between the S1 level and the T1 level of the compound including a bicarbazole skeleton and a benzofuropyrimidine skeleton or a benzothienopyrimidine skeleton is greater than 0 eV and less than or equal to 0.3 eV is described; however, one embodiment of the present invention is not limited thereto. Depending on circumstances or conditions, in one embodiment of the present invention, for example, the energy difference between the S1 level and the T1 level of the compound may be greater than 0.3 eV. In one embodiment of the present invention, an example in which the EL layer includes the compound including a bicarbazole skeleton and a benzofuropyrimidine skeleton or a benzothienopyrimidine skeleton is described; however, one embodiment of the present invention is not limited thereto. Depending on circumstances or conditions, in one embodiment of the present invention, for example, the EL layer does not need to include the compound including a bicarbazole skeleton and a benzofuropyrimidine skeleton or a benzothienopyrimidine skeleton. Alternatively, the EL layer may include a compound that does not include a bicarbazole skeleton, a benzofuropyrimidine skeleton, or a benzothienopyrimidine skeleton.

The structure described above in this embodiment can be combined with any of the structures described in the other embodiments as appropriate.

Embodiment 4

In this embodiment, a light-emitting element having a structure different from that described in Embodiment 3 and light emission mechanisms of the light-emitting element are described below with reference to FIGS. 4A to 4C and FIGS.

5A and 5B. In FIG. 4A, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

Structure Example 1 of Light-Emitting Element

Figure 4A:
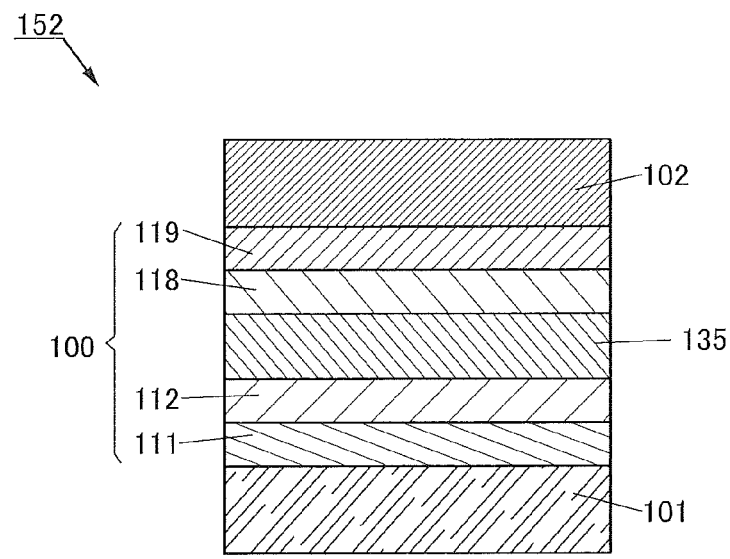
FIGS. 4A and 4B are schematic cross-sectional views illustrating a light-emitting element of one embodiment of the present invention and FIG. 4C is a schematic diagram illustrating the correlation of energy levels in a light-emitting layer.

FIG. 4A is a schematic cross-sectional view of a light-emitting element 152 of one embodiment of the present invention.

The light-emitting element 152 includes a pair of electrodes (an electrode 101 and an electrode 102) and an EL layer 100 between the pair of electrodes. The EL layer 100 includes at least a light-emitting layer 135.

Note that the electrode 101 functions as an anode and the electrode 102 functions as a cathode in the following description of the light-emitting element 152; however, the functions may be interchanged in the light-emitting element 152.

Figure 4B:
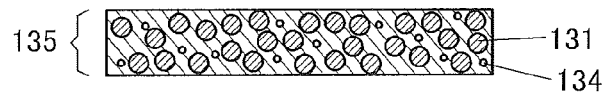

FIG. 4B is a schematic cross-sectional view illustrating an example of the light-emitting layer 135 in FIG. 4A. The light-emitting layer 135 in FIG. 4B includes the material 131 and a guest material 134.

The guest material 134 may be a light-emitting organic material, and the light-emitting organic material is preferably a material capable of emitting phosphorescence (hereinafter also referred to as a phosphorescent material). A structure in which a phosphorescent material is used as the guest material 134 will be described below. The guest material 134 may be rephrased as the phosphorescent material.

Figure 4C:
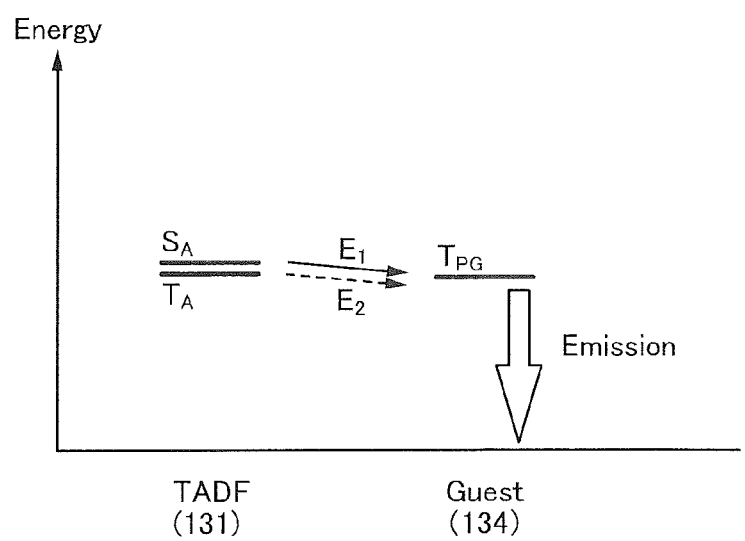

FIG. 4C shows the correlation of energy levels of the material 131 and the guest material 134. The following explains what the terms and signs in FIG. 4C represent:

TADF (131): the material 131;
Guest (134): the guest material 134 (phosphorescent material);
$S_A$: the S1 level of the material 131;
$T_A$: the T1 level of the material 131; and
$T_{PG}$: the T1 level of the guest material 134 (phosphorescent material).

Carriers are recombined in the light-emitting layer 130 and the singlet excited state and the triplet excited state are formed in the material 131.

By transferring both the singlet excitation energy and the triplet excitation energy of the material 131 to the T1 level ($Tp_G$) of the guest material 134 (phosphorescent material), light emission can be obtained from the guest material 134 (see Routes $E_1$ and $E_2$ in FIG. 4C).

The T1 level ($T_A$) of the material 131 is preferably higher than the T1 level ($Tp_G$) of the guest material 134. With such a relation between the S1 levels, the singlet excitation energy and the triplet excitation energy of the material 131 can transfer from the S1 level ($S_A$) and the T1 level ($T_A$) of the material 131 to the T1 level ($T_{PG}$) of the guest material 134.

When the light-emitting layer 130 has the above-described structure, light emission from the guest material 134 (phosphorescent material) of the light-emitting layer 130 can be obtained efficiently.

Note that in the case where carrier recombination occurs in the material 131, the energy difference between the S1 level and the T1 level of the material 131 is preferably small in order to reduce the drive voltage of the light-emitting element 152. Therefore, the compound of one embodiment of the present invention which includes a bicarbazole skeleton and a benzofuropyrimidine skeleton or a benzothienopyrimidine skeleton and is described in Embodiment 1 is preferably used as the material 131. In this embodiment, the material 131 does not necessarily has high efficiency of reverse intersystem crossing from $T_A$ to $S_A$, and the emission quantum yield from $S_A$ does not need to be high; therefore, the material 131 does not necessarily emit thermally activated delayed fluorescence.

Furthermore, the mechanism of the energy transfer process between the molecules of the material 131 and the guest material 134 can be described using two mechanisms, i.e., Förster mechanism (dipole-dipole interaction) and Dexter mechanism (electron exchange interaction), as in Embodiment 3. For Förster mechanism and Dexter mechanism, Embodiment 3 can be referred to.

<<Concept for Promoting Energy Transfer>>

In energy transfer by Förster mechanism, the energy transfer efficiency $\phi_{ET}$ is higher when the emission quantum yield $\phi$ (the fluorescence quantum yield when energy transfer from a singlet excited state is discussed) is higher. Furthermore, it is preferable that the emission spectrum (the fluorescent spectrum in the case where energy transfer from a singlet excited state is discussed) of the material 131 largely overlap with the absorption spectrum (absorption corresponding to the transition from the singlet ground state to the triplet excited state) of the guest material 134. Moreover, it is preferable that the molar absorption coefficient of the guest material 134 be also high. This means that the emission spectrum of the material 131 overlaps with the absorption band of the guest material 134 which is on the longest wavelength side.

In energy transfer by Dexter mechanism, in order to increase the rate constant $k_{h^* \to g}$, it is preferable that an emission spectrum of the material 131 (a fluorescent spectrum in the case where energy transfer from a singlet excited state is discussed) largely overlap with an absorption spectrum of the guest material 134 (absorption corresponding to transition from a singlet ground state to a triplet excited state). Therefore, the energy transfer efficiency can be optimized by making the emission spectrum of the material 131 overlap with the absorption band of the guest material 134 which is on the longest wavelength side.

Structure Example 2 of Light-Emitting Element

Next, a light-emitting element with a structure different from the above structure is described below with reference to FIGS. 5A and 5B. For details of components in this structure example similar to those in the above-described structures, the above structure examples can be referred to.

Figure 5A:
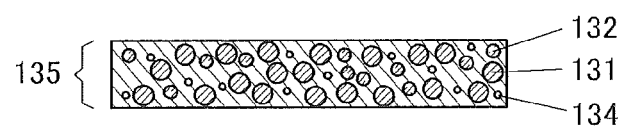
FIG. 5A is a schematic cross-sectional view of a light-emitting layer of a light-emitting element of one embodiment of the present invention and FIG. 5B is a schematic diagram illustrating the correlation of energy levels.

FIG. 5A is a schematic cross-sectional view illustrating an example of the light-emitting layer 135 in FIG. 4A. The light-emitting layer 135 in FIG. 5A includes at least the material 131, the host material 132, and the guest material 134.

In the light-emitting layer 135, the material 131 or the host material 132 is present in the highest proportion by weight, and the guest material 134 is dispersed in the material 131 and the host material 132. Here, the structure in which a phosphorescent material is used as the guest material 134 is described.

Figure 5B:
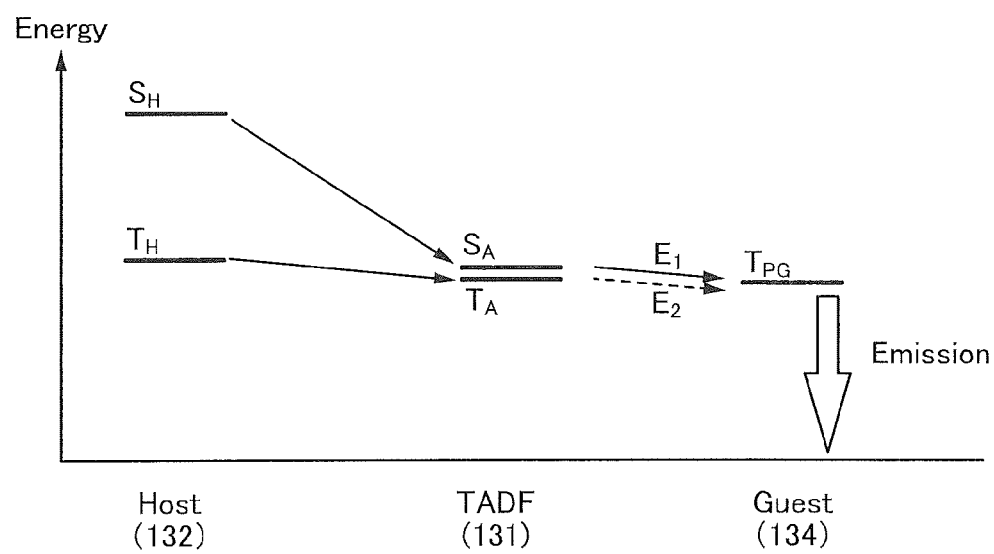

In order to describe the energy transfer process of the material 131, the host material 132, and the guest material 134, a schematic diagram illustrating the correlation of energy levels is shown in FIG. 5B. The following explains what terms and signs in FIG. 5B represent. The other terms and signs in FIG. 5B are similar to those in FIG. 4C.

Host (132): the host material 132
$S_H$: the S1 level of the host material 132
$T_H$: the T1 level of the host material 132

In the case where carriers are recombined in the light-emitting layer 135 and the singlet excited state and the triplet excited state of the host material 132 are formed, energy of the singlet excited state can transfer from the S1 level ($S_H$) of the host material 132 to the S1 level ($S_A$) of the material 131, and energy of the triplet excited state can transfer from the T1 level ($T_H$) of the host material 132 to the T1 level ($T_A$) of the material 131.

When the singlet excited state and the triplet excited state of the material 131 are formed by energy transfer from the host material 132 or carrier recombination in the material 131, both the singlet excitation energy and the triplet excitation energy of the material 131 transfer to the T1 level ($T_{PG}$) of the guest material 134 through Route $E_1$ and Route $E_2$ in FIG. 5B as in the description of FIG. 4C, so that the guest material 134 is brought into the triplet excited state. Phosphorescence is obtained from the guest material 134 in the triplet excited state.

Note that in the case where carrier recombination occurs in the material 131, the energy difference between the S1 level and the T1 level of the material 131 is preferably small in order to reduce the drive voltage of the light-emitting element 152. Therefore, the compound of one embodiment of the present invention which includes a bicarbazole skeleton and a benzofuropyrimidine skeleton or a benzothienopyrimidine skeleton and is described in Embodiment 1 is preferably used as the material 131. In this structure example, the material 131 does not necessarily has high efficiency of reverse intersystem crossing from $T_A$ to $S_A$, and the emission quantum yield from $S_A$ does not need to be high; therefore, the material 131 does not necessarily emit thermally activated delayed fluorescence.

The S1 level ($S_H$) of the host material 132 is preferably greater than or equal to the S1 level ($S_A$) of the material 131, and the T1 level ($T_H$) of the host material 132 is preferably greater than or equal to the T1 level ($T_A$) of the material 131. Thus, quenching of the singlet excitation energy and the triplet excitation energy of the material 131 by the host material 132 is less likely to occur; accordingly, energy transfers to the guest material 134 efficiently.

The T1 level ($T_A$) of the material 131 is preferably higher than the T1 level ($T_{PG}$) of the guest material 134. Thus, quenching of the triplet excitation energy of the material 131 caused by the guest material 134 is less likely to occur, which causes efficient reverse intersystem crossing.

In the case where the combination of the host material 132 and the material 131 is a combination of a material having a function of transporting a hole and a material having a function of transporting an electron, the carrier balance can be easily controlled depending on the mixture ratio. Specifically, the weight ratio of the material having a function of transporting a hole to the material having a function of transporting an electron is preferably within a range of 1:9 to 9:1. Since the carrier balance can be easily controlled with the structure, a carrier recombination region can also be controlled easily.

When the light-emitting layer 130 has the above-described structure, light emission from the guest material 134 of the light-emitting layer 130 can be obtained efficiently.

Example of Material that can be Used in Light-Emitting Layer

Next, materials that can be used in the light-emitting layer 135 are described below.

An energy difference between the S1 level and the T1 level of the material 131 is preferably small. Specifically, the energy difference between the S1 level and the T1 level is preferably greater than 0 eV and less than or equal to 0.3 eV, more preferably greater than 0 eV and less than or equal to 0.2 eV, more preferably greater than 0 eV and less than or equal to 0.1 eV. A material with a small energy difference is, for example, a thermally activated delayed fluorescence material. As the thermally activated delayed fluorescence material, the compound described in Embodiment 1 is preferably used.

Note that the material 131 does not necessarily have a function of emitting thermally activated delayed fluorescence as long as the energy difference between the S1 level and the T1 level is small.

Examples of the host material 132 are, but not particularly limited to, zinc- and aluminum-based metal complexes; heteroaromatic compounds such as an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative; and an aromatic amine and a carbazole derivative which are given as the electron-transport material and the hole-transport material in Embodiment 3.

<<Guest Material 134>>

As the guest material 134, an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

Examples of the substance that has an emission peak in the blue or green wavelength range include organometallic iridium complexes having a 4H-triazole skeleton, such as tris{2-[5-(2-methylphenyl)-4-(2,6-dimethylphenyl)-4H-1,2,4-triazol-3-yl-κN2]phenyl-κ C}iridium(II) (abbreviation: Ir(mpptz-dmp)$_3$), tris(5-methyl-3,4-diphenyl-4H-1,2,4-triazolato)iridium(III) (abbreviation: Ir(Mptz)$_3$), tris[4-(3-biphenyl)-5-isopropyl-3-phenyl-4H-1,2,4-triazolato]iridium (III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium (III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis {2-[3',5'-bis(trifluoromethyl)phenyl]pyridinato-N,C$^{2'}$}iridium(III)picolinate (abbreviation: Ir(CF$_3$ppy)$_2$(pic)), and bis[2-(4',6'-difluorophenyl)pyridinato-N,C$^{2'}$] iridium(III) acetylacetonate (abbreviation: FIr(acac)).

Among the materials given above, the organometallic iridium complexes having a 4H-triazole skeleton have high reliability and high emission efficiency and are thus especially preferable.

Examples of the substance that has an emission peak in the green or yellow wavelength range include organometallic iridium complexes having a pyrimidine skeleton, such as tris(4-methyl-6-phenylpyrimidinato)iridium(III) (abbreviation: Ir(mppm)$_3$), tris(4-t-butyl-6-phenylpyrimidinato) iridium(III) (abbreviation: Ir(tBuppm)$_3$), (acetylacetonato) bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)(acac)), (acetylacetonato)bis {4,6-dimethyl-2-[6-(2,6-dimethylphenyl)-4-pyrimidinyl-xN3]phenyl-κC}iridium(III) (abbreviation: Ir(dmppm-dmp)$_2$(acac)), (acetylacetonato)bis(4,6-diphenylpyrimidinato)iridium(III) (abbreviation: Ir(dppm)$_2$(acac)); organometallic iridium complexes having a pyrazine skeleton, such as (acetylacetonato)bis(3,5-dimethyl-2-phenylpyrazinato)iridium(III) (abbreviation: Ir(mppr-Me)$_2$(acac)) and (acetylacetonato) (5-isopropyl-3-methyl-2-phenylpyrazinato)iridium(III) (abbreviation: Ir(mppr-iPr)$_2$(acac)); organometallic iridium complexes having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato) iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(II) (abbreviation: Ir(pq)$_3$), and bis(2-phenylquinolinato-N,C$^{2'}$)iridium (III) acetylacetonate (abbreviation: Ir(pq)$_2$(acac)); organometallic iridium complexes such as bis(2,4-diphenyl-1,3-oxazolato-N,C$^{2'}$)iridium(III)acetylacetonate (abbreviation: Ir(dpo)$_2$(acac)), bis{2-[4'-(perfluorophenyl)phenyl]pyridinato-N,C$^{2'}$}iridium(III)acetylacetonate (abbreviation: Ir(p-PF-ph)$_2$(acac)), and bis(2-phenylbenzothiazolato-N,C$^{2'}$) iridium(III)acetylacetonate (abbreviation: Ir(bt)$_2$(acac)); and a rare earth metal complex such as tris(acetylacetonatoXmonophenanthroline)terbium(III) (abbreviation: Tb(acac)$_3$ (Phen)). Among the materials given above, the organometallic iridium complexes having a pyrimidine skeleton have distinctively high reliability and emission efficiency and are thus particularly preferable.

Examples of the substance that has an emission peak in the yellow or red wavelength range include organometallic iridium complexes having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis [4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(dlnpm)$_2$(dpm)); organometallic iridium complexes having a pyrazine skeleton, such as (acetylacetonato)bis(2,3,5-triphenylpyrazinato)iridium (III) (abbreviation: Ir(tppr)$_2$(acac)), bis(2,3,5-triphenylpyrazinato) (dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes having a pyridine skeleton, such as tris(1-phenylisoquinolinato-N,C$^{2'}$)iridium(III) (abbreviation: Ir(piq)$_3$) and bis(1-phenylisoquinolinato-N,C$^{2'}$)iridium(III)acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionatoXmonophenanthroline)europium(II) (abbreviation: Eu(DBM)$_3$(Phen)) and tris [1-(2-thenoyl)-3,3,3-trifluoroacetonato](monophenanthroline)europium(III) (abbreviation: Eu(TTA)$_3$(Phen)). Among the materials given above, the organometallic iridium complexes having a pyrimidine skeleton have distinctively high reliability and emission efficiency and are thus particularly preferable. Further, the organometallic iridium complexes having a pyrazine skeleton can provide red light emission with favorable chromaticity.

As the light-emitting material included in the light-emitting layer 130, any material can be used as long as the material can convert the triplet excitation energy into light emission. As an example of the material that can convert triplet excitation energy into light emission, a thermally activated delayed fluorescence (TADF) material can be given in addition to the phosphorescent material. Therefore, the term "phosphorescent material" in the description can be replaced with the term "thermally activated delayed fluorescence material". The thermally activated delayed fluorescence material is a material having a small energy difference between the S1 level and the T1 level and has a function of converting the triplet excitation energy into the singlet excitation energy by reverse intersystem crossing. Thus, the thermally activated delayed fluorescence material can up-convert a triplet excited state into a singlet excited state (i.e., reverse intersystem crossing is possible) using a little thermal energy and efficiently exhibit light emission (fluorescence) from the singlet excited state. Conditions for efficiently obtaining thermally activated delayed fluorescence are as follows: the energy difference between the S1 level and the T1 level is preferably greater than 0 eV and less than or equal to 0.3 eV, more preferably greater than 0 eV and less than or equal to 0.2 eV, further more preferably greater than 0 eV and less than or equal to 0.1 eV.

In the case where the thermally activated delayed fluorescence material is composed of one kind of material, any of the following materials can be used, for example.

First, a fullerene, a derivative thereof, an acridine derivative such as proflavine, eosin, and the like can be given. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)).

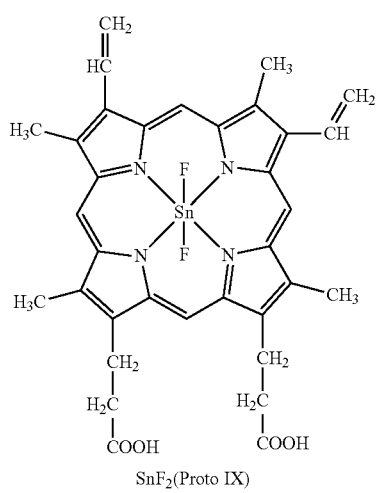
SnF$_2$(Proto IX)
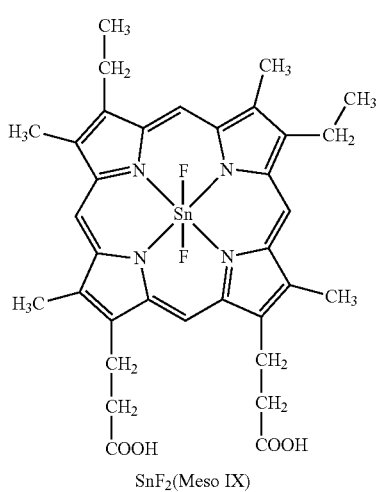
SnF$_2$(Meso IX)
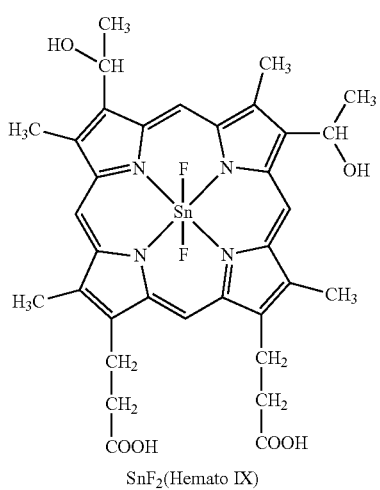
SnF$_2$(Hemato IX)
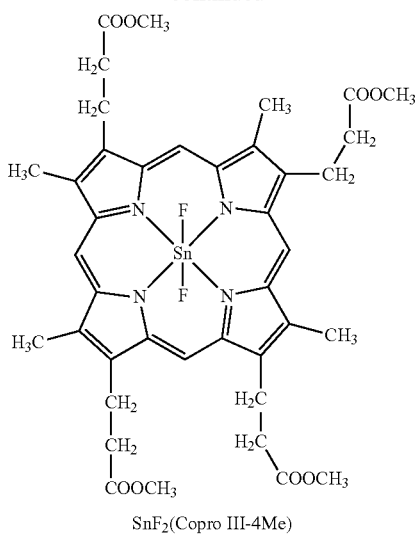
SnF$_2$(Copro III-4Me)
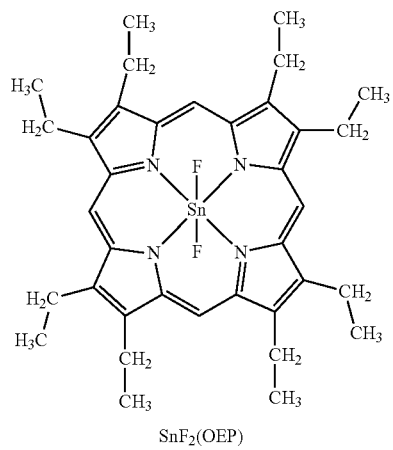
SnF$_2$(OEP)
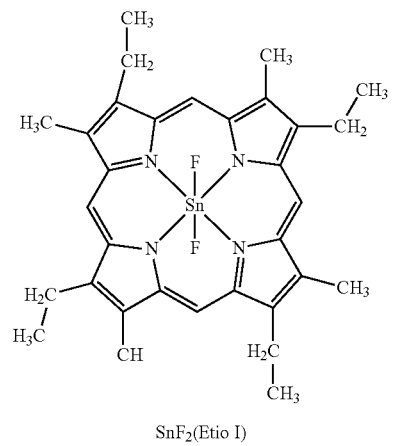
SnF$_2$(Etio I)

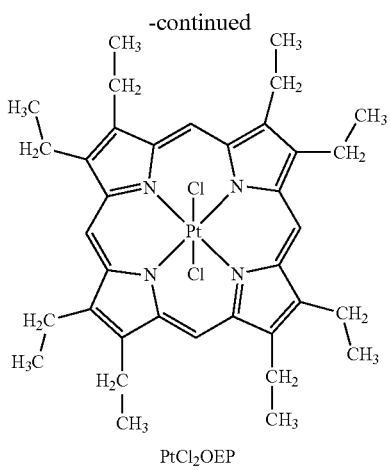

PtCl₂OEP

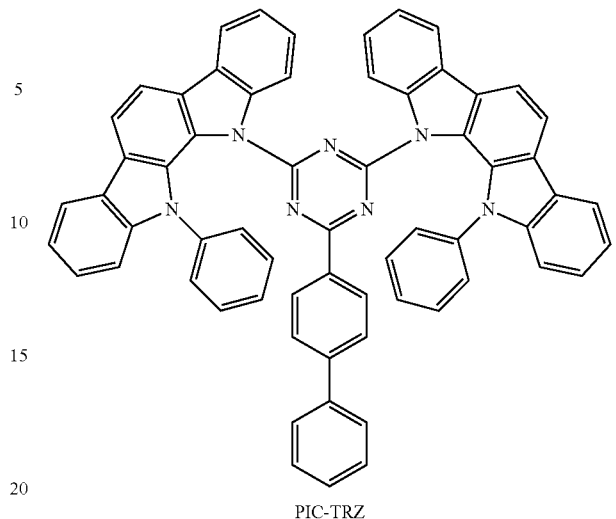

PIC-TRZ

As the thermally activated delayed fluorescence material composed of one kind of material, a heterocyclic compound including a π-electron rich heteroaromatic ring and a π-electron deficient heteroaromatic ring can also be used. Specifically, 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H, 10'H-spiro[acridin-9,9'-anthracen]-10'-one (abbreviation: ACRSA) can be used. The heterocyclic compound is preferably used because of having the π-electron rich heteroaromatic ring and the π-electron deficient heteroaromatic ring, for which the electron-transport property and the hole-transport property are high. Among skeletons having the π-electron deficient heteroaromatic ring, a diazine skeleton (a pyrimidine skeleton, a pyrazine skeleton, or a pyridazine skeleton) and a triazine skeleton have stability and high reliability and are particularly preferable. Among skeletons having the π-electron rich heteroaromatic ring, an acridine skeleton, a phenoxazine skeleton, a phenothiazine skeleton, a furan skeleton, a thiophene skeleton, and a pyrrole skeleton have stability and high reliability; therefore, one or more of these skeletons are preferably included. As the pyrrole skeleton, an indole skeleton, a carbazole skeleton, or a 9-phenyl-3,3'-bi-9H-carbazole skeleton is particularly preferred. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the difference between the level of the singlet excited state and the level of the triplet excited state becomes small.

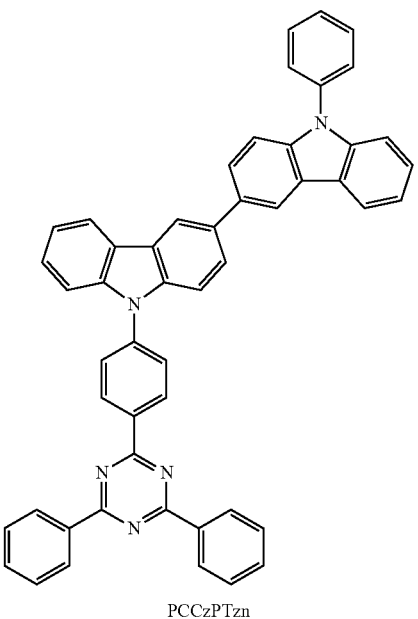

PCCzPTzn

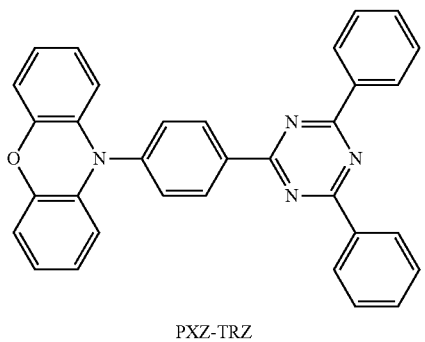

PXZ-TRZ

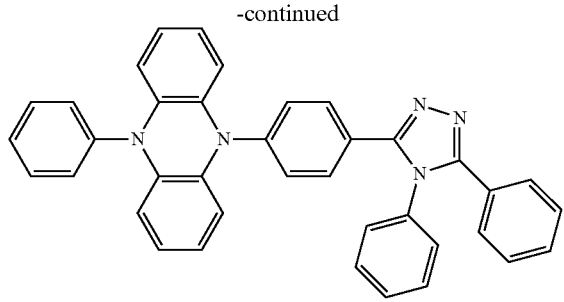

PPZ-3TPT

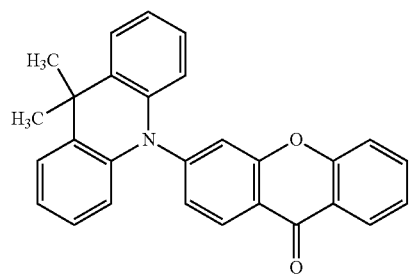

ACRXTN

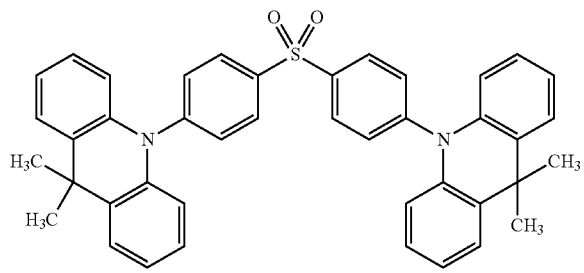

DMAC-DPS

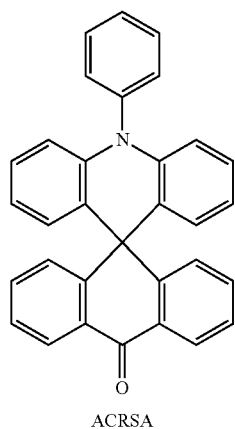

ACRSA

It is preferable that the material 131 and the guest material 134 (the phosphorescent material) be selected such that the emission peak of the material 131 overlaps with an absorption band, specifically an absorption band on the longest wavelength side, of a triplet metal to ligand charge transfer (MLCT) transition of the guest material 134 (the phosphorescent material). This makes it possible to provide a light-emitting element with drastically improved emission efficiency. Note that in the case where a thermally activated delayed fluorescent material is used instead of the phosphorescent material, it is preferable that the absorption band on the longest wavelength side be a singlet absorption band.

The light-emitting layer 135 can have a structure in which two or more layers are stacked. For example, in the case where the light-emitting layer 135 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

The light-emitting layer 135 may contain a material other than the material 131, the host material 132, and the guest material 134.

Note that the light-emitting layer 135 can be formed by an evaporation method (including a vacuum evaporation method), an inkjet method, a coating method, gravure printing, or the like. Besides the above-mentioned materials, an inorganic compound such as a quantum dot or a high molecular compound (e.g., an oligomer, a dendrimer, and a polymer) may be used.

The structure described in this embodiment can be used in appropriate combination with any of the structures described in the other embodiments.

Embodiment 5

In this embodiment, a light-emitting element having a structure different from the structures described in Embodiments 3 and 4 and light emission mechanisms of the light-emitting element are described below with reference to FIGS. 6A to 6C and FIGS. 7A to 7C. In FIGS. 6A to 6C and FIGS. 7A to 7C, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

Structure Example 1 of Light-Emitting Element

Figure 6A:
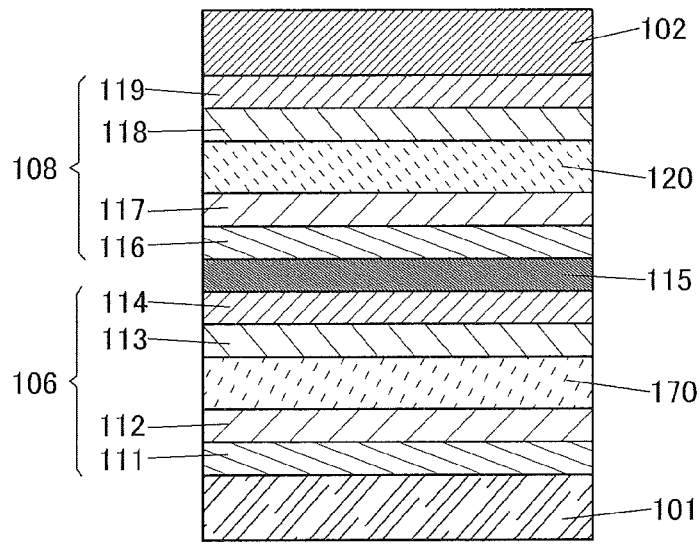
FIGS. 6A and 6B are schematic cross-sectional views illustrating a light-emitting element of one embodiment of the present invention and FIG. 6C is a schematic diagram illustrating the correlation of energy levels in a light-emitting layer.

FIG. 6A is a schematic cross-sectional view of a light-emitting element 250.

The light-emitting element 250 illustrated in FIG. 6A includes a plurality of light-emitting units (a light-emitting unit 106 and a light-emitting unit 108 in FIG. 6A) between a pair of electrodes (the electrode 101 and the electrode 102). One of light-emitting units preferably has the same structure as the EL layer 100. That is, it is preferable that each of the light-emitting element 150 and the light-emitting element 152 in FIGS. 1A to 1C to FIGS. 5A and 5B include one light-emitting unit, while the light-emitting element 250 include a plurality of light-emitting units. Note that the electrode 101 functions as an anode and the electrode 102 functions as a cathode in the following description of the light-emitting element 250; however, the functions may be interchanged in the light-emitting element 250.

In the light-emitting element 250 illustrated in FIG. 6A, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable that the EL layer 100 be used in the light-emitting unit 106.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 108 includes a hole-injection layer 116, a hole-transport layer 117, an electron-transport layer 118, and an electron-injection layer 119 in addition to the light-emitting layer 120.

The charge-generation layer 115 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 115 contains a composite material of an organic compound and an acceptor substance, the composite material that can be used for the hole-injection layer 111 described in Embodiment 3 may be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A material having a hole mobility of $1 \times 10^{-6}$ cm²/Vs or higher is preferably used as the organic compound. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 115, the charge-generation layer 115 can also serve as a hole-injection layer or a hole-transport layer of the light-emitting unit; thus, a hole-injection layer or a hole-transport layer is not necessarily included in the light-emitting unit. Alternatively, when a surface of the light-emitting unit on the cathode side is in contact with the charge-generation layer 115, the charge-generation layer 115 can also serve as an electron-injection layer or an electron-transport layer of the light-emitting unit; thus, an electron-injection layer or an electron-transport layer is not necessarily included in the light-emitting unit.

The charge-generation layer 115 may have a stacked structure of a layer containing the composite material of an organic compound and an acceptor substance and a layer containing another material. For example, the charge-generation layer 115 may be formed using a combination of a layer containing the composite material of an organic compound and an acceptor substance with a layer containing one compound selected from among electron-donating materials and a compound having a high electron-transport property. Furthermore, the charge-generation layer 115 may be formed using a combination of a layer containing the composite material of an organic compound and an acceptor substance with a layer containing a transparent conductive film.

The charge-generation layer 115 provided between the light-emitting unit 106 and the light-emitting unit 108 may have any structure as long as electrons can be injected to the light-emitting unit on one side and holes can be injected into the light-emitting unit on the other side in the case where a voltage is applied between the electrode 101 and the electrode 102. For example, in FIG. 6A, the charge-generation layer 115 injects electrons into the light-emitting unit 106 and holes into the light-emitting unit 108 when a voltage is applied such that the potential of the electrode 101 is higher than that of the electrode 102.

Note that in terms of light extraction efficiency, the charge-generation layer 115 preferably has a visible light transmittance (specifically, a visible light transmittance of higher than or equal to 40%). The charge-generation layer 115 functions even if it has lower conductivity than the pair of electrodes (the electrodes 101 and 102).

Note that forming the charge-generation layer 115 by using any of the above materials can suppress an increase in drive voltage caused by the stack of the light-emitting layers.

The light-emitting element having two light-emitting units has been described with reference to FIG. 6A; however, a similar structure can be applied to a light-emitting element in which three or more light-emitting units are stacked. With a plurality of light-emitting units partitioned by the charge-generation layer between a pair of electrodes as in the light-emitting element 250, it is possible to provide a light-emitting element which can emit light having high luminance with the current density kept low and has a long lifetime. A light-emitting element with low power consumption can be provided.

When the structure with the compound of one embodiment of the present invention described in Embodiment 1 is used for at least one of the plurality of units, a light-emitting element with high emission efficiency can be provided.

It is preferable that the light-emitting layer 170 included in the light-emitting unit 106 have the structure of the light-emitting layer 130 or the light-emitting layer 135 described in Embodiments 3 and 4. In that case, the light-emitting element 250 has high emission efficiency.

Figure 6B:
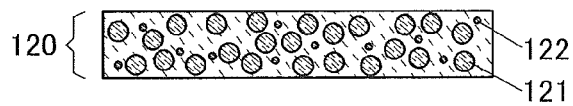

The light-emitting layer 120 included in the light-emitting unit 106 contains a host material 121 and a guest material 122 as illustrated in FIG. 6B. Note that the guest material 122 is described below as a fluorescent material.

<<Light Emission Mechanism of Light-Emitting Layer 120>>

The light emission mechanism of the light-emitting layer 120 is described below.

By recombination of the electrons and holes injected from the pair of electrodes (the electrode 101 and the electrode 102) or the charge-generation layer in the light-emitting layer 120, excitons are formed. Because the amount of the host material 121 is larger than that of the guest material 122, the host material 121 is brought into an excited state by the exciton generation.

In the case where the formed excited state of the host material 121 is a singlet excited state, singlet excitation energy transfers from the S1 level of the host material 121 to the S1 level of the guest material 122, thereby forming the singlet excited state of the guest material 122.

Since the guest material 122 is a fluorescent material, when a singlet excited state is formed in the guest material 122, the guest material 122 immediately emits light. To obtain high light emission efficiency in this case, the fluorescence quantum yield of the guest material 122 is preferably high. The same can apply to a case where a singlet excited state is formed by recombination of carriers in the guest material 122.

Figure 6C:
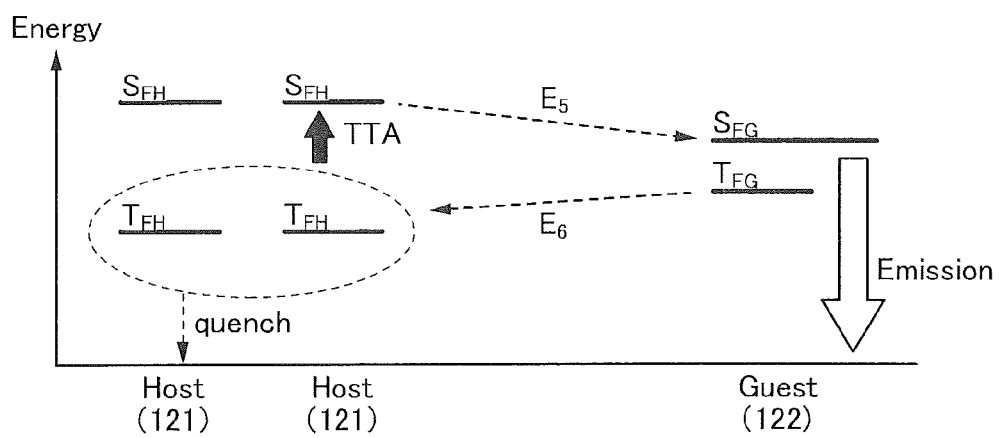

Next, a case where recombination of carriers forms a triplet excited state of the host material 121 is described. The correlation of energy levels of the host material 121 and the guest material 122 in this case is shown in FIG. 6C. The following explains what terms and signs in FIG. 6C represent. Note that because it is preferable that the T1 level of the host material 121 be lower than the T1 level of the guest material 122, FIG. 6C shows this preferable case. However, the T1 level of the host material 121 may be higher than the T1 level of the guest material 122.

Host (121): the host material 121;
Guest (122): the guest material 122 (fluorescent material);
$S_{FH}$: the S1 level of the host material 121;
$T_{FH}$: the T1 level of the host material 121;

$S_{FG}$: the S1 level of the guest material 122 (fluorescent material); and $T_{FG}$: the T1 level of the guest material 122 (fluorescent material).

As illustrated in FIG. 6C, triplet-triplet annihilation (TTA) occurs, that is, triplet excitons formed by carrier recombination interact with each other, and excitation energy is transferred and spin angular momenta are exchanged; as a result, a reaction in which the triplet excitons are converted into singlet exciton having energy of the S1 level of the host material 121 ($S_{FH}$) (see TTA in FIG. 6C). The singlet excitation energy of the host material 121 is transferred from $S_{FH}$ to the S1 level of the guest material 122 ($S_{FG}$) having a lower energy than $S_{FH}$ (see Route $E_5$ in FIG. 6C), and a singlet excited state of the guest material 122 is formed, whereby the guest material 122 emits light.

Note that in the case where the density of triplet excitons in the light-emitting layer 120 is sufficiently high (e.g., $1 \times 10^{-12}$ cm$^{-3}$ or higher), only the reaction of two triplet excitons close to each other can be considered whereas deactivation of a single triplet exciton can be ignored.

In the case where a triplet excited state of the guest material 122 is formed by carrier recombination, the triplet excited state of the guest material 122 is thermally deactivated and is difficult to use for light emission. However, in the case where the T1 level of the host material 121 ($T_{FH}$) is lower than the T1 level of the guest material 122 ($T_{FG}$), the triplet excitation energy of the guest material 122 can be transferred from the T1 level of the guest material 122 ($T_{FG}$) to the T1 level of the host material 121 ($T_{FH}$) (see Route $E_6$ in FIG. 6C) and then is utilized for TTA.

In other words, the host material 121 preferably has a function of converting triplet excitation energy into singlet excitation energy by causing TTA, so that the triplet excitation energy generated in the light-emitting layer 120 can be partly converted into singlet excitation energy by TTA in the host material 121. The singlet excitation energy can be transferred to the guest material 122 and extracted as fluorescence. In order to achieve this, the S1 level of the host material 121 ($S_{FH}$) is preferably higher than the S1 level of the guest material 122 ($S_{FG}$). In addition, the T1 level of the host material 121 ($T_{FH}$) is preferably lower than the T1 level of the guest material 122 ($T_{FG}$).

Note that particularly in the case where the T1 level ($T_{FG}$) of the guest material 122 is lower than the T1 level ($T_{FH}$) of the host material 121, the weight ratio of the guest material 122 to the host material 121 is preferably low. Specifically, the weight ratio of the guest material 122 to the host material 121 is preferably greater than 0 and less than or equal to 0.05, in which case the probability of carrier recombination in the guest material 122 can be reduced. In addition, the probability of energy transfer from the T1 level ($T_{FH}$) of the host material 121 to the T1 level ($T_{FG}$) of the guest material 122 can be reduced.

Note that the host material 121 may be composed of a single compound or a plurality of compounds.

In the case where the light-emitting units 106 and 108 contain guest materials with different colors, light emitted from the light-emitting layer 120 preferably has an emission peak on the shorter wavelength side than light emitted from the light-emitting layer 170. Since the luminance of a light-emitting element using a material having a high triplet excitation energy level tends to be degraded quickly, TTA is utilized in the light-emitting layer emitting light with a short wavelength so that a light-emitting element with less degradation of luminance can be provided.

Structure Example 2 of Light-Emitting Element

Figure 7A:
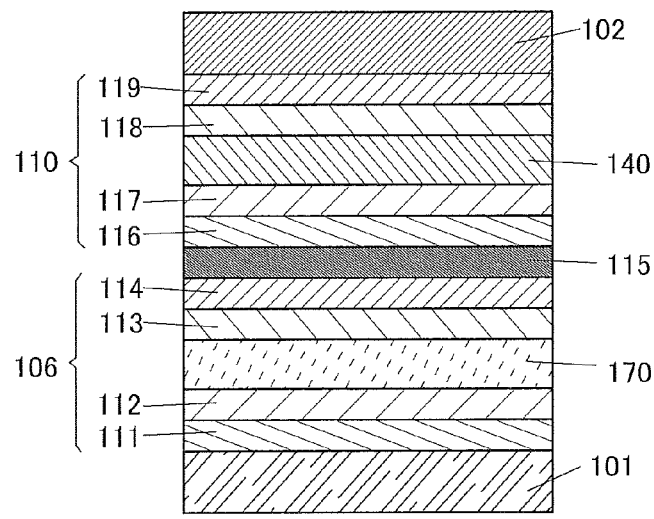
FIGS. 7A and 7B are schematic cross-sectional views illustrating a light-emitting element of one embodiment of the present invention and FIG. 7C is a schematic diagram illustrating the correlation of energy levels in a light-emitting layer.

FIG. 7A is a schematic cross-sectional view of a light-emitting element 252.

The light-emitting element 252 illustrated in FIG. 7A includes, like the light-emitting element 250 described above, a plurality of light-emitting units (the light-emitting unit 106 and a light-emitting unit 110 in FIG. 7A) between a pair of electrodes (the electrode 101 and the electrode 102). At least one of the light-emitting units has a structure similar to that of the EL layer 100 in FIG. 1A. Note that the light-emitting unit 106 and the light-emitting unit 110 may have the same structure or different structures.

In the light-emitting element 252 illustrated in FIG. 7A, the light-emitting unit 106 and the light-emitting unit 110 are stacked, and a charge-generation layer 115 is provided between the light-emitting unit 106 and the light-emitting unit 110. For example, it is preferable that the EL layer 100 be used in the light-emitting unit 106.

The light-emitting element 252 includes a light-emitting layer 140 and the light-emitting layer 170. The light-emitting unit 106 includes the hole-injection layer 111, the hole-transport layer 112, an electron-transport layer 113, and an electron-injection layer 114 in addition to the light-emitting layer 170. The light-emitting unit 110 includes a hole-injection layer 116, a hole-transport layer 117, an electron-transport layer 118, and an electron-injection layer 119 in addition to the light-emitting layer 140.

When the structure with the compound of one embodiment of the present invention described in Embodiment 1 is used for at least one of the plurality of units, a light-emitting element with high emission efficiency can be provided.

The light-emitting layer of the light-emitting unit 110 preferably includes a phosphorescent material. The light-emitting layer 140 included in the light-emitting unit 110 preferably includes a phosphorescent material and the light-emitting layer 170 included in the light-emitting unit 106 preferably includes the compound of one embodiment of the present invention described in Embodiment 1. In other words, it is preferable that the light-emitting layer 170 included in the light-emitting unit 110 have the structure of the light-emitting layer 130 or the light-emitting layer 135 described in Embodiments 3 and 4. A structure example of the light-emitting element 252 in this case is described below.

Figure 7B:
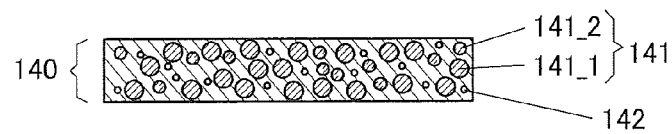

The light-emitting layer 140 included in the light-emitting unit 110 includes a host material 141 and a guest material 142 as illustrated in FIG. 7B. The host material 141 includes an organic compound 141_1 and an organic compound 141_2. In the following description, the guest material 142 included in the light-emitting layer 140 is a phosphorescent material.

<Light Emission Mechanism of Light-Emitting Layer 140>

Next, the light emission mechanism of the light-emitting layer 140 is described below.

The organic compound 141_1 and the organic compound 141_2 which are included in the light-emitting layer 140 form an exciplex.

Although it is acceptable as long as the combination of the organic compound 141_1 and the organic compound 141_2 can form an exciplex, it is preferable that one of them be a compound having a hole-transport property and the other be a compound having an electron-transport property.

Figure 7C:
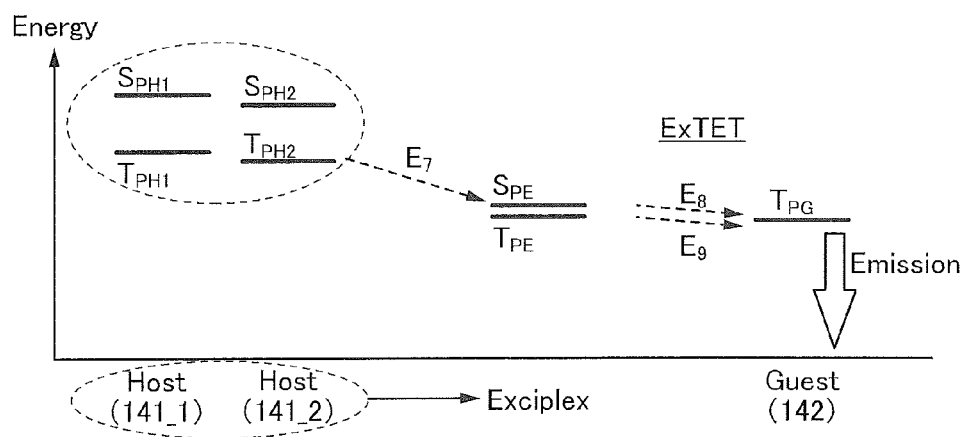

FIG. 7C shows a correlation between the energy levels of the organic compound 141_1, the organic compound 141_2, and the guest material 142 in the light-emitting layer 140. The following explains what terms and numerals in FIG. 7C represent:

Host (141_1): the organic compound 141_1 (host material);

Host (141_2): the organic compound 141_2 (host material);

Guest (142): the guest material 142 (phosphorescent material);

$Sp_H$: the S1 level of the organic compound 141_1 (host material);

$T_{PH}$: the T1 level of the organic compound 141_1 (host material);

$T_{PG}$: the T1 level of the guest material 142 (phosphorescent material);

$S_{PE}$: the S1 level of the exciplex; and $T_{PE}$: the T1 level of the exciplex.

The organic compound 141_1 and the organic compound 1412 form an exciplex, and the S1 level ($S_{PE}$) and the T1 level ($T_{PE}$) of the exciplex are energy levels adjacent to each other (see Route $E_7$ in FIG. 7C).

One of the organic compounds 141_1 and the organic compound 141_2 receives a hole and the other receives an electron to readily form an exciplex. Alternatively, when one of the organic compounds is brought into an excited state, the other immediately interacts with the one to form an exciplex. Consequently, most excitons in the light-emitting layer 140 exist as exciplexes. Because the excitation energy levels ($S_{PE}$ and $T_{PE}$) of the exciplex are lower than the S1 levels ($S_{PH1}$ and $S_{PH2}$) of the host materials (the organic compounds 141_1 and 141_2) that form the exciplex, the excited state of the host material 141 can be formed with lower excitation energy. This can reduce the drive voltage of the light emitting element.

Both energies of $S_{PE}$ and $T_{PE}$ of the exciplex are then transferred to the T1 level of the guest material 142 (the phosphorescent material); thus, light emission is obtained (see Routes $E_8$ and $E_9$ in FIG. 7C).

Furthermore, the T1 level ($T_{PE}$) of the exciplex is preferably higher than the T1 level ($T_{PG}$) of the guest material 142. With such a relation between the T1 levels, the singlet excitation energy and the triplet excitation energy of the formed exciplex can be transferred from the S1 level ($S_{PE}$) and the T1 level ($T_{PE}$) of the exciplex to the T1 level ($T_{PG}$) of the guest material 142.

Note that in order to efficiently transfer excitation energy from the exciplex to the guest material 142, the T1 level ($T_{PE}$) of the exciplex is preferably lower than or equal to the T1 levels ($T_{PH1}$ and $T_{PH2}$) of the organic compounds (the organic compound 141_1 and the organic compound 141_2) which form the exciplex. Thus, quenching of the triplet excitation energy of the exciplex due to the organic compounds (the organic compounds 141_1 and 141_2) is less likely to occur, resulting in efficient energy transfer from the exciplex to the guest material 142.

In the case where the combination of the organic compounds 141_1 and 141_2 is a combination of a compound having a hole-transport property and a compound having an electron-transport property, the carrier balance can be easily controlled by adjusting the mixture ratio. Specifically, the weight ratio of the compound having a hole-transport property to the compound having an electron-transport property is preferably within a range of 1:9 to 9:1. Since the carrier balance can be easily controlled with the structure, a carrier recombination region can also be controlled easily.

Furthermore, the mechanism of the energy transfer process between the molecules of the host material 141 (exciplex) and the guest material 142 can be described using two mechanisms, i.e., Förster mechanism (dipole-dipole interaction) and Dexter mechanism (electron exchange interaction), as in Embodiment 4. For Förster mechanism and Dexter mechanism, Embodiment 3 can be referred to.

In order to facilitate energy transfer from the singlet excited state of the host material (exciplex) to the triplet excited state of the guest material 142 serving as an energy acceptor, it is preferable that the emission spectrum of the exciplex overlap with the absorption band of the guest material 142 which is on the longest wavelength side (lowest energy side). Thus, the efficiency of generating the triplet excited state of the guest material 142 can be increased.

When the light-emitting layer 140 has the above-described structure, light emission from the guest material 142 (the phosphorescent material) of the light-emitting layer 140 can be obtained efficiently.

Note that the above-described processes through Routes $E_7$, $E_8$, and $E_9$ may be referred to as exciplex-triplet energy transfer (ExTET) in this specification and the like. In other words, in the light-emitting layer 140, excitation energy is transferred from the exciplex to the guest material 142. In this case, the efficiency of reverse intersystem crossing from $T_{PE}$ to $S_{PE}$ and the emission quantum yield from $S_{PE}$ are not necessarily high; thus, materials can be selected from a wide range of options.

Note that light emitted from the light-emitting layer 170 preferably has a peak on the shorter wavelength side than light emitted from the light-emitting layer 140. Since the luminance of a light-emitting element using a phosphorescent material emitting light with a short wavelength tends to be degraded quickly, fluorescence with a short wavelength is employed so that a light-emitting element with less degradation of luminance can be provided.

Note that in each of the above-described structures, the emission colors of the guest materials used in the light-emitting unit 106 and the light-emitting unit 108 or in the light-emitting unit 106 and the light-emitting unit 110 may be the same or different. In the case where the same guest materials emitting light of the same color are used for the light-emitting unit 106 and the light-emitting unit 108 or for the light-emitting unit 106 and the light-emitting unit 110, the light-emitting element 250 and the light-emitting element 252 can exhibit high emission luminance at a small current value, which is preferable. In the case where guest materials emitting light of different colors are used for the light-emitting unit 106 and the light-emitting unit 108 or for the light-emitting unit 106 and the light-emitting unit 110, the light-emitting element 250 and the light-emitting element 252 can exhibit multi-color light emission, which is preferable. In that case, when a plurality of light-emitting materials with different emission wavelengths are used in one or both of the light-emitting layers 120 and 170 or in one or both of the light-emitting layers 140 and 170, lights with different emission peaks synthesize light emission from the light-emitting element 250 and the light-emitting element 252. That is, the emission spectrum of the light-emitting element 250 has at least two maximum values.

The above structure is also suitable for obtaining white light emission. When the light-emitting layer 120 and the light-emitting layer 170 or the light-emitting layer 140 and the light-emitting layer 170 emit light of complementary colors, white light emission can be obtained. It is particularly favorable to select the guest materials so that white light emission with high color rendering properties or light emission of at least red, green, and blue can be obtained.

At least one of the light-emitting layers 120, 140, and 170 may be divided into layers and each of the divided layers may contain a different light-emitting material. That is, at least one of the light-emitting layers 120, 140, and 170 may consist of two or more layers. For example, in the case where the light-emitting layer is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. In that case, a light-emitting material included in the first light-emitting layer may be the same as or different from a light-emitting material included in the second light-emitting layer. In addition, the materials may have functions of emitting light of the same color or light of different colors. White light emission with a high color rendering property that is formed of three primary colors or four or more colors can be obtained by using a plurality of light-emitting materials emitting light of different colors.

<Material that can be Used in Light-Emitting Layers>

Next, materials that can be used in the light-emitting layers 120, 140, and 170 are described.

<<Material that can be Used in Light-Emitting Layer 120>>

In the light-emitting layer 120, the host material 121 is present in the largest proportion by weight, and the guest material 122 (the fluorescent material) is dispersed in the host material 121. The S1 level of the host material 121 is preferably higher than the S1 level of the guest material 122 (the fluorescent material) while the T1 level of the host material 121 is preferably lower than the T1 level of the guest material 122 (the fluorescent material).

In the light-emitting layer 120, although the guest material 122 is not particularly limited, for example, any of the materials described as examples of the guest material 133 in Embodiment 3 can be used.

Although there is no particular limitation on a material that can be used as the host material 121 in the light-emitting layer 120, any of the following materials can be used, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[gp]chrysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N,N',N'',N'',N'''-octaphenyldibenzo[gp]chrysene-2,7,10,15-tetramine (abbreviation: DBC 1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), and the like. One or more substances having a wider energy gap than the guest material 122 is preferably selected from these substances and known substances. In addition, the compound of one embodiment of the present invention described in Embodiment 1 can be used.

The light-emitting layer 120 can have a structure in which two or more layers are stacked. For example, in the case where the light-emitting layer 120 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

In the light-emitting layer 120, the host material 121 may be composed of one kind of compound or a plurality of compounds. Alternatively, the light-emitting layer 120 may contain another material in addition to the host material 121 and the guest material 122.

<<Material that can be Used in Light-Emitting Layer 140>>

In the light-emitting layer 140, the host material 141 is present in the largest proportion by weight, and the guest material 142 (phosphorescent material) is dispersed in the host material 141. The T1 levels of the host materials 141 (organic compounds 141_1 and 141_2) of the light-emitting layer 140 are preferably higher than the T1 level of the guest material 142 of the light-emitting layer 140.

Examples of the organic compound 141_1 include a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples are an aromatic amine and a carbazole derivative. Specifically, the electron-transport material and the hole-transport material described in Embodiment 3 can be used.

As the organic compound 141_2, a substance which can form an exciplex together with the organic compound 141_1 is preferably used. Specifically, the electron-transport material and the hole-transport material described in Embodiment 3 can be used. In that case, it is preferable that the organic compound 141_1, the organic compound 141_2, and the guest material 142 (phosphorescent material) be selected such that the emission peak of the exciplex formed by the organic compound 141_1 and the organic compound 141_2 overlaps with an absorption band, specifically an absorption band on the longest wavelength side, of a triplet metal to ligand charge transfer (MLCT) transition of the guest material 142 (phosphorescent material). This makes it possible to provide a light-emitting element with drastically improved emission efficiency. Note that in the case where a thermally activated delayed fluorescence material is used instead of the phosphorescent material, it is preferable that the absorption band on the longest wavelength side be a singlet absorption band. The compound of one embodiment of the present invention described in Embodiment 1 is suitably used as one of the organic compound 141_1 and the organic compound 141_2 because including a skeleton with a high donor property and a high acceptor property.

As the guest material 142 (phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given. Specifically, the material described in Embodiment 4 as an example of the guest material 134 can be used.

As the light-emitting material included in the light-emitting layer 140, any material can be used as long as the material can convert the triplet excitation energy into light emission. As an example of the material that can convert the triplet excitation energy into light emission, a thermally activated delayed fluorescent material can be given in addition to a phosphorescent material. Therefore, it is acceptable that the "phosphorescent material" in the description is replaced with the "thermally activated delayed fluorescence material".

The material that exhibits thermally activated delayed fluorescence may be a material that can form a singlet excited state from a triplet excited state by reverse intersystem crossing or may be a combination of a plurality of materials which form an exciplex.

In the case where the material exhibiting thermally activated delayed fluorescence is formed of one kind of material, any of the compound of one embodiment of the present invention described in Embodiment 1 and the thermally activated delayed fluorescence materials described in Embodiment 4 can be specifically used.

In the case where the thermally activated delayed fluorescence material is used as the host material, it is preferable to use a combination of two kinds of compounds which form an exciplex. In this case, it is particularly preferable to use the above-described combination of a compound that easily accepts electrons and a compound that easily accepts holes, which forms an exciplex.

<<Material that can be Used in Light-Emitting Layer 170>>

As a material that can be used in the light-emitting layer 170, a material that can be used in the light-emitting layer in Embodiment 3 or 4 or the compound of one embodiment of the present invention described in Embodiment 1 can be used. Thus, a light-emitting element with high emission efficiency can be fabricated.

There is no limitation on the emission colors of the light-emitting materials contained in the light-emitting layers 120, 140, and 170, and they may be the same or different. Light emitted from the light-emitting materials is mixed and extracted out of the element; therefore, for example, in the case where their emission colors are complementary colors, the light-emitting element can emit white light.

Note that the light-emitting units 106, 108, and 110 and the charge-generation layer 115 can be formed by an evaporation method (including a vacuum evaporation method), an ink jet method, a coating method, gravure printing, or the like.

The structure described in this embodiment can be used in appropriate combination with any of the structures described in the other embodiments.

Embodiment 6

In this embodiment, examples of light-emitting elements having structures different from those described in Embodiments 3 to 5 are described below with reference to FIGS. 8A and 8B, FIGS. 9A and 9B, FIGS. 10A to 10C, and FIGS. 11A to 11C.

Structure Example 1 of Light-Emitting Element

Figure 8A:
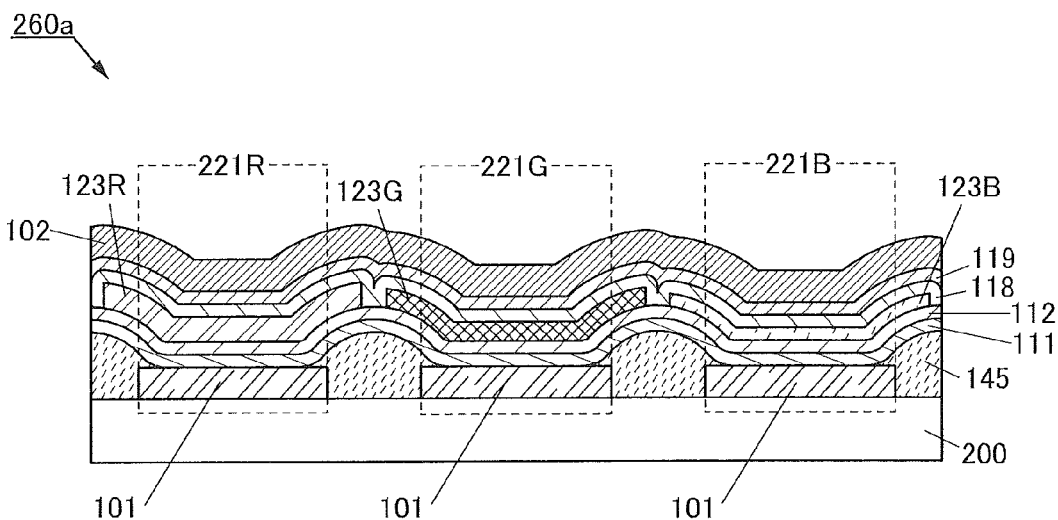
FIGS. 8A and 8B are schematic cross-sectional views each illustrating a light-emitting element of one embodiment of the present invention.
Figure 8B:
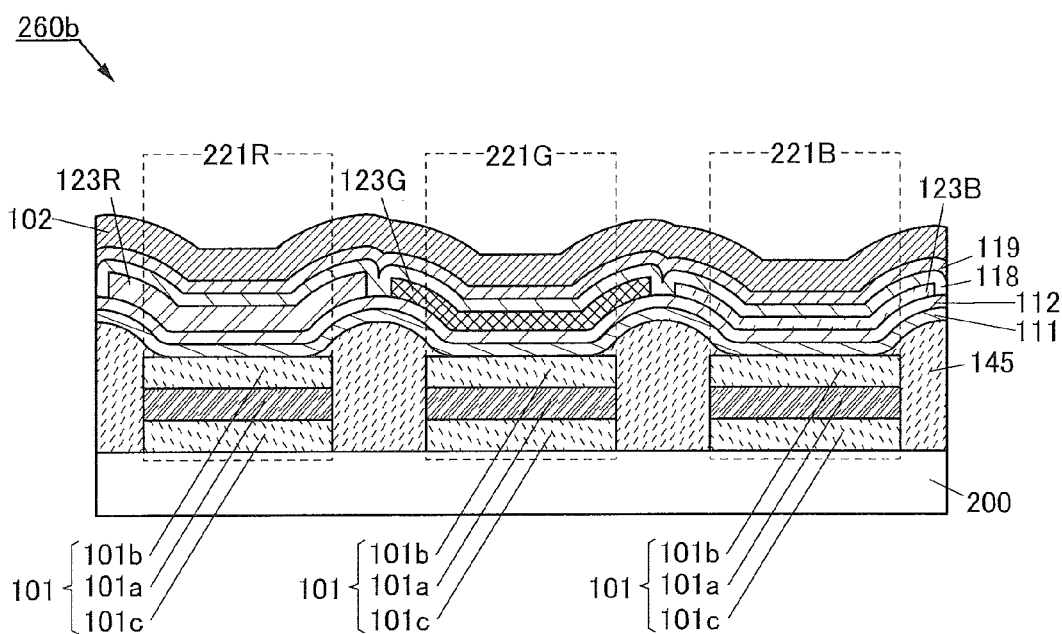

FIGS. 8A and 8B are cross-sectional views each illustrating a light-emitting element of one embodiment of the present invention. In FIGS. 8A and 8B, a portion having a function similar to that in FIG. 1A is represented by the same hatch pattern as in FIG. 1A and not especially denoted by a reference numeral in some cases. In addition, common reference numerals are used for portions having similar functions, and a detailed description of the portions is omitted in some cases.

Light-emitting elements 260a and 260b in FIGS. 8A and 8B may have a bottom-emission structure in which light is extracted through the substrate 200 or may have a top-emission structure in which light emitted from the light-emitting element is extracted in the direction opposite to the substrate 200. However, one embodiment of the present invention is not limited to this structure, and a light-emitting element having a dual-emission structure in which light emitted from the light-emitting element is extracted in both top and bottom directions of the substrate 200 may be used.

In the case where the light-emitting elements 260a and 260b each have a bottom emission structure, the electrode 101 preferably has a function of transmitting light and the electrode 102 preferably has a function of reflecting light. Alternatively, in the case where the light-emitting elements 260a and 260b each have a top emission structure, the electrode 101 preferably has a function of reflecting light and the electrode 102 preferably has a function of transmitting light.

The light-emitting elements 260a and 260b each include the electrode 101 and the electrode 102 over the substrate 200. Between the electrodes 101 and 102, a light-emitting layer 123B, a light-emitting layer 123G, and a light-emitting layer 123R are provided. The hole-injection layer 111, the hole-transport layer 112, the electron-transport layer 118, and the electron-injection layer 119 are also provided.

The light-emitting element 260b includes, as part of the electrode 101, a conductive layer 101a, a conductive layer 101b over the conductive layer 101a, and a conductive layer 101c under the conductive layer 101a. In other words, the light-emitting element 260b includes the electrode 101 having a structure in which the conductive layer 101a is sandwiched between the conductive layer 101b and the conductive layer 101c.

In the light-emitting element 260b, the conductive layer 101b and the conductive layer 101c may be formed with different materials or the same material. The electrode 101 preferably has a structure in which the conductive layer 101a is sandwiched by the layers formed of the same conductive material, in which case patterning by etching in the process for forming the electrode 101 can be performed easily.

In the light-emitting element 260b, the electrode 101 may include one of the conductive layer 101b and the conductive layer 101c.

For each of the conductive layers 101a, 101b, and 101c, which are included in the electrode 101, the structure and materials of the electrode 101 or 102 described in Embodiment 3 can be used.

In FIGS. 8A and 8B, a partition wall 145 is provided between a region 221B, a region 221G, and a region 221R, which are sandwiched between the electrode 101 and the electrode 102. The partition wall 145 has an insulating property. The partition wall 145 covers end portions of the electrode 101 and has openings overlapping with the electrode. With the partition wall 145, the electrode 101 provided over the substrate 200 in the regions can be divided into island shapes.

Note that the light-emitting layer 123B and the light-emitting layer 123G may overlap with each other in a region where they overlap with the partition wall 145. The light-emitting layer 123G and the light-emitting layer 123R may overlap with each other in a region where they overlap with the partition wall 145. The light-emitting layer 123R and the light-emitting layer 123B may overlap with each other in a region where they overlap with the partition wall 145.

The partition wall 145 has an insulating property and is foiled using an inorganic or organic material. Examples of the inorganic material include silicon oxide, silicon oxynitride, silicon nitride oxide, silicon nitride, aluminum oxide, and aluminum nitride. Examples of the organic material include photosensitive resin materials such as an acrylic resin and a polyimide resin.

Note that a silicon oxynitride film refers to a film in which the proportion of oxygen is higher than that of nitrogen. The silicon oxynitride film preferably contains oxygen, nitrogen, silicon, and hydrogen in the ranges of 55 atomic % to 65 atomic %, 1 atomic % to 20 atomic %, 25 atomic % to 35 atomic %, and 0.1 atomic % to 10 atomic %, respectively. A silicon nitride oxide film refers to a film in which the proportion of nitrogen is higher than that of oxygen. The silicon nitride oxide film preferably contains nitrogen, oxygen, silicon, and hydrogen in the ranges of 55 atomic % to 65 atomic %, 1 atomic % to 20 atomic %, 25 atomic % to 35 atomic %, and 0.1 atomic % to 10 atomic %, respectively.

The light-emitting layers 123R, 123G, and 123B preferably contain light-emitting materials having functions of emitting light of different colors. For example, when the light-emitting layer 123R contains a light-emitting material having a function of emitting red, the region 221R emits red light. When the light-emitting layer 123G contains a light-emitting material having a function of emitting green, the region 221G emits green light. When the light-emitting layer 123B contains a light-emitting material having a function of emitting blue, the region 221B emits blue light. The light-emitting element 260a or 260b having such a structure is used in a pixel of a display device, whereby a full-color display device can be fabricated. The thicknesses of the light-emitting layers may be the same or different.

Any one or more of the light-emitting layers 123B, 123G, and 123R preferably include at least one of the light-emitting layer 130 described in Embodiment 3 and the light-emitting layer 135 described in Embodiment 4, in which case a light-emitting element with high emission efficiency can be fabricated.

One or more of the light-emitting layers 123B, 123G, and 123R may include two or more stacked layers.

When at least one light-emitting layer includes the light-emitting layer described in Embodiment 3 or 4 as described above and the light-emitting element 260a or 260b including the light-emitting layer is used in pixels in a display device, a display device with high emission efficiency can be fabricated. The display device including the light-emitting element 260a or 260b can thus have reduced power consumption.

By providing an optical element (e.g., a color filter, a polarizing plate, and an anti-reflection film) on the light extraction side of the electrode through which light is extracted, the color purity of each of the light-emitting elements 260a and 260b can be improved. Therefore, the color purity of a display device including the light-emitting element 260a or 260b can be improved. Alternatively, the reflection of external light by each of the light-emitting elements 260a and 260b can be reduced. Therefore, the contrast ratio of a display device including the light-emitting element 260a or 260b can be improved.

For the other components of the light-emitting elements 260a and 260b, the components of the light-emitting elements in Embodiments 3 to 5 may be referred to.

Structure Example 2 of Light-Emitting Element

Next, structure examples different from the light-emitting elements illustrated in FIGS. 8A and 8B will be described below with reference to FIGS. 9A and 9B.

Figure 9A:
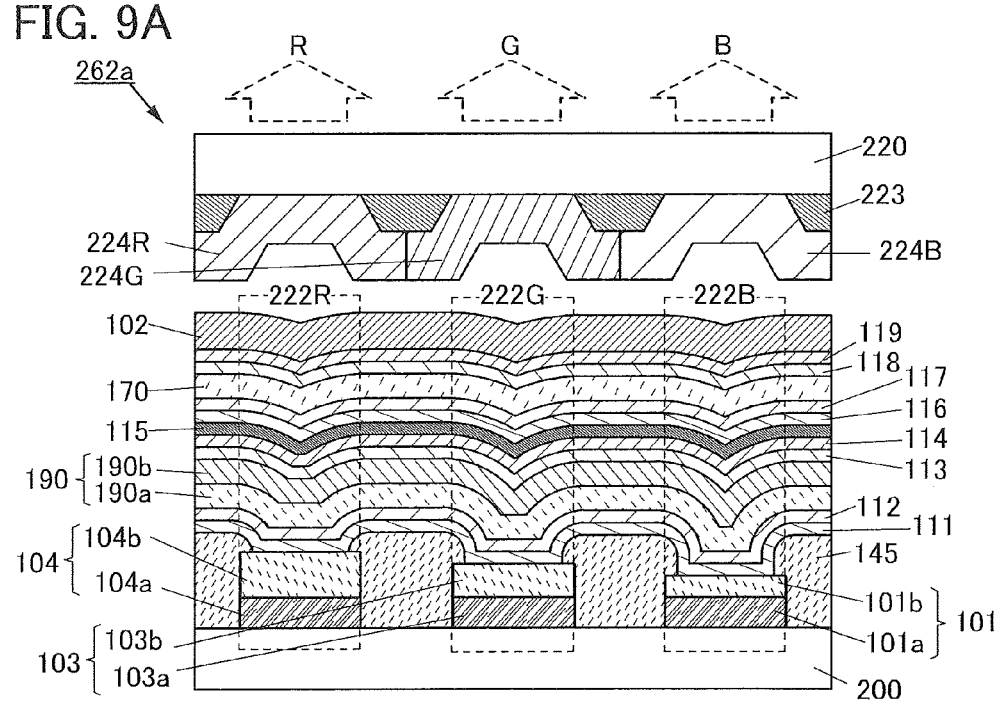
FIGS. 9A and 9B are schematic cross-sectional views each illustrating a light-emitting element of one embodiment of the present invention.
Figure 9B:
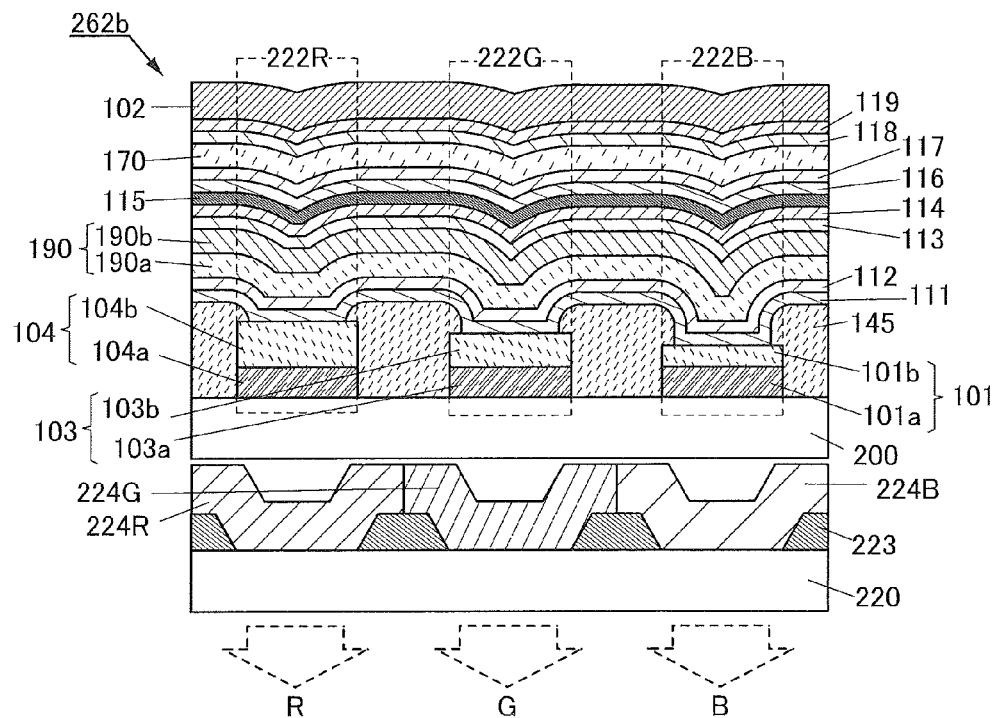

FIGS. 9A and 9B are cross-sectional views of a light-emitting element of one embodiment of the present invention. In FIGS. 9A and 9B, a portion having a function similar to that in FIGS. 8A and 8B is represented by the same hatch pattern as in FIGS. 8A and 8B and not especially denoted by a reference numeral in some cases. In addition, common reference numerals are used for portions having similar functions, and a detailed description of such portions is not repeated in some cases.

FIGS. 9A and 9B illustrate structure examples of a light-emitting element including the light-emitting layer between a pair of electrodes. A light-emitting element 262a illustrated in FIG. 9A has a top-emission structure in which light is extracted in a direction opposite to the substrate 200, and a light-emitting element 262b illustrated in FIG. 9B has a bottom-emission structure in which light is extracted to the substrate 200 side. However, one embodiment of the present invention is not limited to these structures and may have a dual-emission structure in which light emitted from the light-emitting element is extracted in both top and bottom directions with respect to the substrate 200 over which the light-emitting element is formed.

The light-emitting elements 262a and 262b each include the electrode 101, the electrode 102, an electrode 103, and an electrode 104 over the substrate 200. At least a light-emitting layer 170, a light-emitting layer 190, and the charge-generation layer 115 are provided between the electrode 101 and the electrode 102, between the electrode 102 and the electrode 103, and between the electrode 102 and the electrode 104. The hole-injection layer 111, the hole-transport layer 112, the electron-transport layer 113, the electron-injection layer 114, the hole-injection layer 116, the hole-transport layer 117, the electron-transport layer 118, and the electron-injection layer 119 are further provided.

The electrode 101 includes a conductive layer 101a and a conductive layer 101b over and in contact with the conductive layer 101a. The electrode 103 includes a conductive layer 103a and a conductive layer 103b over and in contact with the conductive layer 103a. The electrode 104 includes a conductive layer 104a and a conductive layer 104b over and in contact with the conductive layer 104a.

The light-emitting element 262a illustrated in FIG. 9A and the light-emitting element 262b illustrated in FIG. 9B each include a partition wall 145 between a region 222B sandwiched between the electrode 101 and the electrode 102, a region 222G sandwiched between the electrode 102 and the electrode 103, and a region 222R sandwiched between the electrode 102 and the electrode 104. The partition wall 145 has an insulating property. The partition wall 145 covers end portions of the electrodes 101, 103, and 104 and has openings overlapping with the electrodes. With the partition wall 145, the electrodes provided over the substrate 200 in the regions can be separated into island shapes.

The charge-generation layer 115 can be formed with a material obtained by adding an electron acceptor (acceptor) to a hole-transport material or a material obtained by adding an electron donor (donor) to an electron-transport material. Note that when the conductivity of the charge-generation layer 115 is as high as that of the pair of electrodes, carriers generated in the charge-generation layer 115 might transfer to an adjacent pixel and light emission might occur in the pixel. In order to prevent such false light emission from an adjacent pixel, the charge-generation layer 115 is preferably formed with a material whose conductivity is lower than that of the pair of electrodes.

The light-emitting elements 262a and 262b each include a substrate 220 provided with an optical element 224B, an optical element 224G, and an optical element 224R in the direction in which light emitted from the region 222B, light emitted from the region 222G, and light emitted from the region 222R are extracted. The light emitted from each region is emitted outside the light-emitting element through each optical element. In other words, the light from the region 222B, the light from the region 222G, and the light from the region 222R are emitted through the optical element 224B, the optical element 224G, and the optical element 224R, respectively.

The optical elements 224B, 224G, and 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

For example, a coloring layer (also referred to as color filter), a band pass filter, a multilayer filter, or the like can be used for the optical elements 224R, 224G, and 224B. Alternatively, color conversion elements can be used as the optical elements. A color conversion element is an optical element that converts incident light into light having a longer wavelength than the incident light. As the color conversion elements, quantum-dot elements can be favorably used. The usage of the quantum dot can increase color reproducibility of the display device.

One or more of optical elements may further be stacked over each of the optical elements 224R, 224G, and 224B. As another optical element, a circularly polarizing plate, an anti-reflective film, or the like can be provided, for example. A circularly polarizing plate provided on the side where light emitted from the light-emitting element of the display device is extracted can prevent a phenomenon in which light entering from the outside of the display device is reflected inside the display device and returned to the outside. An anti-reflective film can weaken external light reflected by a surface of the display device. This leads to clear observation of light emitted from the display device.

Note that in FIGS. 9A and 9B, blue light (B), green light (G), and red light (R) emitted from the regions through the optical elements are schematically illustrated by arrows of dashed lines.

A light-blocking layer 223 is provided between the optical elements. The light-blocking layer 223 has a function of blocking light emitted from the adjacent regions. Note that a structure without the light-blocking layer 223 may also be employed.

The light-blocking layer 223 has a function of reducing the reflection of external light. The light-blocking layer 223 has a function of preventing mixture of light emitted from an adjacent light-emitting element. As the light-blocking layer 223, a metal, a resin containing black pigment, carbon black, a metal oxide, a composite oxide containing a solid solution of a plurality of metal oxides, or the like can be used.

Note that the optical element 224B and the optical element 224G may overlap with each other in a region where they overlap with the light-blocking layer 223. In addition, the optical element 224G and the optical element 224R may overlap with each other in a region where they overlap with the light-blocking layer 223. In addition, the optical element 224R and the optical element 224B may overlap with each other in a region where they overlap with the light-blocking layer 223.

For the substrate 200 and the substrate 220 provided with the optical elements, the substrate in Embodiment 3 may be referred to.

Furthermore, the light-emitting elements 262a and 262b have a microcavity structure.

<Microcavity Structure>>

Light emitted from the light-emitting layer 170 and the light-emitting layer 190 resonates between a pair of electrodes (e.g., the electrode 101 and the electrode 102). The light-emitting layer 170 and the light-emitting layer 190 are formed at such a position as to intensify the light of a desired wavelength among light to be emitted. For example, by adjusting the optical length from a reflective region of the electrode 101 to the light-emitting region of the light-emitting layer 170 and the optical length from a reflective region of the electrode 102 to the light-emitting region of the light-emitting layer 170, the light of a desired wavelength among light emitted from the light-emitting layer 170 can be intensified. By adjusting the optical length from the reflective region of the electrode 101 to the light-emitting region of the light-emitting layer 190 and the optical length from the reflective region of the electrode 102 to the light-emitting region of the light-emitting layer 190, the light of a desired wavelength among light emitted from the light-emitting layer 190 can be intensified. In the case of a light-emitting element in which a plurality of light-emitting layers (here, the light-emitting layers 170 and 190) are stacked, the optical lengths of the light-emitting layers 170 and 190 are preferably optimized.

In each of the light-emitting elements 262a and 262b, by adjusting the thicknesses of the conductive layers (the conductive layer 101b, the conductive layer 103b, and the conductive layer 104b) in each region, the light of a desired wavelength among light emitted from the light-emitting layers 170 and 190 can be increased. Note that the thickness of at least one of the hole-injection layer 111 and the hole-transport layer 112, or the thickness of at least one of the electron-injection layer 119 and the electron-transport layer 118 may differ between the regions to increase the light emitted from the light-emitting layers 170 and 190.

For example, in the case where the refractive index of the conductive material having a function of reflecting light in the electrodes 101 to 104 is lower than the refractive index of the light-emitting layer 170 or 190, the thickness of the conductive layer 101b of the electrode 101 is adjusted so that the optical length between the electrode 101 and the electrode 102 is $m_B \lambda_B/2$ ($m_B$ is a natural number and $\lambda_B$ is the wavelength of light intensified in the region 222B). Similarly, the thickness of the conductive layer 103b of the electrode 103 is adjusted so that the optical length between the electrode 103 and the electrode 102 is $m_G \lambda_G/2$ ($m_G$ is a natural number and $\lambda_G$ is the wavelength of light intensified in the region 222G). Furthermore, the thickness of the conductive layer 104b of the electrode 104 is adjusted so that the optical length between the electrode 104 and the electrode 102 is $m_R \lambda_R/2$ ($m_R$ is a natural number and $\lambda_R$ is the wavelength of light intensified in the region 222R).

In the case where it is difficult to precisely determine the reflective regions of the electrodes 101 to 104, the optical length for intensifying light emitted from the light-emitting layer 170 or the light-emitting layer 190 may be derived on the assumption that certain regions of the electrodes 101 to 104 are the reflective regions. In the case where it is difficult to precisely determine the light-emitting regions of the light-emitting layer 170 and the light-emitting layer 190, the optical length for intensifying light emitted from the light-emitting layer 170 and the light-emitting layer 190 may be derived on the assumption that certain regions of the light-emitting layer 170 and the light-emitting layer 190 are the light-emitting regions.

In the above manner, with the microcavity structure, in which the optical length between the pair of electrodes in the respective regions is adjusted, scattering and absorption of light in the vicinity of the electrodes can be suppressed, resulting in high light extraction efficiency.

In the above structure, the conductive layers 101b, 103b, and 104b preferably have a function of transmitting light. The materials of the conductive layers 101b, 103b, and 104b may be the same or different. It is preferable to use the same material for the conductive layer 101b, the conductive layer 103b, and the conductive layer 104b because patterning by etching in the formation process of the electrode 101, the electrode 103, and the electrode 104 can be performed easily. Each of the conductive layers 101b, 103b, and 104b may have a stacked structure of two or more layers.

Since the light-emitting element 262a illustrated in FIG. 9A has a top-emission structure, it is preferable that the conductive layer 101a, the conductive layer 103a, and the conductive layer 104a have a function of reflecting light. In addition, it is preferable that the electrode 102 have functions of transmitting light and reflecting light.

Since the light-emitting element 262b illustrated in FIG. 9B has a bottom-emission structure, it is preferable that the conductive layer 101a, the conductive layer 103a, and the conductive layer 104a have functions of transmitting light and reflecting light. In addition, it is preferable that the electrode 102 have a function of reflecting light.

In each of the light-emitting elements 262a and 262b, the conductive layers 101a, 103a, and 104a may be formed of different materials or the same material. When the conductive layers 101a, 103a, and 104a are formed of the same material, manufacturing cost of the light-emitting elements 262a and 262b can be reduced. Note that each of the conductive layers 101a, 103a, and 104a may have a stacked structure including two or more layers.

At least one of the light-emitting layers 170 and 190 in the light-emitting elements 262a and 262b preferably has at least one of the structures described in Embodiments 3 to 5, in which case light-emitting elements with high emission efficiency can be fabricated.

Either or both of the light-emitting layers 170 and 190 may have a stacked structure of two layers, like a light-emitting layer 190a and a light-emitting layer 190b, for example. Two kinds of light-emitting materials (a first compound and a second compound) having functions of emitting light of different colors are used in the two light-emitting layers, so that light of a plurality of emission colors can be obtained at the same time. It is particularly preferable to select the light-emitting materials of the light-emitting layers so that white light can be obtained by combining light emissions from the light-emitting layers 170 and 190.

Either or both of the light-emitting layers 170 and 190 may have a stacked structure of three or more layers, in which a layer not including a light-emitting material may be included.

In the above-described manner, the light-emitting element 262a or 262b including at least one of the light-emitting layers which have the structures described in Embodiments 3 to 5 is used in pixels in a display device, whereby a display device with high emission efficiency can be fabricated. Accordingly, the display device including the light-emitting element 262a or 262b can have low power consumption.

For the other components of the light-emitting elements 262a and 262b, the components of the light-emitting elements 260a and 260b and the light-emitting elements in Embodiments 3 to 5 may be referred to.

<Fabrication Method of Light-Emitting Element>

Next, a method for fabricating a light-emitting element of one embodiment of the present invention is described below with reference to FIGS. 10A to 10C and FIGS. 11A to 11C. Here, a method for fabricating the light-emitting element 262a illustrated in FIG. 9A is described.

FIGS. 10A to 10C and FIGS. 11A to 11C are cross-sectional views illustrating a method for fabricating the light-emitting element of one embodiment of the present invention.

The method for manufacturing the light-emitting element 262a described below includes first to seventh steps.

<<First Step>>

Figure 10A:
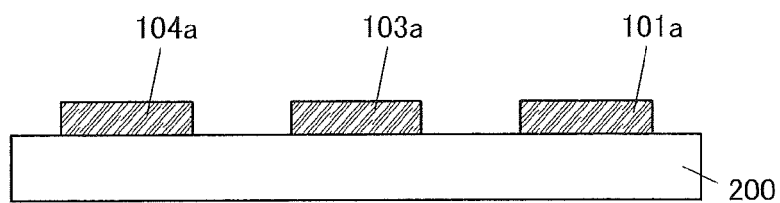
FIGS. 10A to 10C are schematic cross-sectional views illustrating a method for manufacturing a light-emitting element of one embodiment of the present invention.

In the first step, the electrodes (specifically the conductive layer 101a of the electrode 101, the conductive layer 103a of the electrode 103, and the conductive layer 104a of the electrode 104) of the light-emitting elements are formed over the substrate 200 (see FIG. 10A).

In this embodiment, a conductive layer having a function of reflecting light is formed over the substrate 200 and processed into a desired shape; whereby the conductive layers 101a, 103a, and 104a are formed. As the conductive layer having a function of reflecting light, an alloy film of silver, palladium, and copper (also referred to as an Ag—Pd—Cu film or APC) is used. The conductive layers 101a, 103a, and 104a are preferably formed through a step of processing the same conductive layer, because the manufacturing cost can be reduced.

Note that a plurality of transistors may be formed over the substrate 200 before the first step. The plurality of transistors may be electrically connected to the conductive layers 101a, 103a, and 104a.

<<Second Step>>

Figure 10B:
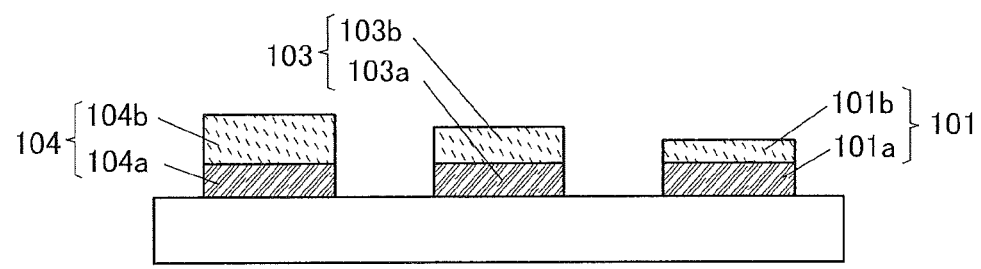

In the second step, the conductive layer 101b having a function of transmitting light is formed over the conductive layer 101a of the electrode 101, the conductive layer 103b having a function of transmitting light is formed over the conductive layer 103a of the electrode 103, and the conductive layer 104b having a function of transmitting light is formed over the conductive layer 104a of the electrode 104 (see FIG. 10B).

In this embodiment, the conductive layers 101b, 103b, and 104b each having a function of transmitting light are formed over the conductive layers 101a, 103a, and 104a each having a function of reflecting light, respectively, whereby the electrode 101, the electrode 103, and the electrode 104 are formed. As the conductive layers 101b, 103b, and 104b, ITSO films are used.

The conductive layers 101b, 103b, and 104b having a function of transmitting light may be formed through a plurality of steps. When the conductive layers 101b, 103b, and 104b having a function of transmitting light are formed through a plurality of steps, they can be formed to have thicknesses which enable microcavity structures appropriate in the respective regions.

<<Third Step>>

Figure 10C:
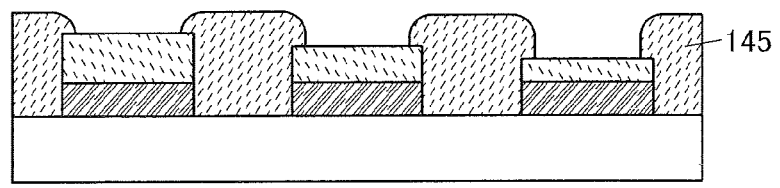

In the third step, the partition wall 145 that covers end portions of the electrodes of the light-emitting element is formed (see FIG. 10C).

The partition wall 145 includes an opening overlapping with the electrode. The conductive film exposed by the opening functions as the anode of the light-emitting element. As the partition wall 145, a polyimide-based resin is used in this embodiment.

In the first to third steps, since there is no possibility of damaging the EL layer (a layer containing an organic compound), a variety of film formation methods and fine processing technologies can be employed. In this embodiment, a reflective conductive layer is formed by a sputtering method, a pattern is formed over the conductive layer by a lithography method, and then the conductive layer is processed into an island shape by a dry etching method or a wet etching method to form the conductive layer 101a of the electrode 101, the conductive layer 103a of the electrode 103, and the conductive layer 104a of the electrode 104. Then, a transparent conductive film is formed by a sputtering method, a pattern is formed over the transparent conductive film by a lithography method, and then the transparent conductive film is processed into island shapes by a wet etching method to form the electrodes 101, 103, and 104.

<<Fourth Step>>

Figure 11A:
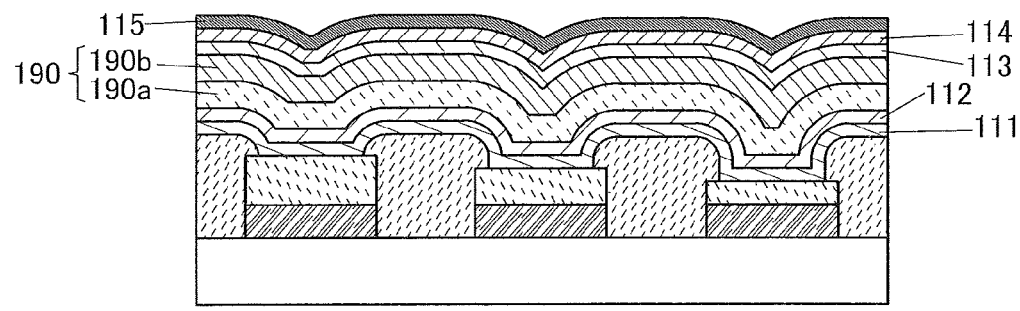
FIGS. 11A to 11C are schematic cross-sectional views illustrating a method for manufacturing a light-emitting element of one embodiment of the present invention.

In the fourth step, the hole-injection layer 111, the hole-transport layer 112, the light-emitting layer 190, the electron-transport layer 113, the electron-injection layer 114, and the charge-generation layer 115 are formed (see FIG. 11A).

The hole-injection layer 111 can be formed by co-evaporating a hole-transport material and a material containing an acceptor substance. Note that a co-evaporation method is an evaporation method in which a plurality of different substances is concurrently vaporized from respective different evaporation sources. The hole-transport layer 112 can be formed by evaporating a hole-transport material.

The light-emitting layer 190 can be formed by evaporating the guest material that emits light of at least one of violet, blue, blue green, green, yellow green, yellow, orange, and red. As the guest material, a fluorescent or phosphorescent organic material can be used. In addition, the light-emitting layer having any of the structures described in Embodiments 3 to 5 is preferably used. The light-emitting layer 190 may have a two-layer structure. In that case, the two light-emitting layers preferably contain light-emitting materials that emit light of different colors.

The electron-transport layer 113 can be formed by evaporating a substance having a high electron-transport property. The electron-injection layer 114 can be formed by evaporating a substance having a high electron-injection property.

The charge-generation layer 115 can be formed by evaporating a material obtained by adding an electron acceptor (acceptor) to a hole-transport material or a material obtained by adding an electron donor (donor) to an electron-transport material.

<<Fifth Step>>

Figure 11B:
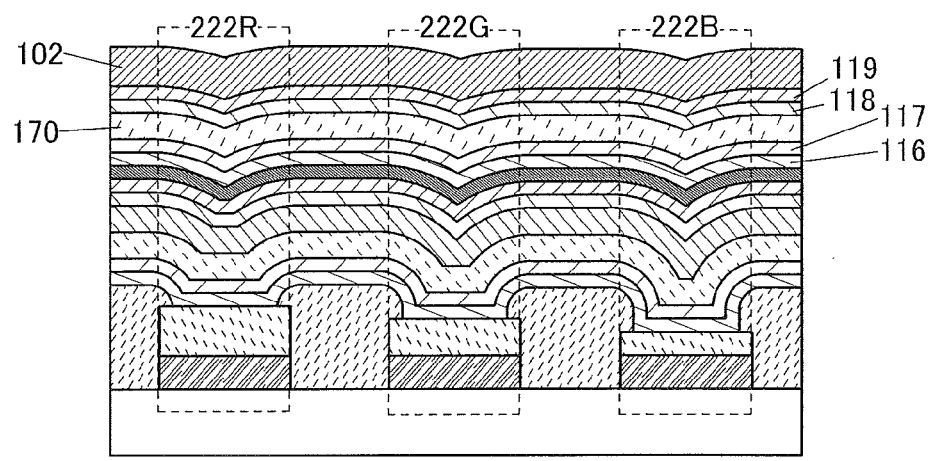

In the fifth step, the hole-injection layer 116, the hole-transport layer 117, the light-emitting layer 170, the electron-transport layer 118, the electron-injection layer 119, and the electrode 102 are formed (see FIG. 11B).

The hole-injection layer 116 can be formed by using a material and a method which are similar to those of the hole-injection layer 111. The hole-transport layer 117 can be formed by using a material and a method which are similar to those of the hole-transport layer 112.

The light-emitting layer 170 can be formed by evaporating the guest material that emits light of at least one color selected from violet, blue, blue green, green, yellow green, yellow, orange, and red. As the guest material, a fluorescent or phosphorescent organic compound can be used. In addition, the light-emitting layer having any of the structures described in Embodiments 3 to 5 is preferably used. Note that at least one of the light-emitting layer 170 and the light-emitting layer 190 preferably has the structure of the light-emitting layer described in Embodiment 3 or 4. The light-emitting layer 170 and the light-emitting layer 190 preferably include light-emitting organic compounds exhibiting light of different colors.

The electron-transport layer 118 can be formed by using a material and a method which are similar to those of the electron-transport layer 113. The electron-injection layer 119 can be formed by using a material and a method which are similar to those of the electron-injection layer 114.

The electrode 102 can be formed by stacking a reflective conductive film and a light-transmitting conductive film. The electrode 102 may have a single-layer structure or a stacked-layer structure.

Through the above-described steps, the light-emitting element including the region 222B, the region 222G, and the region 222R over the electrode 101, the electrode 103, and the electrode 104, respectively, are formed over the substrate 200.

<<Sixth Step>>

Figure 11C:
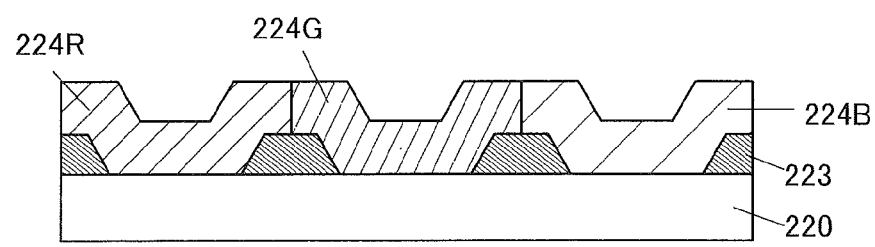

In the sixth step, the light-blocking layer 223, the optical element 224B, the optical element 224G, and the optical element 224R are formed over the substrate 220 (see FIG. 11C).

As the light-blocking layer 223, a resin film containing black pigment is formed in a desired region. Then, the optical element 224B, the optical element 224G, and the optical element 224R are formed over the substrate 220 and the light-blocking layer 223. As the optical element 224B, a resin film containing blue pigment is formed in a desired region. As the optical element 224G, a resin film containing green pigment is formed in a desired region. As the optical element 224R, a resin film containing red pigment is formed in a desired region.

<<Seventh Step>>

In the seventh step, the light-emitting element formed over the substrate 200 is attached to the light-blocking layer 223, the optical element 224B, the optical element 224G, and the optical element 224R formed over the substrate 220, and sealed with a sealant (not illustrated).

Through the above-described steps, the light-emitting element 262a illustrated in FIG. 9A can be formed.

Note that the structures described in this embodiment can be used in appropriate combination with any of the structures described in the other embodiments.

Embodiment 7

This embodiment shows an example of a mode where the compound described in Embodiment 1 is used in an active layer of a vertical transistor (a static induction transistor (SIT)), which is a kind of an organic semiconductor element.

Figure 12:
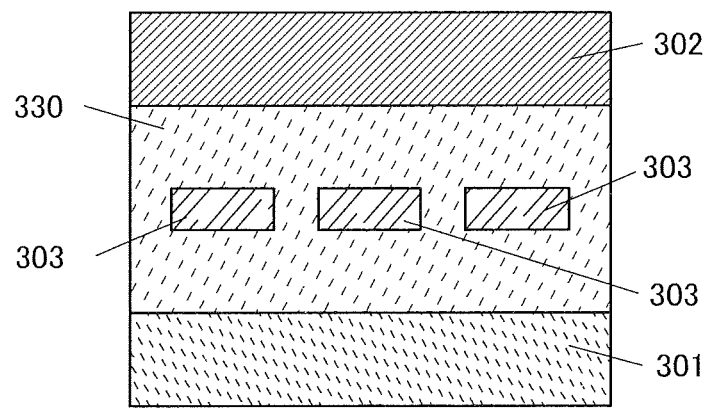
FIG. 12 is a schematic cross-sectional view of a semiconductor element of one embodiment of the present invention.

In an element structure, between a source electrode 301 and a drain electrode 302, a thin-film active layer 330 including the compound which is described in Embodiment 1 and includes a bicarbazole skeleton and a benzofuropyrimidine skeleton or a benzothienopyrimidine skeleton is provided and gate electrodes 303 are embedded in the active layer 330, as illustrated in FIG. 12. The gate electrodes 303 are electrically connected to a means for applying a gate voltage, and the source electrode 301 and the drain electrode 302 are electrically connected to a means for controlling a voltage between the source electrode and the drain electrode. Note that the functions of the source electrode and the drain electrode may be replaced with each other.

In such an element structure, when a voltage is applied between the source electrode and the drain electrode without applying a voltage to the gate electrodes 303, a current flows (the element is turned on). Then, when a voltage is applied to the gate electrodes 303 in that state, a depletion layer is formed in the periphery of the gate electrodes 303, so that the current ceases flowing (the element is turned off). With such a mechanism, an organic semiconductor element 300 operates as a transistor.

In a vertical transistor, a material having both a carrier-transport property and a favorable film quality is required for an active layer like in a light-emitting element. Since the compound described in Embodiment 1 sufficiently meets these requirements, it can be suitably used.

Note that the structure described in this embodiment can be combined as appropriate with any of the structures described in the other embodiments.

Embodiment 8

In this embodiment, a display device of one embodiment of the present invention is described below with reference to FIGS. 13A and 13B, FIGS. 14A and 14B, FIG. 15, FIGS. 16A and 16B, FIGS. 17A and 17B, FIG. 18, FIGS. 19A and 19B, FIG. 20, and FIGS. 21A and 21B.

Structure Example 1 of Display Device

Figure 13A:
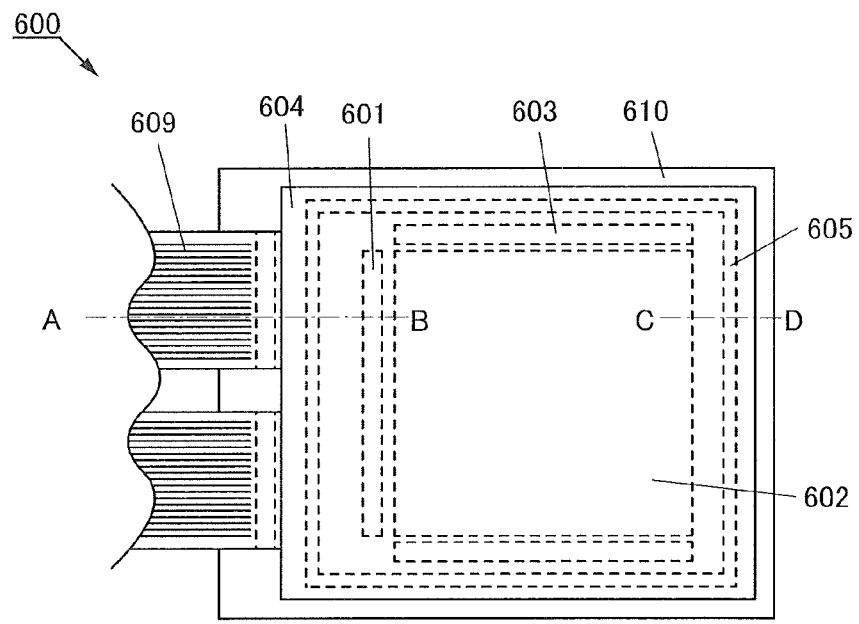
FIGS. 13A and 13B are a top view and a schematic cross-sectional view illustrating a display device of one embodiment of the present invention.
Figure 13B:
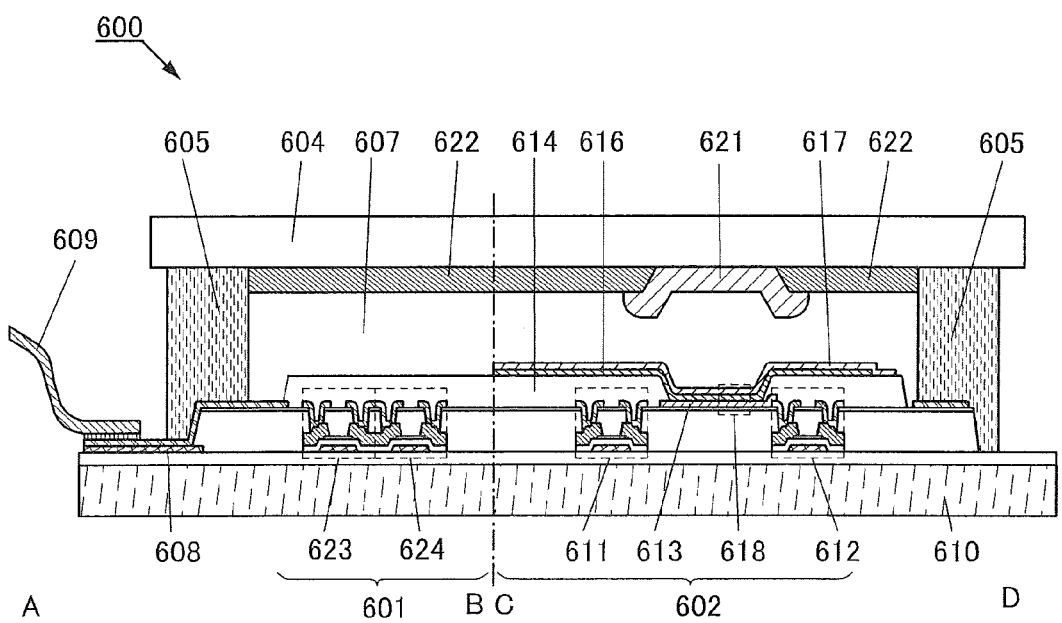

FIG. 13A is a top view illustrating a display device 600 and FIG. 13B is a cross-sectional view taken along the dashed-dotted line A-B and the dashed-dotted line C-D in FIG. 13A. The display device 600 includes driver circuit portions (a signal line driver circuit portion 601 and a scan line driver circuit portion 603) and a pixel portion 602. Note that the signal line driver circuit portion 601, the scan line driver circuit portion 603, and the pixel portion 602 have a function of controlling light emission from a light-emitting element.

The display device 600 also includes an element substrate 610, a sealing substrate 604, a sealant 605, a region 607 surrounded by the sealant 605, a lead wiring 608, and an FPC 609.

Note that the lead wiring 608 is a wiring for transmitting signals to be input to the signal line driver circuit portion 601 and the scan line driver circuit portion 603 and for receiving a video signal, a clock signal, a start signal, a reset signal, and the like from the FPC 609 serving as an external input terminal. Although only the FPC 609 is illustrated here, the FPC 609 may be provided with a printed wiring board (PWB).

As the signal line driver circuit portion 601, a CMOS circuit in which an n-channel transistor 623 and a p-channel transistor 624 are combined is formed. As the signal line driver circuit portion 601 or the scan line driver circuit portion 603, various types of circuits such as a CMOS circuit, a PMOS circuit, or an NMOS circuit can be used. Although a driver in which a driver circuit portion is formed and a pixel are formed over the same surface of a substrate in the display device of this embodiment, the driver circuit portion is not necessarily formed over the substrate and can be formed outside the substrate.

The pixel portion 602 includes a switching transistor 611, a current control transistor 612, and a lower electrode 613 electrically connected to a drain of the current control transistor 612. Note that a partition wall 614 is formed to cover end portions of the lower electrode 613. As the partition wall 614, for example, a positive type photosensitive acrylic resin film can be used.

In order to obtain favorable coverage, the partition wall 614 is formed to have a curved surface with curvature at its upper or lower end portion. For example, in the case of using a positive photosensitive acrylic as a material of the partition wall 614, it is preferable that only the upper end portion of the partition wall 614 have a curved surface with curvature (the radius of the curvature being 0.2 μm to 3 μm). As the partition wall 614, either a negative photosensitive resin or a positive photosensitive resin can be used.

Note that there is no particular limitation on a structure of each of the transistors (the transistors 611, 612, 623, and 624). For example, a staggered transistor can be used. In addition, there is no particular limitation on the polarity of these transistors. For these transistors, n-channel and p-channel transistors may be used, or either n-channel transistors or p-channel transistors may be used, for example. Furthermore, there is no particular limitation on the crystallinity of a semiconductor film used for these transistors. For example, an amorphous semiconductor film or a crystalline semiconductor film can be used. Examples of a semiconductor material include Group 14 semiconductors (e.g., a semiconductor including silicon), compound semiconductors (including oxide semiconductors), organic semiconductors, and the like. For example, it is preferable to use an oxide semiconductor that has an energy gap of 2 eV or more, preferably 2.5 eV or more and further preferably 3 eV or more, for the transistors, so that the off-state current of the transistors can be reduced. Examples of the oxide semiconductor include an In—Ga oxide, an In-M-Zn oxide (M is aluminum (Al), gallium (Ga), yttrium (Y), zirconium (Zr), lanthanum (La), cerium (Ce), tin (Sn), hafnium (Hf), or neodymium (Nd)), and the like.

An EL layer 616 and an upper electrode 617 are formed over the lower electrode 613. Here, the lower electrode 613 functions as an anode and the upper electrode 617 functions as a cathode.

In addition, the EL layer 616 is formed by any of a variety of methods such as an evaporation method with an evaporation mask, an inkjet method, and a spin coating method. As another material included in the EL layer 616, a low molecular compound or a high molecular compound (including an oligomer or a dendrimer) may be used.

Note that a light-emitting element 618 is formed with the lower electrode 613, the EL layer 616, and the upper electrode 617. The light-emitting element 618 preferably has any of the structures described in Embodiments 3 to 6. In the case where the pixel portion includes a plurality of light-emitting elements, the pixel portion may include both any of the light-emitting elements described in Embodiments 3 to 6 and a light-emitting element having a different structure.

When the sealing substrate 604 and the element substrate 610 are attached to each other with the sealant 605, the light-emitting element 618 is provided in the region 607 surrounded by the element substrate 610, the sealing substrate 604, and the sealant 605. The region 607 is filled with a filler. In some cases, the region 607 is filled with an inert gas (nitrogen, argon, or the like) or filled with an ultraviolet curable resin or a thermosetting resin which can be used for the sealant 605. For example, a polyvinyl chloride (PVC)-based resin, an acrylic-based resin, a polyimide-based resin, an epoxy-based resin, a silicone-based resin, a polyvinyl butyral (PVB)-based resin, or an ethylene vinyl acetate (EVA)-based resin can be used. It is preferable that the sealing substrate be provided with a recessed portion and a desiccant be provided in the recessed portion, in which case deterioration due to influence of moisture can be inhibited.

An optical element 621 is provided below the sealing substrate 604 to overlap with the light-emitting element 618. A light-blocking layer 622 is provided below the sealing substrate 604. The structures of the optical element 621 and the light-blocking layer 622 can be the same as those of the optical element and the light-blocking layer in Embodiment 6, respectively.

An epoxy-based resin or glass fit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), polyester, acrylic, or the like can be used.

In the above-described manner, the display device including any of the light-emitting elements and the optical elements which are described in Embodiments 3 to 6 can be obtained.

Structure Example 2 of Display Device

Figure 15:
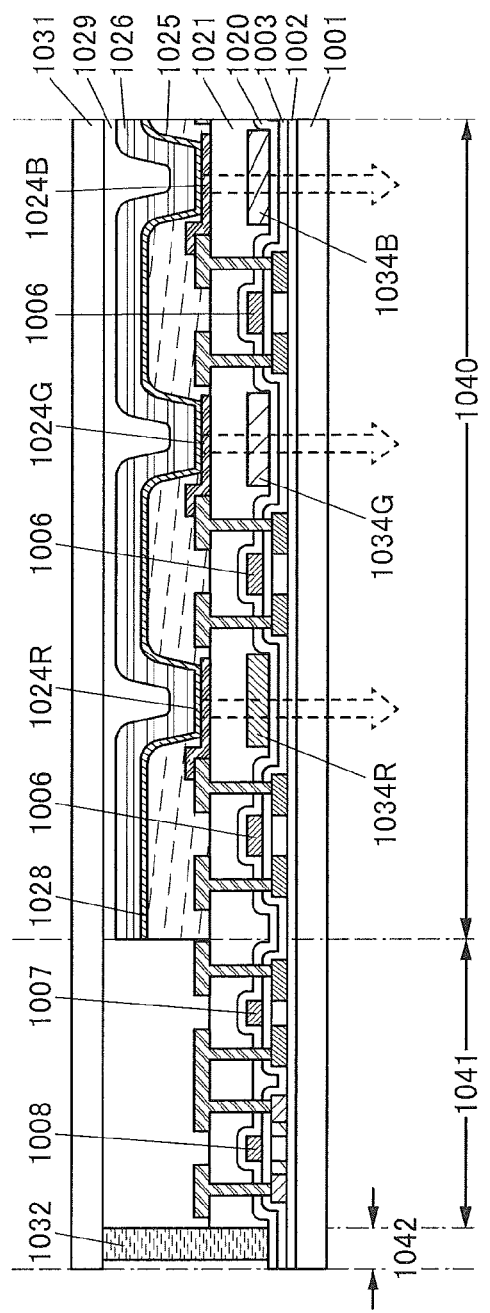
FIG. 15 is a schematic cross-sectional view illustrating a display device of one embodiment of the present invention.

Next, another example of the display device is described with reference to FIGS. 14A and 14B and FIG. 15. Note that FIGS. 14A and 14B and FIG. 15 are each a cross-sectional view of a display device of one embodiment of the present invention.

In FIG. 14A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, lower electrodes 1024R, 1024G, and 1024B of light-emitting elements, a partition wall 1025, an EL layer 1028, an upper electrode 1026 of the light-emitting elements, a sealing layer 1029, a sealing substrate 1031, a sealant 1032, and the like are illustrated.

In FIG. 14A, as examples of the optical elements, coloring layers (a red coloring layer 1034R, a green coloring layer 1034G, and a blue coloring layer 1034B) are provided on a transparent base material 1033. A light-blocking layer 1035 may further be provided. The transparent base material 1033 provided with the coloring layers and the light-blocking layer is positioned and fixed to the substrate 1001. Note that the coloring layers and the light-blocking layer are covered with an overcoat layer 1036. In the structure in FIG. 14A, red light, green light, and blue light are transmitted through the coloring layers, and thus an image can be displayed with the use of pixels of three colors.

FIG. 14B illustrates an example in which, as examples of the optical elements, the coloring layers (the red coloring layer 1034R, the green coloring layer 1034G, and the blue coloring layer 1034B) are provided between the gate insulating film 1003 and the first interlayer insulating film 1020. As in this structure, the coloring layers may be provided between the substrate 1001 and the sealing substrate 1031.

FIG. 15 illustrates an example in which, as examples of the optical elements, the coloring layers (the red coloring layer 1034R, the green coloring layer 1034G, and the blue coloring layer 1034B) are provided between the first interlayer insulating film 1020 and the second interlayer insulating film 1021. As in this structure, the coloring layers may be provided between the substrate 1001 and the sealing substrate 1031.

The above-described display device has a structure in which light is extracted from the substrate 1001 side where the transistors are formed (a bottom-emission structure), but may have a structure in which light is extracted from the sealing substrate 1031 side (a top-emission structure).

Structure Example 3 of Display Device

Figure 16A:
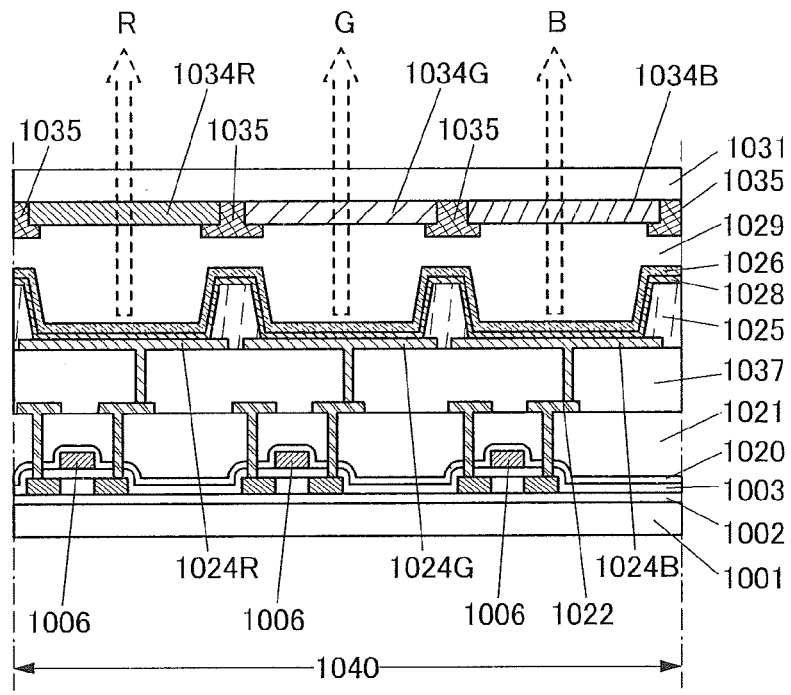
FIGS. 16A and 16B are schematic cross-sectional views each illustrating a display device of one embodiment of the present invention.
Figure 16B:
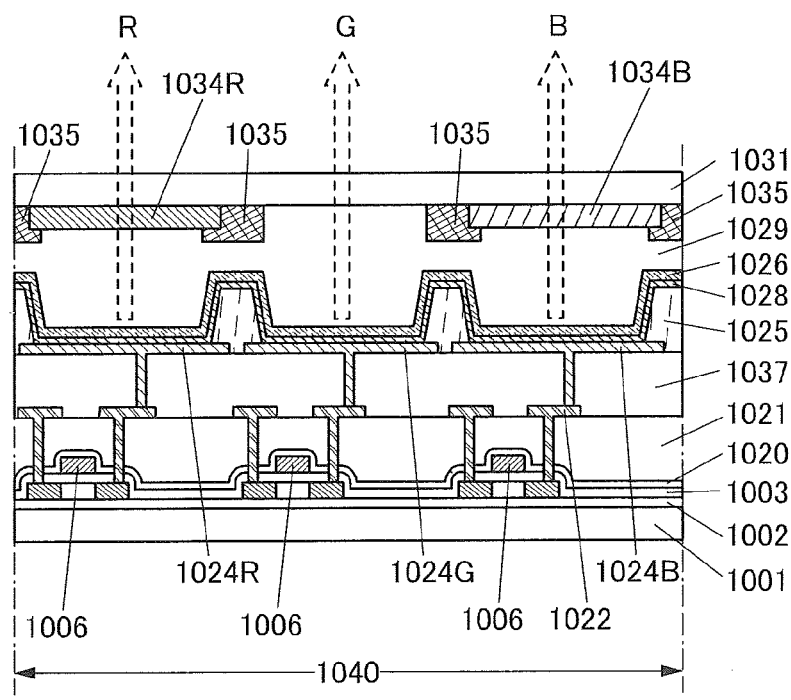

FIGS. 16A and 16B are each an example of a cross-sectional view of a display device having a top emission structure. Note that FIGS. 16A and 16B are each a cross-sectional view illustrating the display device of one embodiment of the present invention, and the driver circuit portion 1041, the peripheral portion 1042, and the like, which are illustrated in FIGS. 14A and 14B and FIG. 15, are not illustrated therein.

In this case, as the substrate 1001, a substrate that does not transmit light can be used. The process up to the step of forming a connection electrode which connects the transistor and the anode of the light-emitting element is performed in a manner similar to that of the display device having a bottom-emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The lower electrodes 1024R, 1024G, and 1024B of the light-emitting elements each function as an anode here, but may function as a cathode. Furthermore, in the case of a display device having a top-emission structure as illustrated in FIGS. 16A and 16B, the lower electrodes 1024R, 1024G, and 1024B preferably have a function of reflecting light. The upper electrode 1026 is provided over the EL layer 1028. It is preferable that the upper electrode 1026 have a function of reflecting light and a function of transmitting light and that a microcavity structure be used between the upper electrode 1026 and the lower electrodes 1024R, 1024G, and 1024B, in which case the intensity of light having a specific wavelength is increased.

In the case of a top-emission structure as illustrated in FIG. 16A, sealing can be performed with the sealing substrate 1031 on which the coloring layers (the red coloring layer 1034R, the green coloring layer 1034G, and the blue coloring layer 1034B) are provided. The sealing substrate 1031 may be provided with the light-blocking layer 1035 which is positioned between pixels. Note that a light-transmitting substrate is favorably used as the sealing substrate 1031.

FIG. 16A illustrates the structure provided with the light-emitting elements and the coloring layers for the light-emitting elements as an example; however, the structure is not limited thereto. For example, as shown in FIG. 16B, a structure including the red coloring layer 1034R and the blue coloring layer 1034B but not including a green coloring layer may be employed to achieve full color display with the three colors of red, green, and blue. The structure as illustrated in FIG. 16A where the light-emitting elements are provided with the coloring layers is effective to suppress reflection of external light. In contrast, the structure as illustrated in FIG. 16B where the light-emitting elements are provided with the red coloring layer and the blue coloring layer and without the green coloring layer is effective to reduce power consumption because of small energy loss of light emitted from the green light-emitting element.

Structure Example 4 of Display Device

Figure 18:
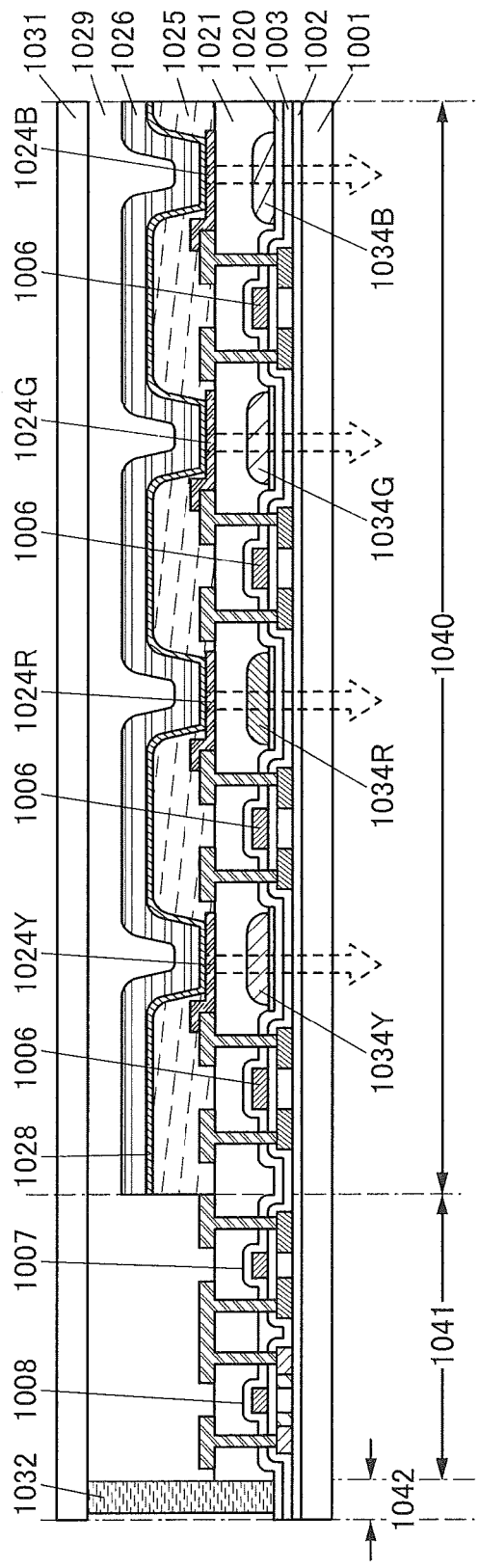
FIG. 18 is a schematic cross-sectional view illustrating a display device of one embodiment of the present invention.

Although a display device including sub-pixels of three colors (red, green, and blue) is described above, the number of colors of sub-pixels may be four (red, green, blue, and yellow, or red, green, blue, and white). FIGS. 17A and 17B, FIG. 18, and FIGS. 19A and 19B illustrate structures of display devices each including the lower electrodes 1024R, 1024G, 1024B, and 1024Y. FIGS. 17A and 17B and FIG. 18 each illustrate a display device having a structure in which light is extracted from the substrate 1001 side on which transistors are formed (a bottom-emission structure), and FIGS. 19A and 19B each illustrate a display device having a structure in which light is extracted from the sealing substrate 1031 side (a top-emission structure).

FIG. 17A illustrates an example of a display device in which optical elements (the coloring layer 1034R, the coloring layer 1034G, the coloring layer 1034B, and a coloring layer 1034Y) are provided on the transparent base material 1033. FIG. 17B illustrates an example of a display device in which optical elements (the coloring layer 1034R, the coloring layer 1034G, the coloring layer 1034B, and the coloring layer 1034Y) are provided between the gate insulating film 1003 and the first interlayer insulating film 1020. FIG. 18 illustrates an example of a display device in which optical elements (the coloring layer 1034R, the coloring layer 1034G, the coloring layer 1034B, and the coloring layer 1034Y) are provided between the first interlayer insulating film 1020 and the second interlayer insulating film 1021.

The coloring layer 1034R has a function of transmitting red light, the coloring layer 1034G has a function of transmitting green light, and the coloring layer 1034B has a function of transmitting blue light. The coloring layer 1034Y has a function of transmitting yellow light or a function of transmitting light of a plurality of colors selected from blue, green, yellow, and red. When the coloring layer 1034Y has a function of transmitting light of a plurality of colors selected from blue, green, yellow, and red, light that has passed through the coloring layer 1034Y may be white light. Since the light-emitting element which exhibits yellow or white light has high emission efficiency, the display device including the coloring layer 1034Y can have lower power consumption.

Figure 19A:
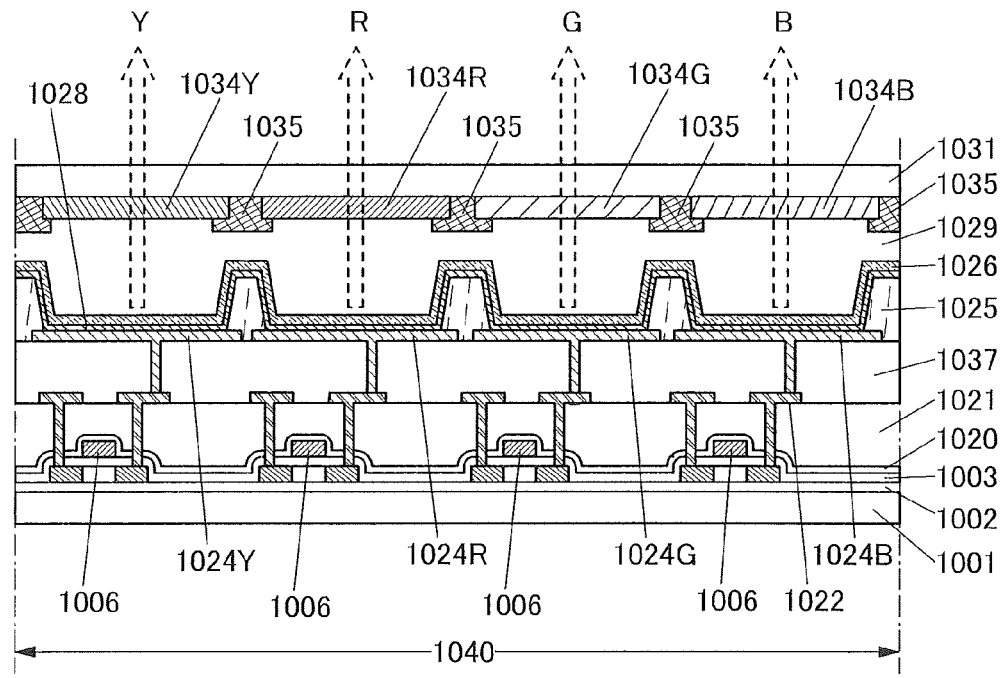
FIGS. 19A and 19B are schematic cross-sectional views each illustrating a display device of one embodiment of the present invention.
Figure 19B:
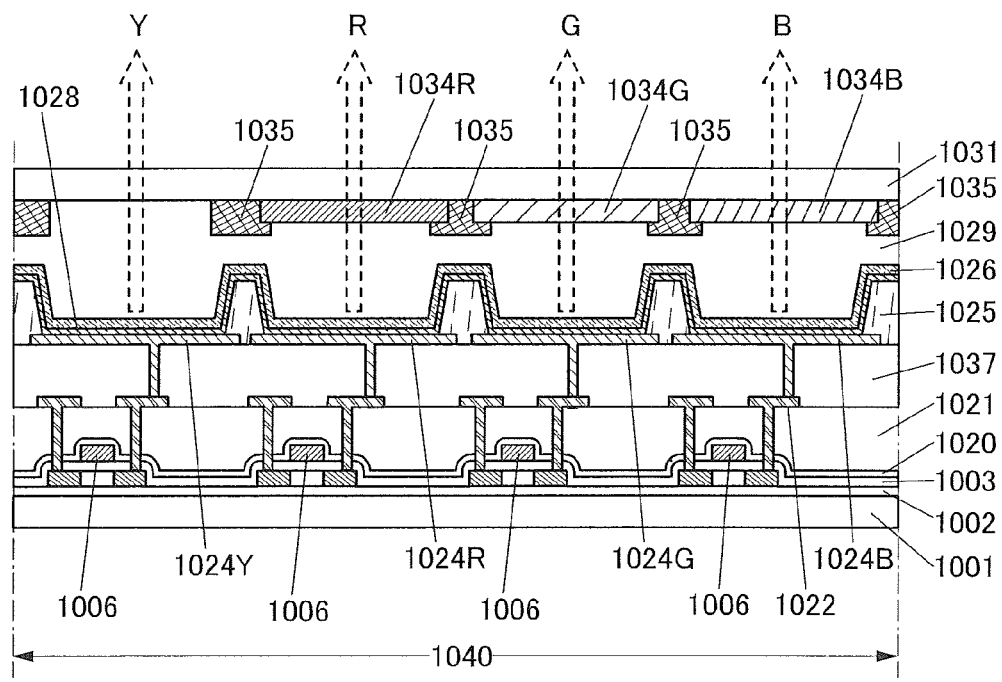

In the top-emission display devices illustrated in FIGS. 19A and 19B, a light-emitting element including the lower electrode 1024Y preferably has a microcavity structure between the lower electrode 1024Y and the upper electrode 1026 as in the display device illustrated in FIG. 16A. In the display device illustrated in FIG. 19A, sealing can be performed with the sealing substrate 1031 on which the coloring layers (the red coloring layer 1034R, the green coloring layer 1034G, the blue coloring layer 1034B, and the yellow coloring layer 1034Y) are provided.

Light emitted through the microcavity and the yellow coloring layer 1034Y has an emission spectrum in a yellow region. Since yellow is a color with a high luminosity factor, a light-emitting element emitting yellow light has high emission efficiency. Therefore, the display device having the structure in FIG. 19A can reduce power consumption.

FIG. 19A illustrates the structure provided with the light-emitting elements and the coloring layers for the light-emitting elements as an example; however, the structure is not limited thereto. For example, as shown in FIG. 19B, a structure including the red coloring layer 1034R, the green coloring layer 1034G, and the blue coloring layer 1034B but not including a yellow coloring layer may be employed to achieve full color display with the four colors of red, green, blue, and yellow or of red, green, blue, and white. The structure as illustrated in FIG. 19A where the light-emitting elements are provided with the coloring layers is effective to suppress reflection of external light. In contrast, the structure as illustrated in FIG. 19B where the light-emitting elements are provided with the red coloring layer, the green coloring layer, and the blue coloring layer and without the yellow coloring layer is effective to reduce power consumption because of small energy loss of light emitted from the yellow or white light-emitting element.

Structure Example 5 of Display Device

Figure 20:
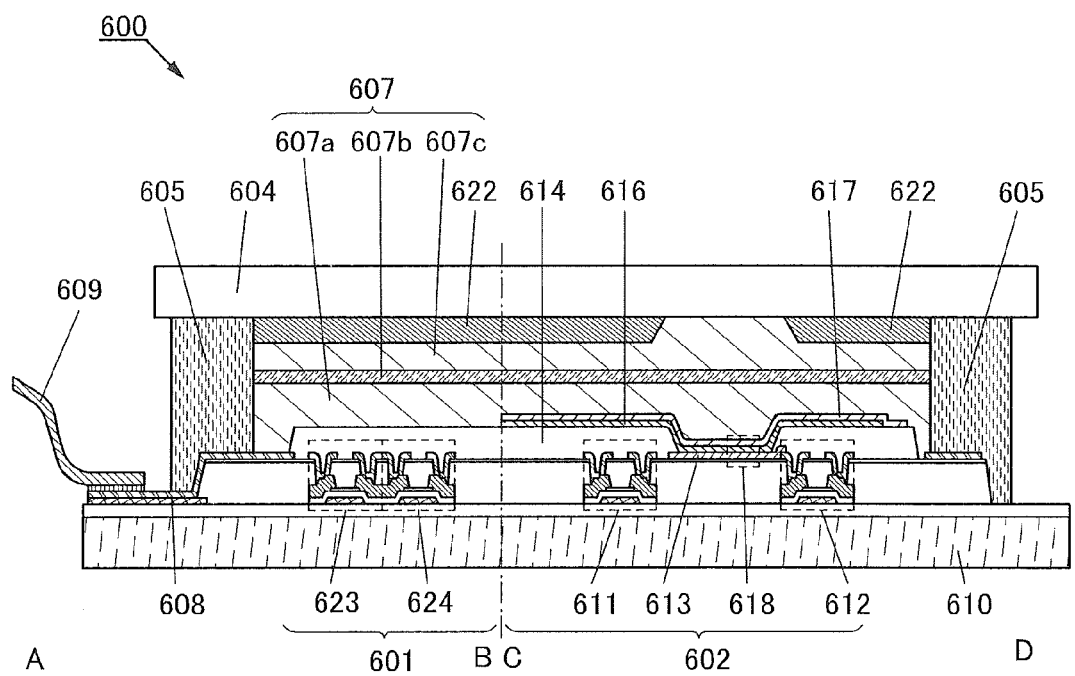
FIG. 20 is a schematic cross-sectional view illustrating a display device of one embodiment of the present invention.

Next, a display device of another embodiment of the present invention is described with reference to FIG. 20. FIG. 20 is a cross-sectional view taken along the dashed-dotted line A-B and the dashed-dotted line C-D in FIG. 13A. Note that in FIG. 20, portions having functions similar to those of portions in FIG. 13B are given the same reference numerals as in FIG. 13B, and a detailed description of the portions is omitted.

The display device 600 in FIG. 20 includes a sealing layer 607a, a sealing layer 607b, and a sealing layer 607c in a region 607 surrounded by the element substrate 610, the sealing substrate 604, and the sealant 605. For one or more of the sealing layer 607a, the sealing layer 607b, and the sealing layer 607c, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride may be used. The formation of the sealing layers 607a, 607b, and 607c is preferable because deterioration of the light-emitting element 618 due to impurities such as water can be prevented. In the case where the sealing layers 607a, 607b, and 607c are formed, the sealant 605 is not necessarily provided.

Alternatively, any one or two of the sealing layers 607a, 607b, and 607c may be provided or four or more sealing layers may be formed. When the sealing layer has a multilayer structure, the impurities such as water can be effectively prevented from entering the light-emitting element 618 which is inside the display device from the outside of the display device 600. In the case where the sealing layer has a multilayer structure, a resin and an inorganic material are preferably stacked.

Structure Example 6 of Display Device

Although the display devices in the structure examples 1 to 4 in this embodiment each have a structure including optical elements, one embodiment of the present invention does not necessarily include an optical element.

Figure 21A:
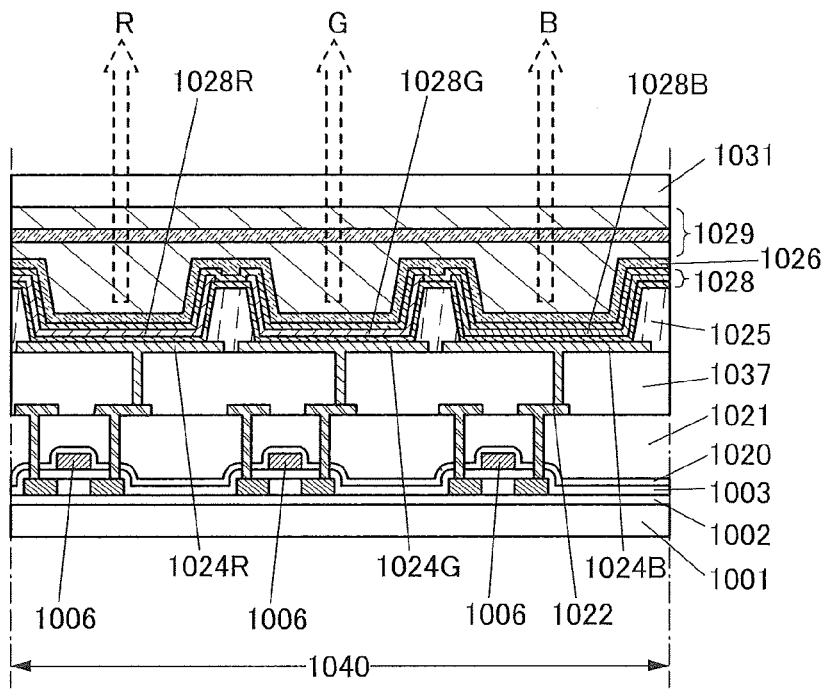
FIGS. 21A and 21B are schematic cross-sectional views each illustrating a display device of one embodiment of the present invention.
Figure 21B:
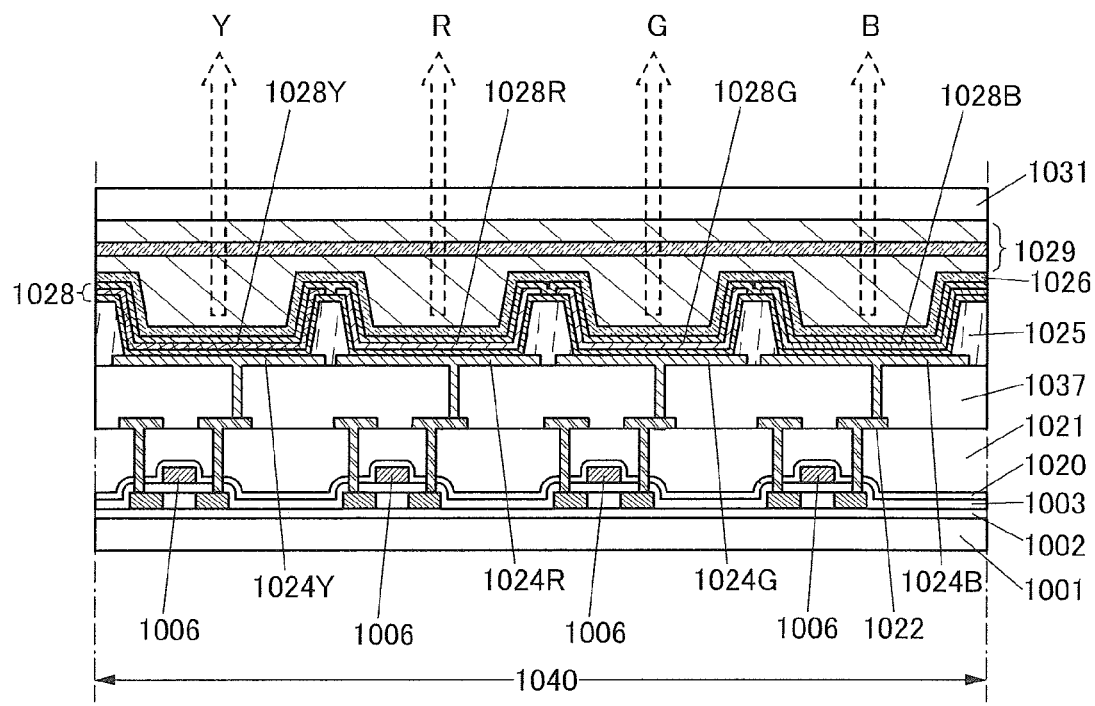

FIGS. 21A and 21B each illustrate a display device having a structure in which light is extracted from the sealing substrate 1031 side (a top-emission display device). FIG. 21A illustrates an example of a display device including a light-emitting layer 1028R, a light-emitting layer 1028G, and a light-emitting layer 1028B. FIG. 21B illustrates an example of a display device including a light-emitting layer 1028R, a light-emitting layer 1028G, a light-emitting layer 1028B, and a light-emitting layer 1028Y.

The light-emitting layer 1028R has a function of exhibiting red light, the light-emitting layer 1028G has a function of exhibiting green light, and the light-emitting layer 1028B has a function of exhibiting blue light. The light-emitting layer 1028Y has a function of exhibiting yellow light or a function of exhibiting light of a plurality of colors selected from blue, green, and red. The light-emitting layer 1028Y may exhibit white light. Since the light-emitting element which exhibits yellow or white light has high light emission efficiency, the display device including the light-emitting layer 1028Y can have lower power consumption.

Each of the display devices in FIGS. 21A and 21B does not necessarily include coloring layers serving as optical elements because EL layers exhibiting light of different colors are included in sub-pixels.

For the sealing layer 1029, a resin such as a polyvinyl chloride (PVC) based resin, an acrylic-based resin, a polyimide-based resin, an epoxy-based resin, a silicone-based resin, a polyvinyl butyral (PVB) based resin, or an ethylene vinyl acetate (EVA) based resin can be used. Alternatively, an inorganic material such as silicon oxide, silicon oxynitride, silicon nitride oxide, silicon nitride, aluminum oxide, or aluminum nitride may be used. The formation of the sealing layer 1029 is preferable because deterioration of the light-emitting element due to impurities such as water can be prevented.

Alternatively, the sealing layer 1029 may have a single-layer or two-layer structure, or four or more sealing layers may be formed as the sealing layer 1029. When the sealing layer has a multilayer structure, the impurities such as water can be effectively prevented from entering the inside of the display device from the outside of the display device. In the case where the sealing layer has a multilayer structure, a resin and an inorganic material are preferably stacked.

Note that the sealing substrate 1031 has a function of protecting the light-emitting element. Thus, for the sealing substrate 1031, a flexible substrate or a film can be used.

The structures described in this embodiment can be combined as appropriate with any of the other structures in this embodiment and the other embodiments.

Embodiment 9

In this embodiment, a display device including a light-emitting element of one embodiment of the present invention is described with reference to FIGS. 22A and 22B, FIGS. 23A and 23B, and FIGS. 24A and 24B.

Figure 22A:
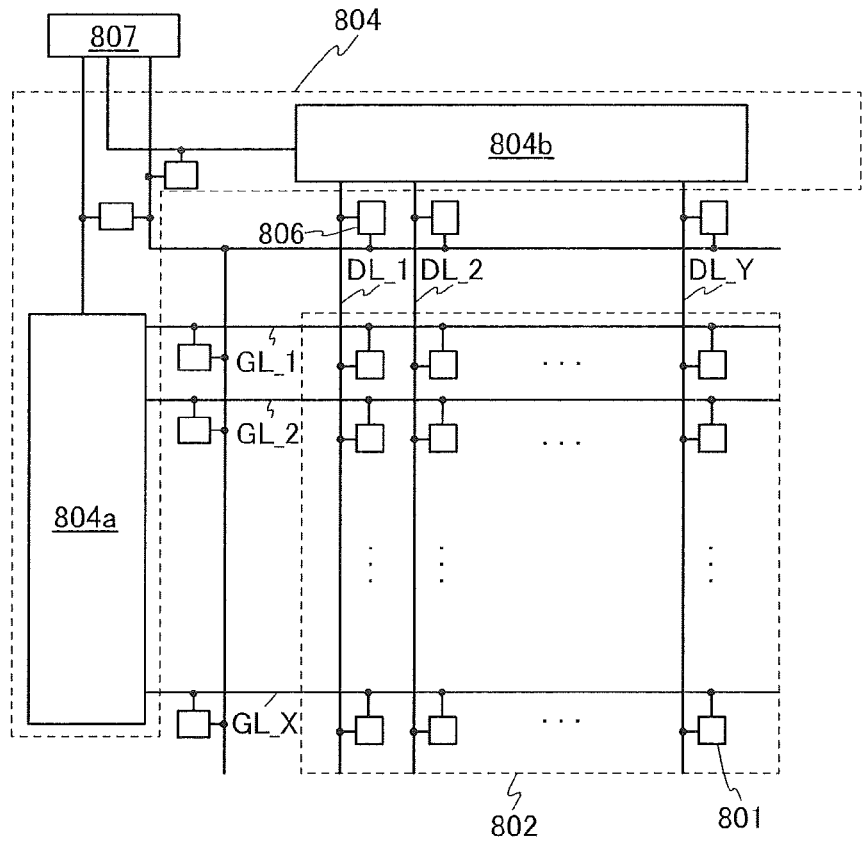
FIGS. 22A and 22B are a block diagram and a circuit diagram, respectively, illustrating a display device of one embodiment of the present invention.
Figure 22B:
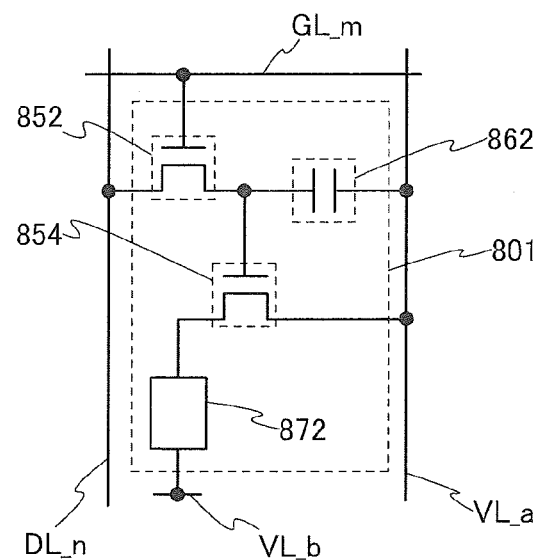

FIG. 22A is a block diagram showing the display device of one embodiment of the present invention, and FIG. 22B is a circuit diagram showing a pixel circuit of the display device of one embodiment of the present invention.

<Description of Display Device>

The display device shown in FIG. 22A includes a region including pixels of display elements (the region is hereinafter referred to as a pixel portion 802), a circuit portion that is provided outside the pixel portion 802 and includes circuits for driving the pixels (the portion is hereinafter referred to as a driver circuit portion 804), circuits having a function of protecting elements (the circuits are hereinafter referred to as protection circuits 806), and a terminal portion 807. Note that the protection circuits 806 are not necessarily provided.

A part or the whole of the driver circuit portion 804 is preferably formed over a substrate over which the pixel portion 802 is formed, in which case the number of components and the number of terminals can be reduced. When a part or the whole of the driver circuit portion 804 is not formed over the substrate over which the pixel portion 802 is formed, the part or the whole of the driver circuit portion 804 can be mounted by COG or tape automated bonding (TAB).

The pixel portion 802 includes a plurality of circuits for driving display elements arranged in X rows (X is a natural number of 2 or more) and Y columns (Y is a natural number of 2 or more) (such circuits are hereinafter referred to as pixel circuits 801). The driver circuit portion 804 includes driver circuits such as a circuit for supplying a signal (a scan signal) to select a pixel (the circuit is hereinafter referred to as a scan line driver circuit 804a) and a circuit for supplying a signal (a data signal) to drive a display element in a pixel (the circuit is hereinafter referred to as a signal line driver circuit 804b).

The scan line driver circuit 804a includes a shift register or the like. Through the terminal portion 807, the scan line driver circuit 804a receives a signal for driving the shift register and outputs a signal. For example, the scan line driver circuit 804a receives a start pulse signal, a clock signal, or the like and outputs a pulse signal. The scan line driver circuit 804a has a function of controlling the potentials of wirings supplied with scan signals (such wirings are hereinafter referred to as scan lines GL_1 to GL_X). Note that a plurality of scan line driver circuits 804a may be provided to control the scan lines GL_1 to GL_X separately. Alternatively, the scan line driver circuit 804a has a function of supplying an initialization signal. Without being limited thereto, the scan line driver circuit 804a can supply another signal.

The signal line driver circuit 804b includes a shift register or the like. The signal line driver circuit 804b receives a signal (an image signal) from which a data signal is derived, as well as a signal for driving the shift register, through the terminal portion 807. The signal line driver circuit 804b has a function of generating a data signal to be written to the pixel circuit 801 which is based on the image signal. In addition, the signal line driver circuit 804*b* has a function of controlling output of a data signal in response to a pulse signal produced by input of a start pulse signal, a clock signal, or the like. Furthermore, the signal line driver circuit 804*b* has a function of controlling the potentials of wirings supplied with data signals (such wirings are hereinafter referred to as data lines DL_1 to DL_Y). Alternatively, the signal line driver circuit 804*b* has a function of supplying an initialization signal. Without being limited thereto, the signal line driver circuit 804*b* can supply another signal.

The signal line driver circuit 804*b* includes a plurality of analog switches or the like, for example. The signal line driver circuit 804*b* can output, as the data signals, signals obtained by time-dividing the image signal by sequentially turning on the plurality of analog switches. The signal line driver circuit 804*b* may include a shift register or the like.

A pulse signal and a data signal are input to each of the plurality of pixel circuits 801 through one of the plurality of scan lines GL supplied with scan signals and one of the plurality of data lines DL supplied with data signals, respectively. Writing and holding of the data signal to and in each of the plurality of pixel circuits 801 are controlled by the scan line driver circuit 804*a*. For example, to the pixel circuit 801 in the m-th row and the n-th column (in is a natural number less than or equal to X, and n is a natural number less than or equal to Y), a pulse signal is input from the scan line driver circuit 804*a* through the scan line GL_m, and a data signal is input from the signal line driver circuit 804*b* through the data line DL_n in accordance with the potential of the scan line GL_m.

The protection circuit 806 shown in FIG. 22A is connected to, for example, the scan line GL between the scan line driver circuit 804*a* and the pixel circuit 801. Alternatively, the protection circuit 806 is connected to the data line DL between the signal line driver circuit 804*b* and the pixel circuit 801. Alternatively, the protection circuit 806 can be connected to a wiring between the scan line driver circuit 804*a* and the terminal portion 807. Alternatively, the protection circuit 806 can be connected to a wiring between the signal line driver circuit 804*b* and the terminal portion 807. Note that the terminal portion 807 means a portion having terminals for inputting power, control signals, and image signals to the display device from external circuits.

The protection circuit 806 is a circuit that electrically connects a wiring connected to the protection circuit to another wiring when a potential out of a certain range is applied to the wiring connected to the protection circuit.

As shown in FIG. 22A, the protection circuits 806 are provided for the pixel portion 802 and the driver circuit portion 804, so that the resistance of the display device to overcurrent generated by electrostatic discharge (ESD) or the like can be improved. Note that the configuration of the protection circuits 806 is not limited to that, and for example, a configuration in which the protection circuits 806 are connected to the scan line driver circuit 804*a* or a configuration in which the protection circuits 806 are connected to the signal line driver circuit 804*b* may be employed. Alternatively, the protection circuits 806 may be configured to be connected to the terminal portion 807.

FIG. 22A shows an example in which the driver circuit portion 804 includes the scan line driver circuit 804*a* and the signal line driver circuit 804*b*; however, the configuration is not limited thereto. For example, only the scan line driver circuit 804*a* may be formed and a separately prepared substrate where a signal line driver circuit is formed (e.g., a driver circuit substrate formed with a single crystal semiconductor film or a polycrystalline semiconductor film) may be mounted.

Configuration Example of Pixel Circuit

Each of the plurality of pixel circuits 801 in FIG. 22A can have a configuration shown in FIG. 22B, for example.

The pixel circuit 801 shown in FIG. 22B includes transistors 852 and 854, a capacitor 862, and a light-emitting element 872.

One of a source electrode and a drain electrode of the transistor 852 is electrically connected to a wiring to which a data signal is supplied (a data line DL_n). A gate electrode of the transistor 852 is electrically connected to a wiring to which a gate signal is supplied (a scan line GL_m).

The transistor 852 has a function of controlling whether to write a data signal.

One of a pair of electrodes of the capacitor 862 is electrically connected to a wiring to which a potential is supplied (hereinafter referred to as a potential supply line VL_a), and the other is electrically connected to the other of the source electrode and the drain electrode of the transistor 852.

The capacitor 862 functions as a storage capacitor for storing written data.

One of a source electrode and a drain electrode of the transistor 854 is electrically connected to the potential supply line VL_a. Furthermore, a gate electrode of the transistor 854 is electrically connected to the other of the source electrode and the drain electrode of the transistor 852.

One of an anode and a cathode of the light-emitting element 872 is electrically connected to a potential supply line VL_b, and the other is electrically connected to the other of the source electrode and the drain electrode of the transistor 854.

As the light-emitting element 872, any of the light-emitting elements described in Embodiments 3 to 6 can be used.

Note that a high power supply potential VDD is supplied to one of the potential supply line VL_a and the potential supply line VL_b, and a low power supply potential VSS is supplied to the other.

In the display device including the pixel circuits 801 in FIG. 22B, the pixel circuits 801 are sequentially selected row by row by the scan line driver circuit 804*a* in FIG. 22A, for example, whereby the transistors 852 are turned on and a data signal is written.

When the transistors 852 are turned off, the pixel circuits 801 in which the data has been written are brought into a holding state. Furthermore, the amount of current flowing between the source electrode and the drain electrode of the transistor 854 is controlled in accordance with the potential of the written data signal. The light-emitting element 872 emits light with a luminance corresponding to the amount of flowing current. This operation is sequentially performed row by row; thus, an image can be displayed.

The pixel circuit may have a function of correcting the effect of a fluctuation in the threshold voltage or the like of a transistor. FIGS. 23A and 23B and FIGS. 24A and 24B show examples of the pixel circuit.

Figure 23A:
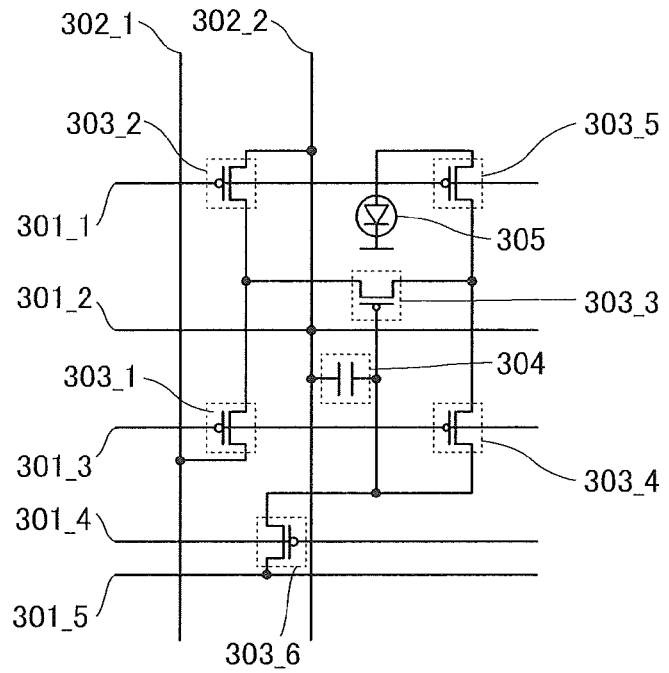
FIGS. 23A and 23B are circuit diagrams each illustrating a pixel circuit of a display device of one embodiment of the present invention.

The pixel circuit shown in FIG. 23A includes six transistors (transistors 303_1 to 303_6), a capacitor 304, and a light-emitting element 305. To the pixel circuit shown in FIG. 23A, wirings 301_1 to 301_5 and wirings 302_1 and 302_2 are electrically connected. Note that as the transistors 303_1 to 303_6, for example, p-channel transistors can be used.

Figure 23B:
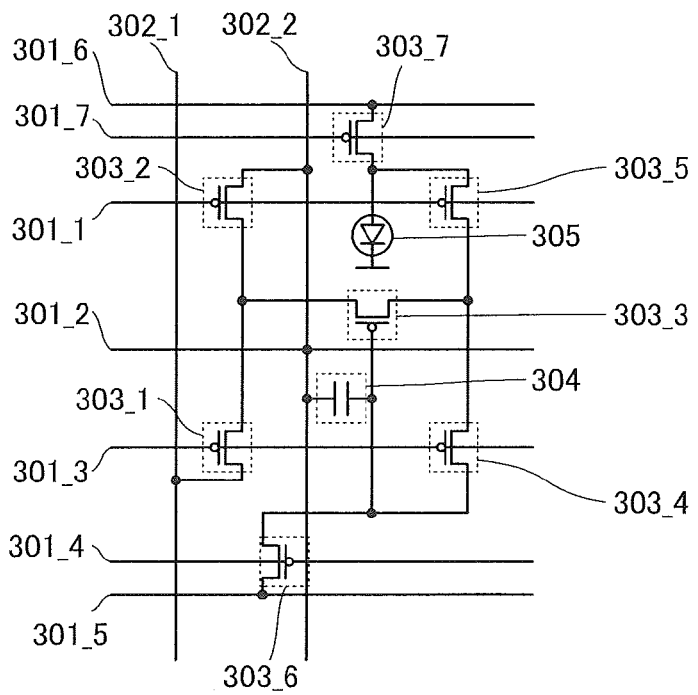

The pixel circuit shown in FIG. 23B has a configuration in which a transistor 303_7 is added to the pixel circuit shown in FIG. 23A. To the pixel circuit shown in FIG. 23B, wirings 301_6 and 301_7 are electrically connected. The wirings 301_5 and 301_6 may be electrically connected to each other. Note that as the transistor 3037, for example, a p-channel transistor can be used.

Figure 24A:
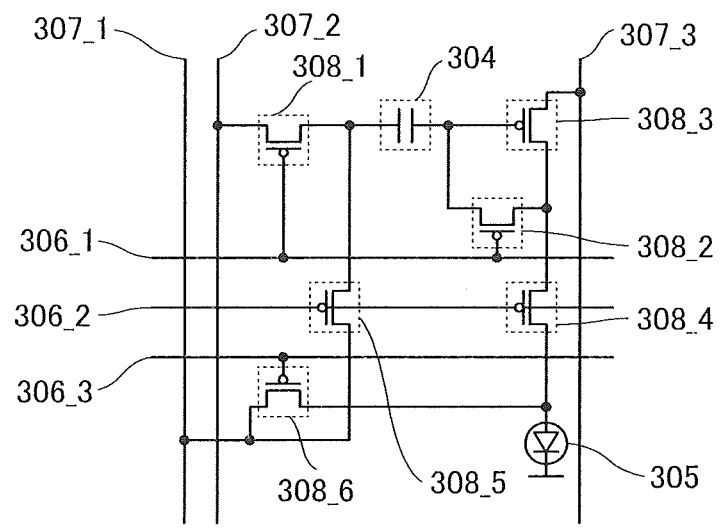
FIGS. 24A and 24B are circuit diagrams each illustrating a pixel circuit of a display device of one embodiment of the present invention.

The pixel circuit shown in FIG. 24A includes six transistors (transistors 308_1 to 3086), the capacitor 304, and the light-emitting element 305. To the pixel circuit shown in FIG. 24A, wirings 306_1 to 306_3 and wirings 307_1 to 307_3 are electrically connected. The wirings 306_1 and 306_3 may be electrically connected to each other. Note that as the transistors 308_1 to 308_6, for example, p-channel transistors can be used.

Figure 24B:
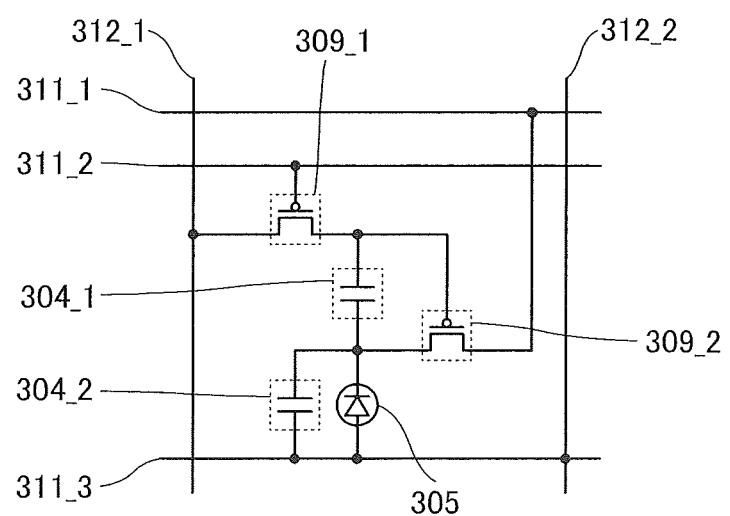

The pixel circuit shown in FIG. 24B includes two transistors (transistors 309_1 and 309_2), two capacitors (capacitors 304_1 and 304_2), and the light-emitting element 305. To the pixel circuit illustrated in FIG. 24B, wirings 311_1 to 311_3 and wirings 312_1 and 312_2 are electrically connected. With the configuration of the pixel circuit shown in FIG. 24B, the pixel circuit can be driven by a voltage inputting current driving method (also referred to as a CVCC method). Note that as the transistors 309_1 and 309_2, for example, p-channel transistors can be used.

A light-emitting element of one embodiment of the present invention can be used for each of an active matrix method in which an active element is included in a pixel of a display device and a passive matrix method in which an active element is not included in a pixel of a display device.

In the active matrix method, as an active element (a non-linear element), not only a transistor but also a variety of active elements (non-linear elements) can be used. For example, a metal insulator metal (MIM), a thin film diode (TFD), or the like can also be used. Since these elements can be formed with a smaller number of manufacturing steps, manufacturing cost can be reduced or yield can be improved. Alternatively, since the size of these elements is small, the aperture ratio can be improved, so that power consumption can be reduced and higher luminance can be achieved.

As a method other than the active matrix method, a passive matrix type in which an active element (a non-linear element) is not used can also be used. Since an active element (a non-linear element) is not used, the number of manufacturing steps is small, so that manufacturing cost can be reduced or yield can be improved. Alternatively, since an active element (a non-linear element) is not used, the aperture ratio can be improved, so that power consumption can be reduced or higher luminance can be achieved, for example.

The structure described in this embodiment can be used in combination with any of the structures described in the other embodiments as appropriate.

Embodiment 10

In this embodiment, a display device including a light-emitting element of one embodiment of the present invention and an electronic device in which the display device is provided with an input device are described with reference to FIGS. 25A and 25B, FIGS. 26A to 26C, FIGS. 27A and 27B, FIGS. 28A and 28B, and FIG. 29.

<Description 1 of Touch Panel>

In this embodiment, a touch panel 2000 including a display device and an input device are described as an example of an electronic device. In addition, an example in which a touch sensor is included as an input device is described.

Figure 25A:
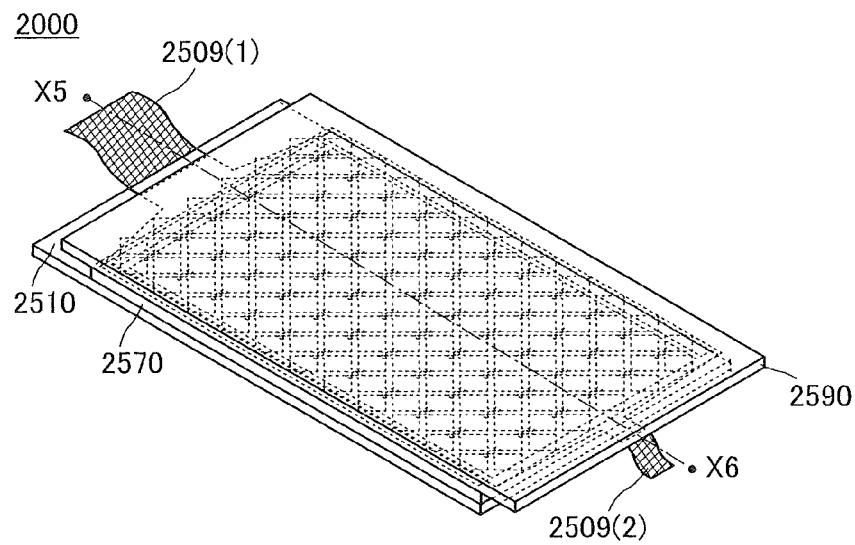
FIGS. 25A and 25B are perspective views illustrating an example of a touch panel of one embodiment of the present invention.
Figure 25B:
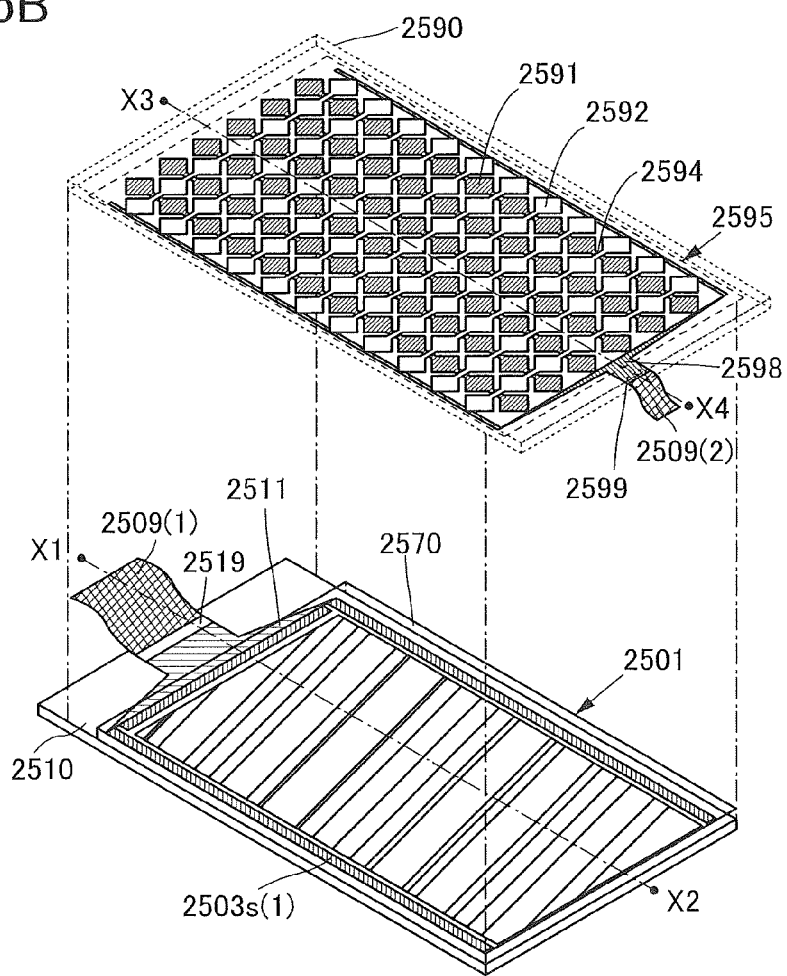

FIGS. 25A and 25B are perspective views of the touch panel 2000. Note that FIGS. 25A and 25B illustrate only main components of the touch panel 2000 for simplicity.

The touch panel 2000 includes a display device 2501 and a touch sensor 2595 (see FIG. 25B). The touch panel 2000 also includes a substrate 2510, a substrate 2570, and a substrate 2590. The substrate 2510, the substrate 2570, and the substrate 2590 each have flexibility. Note that one or all of the substrates 2510, 2570, and 2590 may be inflexible.

The display device 2501 includes a plurality of pixels over the substrate 2510 and a plurality of wirings 2511 through which signals can be supplied to the pixels. The plurality of wirings 2511 are led to a peripheral portion of the substrate 2510, and parts of the plurality of wirings 2511 form a terminal 2519. The terminal 2519 is electrically connected to an FPC 2509(1). The plurality of wirings 2511 can supply signals from a signal line driver circuit $2503s(1)$ to the plurality of pixels.

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal. The terminal is electrically connected to an FPC 2509(2). Note that in FIG. 25B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive type is preferable because multiple points can be sensed simultaneously.

Note that the touch sensor 2595 illustrated in FIG. 25B is an example of using a projected capacitive touch sensor.

Note that a variety of sensors that can sense proximity or touch of a sensing target such as a finger can be used as the touch sensor 2595.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598.

The electrodes 2592 each have a shape of a plurality of quadrangles arranged in one direction with one corner of a quadrangle connected to one corner of another quadrangle as illustrated in FIGS. 25A and 25B.

The electrodes 2591 each have a quadrangular shape and are arranged in a direction intersecting with the direction in which the electrodes 2592 extend.

A wiring 2594 electrically connects two electrodes 2591 between which the electrode 2592 is positioned. The intersecting area of the electrode 2592 and the wiring 2594 is preferably as small as possible. Such a structure allows a reduction in the area of a region where the electrodes are not provided, reducing variation in transmittance. As a result, variation in the luminance of light passing through the touch sensor 2595 can be reduced.

Note that the shapes of the electrodes 2591 and the electrodes 2592 are not limited thereto and can be any of a variety of shapes. For example, a structure may be employed in which the plurality of electrodes 2591 are arranged so that gaps between the electrodes 2591 are reduced as much as possible, and the electrodes 2592 are spaced apart from the electrodes 2591 with an insulating layer interposed therebetween to have regions not overlapping with the electrodes 2591. In this case, it is preferable to provide, between two adjacent electrodes 2592, a dummy electrode electrically insulated from these electrodes because the area of regions having different transmittances can be reduced.

<Description of Display Device>

Figure 26A:
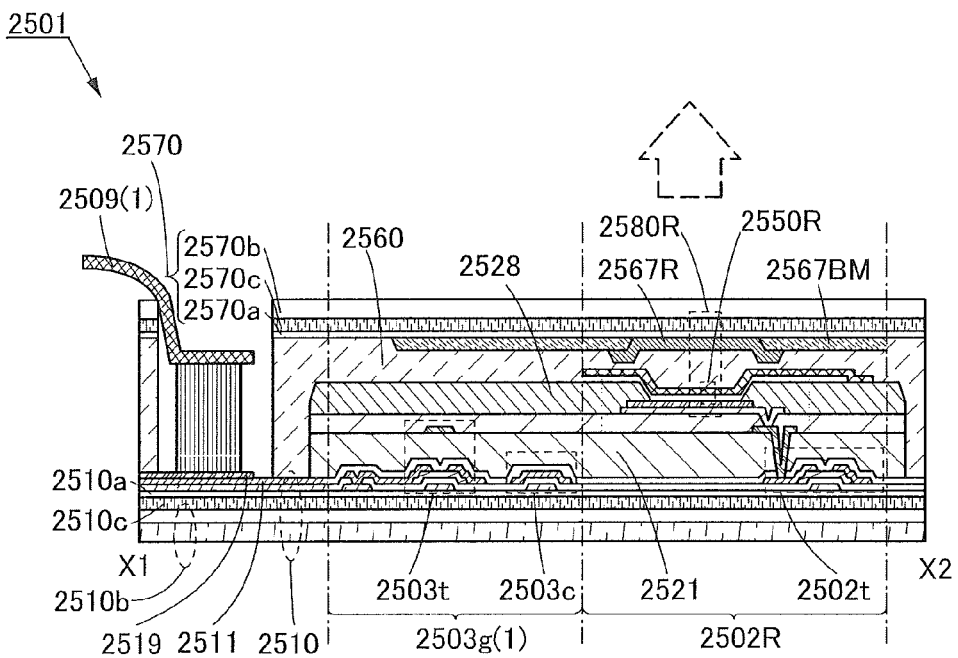
FIGS. 26A to 26C are cross-sectional views illustrating examples of a display device and a touch sensor of one embodiment of the present invention.

Next, the display device 2501 is described in detail with reference to FIG. 26A. FIG. 26A corresponds to a cross-sectional view taken along the dashed-dotted line X1-X2 in FIG. 25B.

The display device 2501 includes a plurality of pixels arranged in a matrix. Each of the pixels includes a display element and a pixel circuit for driving the display element.

In the following description, an example of using a light-emitting element that emits white light as a display element is described; however, the display element is not limited to such an element. For example, light-emitting elements that emit light of different colors may be included so that the light of different colors can be emitted from adjacent pixels.

For the substrate 2510 and the substrate 2570, for example, a flexible material with a vapor permeability lower than or equal to $1\times10^{-5}$ g·m$^{-2}$·day$^{-1}$, preferably lower than or equal to $1\times10^{-6}$ g·m$^{-2}$·day$^{-1}$ can be favorably used. Alternatively, materials whose thermal expansion coefficients are substantially equal to each other are preferably used for the substrate 2510 and the substrate 2570. For example, the coefficients of linear expansion of the materials are preferably lower than or equal to $1\times10^{-3}$/K, further preferably lower than or equal to $5\times10^{-5}$/K, and still further preferably lower than or equal to $1\times10^{-5}$/K.

Note that the substrate 2510 is a stacked body including an insulating layer 2510a for preventing impurity diffusion into the light-emitting element, a flexible substrate 2510b, and an adhesive layer 2510c attaching the insulating layer 2510a and the flexible substrate 2510b to each other. The substrate 2570 is a stacked body including an insulating layer 2570a preventing impurity diffusion into the light-emitting element, a flexible substrate 2570b, and an adhesive layer 2570c attaching the insulating layer 2570a and the flexible substrate 2570b to each other.

For the adhesive layer 2510c and the adhesive layer 2570c, for example, polyester, polyolefin, polyamide (e.g., nylon or aramid), polyimide, polycarbonate, or an acrylic resin, polyurethane, or an epoxy resin can be used. Alternatively, a material that includes a resin having a siloxane bond such as silicone can be used.

A sealing layer 2560 is provided between the substrate 2510 and the substrate 2570. The sealing layer 2560 preferably has a refractive index higher than the air. In the case where light is extracted to the sealing layer 2560 side as illustrated in FIG. 26A, the sealing layer 2560 can also serve as an optical adhesive layer.

A sealant may be formed in the peripheral portion of the sealing layer 2560. With the use of the sealant, a light-emitting element 2550R can be provided in a region surrounded by the substrate 2510, the substrate 2570, the sealing layer 2560, and the sealant. Note that an inert gas (such as nitrogen and argon) may be used instead of the sealing layer 2560. A desiccant may be provided in the inert gas so as to adsorb moisture or the like. A resin such as an acrylic resin or an epoxy resin may be used. An epoxy-based resin or a glass frit is preferably used as the sealant. As a material used for the sealant, a material which is impermeable to moisture and oxygen is preferably used.

The display device 2501 includes a pixel 2502R. The pixel 2502R includes a light-emitting module 2580R.

The pixel 2502R includes the light-emitting element 2550R and a transistor 2502t that can supply electric power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode. As the light-emitting element 2550R, any of the light-emitting elements described in Embodiments 3 to 6 can be used.

A microcavity structure may be employed between the lower electrode and the upper electrode so as to increase the intensity of light having a specific wavelength.

In the case where the sealing layer 2560 is provided on the light extraction side, the sealing layer 2560 is in contact with the light-emitting element 2550R and the coloring layer 2567R.

The coloring layer 2567R is positioned in a region overlapping with the light-emitting element 2550R. Accordingly, part of light emitted from the light-emitting element 2550R passes through the coloring layer 2567R and is emitted to the outside of the light-emitting module 2580R as indicated by the arrow in the drawing.

The display device 2501 includes a light-blocking layer 2567BM on the light extraction side. The light-blocking layer 2567BM is provided so as to surround the coloring layer 2567R.

The coloring layer 2567R is a coloring layer having a function of transmitting light in a particular wavelength range. For example, a color filter for transmitting light in a red wavelength range, a color filter for transmitting light in a green wavelength range, a color filter for transmitting light in a blue wavelength range, a color filter for transmitting light in a yellow wavelength range, or the like can be used. Each color filter can be formed with any of various materials by a printing method, an inkjet method, an etching method using a photolithography technique, or the like.

An insulating layer 2521 is provided in the display device 2501. The insulating layer 2521 covers the transistor 2502t. Note that the insulating layer 2521 has a function of covering unevenness caused by the pixel circuit. The insulating layer 2521 may have a function of suppressing impurity diffusion. This can prevent the reliability of the transistor 2502t or the like from being lowered by impurity diffusion.

The light-emitting element 2550R is formed above the insulating layer 2521. A partition wall 2528 is provided so as to overlap with an end portion of the lower electrode of the light-emitting element 2550R. Note that a spacer controlling the distance between the substrate 2510 and the substrate 2570 may be formed over the partition wall 2528.

A scan line driver circuit 2503g(1) includes a transistor 2503t and a capacitor 2503c. Note that the driver circuit can be formed in the same process and over the same substrate as those of the pixel circuits.

The wirings 2511 through which signals can be supplied are provided over the substrate 2510. The terminal 2519 is provided over the wirings 2511. The FPC 2509(1) is electrically connected to the terminal 2519. The FPC 2509(1) has a function of supplying a video signal, a clock signal, a start signal, a reset signal, or the like. Note that the FPC 2509(1) may be provided with a printed wiring board (PWB).

Figure 26B:
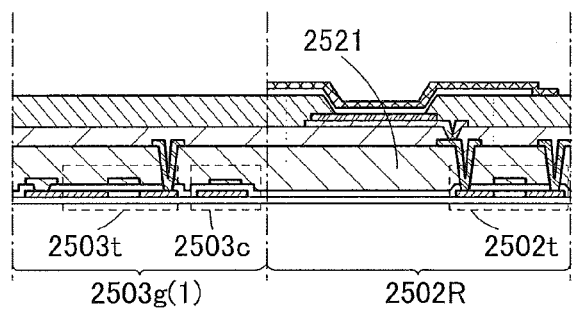

In the display device 2501, transistors with any of a variety of structures can be used. FIG. 26A illustrates an example of using bottom-gate transistors; however, the present invention is not limited to this example, and top-gate transistors may be used in the display device 2501 as illustrated in FIG. 26B.

In addition, there is no particular limitation on the polarity of the transistor 2502t and the transistor 2503t. For these transistors, n-channel and p-channel transistors may be used, or either n-channel transistors or p-channel transistors may be used, for example. Furthermore, there is no particular limitation on the crystallinity of a semiconductor film used for the transistors 2502t and 2503t. For example, an amorphous semiconductor film or a crystalline semiconductor film can be used. Examples of semiconductor materials include Group 14 semiconductors (e.g., a semiconductor including silicon), compound semiconductors (including oxide semiconductors), organic semiconductors, and the like. An oxide semiconductor that has an energy gap of 2 eV or more, preferably 2.5 eV or more, further preferably 3 eV or more is preferably used for one of the transistors 2502t and 2503t or both, so that the off-state current of the transistors can be reduced. Examples of the oxide semiconductors include an In—Ga oxide, an In-M-Zn oxide (M represents Al, Ga, Y, Zr, La, Ce, Sn, Hf, or Nd), and the like.

<Description of Touch Sensor>

Figure 26C:
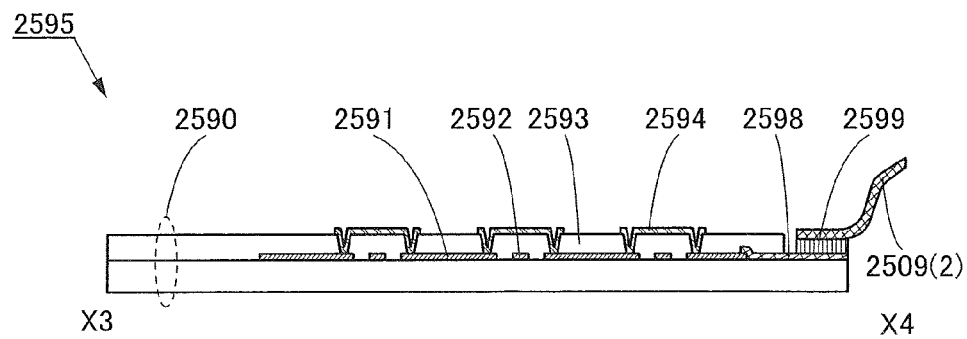

Next, the touch sensor 2595 is described in detail with reference to FIG. 26C. FIG. 26C corresponds to a cross-sectional view taken along the dashed-dotted line X3-X4 in FIG. 25B.

The touch sensor 2595 includes the electrodes 2591 and the electrodes 2592 provided in a staggered arrangement on the substrate 2590, an insulating layer 2593 covering the electrodes 2591 and the electrodes 2592, and the wiring 2594 that electrically connects the adjacent electrodes 2591 to each other.

The electrodes 2591 and the electrodes 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene can be used as well. The film including graphene can be formed, for example, by reducing a film containing graphene oxide. As a reducing method, a method with application of heat or the like can be employed.

The electrodes 2591 and the electrodes 2592 may be formed by, for example, depositing a light-transmitting conductive material on the substrate 2590 by a sputtering method and then removing an unnecessary portion by any of various pattern forming techniques such as a photolithography method.

Examples of a material used for the insulating layer 2593 are a resin such as an acrylic resin or an epoxy resin, a resin having a siloxane bond such as silicone, an inorganic insulating material such as silicon oxide, silicon oxynitride, or aluminum oxide, and the like.

Openings reaching the electrodes 2591 are formed in the insulating layer 2593, and the wiring 2594 is electrically connected to the adjacent electrodes 2591. A light-transmitting conductive material can be favorably used as the wiring 2594 because the aperture ratio of the touch panel can be increased. Moreover, a material with higher conductivity than the conductivities of the electrodes 2591 and 2592 can be favorably used for the wiring 2594 because electric resistance can be reduced.

One electrode 2592 extends in one direction, and a plurality of electrodes 2592 are provided in the form of stripes. The wiring 2594 intersects with the electrode 2592.

Adjacent electrodes 2591 are provided with one electrode 2592 provided therebetween. The wiring 2594 electrically connects the adjacent electrodes 2591.

Note that the plurality of electrodes 2591 are not necessarily arranged in the direction orthogonal to one electrode 2592 and may be arranged to intersect with one electrode 2592 at an angle more than 0 degrees and less than 90 degrees.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Note that an insulating layer that covers the insulating layer 2593 and the wiring 2594 may be provided to protect the touch sensor 2595.

A connection layer 2599 electrically connects the wiring 2598 to the FPC 2509(2).

As the connection layer 2599, any of various anisotropic conductive films (ACF), anisotropic conductive pastes (ACP), or the like can be used.

<Description 2 of Touch Panel>

Figure 27A:
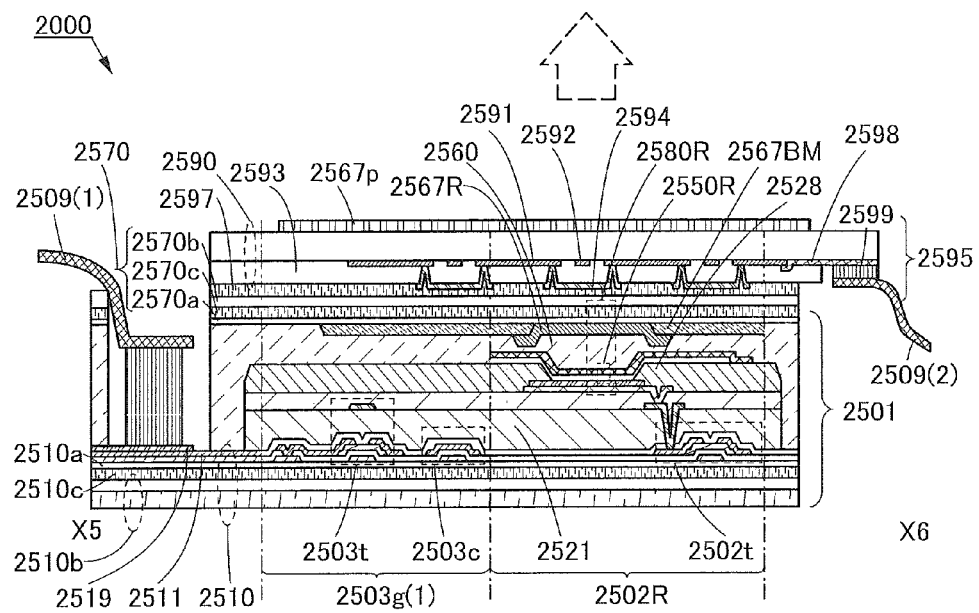
FIGS. 27A and 27B are cross-sectional views each illustrating an example of a touch panel of one embodiment of the present invention.

Next, the touch panel 2000 is described in detail with reference to FIG. 27A. FIG. 27A corresponds to a cross-sectional view taken along the dashed-dotted line X5-X6 in FIG. 25A.

In the touch panel 2000 illustrated in FIG. 27A, the display device 2501 described with reference to FIG. 26A and the touch sensor 2595 described with reference to FIG. 26C are attached to each other.

The touch panel 2000 illustrated in FIG. 27A includes an adhesive layer 2597 and an anti-reflective layer 2567p in addition to the components described with reference to FIGS. 26A and 26C.

The adhesive layer 2597 is provided in contact with the wiring 2594. Note that the adhesive layer 2597 attaches the substrate 2590 to the substrate 2570 so that the touch sensor 2595 overlaps with the display device 2501. The adhesive layer 2597 preferably has a light-transmitting property. A heat curable resin or an ultraviolet curable resin can be used for the adhesive layer 2597. For example, an acrylic resin, a urethane-based resin, an epoxy-based resin, or a siloxane-based resin can be used.

The anti-reflective layer 2567p is positioned in a region overlapping with pixels. As the anti-reflective layer 2567p, a circularly polarizing plate can be used, for example.

Next, a touch panel having a structure different from that illustrated in FIG. 27A is described with reference to FIG. 27B.

Figure 27B:
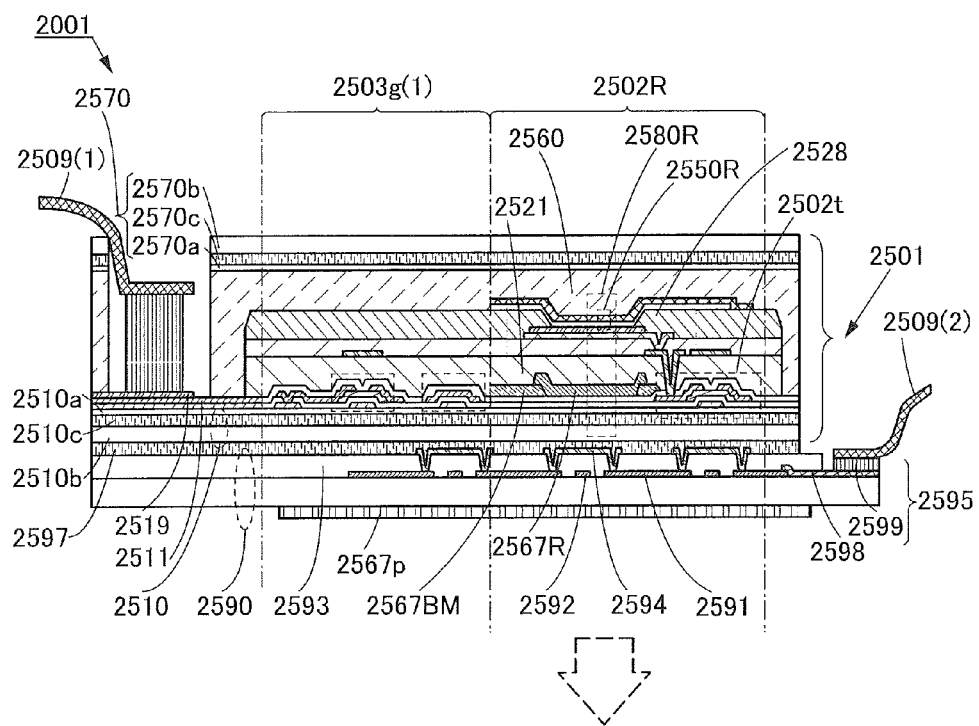

FIG. 27B is a cross-sectional view of a touch panel 2001. The touch panel 2001 illustrated in FIG. 27B differs from the touch panel 2000 illustrated in FIG. 27A in the position of the touch sensor 2595 relative to the display device 2501. Different parts are described in detail below, and the above description of the touch panel 2000 is referred to for the other similar parts.

The coloring layer 2567R is positioned in a region overlapping with the light-emitting element 2550R. The light-emitting element 2550R illustrated in FIG. 27B emits light to the side where the transistor 2502t is provided. Accordingly, part of light emitted from the light-emitting element 2550R passes through the coloring layer 2567R and is emitted to the outside of the light-emitting module 2580R as indicated by the arrow in the drawing.

The touch sensor 2595 is provided on the substrate 2510 side of the display device 2501.

The adhesive layer 2597 is provided between the substrate 2510 and the substrate 2590 and attaches the touch sensor 2595 to the display device 2501.

As illustrated in FIG. 27A or 27B, light may be emitted from the light-emitting element through one or both of the substrate 2510 and the substrate 2570.

<Description of Method for Driving Touch Panel>

Next, an example of a method for driving a touch panel is described with reference to FIGS. 28A and 28B.

Figure 28A:
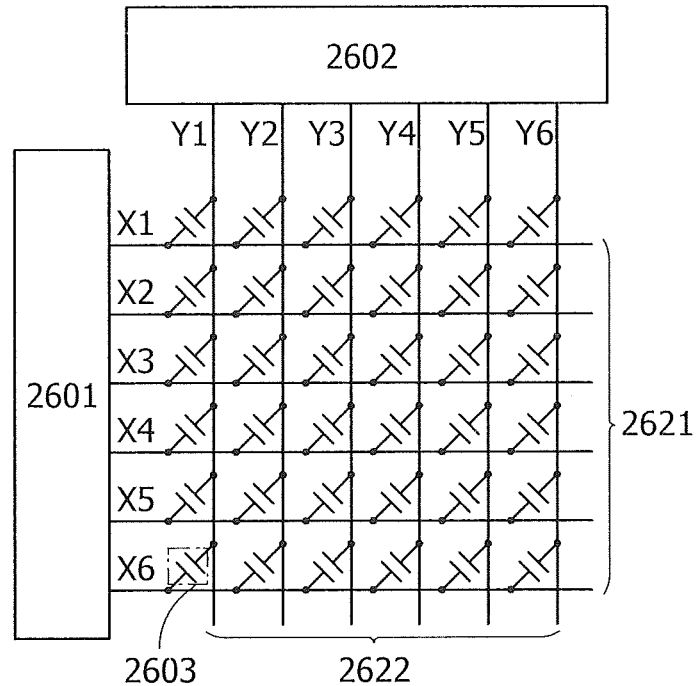
FIGS. 28A and 28B are a block diagram and a timing chart of a touch sensor of one embodiment of the present invention.

FIG. 28A is a block diagram showing the configuration of a mutual capacitive touch sensor. FIG. 28A shows a pulse voltage output circuit 2601 and a current sensing circuit 2602. Note that in FIG. 28A, six wirings X1 to X6 represent the electrodes 2621 to which a pulse voltage is applied, and six wirings Y1 to Y6 represent the electrodes 2622 that detect changes in current. FIG. 28A also shows capacitors 2603 which are each formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in mutual capacitance of the capacitor 2603. The approach or contact of a sensing target can be sensed by utilizing this change.

The current sensing circuit 2602 is a circuit for sensing changes in current flowing through the wirings Y1 to Y6 which are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 28B:
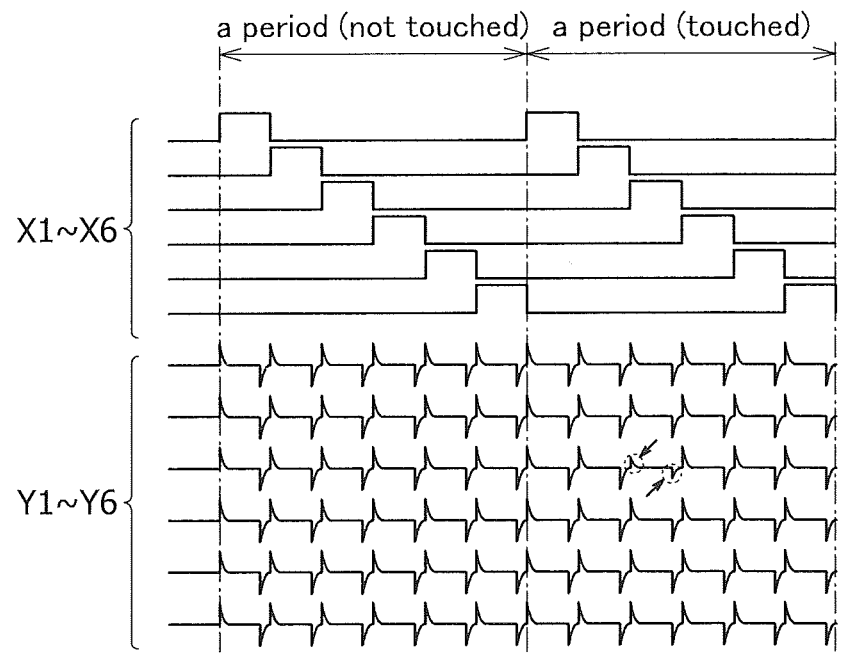

FIG. 28B is a timing chart showing input and output waveforms in the mutual capacitive touch sensor shown in FIG. 28A. In FIG. 28B, sensing of a sensing target is performed in all the rows and columns in one frame period. FIG. 28B shows a period when a sensing target is not sensed (not touched) and a period when a sensing target is sensed (touched). In FIG. 28B, sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes.

By sensing a change in mutual capacitance in this manner, the approach or contact of a sensing target can be sensed.

<Description of Sensor Circuit>

Figure 29:
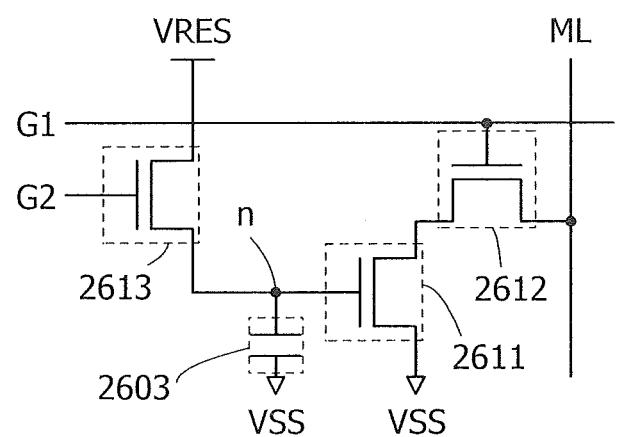
FIG. 29 is a circuit diagram of a touch sensor of one embodiment of the present invention.

Although FIG. 28A shows a passive matrix type touch sensor in which only the capacitor 2603 is provided at the intersection of wirings as a touch sensor, an active matrix type touch sensor including a transistor and a capacitor may be used. FIG. 29 shows an example of a sensor circuit included in an active matrix type touch sensor.

The sensor circuit in FIG. 29 includes the capacitor 2603 and transistors 2611, 2612, and 2613.

A signal G2 is input to a gate of the transistor 2613. A voltage VRES is applied to one of a source and a drain of the transistor 2613, and the other is electrically connected to one electrode of the capacitor 2603 and a gate of the transistor 2611. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 29 is described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained.

Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

The structure described in this embodiment can be used in combination with any of the structures described in the other embodiments as appropriate.

Embodiment 11

In this embodiment, a display module and electronic devices including a light-emitting element of one embodiment of the present invention are described with reference to FIG. 30, FIGS. 31A to 31G, FIGS. 32A to 32F, FIGS. 33A to 33D, and FIGS. 34A and 34B.

<Display Module>

Figure 30:
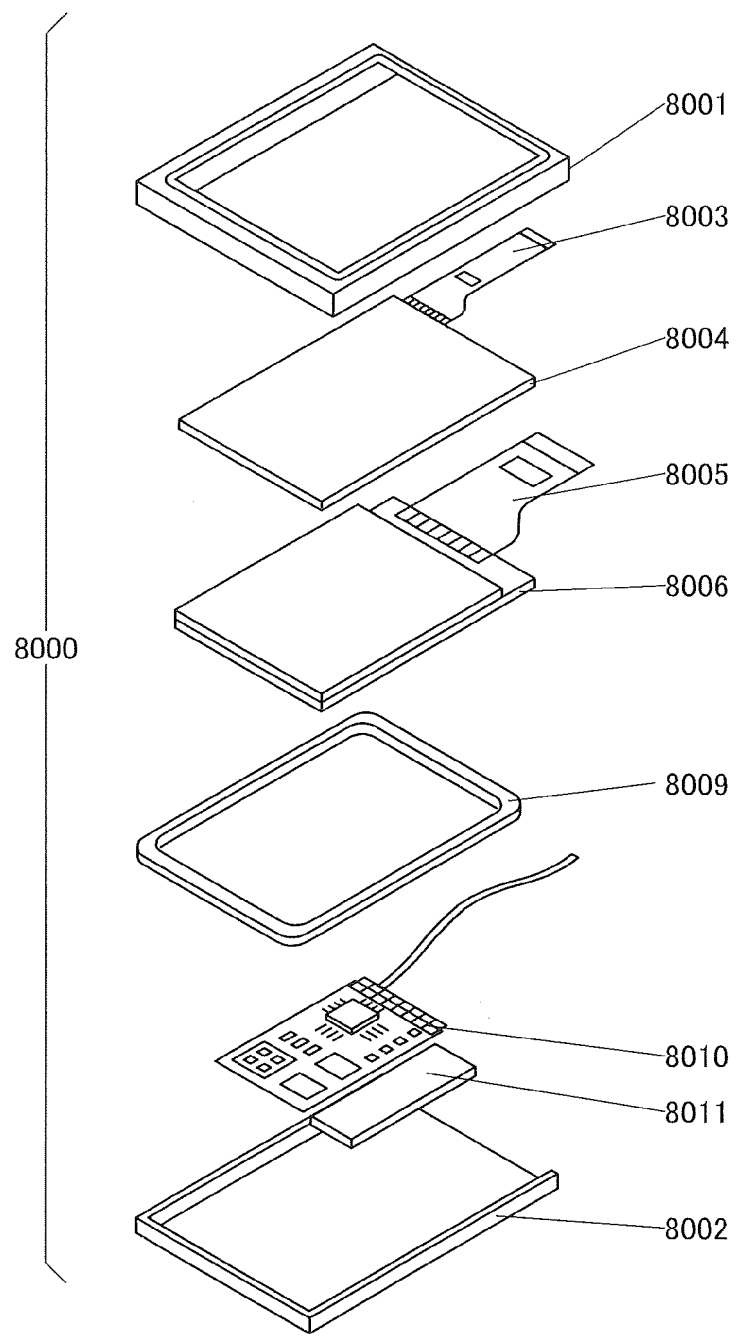
FIG. 30 is a perspective view of a display module of one embodiment of the present invention.

In a display module 8000 in FIG. 30, a touch sensor 8004 connected to an FPC 8003, a display device 8006 connected to an FPC 8005, a frame 8009, a printed board 8010, and a battery 8011 are provided between an upper cover 8001 and a lower cover 8002.

The light-emitting element of one embodiment of the present invention can be used for the display device 8006, for example.

The shapes and sizes of the upper cover 8001 and the lower cover 8002 can be changed as appropriate in accordance with the sizes of the touch sensor 8004 and the display device 8006.

The touch sensor 8004 can be a resistive touch sensor or a capacitive touch sensor and overlap with the display device 8006. A counter substrate (sealing substrate) of the display device 8006 can have a touch sensor function. A photosensor may be provided in each pixel of the display device 8006 so that an optical touch sensor is obtained.

The frame 8009 protects the display device 8006 and also serves as an electromagnetic shield for blocking electromagnetic waves generated by the operation of the printed board 8010. The frame 8009 may serve as a radiator plate.

The printed board 8010 has a power supply circuit and a signal processing circuit for outputting a video signal and a clock signal. As a power source for supplying power to the power supply circuit, an external commercial power source or the battery 8011 provided separately may be used. The battery 8011 can be omitted in the case of using a commercial power source.

The display module 8000 can be additionally provided with a member such as a polarizing plate, a retardation plate, or a prism sheet.

<Electronic Devices>

FIGS. 31A to 31G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone 9008, and the like. In addition, the sensor 9007 may have a function of measuring biological information like a pulse sensor and a finger print sensor.

The electronic devices illustrated in FIGS. 31A to 31G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 31A to 31G are not limited to those described above, and the electronic devices can have a variety of functions. Although not illustrated in FIGS. 31A to 31G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 31A to 31G are described in detail below.

Figure 31A:
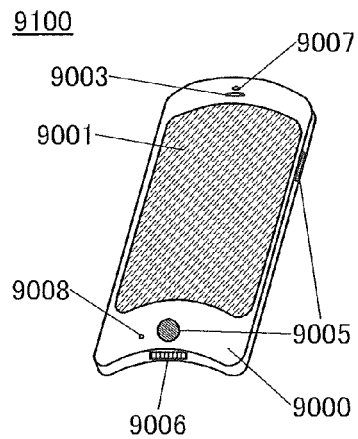
FIGS. 31A to 31G illustrate electronic devices of embodiments of the present invention.

FIG. 31A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 31D:
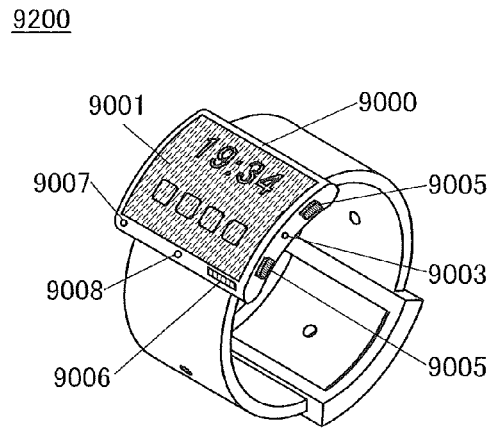
Figure 31B:
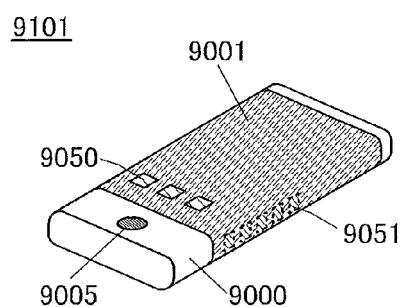

FIG. 31B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not illustrated in the drawing, can be positioned in the portable information terminal 9101 as in the portable information terminal 9100 illustrated in FIG. 31A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 are display indicating reception of an incoming email, social networking service (SNS) message, call, and the like, the title and sender of an email and SNS message, the date, the time, remaining battery, display indicating the intensity of a received signal such as a radio wave, and the like. Instead of the information 9051, the operation buttons 9050 or the like may be displayed on the position where the information 9051 is displayed.

As a material of the housing 9000, an alloy, plastic, ceramic, or a material containing carbon fiber can be used. As the material containing carbon fiber, carbon fiber reinforced plastic (CFRP) has advantages of lightweight and corrosion-free; however, it is black and thus limits the exterior and design of the housing. The CFRP can be regarded as a kind of reinforced plastic, which may use glass fiber or aramid fiber. Since the fiber might be separated from a resin by high impact, the alloy is preferred. As the alloy, an aluminum alloy and a magnesium alloy can be given. An amorphous alloy (also referred to as metallic glass) containing zirconium, copper, nickel, and titanium especially has high elastic strength. This amorphous alloy has a glass transition region at room temperature, which is also referred to as a bulk-solidifying amorphous alloy and substantially has an amorphous atomic structure. An alloy material is molded in a mold of at least the part of the housing and coagulated by a solidification casting method, whereby part of the housing is formed with the bulk-solidifying amorphous alloy. The amorphous alloy may contain beryllium, silicon, niobium, boron, gallium, molybdenum, tungsten, manganese, iron, cobalt, yttrium, vanadium, phosphorus, carbon, or the like in addition to zirconium, copper, nickel, and titanium. The amorphous alloy may be formed by a vacuum evaporation method, a sputtering method, an electroplating method, an electroless plating method, or the like instead of the solidification casting method. The amorphous alloy may include a microcrystal or a nanocrystal as long as a state without a long-range order (a periodic structure) is maintained as a whole. Note that the term alloy includes both a complete solid solution alloy having a single solid-phase structure and a partial solution having two or more phases. The housing 9000 using the amorphous alloy can have high elastic strength. Even if the portable information terminal 9101 is dropped and the impact causes temporary deformation, the use of the amorphous alloy in the housing

9000 allows a return to the original shape; thus, the impact resistance of the portable information terminal 9101 can be improved.

Figure 31E:
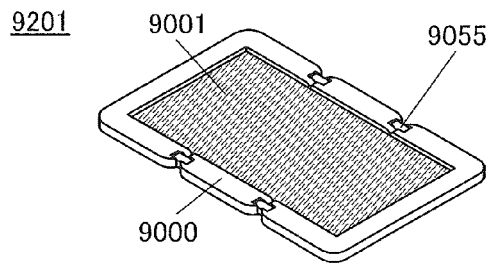
Figure 31C:
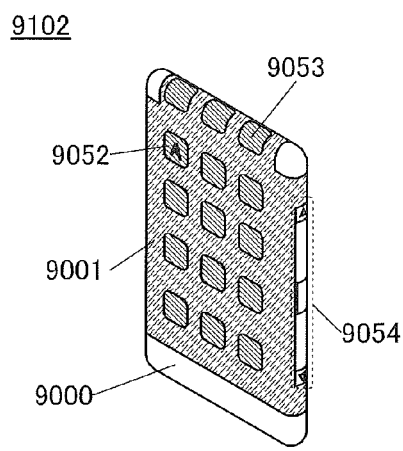

FIG. 31C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 31D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 31F:
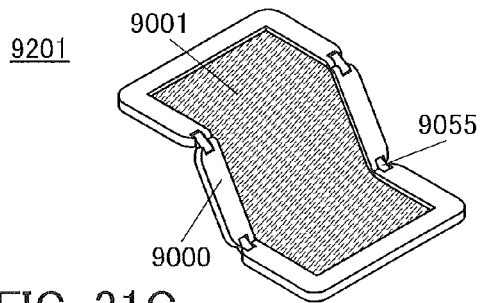
Figure 31G:
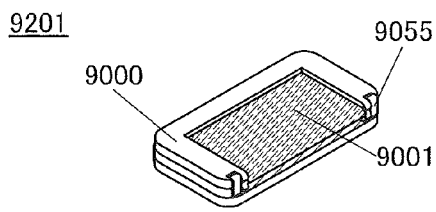

FIGS. 31E, 31F, and 31G are perspective views of a foldable portable information terminal 9201. FIG. 31E is a perspective view illustrating the portable information terminal 9201 which is opened. FIG. 31F is a perspective view illustrating the portable information terminal 9201 which is being opened or being folded. FIG. 31G is a perspective view illustrating the portable information terminal 9201 which is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature greater than or equal to 1 mm and less than or equal to 150 mm.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a goggle-type display (head mounted display), a portable game machine, a portable information terminal, an audio reproducing device, a large-sized game machine such as a pachinko machine, and the like.

Furthermore, the electronic device of one embodiment of the present invention may include a secondary battery. It is preferable that the secondary battery be capable of being charged by non-contact power transmission.

Examples of the secondary battery include a lithium ion secondary battery such as a lithium polymer battery using a gel electrolyte (lithium ion polymer battery), a lithium-ion battery, a nickel-hydride battery, a nickel-cadmium battery, an organic radical battery, a lead storage battery, an air secondary battery, a nickel-zinc battery, a silver-zinc battery, and the like.

The electronic device of one embodiment of the present invention may include an antenna. When a signal is received by the antenna, the electronic device can display an image, data, or the like on a display portion. When the electronic device includes a secondary battery, the antenna may be used for non-contact power transmission.

Figure 32A:
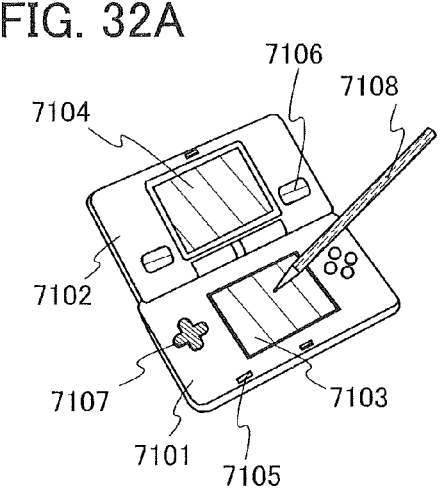
FIGS. 32A to 32F illustrate electronic devices of embodiments of the present invention.

FIG. 32A illustrates a portable game machine including a housing 7101, a housing 7102, display portions 7103 and 7104, a microphone 7105, speakers 7106, an operation key 7107, a stylus 7108, and the like. When the light-emitting device of one embodiment of the present invention is used as the display portion 7103 or 7104, it is possible to provide a user-friendly portable game machine with quality that hardly deteriorates. Although the portable game machine illustrated in FIG. 32A includes two display portions, the display portions 7103 and 7104, the number of display portions included in the portable game machine is not limited to two.

Figure 32B:
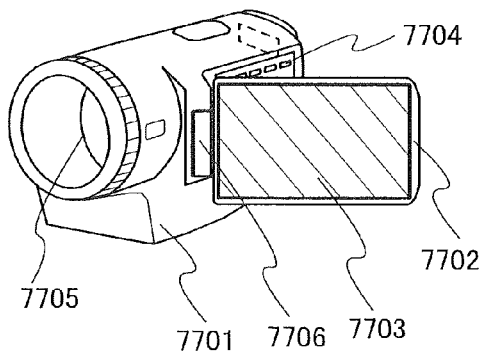

FIG. 32B illustrates a video camera including a housing 7701, a housing 7702, a display portion 7703, operation keys 7704, a lens 7705, a joint 7706, and the like. The operation keys 7704 and the lens 7705 are provided for the housing 7701, and the display portion 7703 is provided for the housing 7702. The housing 7701 and the housing 7702 are connected to each other with the joint 7706, and the angle between the housing 7701 and the housing 7702 can be changed with the joint 7706. Images displayed on the display portion 7703 may be switched in accordance with the angle at the joint 7706 between the housing 7701 and the housing 7702.

Figure 32C:
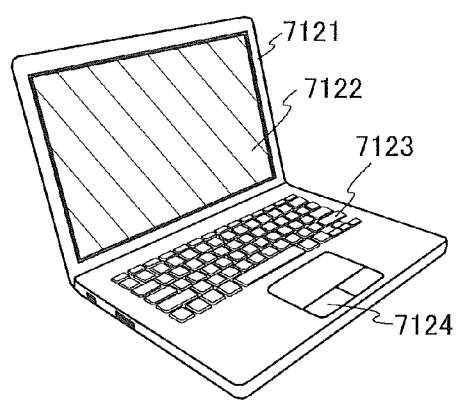

FIG. 32C illustrates a notebook personal computer including a housing 7121, a display portion 7122, a keyboard 7123, a pointing device 7124, and the like. Note that the display portion 7122 is small- or medium-sized but can perform 8 k display because it has high pixel density and high resolution; therefore, a significantly clear image can be obtained.

Figure 32D:
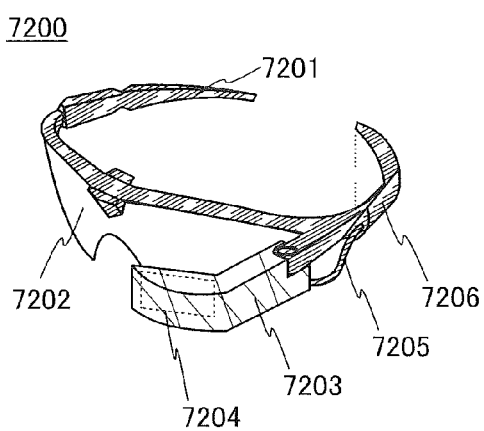

FIG. 32D is an external view of a head-mounted display 7200.

The head-mounted display 7200 includes a mounting portion 7201, a lens 7202, a main body 7203, a display portion 7204, a cable 7205, and the like. The mounting portion 7201 includes a battery 7206.

Power is supplied from the battery 7206 to the main body 7203 through the cable 7205. The main body 7203 includes a wireless receiver or the like to receive video data, such as image data, and can display it on the display portion 7204. The movement of the eyeball and the eyelid of a user is captured by a camera in the main body 7203 and then coordinates of the points the user looks at are calculated using the captured data to utilize the eye point of the user as an input means.

The mounting portion 7201 may include a plurality of electrodes so as to be in contact with the user. The main body 7203 may be configured to sense current flowing through the electrodes with the movement of the user's eyeball to recognize the direction of his or her eyes. The main body 7203 may be configured to sense current flowing through the electrodes to monitor the user's pulse. The mounting portion 7201 may include sensors, such as a temperature sensor, a pressure sensor, or an acceleration sensor, so that the user's biological information can be displayed on the display portion 7204. The main body 7203 may be configured to sense the movement of the user's head or the like to move an image displayed on the display portion 7204 in synchronization with the movement of the user's head or the like.

Figure 32E:
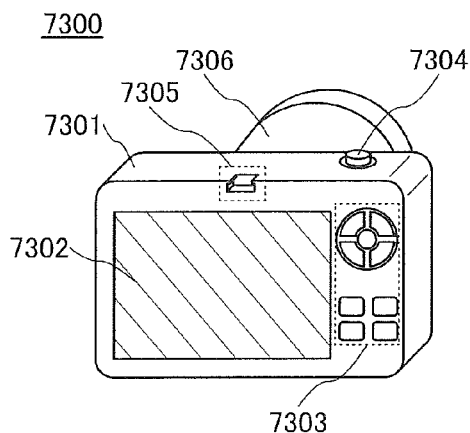

FIG. 32E is an external view of a camera 7300. The camera 7300 includes a housing 7301, a display portion 7302, an operation button 7303, a shutter button 7304, a connection portion 7305, and the like. A lens 7306 can be put on the camera 7300.

The connection portion 7305 includes an electrode to connect with a finder 7400, which is described below, a stroboscope, or the like.

Although the lens 7306 of the camera 7300 here is detachable from the housing 7301 for replacement, the lens 7306 may be included in the housing 7301.

Images can be taken at the touch of the shutter button 7304. In addition, images can be taken by operation of the display portion 7302 including a touch sensor.

In the display portion 7302, the display device of one embodiment of the present invention or a touch sensor can be used.

Figure 32F:
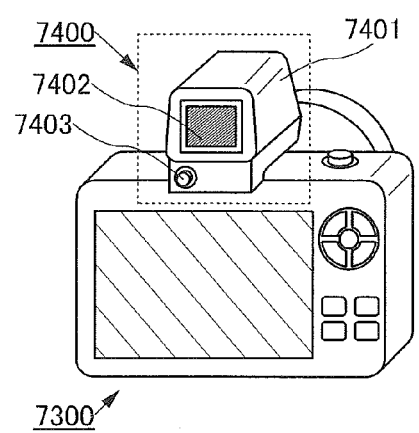

FIG. 32F illustrates the camera 7300 with the finder 7400 connected.

The finder 7400 includes a housing 7401, a display portion 7402, a button 7403, and the like.

The housing 7401 includes a connection portion for engagement with the connection portion 7305 of the camera 7300 so that the finder 7400 can be connected to the camera 7300. The connection portion includes an electrode, and an image or the like received from the camera 7300 through the electrode can be displayed on the display portion 7402.

The button 7403 has a function of a power button, and the display portion 7402 can be turned on and off with the button 7403.

Although the camera 7300 and the finder 7400 are separate and detachable electronic devices in FIGS. 32E and 32F, the housing 7301 of the camera 7300 may include a finder having a display device of one embodiment of the present invention or a touch sensor.

Figure 33A:
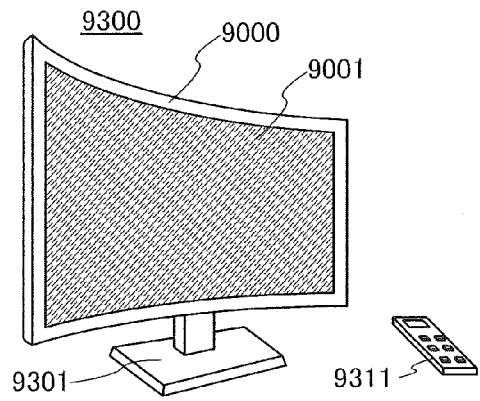
FIGS. 33A to 33D illustrate electronic devices of embodiments of the present invention.

FIG. 33A illustrates an example of a television set. In the television set 9300, the display portion 9001 is incorporated into the housing 9000. Here, the housing 9000 is supported by a stand 9301.

The television set 9300 illustrated in FIG. 33A can be operated with an operation switch of the housing 9000 or a separate remote controller 9311. The display portion 9001 may include a touch sensor. The television set 9300 may be operated by touching the display portion 9001 with a finger or the like. The remote controller 9311 may be provided with a display portion for displaying data output from the remote controller 9311. With operation keys or a touch panel of the remote controller 9311, channels or volume can be controlled and images displayed on the display portion 9001 can be controlled.

The television set 9300 is provided with a receiver, a modem, or the like. A general television broadcast can be received with the receiver. When the television set is connected to a communication network with or without wires via the modem, one-way (from a transmitter to a receiver) or two-way (between a transmitter and a receiver or between receivers) data communication can be performed.

The electronic device or the lighting device of one embodiment of the present invention has flexibility and therefore can be incorporated along a curved inside/outside wall surface of a house or a building or a curved interior/exterior surface of a car.

Figure 33B:
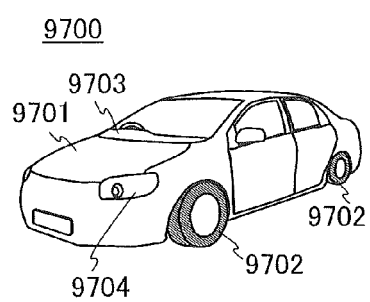
Figure 33C:
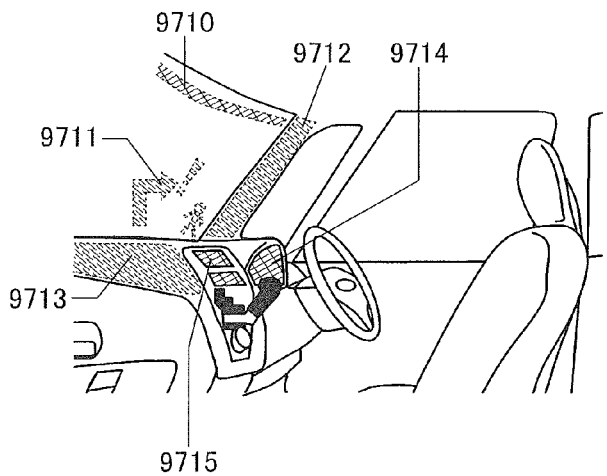

FIG. 33B is an external view of an automobile 9700. FIG. 33C illustrates a driver's seat of the automobile 9700. The automobile 9700 includes a car body 9701, wheels 9702, a dashboard 9703, lights 9704, and the like. The display device, the light-emitting device, or the like of one embodiment of the present invention can be used in a display portion or the like of the automobile 9700. For example, the display device, the light-emitting device, or the like of one embodiment of the present invention can be used in display portions 9710 to 9715 illustrated in FIG. 33C.

The display portion 9710 and the display portion 9711 are each a display device provided in an automobile windshield. The display device, the light-emitting device, or the like of one embodiment of the present invention can be a see-through display device, through which the opposite side can be seen, using a light-transmitting conductive material for its electrodes and wirings. Such a see-through display portion 9710 or 9711 does not hinder driver's vision during driving the automobile 9700. Thus, the display device, the light-emitting device, or the like of one embodiment of the present invention can be provided in the windshield of the automobile 9700. Note that in the case where a transistor or the like for driving the display device, the light-emitting device, or the like is provided, a transistor having a light-transmitting property, such as an organic transistor using an organic semiconductor material or a transistor using an oxide semiconductor, is preferably used.

The display portion 9712 is a display device provided on a pillar portion. For example, an image taken by an imaging unit provided in the car body is displayed on the display portion 9712, whereby the view hindered by the pillar can be compensated. The display portion 9713 is a display device provided on a dashboard portion. For example, an image taken by an imaging unit provided in the car body is displayed on the display portion 9713, whereby the view hindered by the dashboard can be compensated. That is, by displaying an image taken by an imaging unit provided on the outside of the automobile, blind areas can be eliminated and safety can be increased. Displaying an image to compensate for the area which a driver cannot see, makes it possible for the driver to confirm safety easily and comfortably.

Figure 33D:
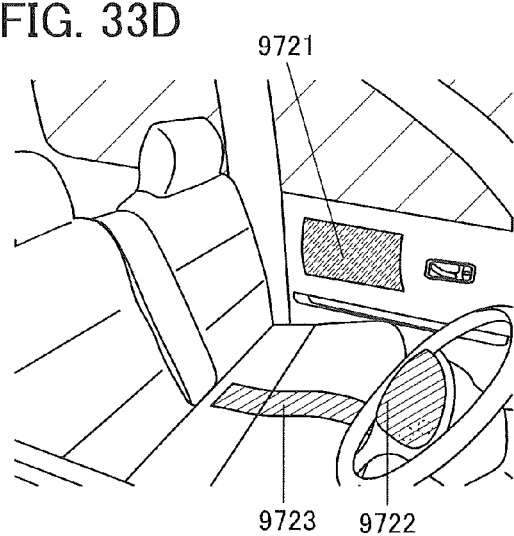

FIG. 33D illustrates the inside of a car in which bench seats are used for a driver seat and a front passenger seat. A display portion 9721 is a display device provided in a door portion. For example, an image taken by an imaging unit provided in the car body is displayed on the display portion 9721, whereby the view hindered by the door can be compensated. A display portion 9722 is a display device provided in a steering wheel. A display portion 9723 is a display device provided in the middle of a seating face of the bench seat. Note that the display device can be used as a seat heater by providing the display device on the seating face or backrest and by using heat generation of the display device as a heat source.

The display portion 9714, the display portion 9715, and the display portion 9722 can provide a variety of kinds of information such as navigation data, a speedometer, a tachometer, a mileage, a fuel meter, a gearshift indicator, and air-condition setting. The content, layout, or the like of the display on the display portions can be changed freely by a user as appropriate. The information listed above can also be displayed on the display portions 9710 to 9713, 9721, and 9723. The display portions 9710 to 9715 and 9721 to 9723 can also be used as lighting devices. The display portions 9710 to 9715 and 9721 to 9723 can also be used as heating devices.

Figure 34A:
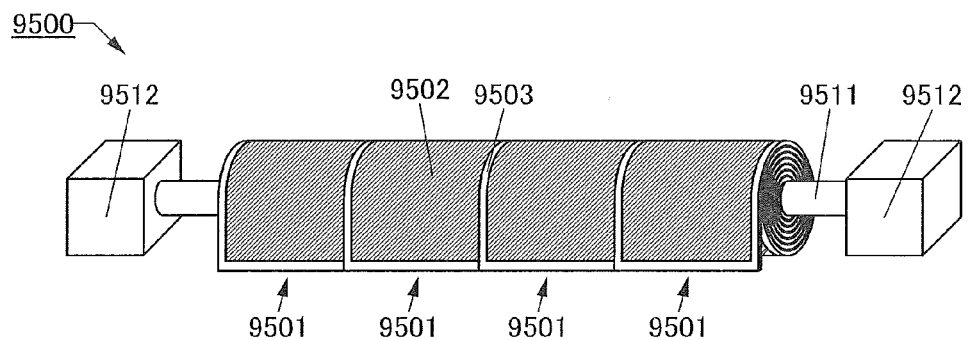
FIGS. 34A and 34B are perspective views illustrating a display device of one embodiment of the present invention.
Figure 34B:
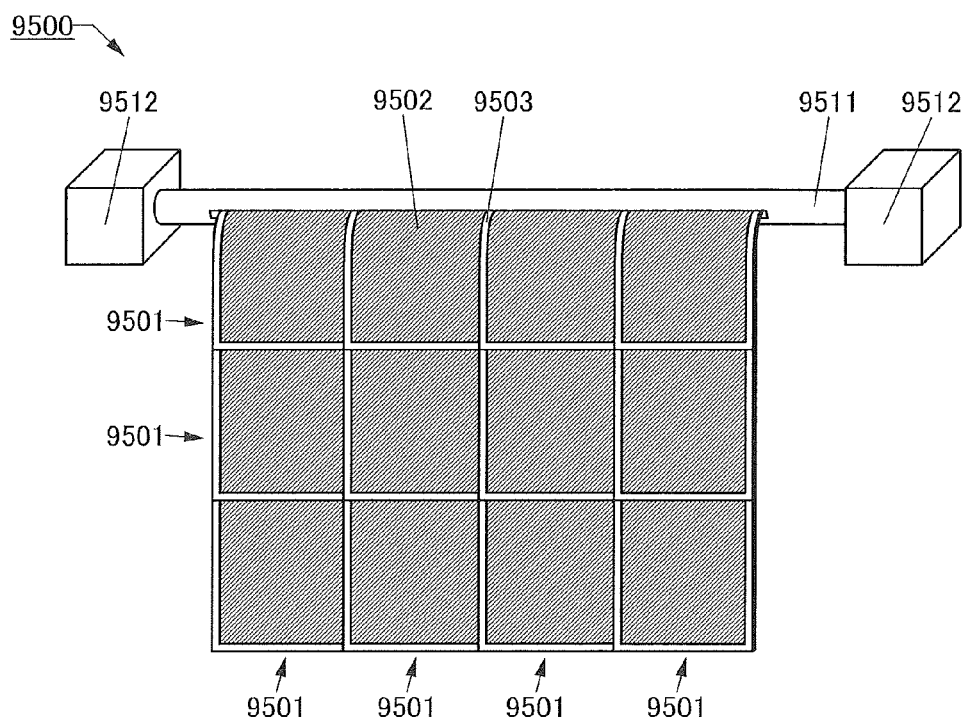

A display device 9500 illustrated in FIGS. 34A and 34B includes a plurality of display panels 9501, a hinge 9511, and a bearing 9512. The plurality of display panels 9501 each include a display region 9502 and a light-transmitting region 9503.

Each of the plurality of display panels 9501 is flexible. Two adjacent display panels 9501 are provided so as to partly overlap with each other. For example, the light-transmitting regions 9503 of the two adjacent display panels 9501 can be overlapped each other. A display device having a large screen can be obtained with the plurality of display panels 9501. The display device is highly versatile because the display panels 9501 can be wound depending on its use.

Moreover, although the display regions 9502 of the adjacent display panels 9501 are separated from each other in FIGS. 34A and 34B, without limitation to this structure, the display regions 9502 of the adjacent display panels 9501 may overlap with each other without any space so that a continuous display region 9502 is obtained, for example.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

The structure described in this embodiment can be used in combination with any of the structures described in the other embodiments as appropriate.

Embodiment 12

In this embodiment, a light-emitting device including the light-emitting element of one embodiment of the present invention is described with reference to FIGS. 35A to 35C and FIGS. 36A to 36D.

Figure 35A:
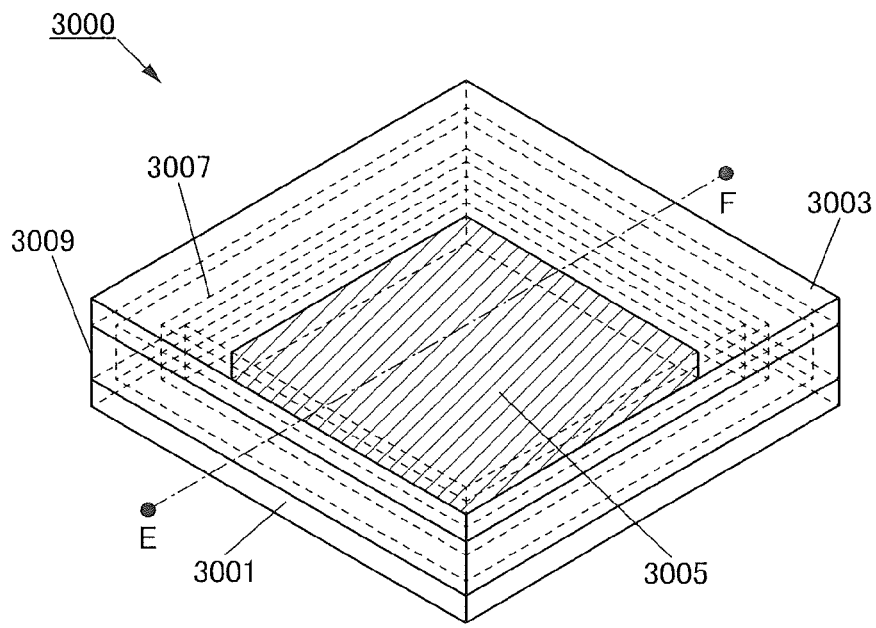
FIGS. 35A to 35C are a perspective view and cross-sectional views illustrating a light-emitting device of one embodiment of the present invention.
Figure 35B:
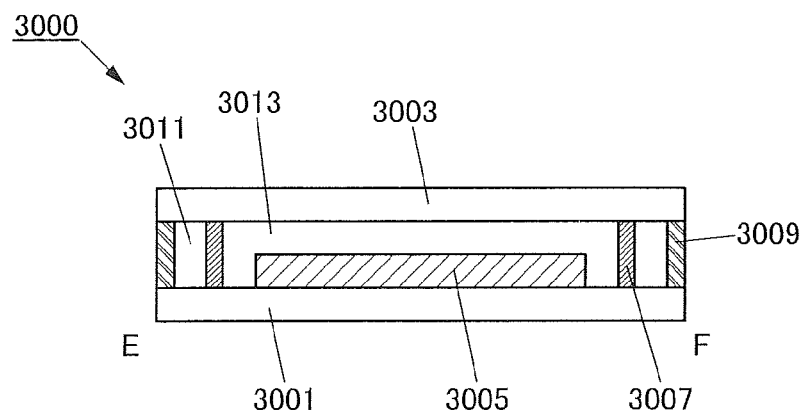

FIG. 35A is a perspective view of a light-emitting device 3000 shown in this embodiment, and FIG. 35B is a cross-sectional view along the dashed-dotted line E-F in FIG. 35A. Note that in FIG. 35A, some components are illustrated by broken lines in order to avoid complexity of the drawing.

The light-emitting device 3000 illustrated in FIGS. 35A and 35B includes a substrate 3001, a light-emitting element 3005 over the substrate 3001, a first sealing region 3007 provided around the light-emitting element 3005, and a second sealing region 3009 provided around the first sealing region 3007.

Light is emitted from the light-emitting element 3005 through one or both of the substrate 3001 and a substrate 3003. In FIGS. 35A and 35B, a structure in which light is emitted from the light-emitting element 3005 to the lower side (the substrate 3001 side) is illustrated.

As illustrated in FIGS. 35A and 35B, the light-emitting device 3000 has a double sealing structure in which the light-emitting element 3005 is surrounded by the first sealing region 3007 and the second sealing region 3009. With the double sealing structure, entry of impurities (e.g., water, oxygen, and the like) from the outside into the light-emitting element 3005 can be favorably suppressed. Note that it is not necessary to provide both the first sealing region 3007 and the second sealing region 3009. For example, only the first sealing region 3007 may be provided.

Note that in FIG. 35B, the first sealing region 3007 and the second sealing region 3009 are each provided in contact with the substrate 3001 and the substrate 3003. However, without limitation to such a structure, for example, one or both of the first sealing region 3007 and the second sealing region 3009 may be provided in contact with an insulating film or a conductive film provided on the substrate 3001. Alternatively, one or both of the first sealing region 3007 and the second sealing region 3009 may be provided in contact with an insulating film or a conductive film provided on the substrate 3003.

The substrate 3001 and the substrate 3003 can have structures similar to those of the substrate 200 and the substrate 220 described in the above embodiment, respectively. The light-emitting element 3005 can have a structure similar to that of any of the light-emitting elements described in the above embodiments.

For the first sealing region 3007, a material containing glass (e.g., a glass frit, a glass ribbon, and the like) can be used. For the second sealing region 3009, a material containing a resin can be used. With the use of the material containing glass for the first sealing region 3007, productivity and a sealing property can be improved. Moreover, with the use of the material containing a resin for the second sealing region 3009, impact resistance and heat resistance can be improved. However, the materials used for the first sealing region 3007 and the second sealing region 3009 are not limited to such, and the first sealing region 3007 may be formed using the material containing a resin and the second sealing region 3009 may be formed using the material containing glass.

The glass frit may contain, for example, magnesium oxide, calcium oxide, strontium oxide, barium oxide, cesium oxide, sodium oxide, potassium oxide, boron oxide, vanadium oxide, zinc oxide, tellurium oxide, aluminum oxide, silicon dioxide, lead oxide, tin oxide, phosphorus oxide, ruthenium oxide, rhodium oxide, iron oxide, copper oxide, manganese dioxide, molybdenum oxide, niobium oxide, titanium oxide, tungsten oxide, bismuth oxide, zirconium oxide, lithium oxide, antimony oxide, lead borate glass, tin phosphate glass, vanadate glass, or borosilicate glass. The glass frit preferably contains at least one kind of transition metal to absorb infrared light.

As the above glass frits, for example, a frit paste is applied to a substrate and is subjected to heat treatment, laser light irradiation, or the like. The frit paste contains the glass frit and a resin (also referred to as a binder) diluted by an organic solvent. Note that an absorber which absorbs light having the wavelength of laser light may be added to the glass frit. For example, an Nd:YAG laser or a semiconductor laser is preferably used as the laser. The shape of laser light may be circular or quadrangular.

As the above material containing a resin, for example, polyester, polyolefin, polyamide (e.g., nylon or aramid), polyimide, polycarbonate, or an acrylic resin, polyurethane, or an epoxy resin can be used. Alternatively, a material that includes a resin having a siloxane bond such as silicone can be used.

Note that in the case where the material containing glass is used for one or both of the first sealing region 3007 and the second sealing region 3009, the material containing glass preferably has a thermal expansion coefficient close to that of the substrate 3001. With the above structure, generation of a crack in the material containing glass or the substrate 3001 due to thermal stress can be suppressed.

For example, the following advantageous effect can be obtained in the case where the material containing glass is used for the first sealing region 3007 and the material containing a resin is used for the second sealing region 3009.

The second sealing region 3009 is provided closer to an outer portion of the light-emitting device 3000 than the first sealing region 3007 is. In the light-emitting device 3000, distortion due to external force or the like increases toward the outer portion. Thus, the outer portion of the light-emitting device 3000 where a larger amount of distortion is generated, that is, the second sealing region 3009 is sealed using the material containing a resin and the first sealing region 3007 provided on an inner side of the second sealing region 3009 is sealed using the material containing glass, whereby the light-emitting device 3000 is less likely to be damaged even when distortion due to external force or the like is generated.

Furthermore, as illustrated in FIG. 35B, a first region 3011 corresponds to the region surrounded by the substrate 3001, the substrate 3003, the first sealing region 3007, and the second sealing region 3009. A second region 3013 corresponds to the region surrounded by the substrate 3001, the substrate 3003, the light-emitting element 3005, and the first sealing region 3007.

The first region 3011 and the second region 3013 are preferably filled with, for example, an inert gas such as a rare gas or a nitrogen gas. Alternatively, the first region 3011 and the second region 3013 are preferably filled with a resin such as an acrylic resin or an epoxy resin. Note that for the first region 3011 and the second region 3013, a reduced pressure state is preferred to atmospheric pressure state.

Figure 35C:
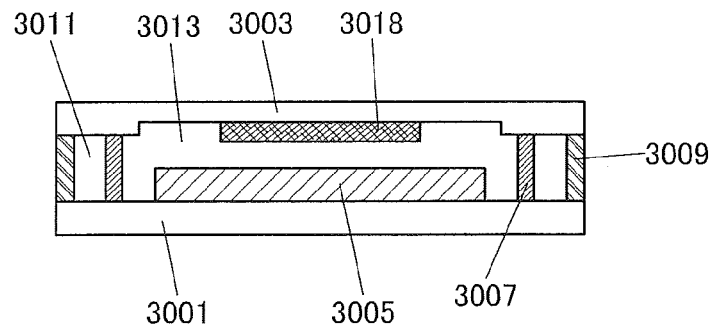

FIG. 35C illustrates a modification example of the structure in FIG. 35B. FIG. 35C is a cross-sectional view illustrating the modification example of the light-emitting device 3000.

FIG. 35C illustrates a structure in which a desiccant 3018 is provided in a recessed portion provided in part of the substrate 3003. The other components are the same as those of the structure illustrated in FIG. 35B.

As the desiccant 3018, a substance which adsorbs moisture and the like by chemical adsorption or a substance which adsorbs moisture and the like by physical adsorption can be used. Examples of the substance that can be used as the desiccant 3018 include alkali metal oxides, alkaline earth metal oxide (e.g., calcium oxide and barium oxide), sulfate, metal halides, perchlorate, zeolite, silica gel, and the like.

Next, modification examples of the light-emitting device 3000 which is illustrated in FIG. 35B are described with reference to FIGS. 36A to 36D. Note that FIGS. 36A to 36D are cross-sectional views illustrating the modification examples of the light-emitting device 3000 illustrated in FIG. 35B.

In each of the light-emitting devices illustrated in FIGS. 36A to 36D, the second sealing region 3009 is not provided but only the first sealing region 3007 is provided. Moreover, in each of the light-emitting devices illustrated in FIGS. 36A to 36D, a region 3014 is provided instead of the second region 3013 illustrated in FIG. 35B.

For the region 3014, for example, polyester, polyolefin, polyamide (e.g., nylon or aramid), polyimide, polycarbonate, or an acrylic resin, polyurethane, or an epoxy resin can be used. Alternatively, a material that includes a resin having a siloxane bond such as silicone can be used.

When the above-described material is used for the region 3014, what is called a solid-sealing light-emitting device can be obtained.

Figure 36A:
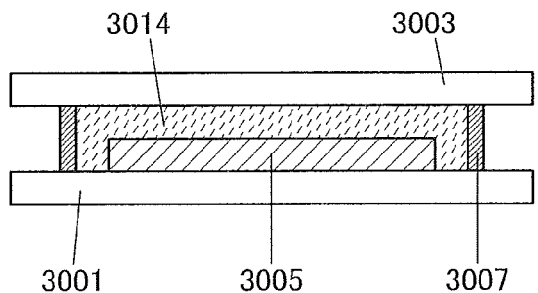
FIGS. 36A to 36D are cross-sectional views each illustrating a light-emitting device of one embodiment of the present invention.
Figure 36B:
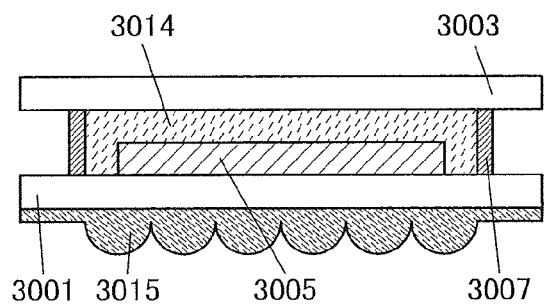

In the light-emitting device illustrated in FIG. 36B, a substrate 3015 is provided on the substrate 3001 side of the light-emitting device illustrated in FIG. 36A.

The substrate 3015 has unevenness as illustrated in FIG. 36B. With a structure in which the substrate 3015 having unevenness is provided on the side through which light emitted from the light-emitting element 3005 is extracted, the efficiency of extraction of light from the light-emitting element 3005 can be improved. Note that instead of the structure having unevenness and illustrated in FIG. 36B, a substrate having a function as a diffusion plate may be provided.

Figure 36C:
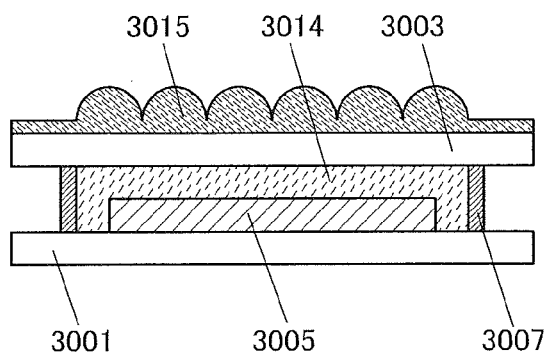

In the light-emitting device illustrated in FIG. 36C, light is extracted through the substrate 3003 side, unlike in the light-emitting device illustrated in FIG. 36A, in which light is extracted through the substrate 3001 side.

The light-emitting device illustrated in FIG. 36C includes the substrate 3015 on the substrate 3003 side. The other components are the same as those of the light-emitting device illustrated in FIG. 36B.

Figure 36D:
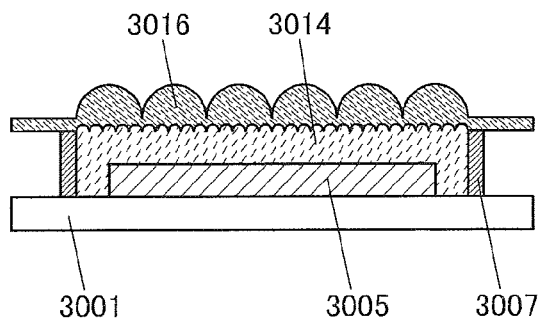

In the light-emitting device illustrated in FIG. 36D, the substrate 3003 and the substrate 3015 included in the light-emitting device illustrated in FIG. 36C are not provided but a substrate 3016 is provided.

The substrate 3016 includes first unevenness positioned closer to the light-emitting element 3005 and second unevenness positioned farther from the light-emitting element 3005. With the structure illustrated in FIG. 36D, the efficiency of extraction of light from the light-emitting element 3005 can be further improved.

Thus, the use of the structure described in this embodiment can provide a light-emitting device in which deterioration of a light-emitting element due to impurities such as moisture and oxygen is suppressed. Alternatively, with the structure described in this embodiment, a light-emitting device having high light extraction efficiency can be obtained.

Note that the structure described in this embodiment can be combined as appropriate with any of the structures described in the other embodiments.

Embodiment 13

In this embodiment, examples in which the light-emitting element of one embodiment of the present invention is used for various lighting devices and electronic devices are described with reference to FIGS. 37A to 37C and FIG. 38.

An electronic device or a lighting device that has a light-emitting region with a curved surface can be obtained with the use of the light-emitting element of one embodiment of the present invention which is manufactured over a substrate having flexibility.

Furthermore, a light-emitting device to which one embodiment of the present invention is applied can also be used for lighting for motor vehicles, examples of which are lighting for a dashboard, a windshield, a ceiling, and the like.

Figure 37A:
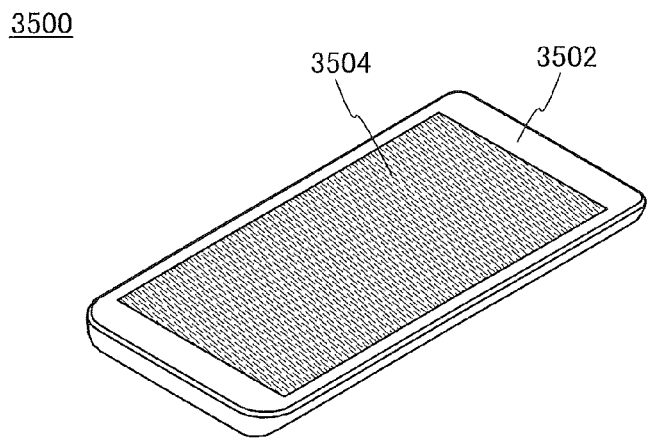
FIGS. 37A to 37C illustrate an electronic device and a lighting device of one embodiment of the present invention.
Figure 37B:
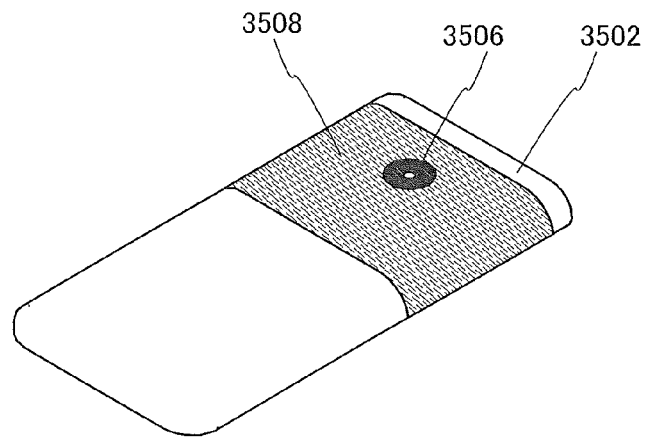

FIG. 37A is a perspective view illustrating one surface of a multifunction terminal 3500, and FIG. 37B is a perspective view illustrating the other surface of the multifunction terminal 3500. In a housing 3502 of the multifunction terminal 3500, a display portion 3504, a camera 3506, lighting 3508, and the like are incorporated. The light-emitting device of one embodiment of the present invention can be used for the lighting 3508.

The lighting 3508 including the light-emitting device of one embodiment of the present invention functions as a planar light source. Thus, unlike a point light source typified by an LED, the lighting 3508 can provide light emission with low directivity. When the lighting 3508 and the camera 3506 are used in combination, for example, imaging can be performed by the camera 3506 with the lighting 3508 lighting or flashing. Because the lighting 3508 functions as a planar light source, a photograph as if taken under natural light can be taken.

Note that the multifunction terminal 3500 illustrated in FIGS. 37A and 37B can have a variety of functions as in the electronic devices illustrated in FIGS. 31A to 31G.

The housing 3502 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. When a detection device including a sensor for detecting inclination, such as a gyroscope or an acceleration sensor, is provided inside the multifunction terminal 3500, display on the screen of the display portion 3504 can be automatically switched by determining the orientation of the multifunction terminal 3500 (whether the multifunction terminal is placed horizontally or vertically for a landscape mode or a portrait mode).

The display portion 3504 may function as an image sensor. For example, an image of a palm print, a fingerprint, or the like is taken when the display portion 3504 is touched with the palm or the finger, whereby personal authentication can be performed. Furthermore, by providing a backlight or a sensing light source which emits near-infrared light in the display portion 3504, an image of a finger vein, a palm vein, or the like can be taken. Note that the light-emitting device of one embodiment of the present invention may be used for the display portion 3504.

Figure 37C:
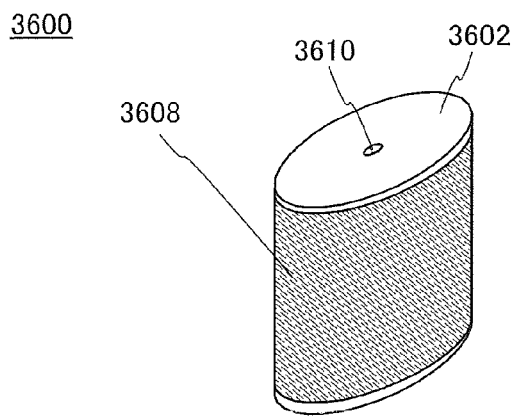

FIG. 37C is a perspective view of a security light 3600. The security light 3600 includes lighting 3608 on the outside of the housing 3602, and a speaker 3610 and the like are incorporated in the housing 3602. The light-emitting device of one embodiment of the present invention can be used for the lighting 3608.

The security light 3600 can emit light when the lighting 3608 is gripped or held, for example. An electronic circuit that can control the manner of light emission from the security light 3600 may be provided in the housing 3602. The electronic circuit may be a circuit that enables light emission once or intermittently a plurality of times or may be a circuit that can adjust the amount of emitted light by controlling the current value for light emission. A circuit with which a loud audible alarm is output from the speaker 3610 at the same time as light emission from the lighting 3608 may be incorporated.

The security light 3600 can emit light in various directions; therefore, it is possible to intimidate a thug or the like with light, or light and sound. Moreover, the security light 3600 may include a camera such as a digital still camera to have a photography function.

Figure 38:
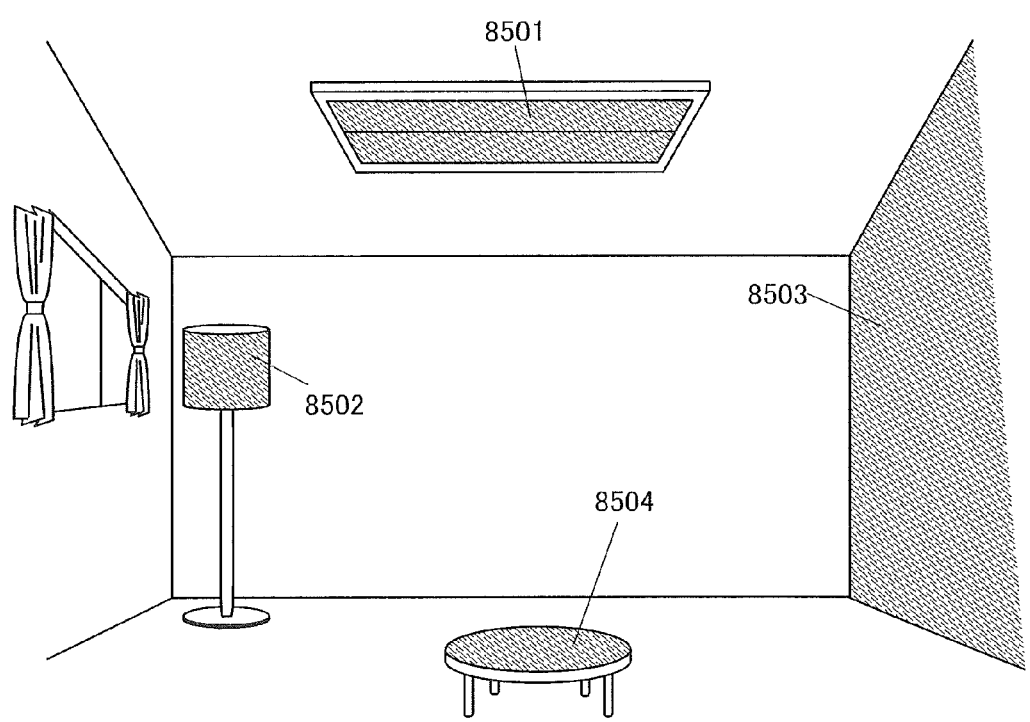
FIG. 38 illustrates lighting devices of embodiments of the present invention.

FIG. 38 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

As described above, lighting devices and electronic devices can be obtained by application of the light-emitting device of one embodiment of the present invention. Note that the light-emitting device can be used for electronic devices in a variety of fields without being limited to the lighting devices and the electronic devices described in this embodiment.

The structure described in this embodiment can be used in combination with any of the structures described in the other embodiments as appropriate.

Example 1

In this example, a method of synthesizing one of the compounds that are described in Embodiment 1 and represented by General Formula (G0), 4-[4-(9'-phenyl-3,3'-bi-9H-carbazol-9-yl)phenyl]benzofuro[3,2-d]pyrimidine (abbreviation: 4PCCzPBfpm) (Structural Formula (100)), and characteristics of the compound are described.

Synthesis Example 1

Step 1: Synthesis of 9-(4-Bromophenyl)-9'-Phenyl-3,3'-bi-9H-carbazole

First, 6.0 g of 9-phenyl-3,3'-bi-9H-carbazole, 8.3 g of 4-bromoiodobenzene, and 6.1 g (44 mmol) of potassium carbonate were put in a three-neck flask equipped with a reflux pipe, and the air in the flask was replaced with nitrogen. To this mixture were added 100 mL of toluene, 1.41 g (23.4 mmol) of ethylenediamine (abbreviation: EDA), and 2.4 g (12.5 mmol) of copper iodide, and the mixture was heated at 125° C. for 46 hours under a nitrogen stream. The obtained reaction liquid was filtered through Celite, and the filtrate was subjected to extraction with ethyl acetate. The obtained solution of the extract was washed with saturated brine. Magnesium sulfate was added and filtration was performed. The solvent of the obtained filtrate was distilled off. Purification was conducted by silica gel column chromatography using a 1:3 toluene-hexane mixed solvent as the developing solvent to give 5.9 g of the desired substance (as a yellow solid in a yield of 71%). The synthesis scheme of Step 1 is shown in the following equation (A-1).

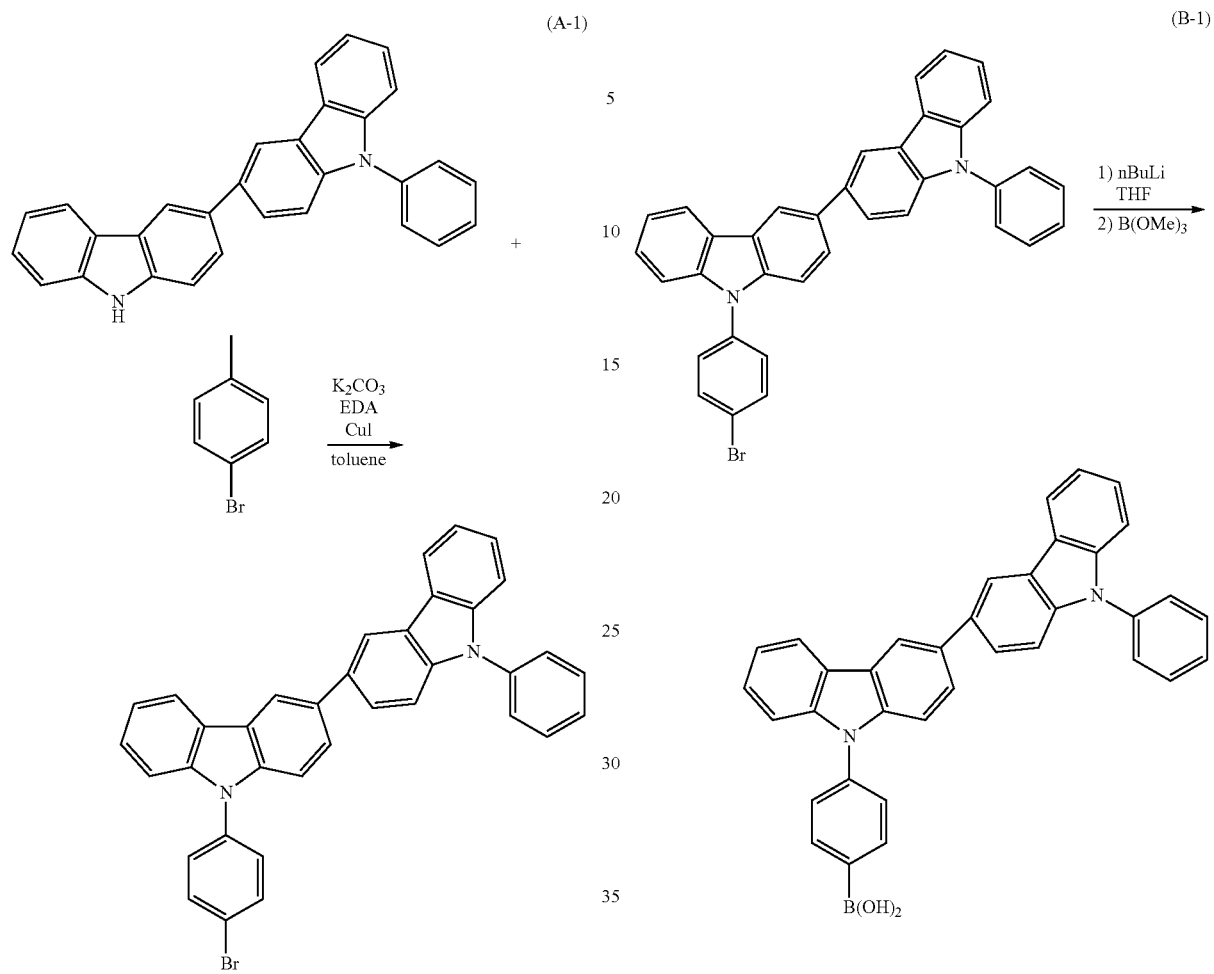

Step 2: Synthesis of B-[4-(9'-phenyl-3,3'-bi-9H-carbazol-9-yl)phenyl]boronic acid Next, 5.9 g (10 mmol) of 9-(4-bromophenyl)-9'-phenyl-3,3'-bi-9H-carbazole synthesized in Step 1 described above was put in a three-neck flask, and the air in the flask was replaced with nitrogen. To this mixture was added 100 mL of tetrahydrofuran (abbreviation: THF). The container was cooled to −78° C., and 10 mL of n-butyllithium (1.6 mol/L) was added dropwise. The mixture was returned to room temperature and stirred for approximately 10 minutes. The container was again cooled to −78° C., and 2.2 g (21 mmol) of trimethyl borate was added dropwise. The mixture was returned to room temperature and stirred for 12 hours. To the obtained reaction substance was added 1M hydrochloric acid, and the mixture was stirred for 30 minutes. Then, the organic layer was extracted with ethyl acetate. The obtained solution of the extract was washed with a saturated aqueous solution of sodium hydrogen carbonate. Magnesium sulfate was added and filtration was performed. The solvent of the obtained filtrate was distilled off. Recrystallization was conducted using a mixed solvent of toluene and hexane to give 2.9 g of the desired substance (as a yellow solid in a yield of 54%). The synthesis scheme of Step 2 is shown in the following equation (B-1).

Step 3: Synthesis of 4PCCzPBfpm

Next, 0.96 g (4.7 mmol) of 4-chloro[1]benzofuro[3,2-d]pyrimidine, 3.0 g (5.6 mmol) of B-[4-(9'-phenyl-3,3'-bi-9H-carbazol-9-yl)phenyl]boronic acid synthesized by the synthesis method in Step 2 described above, 2.8 mL of a 2M aqueous solution of potassium carbonate, 24 mL of toluene, and 2.4 mL of ethanol were put in a three-neck flask equipped with a reflux pipe, and the air in the flask was replaced with nitrogen. To this mixture was added 0.43 g (0.38 mmol) of tetrakis(triphenylphosphine)palladium(0), and the mixture was heated and stirred at 80° C. for 16 hours. The obtained reaction substance was filtered, and washing with water and ethanol was performed. The obtained residue was dissolved in hot toluene, and the mixture was filtered through a filter aid in which Celite, aluminum oxide, and Celite were filled in this order. The solvent of the obtained filtrate was distilled off, and purification was conducted by silica gel column chromatography using chloroform as the developing solvent. Then, recrystallization was conducted using a mixed solvent of toluene and hexane to give 2.2 g of 4PCCzPBfpm, which was the desired substance (as a yellow solid in a yield of 71%). Then, 2.2 g of the yellow solid was purified by a train sublimation method. In the purification by sublimation, the yellow solid was heated at 320° C. under a pressure of 2.7 Pa with argon gas at a flow rate of 5 mL/min. After the purification by sublimation, 1.6 g of a yellowish white solid of the desired substance was obtained at a collection rate of 72%. The synthesis scheme of Step 3 is shown in the following equation (C-1).

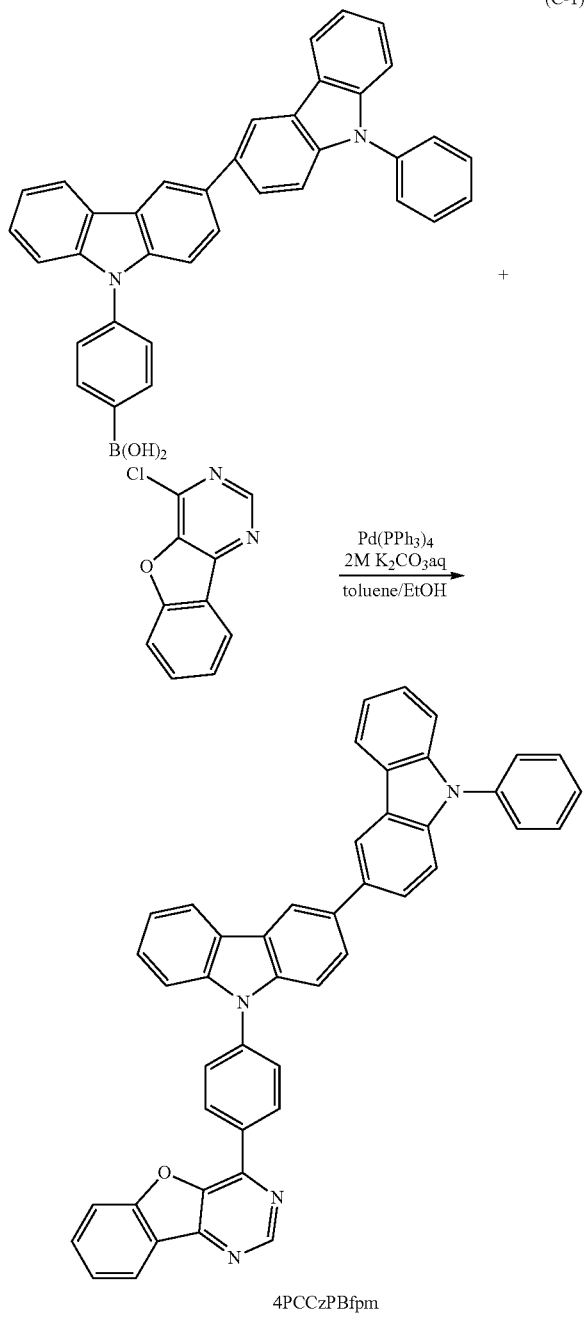

Figure 39:
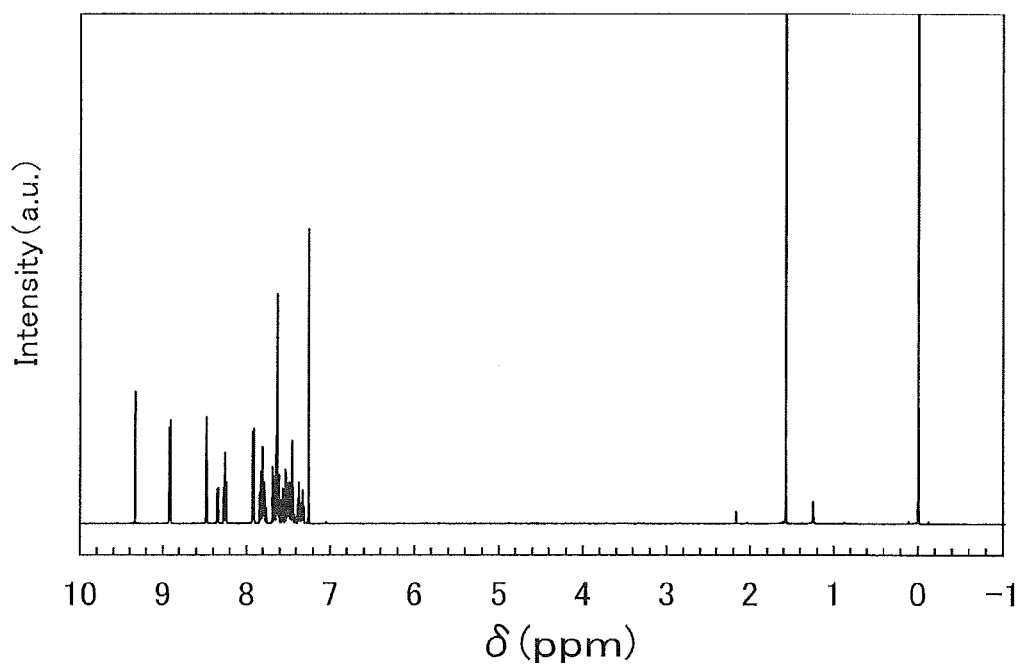
FIG. 39 is an NMR chart of a compound of Example.

Measurement results obtained by nuclear magnetic resonance ($^1$H-NMR) spectroscopy of the yellowish white solid obtained in Step 3 described above are shown below. The $^1$H-NMR chart is shown in FIG. 39. These results reveal that 4PCCzPBfpm, which is one embodiment of the present invention, was obtained in Synthesis Example 1.

$^1$H-NMR. δ(CDCl$_3$): 7.31-7.34 (t, 1H), 7.35-7.38 (t, 1H), 7.44 (d, 2H), 7.46-7.51 (m, 2H), 7.53 (d, 1H), 7.55-7.58 (t, 1H), 7.61-7.69 (m, 6H), 7.76-7.83 (m, 4H), 7.92 (d, 2H), 8.24-8.28 (t, 2H), 8.35 (d, 1H), 8.45 (ts, 2H), 8.91 (d, 2H), 9.33 (s, 1H).

<Characteristics of 4PCCzPBfpm>

Next, mass spectrometry (MS) analysis of 4PCCzPBfpm which was obtained was carried out by liquid chromatography mass spectrometry (abbreviation: LC/MS analysis).

In the LC/MS analysis, liquid chromatography (LC) separation was carried out with ACQUITY UPLC (manufactured by Waters Corporation), and mass spectrometry (MS) analysis was carried out with Xevo G2 Tof MS (manufactured by Waters Corporation). As a column for the LC separation, ACQUITY UPLC BEH C8 (2.1×100 mm, 1.7 μm) was used and the column temperature was set to 40° C. Acetonitrile was used for Mobile Phase A and a 0.1% formic acid aqueous solution was used for Mobile Phase B. A sample was prepared in such a manner that 4PCCzPBfpm was dissolved in chloroform at a given concentration and the solution was diluted with acetonitrile. The injection amount was set to 5.0 μL.

In the MS analysis, ionization was carried out by an electrospray ionization (abbreviation: ESI) method. At this time, the capillary voltage and the sample cone voltage were set to 3.0 kV and 50 V, respectively, and detection was performed in a positive mode. A component with m/z of 653.23 which underwent the ionization under the above-described conditions was collided with an argon gas in a collision cell to dissociate into product ions. Energy (collision energy) for the collision with argon was set to 70 eV. The measurement mass range was set to m/z=100 to 1200. The detection results of the dissociated product ions by time-of-flight (TOF) MS are shown in FIG. 40.

Figure 40:
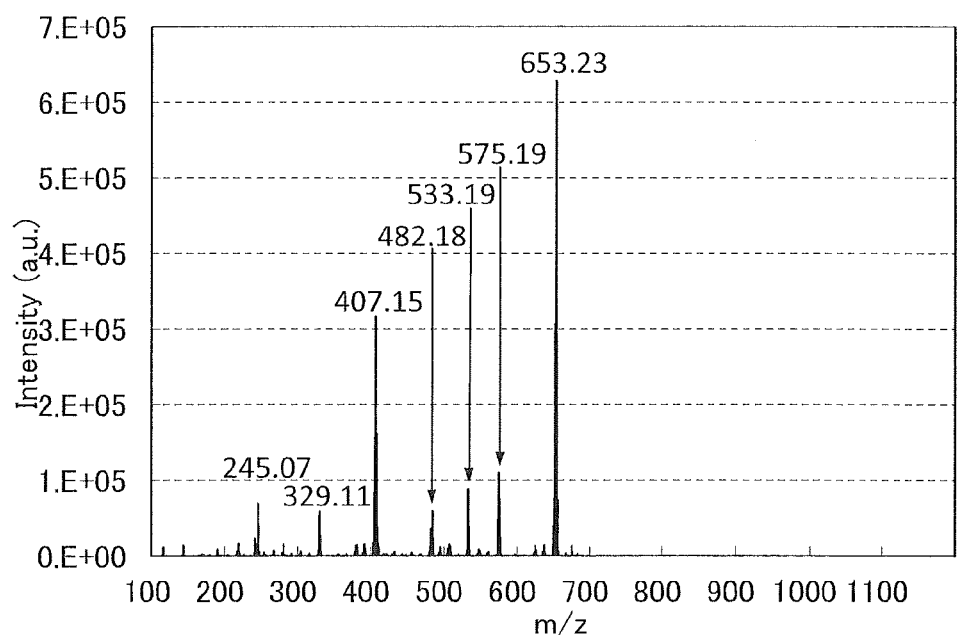
FIG. 40 is a graph showing an MS spectrum of a compound of Example.

FIG. 40 shows that product ions of 4PCCzPBfpm are mainly detected around m/z=575, 533, 482, 407, 329, and 245. The results in FIG. 40 show characteristics derived from 4PCCzPBfpm and can thus be regarded as important data for identifying 4PCCzPBfpm contained in a mixture.

The product ion around m/z=482 is presumed to be a cation in the state where diphenylbicarbazole is dissociated from 4PCCzPBfpm. The product ion around m/z=407 is presumed to be a cation in the state where phenylbicarbazole is further dissociated from the above cation. The product ion around m/z=329 is presumed to be a cation in the state where bicarbazole is further dissociated from the above cation. These data suggest that 4PCCzPBfpm includes diphenylbicarbazole. Furthermore, the product ion around m/z=245 is presumed to be a cation in the state where phenylbenzofuropyrimidine is dissociated from 4PCCzPBfpm, which suggests that 4PCCzPBfpm includes phenylbenzofuropyrimidine.

Figure 41:
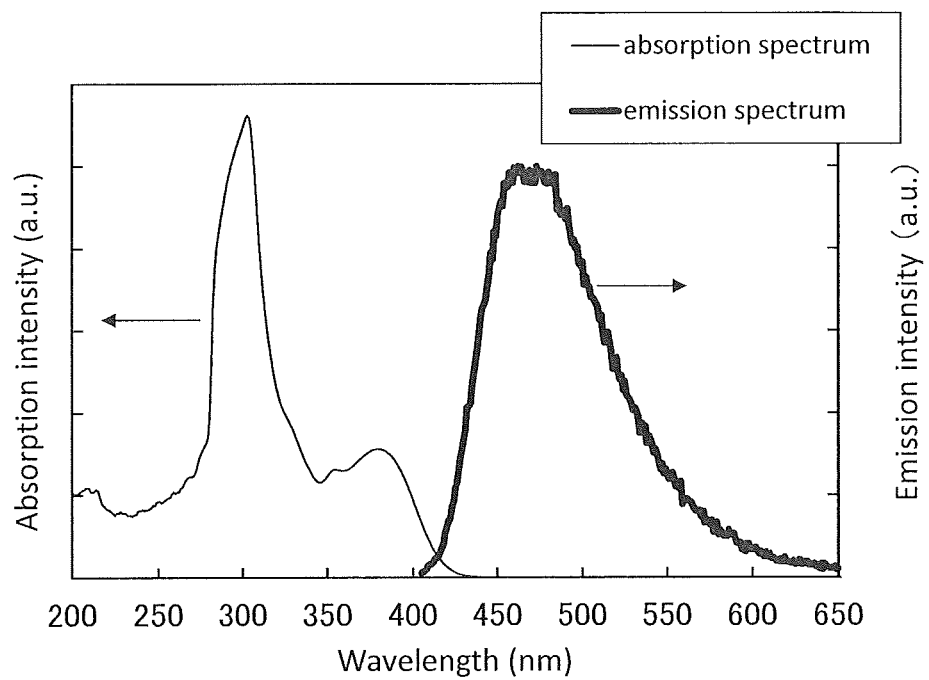
FIG. 41 is a graph showing absorption and emission spectra of a compound of Example.
Figure 42:
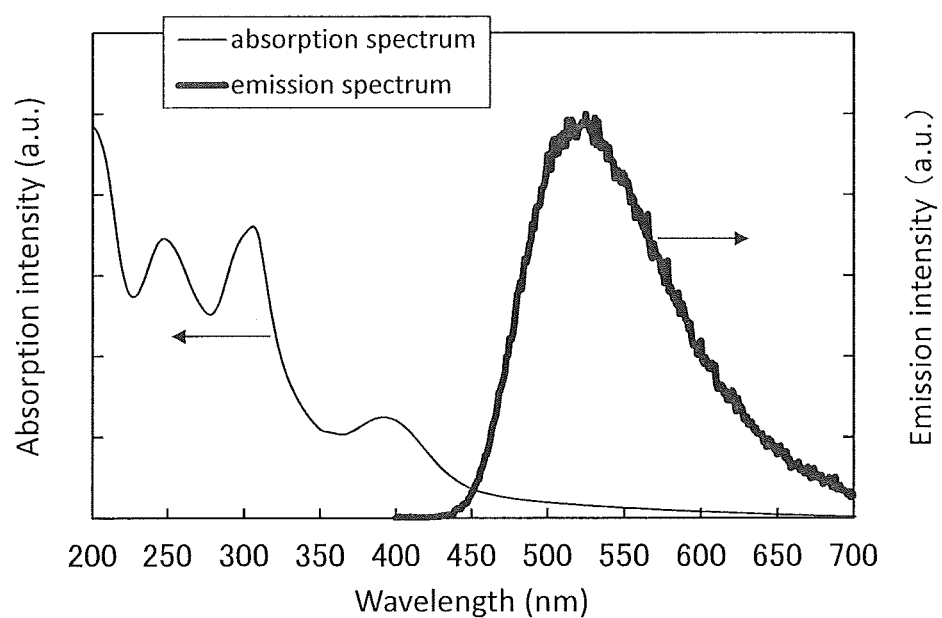
FIG. 42 is a graph showing absorption and emission spectra of a compound of Example.

Absorption and emission spectra of 4PCCzPBfpm in a toluene solution of 4PCCzPBfpm are shown in FIG. 41, and absorption and emission spectra of a thin film of 4PCCzPBfpm are shown in FIG. 42.

The absorption spectra were measured using an ultraviolet-visible spectrophotometer (V-550, produced by JASCO Corporation). The absorption spectrum of 4PCCzPBfpm in the toluene solution was obtained by subtraction of the absorption spectra of toluene and a quartz cell from the absorption spectrum of the toluene solution of 4PCCzPBfpm put in the quartz cell, and is shown in the figure. In addition, as for the absorption spectrum of the thin film, a sample was formed by evaporation of 4PCCzPBfpm over a quartz substrate, and the absorption spectrum obtained by subtraction of the absorption spectrum of quartz from the absorption spectrum of this sample is shown in the figure. The emission spectra were measured with a PL-EL measurement apparatus (manufactured by Hamamatsu Photonics K.K.). The emission spectrum of 4PCCzPBfpm in the toluene solution was measured with the toluene solution of 4PCCzPBfpm put in a quartz cell. The emission spectrum of the thin film was measured with a sample formed by evaporation of 4PCCzPBfpm over a quartz substrate. The thin film whose absorption and emission spectra were measured was formed over a quartz substrate by a vacuum evaporation method.

The maximum absorption wavelength of 4PCCzPBfpm in the toluene solution was around 380 nm, and the maximum emission wavelength thereof was around 473 nm (an excitation wavelength of 390 nm). Furthermore, the maximum absorption wavelength of the thin film was around 392 nm, and the maximum emission wavelength thereof was around 525 nm (an excitation wavelength of 392 nm).

The ionization potential of the thin film of 4PCCzPBfpm was measured in the air with a photoelectron spectrometer (AC-3, produced by Riken Keiki, Co., Ltd.). The obtained value of the ionization potential was converted into a negative value, and the HOMO level of 4PCCzPBfpm was −5.82 eV. From the data of the absorption spectrum of the thin film in FIG. 42, the absorption edge of 4PCCzPBfpm, which was obtained from Tauc plot with an assumption of direct transition, was 2.82 eV. Thus, the optical energy gap of 4PCCzPBfpm in the solid state was estimated at 2.82 eV; from the values of the HOMO level obtained above and this energy gap, the LUMO level of 4PCCzPBfpm can be estimated at −3.00 eV. This reveals that 4PCCzPBfpm in the solid state has an energy gap as wide as 2.82 eV.

The electrochemical characteristics (oxidation reaction characteristics and reduction reaction characteristics) of 4PCCzPBfpm were measured by cyclic voltammetry (CV) measurement. Note that for the measurement, an electrochemical analyzer (ALS model 600A or 600C, produced by BAS Inc.) was used, and the measurement was performed on a solution obtained by dissolving the compound in N,N-dimethylformamide (abbreviation: DMF). In the measurement, the potential of a working electrode with respect to the reference electrode was changed within an appropriate range, so that the oxidation peak potential and the reduction peak potential were obtained. In addition, the HOMO and LUMO levels of the compound were calculated from the estimated redox potential of the reference electrode of −4.94 eV and the obtained peak potentials.

The CV measurement results reveal that the oxidation potential of 4PCCzPBfpm is 0.70 V and the reduction potential is −1.94 V. In addition, the HOMO level and LUMO level of 4PCCzPBfpm, which are calculated from the CV measurement results, are −5.64 eV and −3.01 eV, respectively. Thus, 4PCCzPBfpm is found to have a low LUMO level and a relatively high HOMO level.

Example 2

In this example, a method of synthesizing one of the compounds that are described in Embodiment 1 and represented by General Formula (G0), 4-(9'-phenyl-3,3'-bi-9H-carbazol-9-yl)benzofuro[3,2-d]pyrimidine (abbreviation: 4PCCzBfpm) (Structural Formula (133)), and characteristics of the compound are described.

Synthesis Example 2

Synthesis of 4Pcczbfpm

First, 0.15 g (3.6 mmol) of sodium hydride (60%) was put into a three-neck flask the air in which was replaced with nitrogen, and 10 mL of N,N-dimethylformamide (abbreviation: DMF) was added dropwise thereinto while stirring was performed. The container was cooled to 0° C., a mixed solution of 1.1 g (2.7 mmol) of 9-phenyl-3,3'-bi-9H-carbazole and 15 mL of DMF was added dropwise, and stirring was performed at room temperature for 30 minutes. Then, the container was cooled to 0° C., a mixed solution of 0.50 g (2.4 mmol) of 4-chloro[1]benzofuro[3,2-d]pyrimidine and 15 mL of DMF was added, and stirring was performed at room temperature for 20 hours. The obtained reaction liquid was put into ice water and toluene was added to the mixture. The organic layer was extracted from the mixture with the use of ethyl acetate and washed with saturated brine. Magnesium sulfate was added and filtration was performed. The solvent of the obtained filtrate was distilled off and purification was conducted by silica gel column chromatography using toluene and then a 1:20 toluene-ethyl acetate mixed solvent as the developing solvent. Recrystallization using a mixed solvent of toluene and hexane was performed, so that 1.0 g of 4PCCzBfpm, which was the desired substance, was obtained (as a yellowish white solid in a yield of 72%). Then, 1.0 g of the yellowish white solid was purified by a train sublimation method. In the purification by sublimation, the yellowish white solid was heated at approximately 270° C. to 280° C. under a pressure of 2.6 Pa with argon gas at a flow rate of 5 mL/min. After the purification by sublimation, 0.7 g of a yellowish white solid, which was the desired substance, was obtained at a collection rate of 69%. The synthesis scheme of this step is shown in the following equation (A-2).

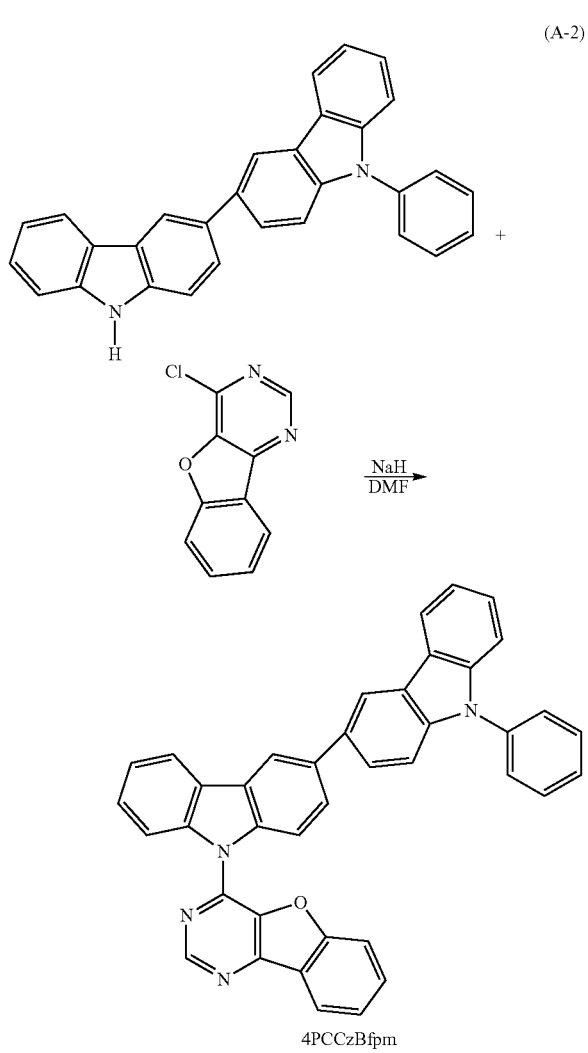

4PCCzBfpm

Figure 43:
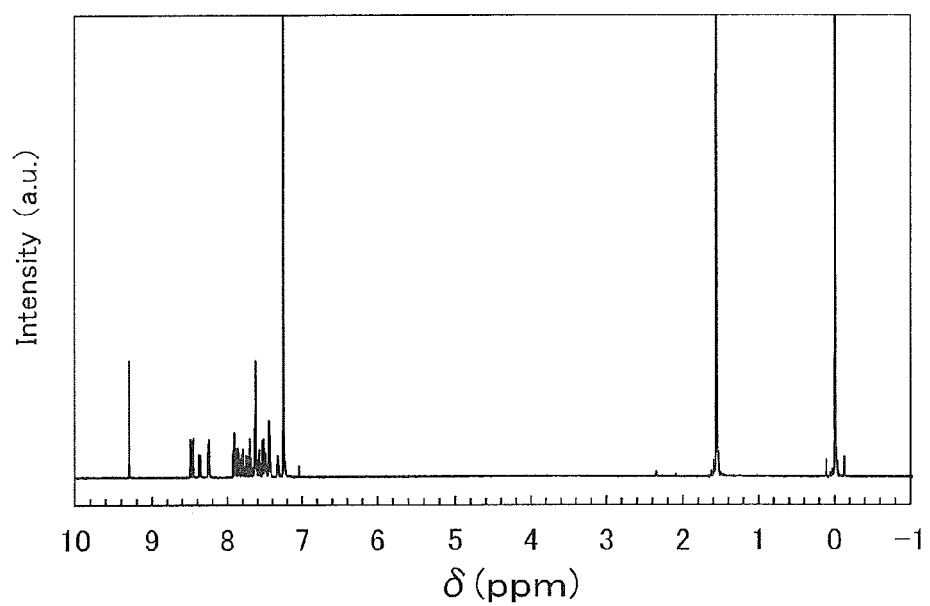
FIG. 43 is an NMR chart of a compound of Example.

Measurement results obtained by nuclear magnetic resonance ($^1$H-NMR) spectroscopy of the yellowish white solid obtained in the above step are shown below. The ¹H-NMR chart is shown in FIG. 43. These results reveal that 4PCC-zBfpm, which is one embodiment of the present invention, was obtained in Synthesis Example 2.

¹H-NMR δ(CDCl₃): 7.31-7.34 (m, 1H), 7.43-7.46 (m, 3H), 7.48-7.54 (m, 3H), 7.57-7.60 (t, 1H), 7.62-7.66 (m, 4H), 7.70 (d, 1H), 7.74-7.77 (dt, 1H), 7.80 (dd, 1H), 7.85 (dd, 1H), 7.88-7.93 (m, 2H), 8.25 (d, 2H), 8.37 (d, 1H), 8.45 (ds, 1H), 8.49 (ds, 1H), 9.30 (s, 1H).

<Characteristics of 4PCCzBfpm>

Next, mass spectrometry (MS) analysis of 4PCCzBfpm which was obtained was carried out by liquid chromatography mass spectrometry (abbreviation: LC/MS analysis).

In the LC/MS analysis, liquid chromatography (LC) separation was carried out with ACQUITY UPLC (manufactured by Waters Corporation), and mass spectrometry (MS) analysis was carried out with Xevo G2 Tof MS (manufactured by Waters Corporation). As a column for the LC separation, ACQUITY UPLC BEH C8 (2.1×100 mm, 1.7 μm) was used and the column temperature was set to 40° C. Acetonitrile was used for Mobile Phase A and a 0.1% formic acid aqueous solution was used for Mobile Phase B. A sample was prepared in such a manner that 4PCCzBfpm was dissolved in toluene at a given concentration and the solution was diluted with acetonitrile. The injection amount was set to 5.0 μL.

In the MS analysis, ionization was carried out by an electrospray ionization (abbreviation: ESI) method. At this time, the capillary voltage and the sample cone voltage were set to 3.0 kV and 50 V, respectively, and detection was performed in a positive mode. A component with m/z of 577.2 which underwent the ionization under the above-described conditions was collided with an argon gas in a collision cell to dissociate into product ions. Energy (collision energy) for the collision with argon was set to 50 eV. The measurement mass range was set to m/z=100 to 1200. The detection results of the dissociated product ions by time-of-flight (TOF) MS are shown in FIG. 44.

Figure 44:
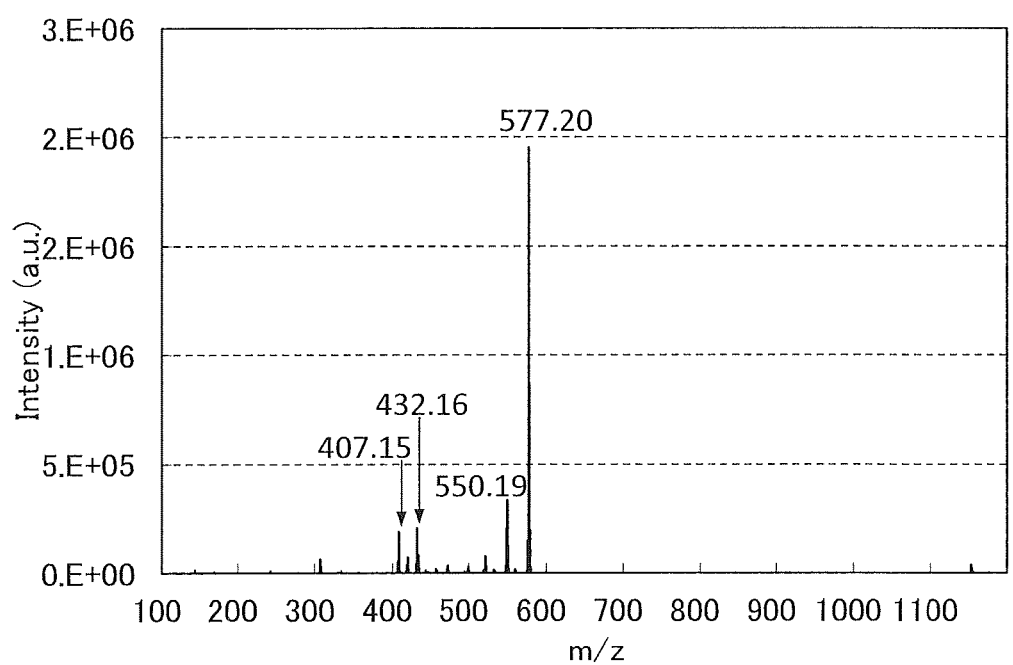
FIG. 44 is a graph showing an MS spectrum of a compound of Example.

FIG. 44 shows that product ions of 4PCCzBfpm are mainly detected around m/z=550, 432, and 407. The results in FIG. 44 show characteristics derived from 4PCCzBfpm and can thus be regarded as important data for identifying 4PCCzBfpm contained in a mixture.

The product ion around m/z=550 is presumed to be a cation generated due to dissociation of nitrile by cleavage of a pyrimidine ring in 4PCCzBfpm. The product ion around m/z=432 is presumed to be a cation generated due to dissociation of benzofuranyl by further cleavage. These data suggest that 4PCCzBfpm includes benzofuropyrimidyl. The product ion around m/z=407 is presumed to be a cation in the state where HPCCz is dissociated from 4PCCzBfpm, which suggests that 4PCCzBfpm includes HPCCz.

Figure 45:
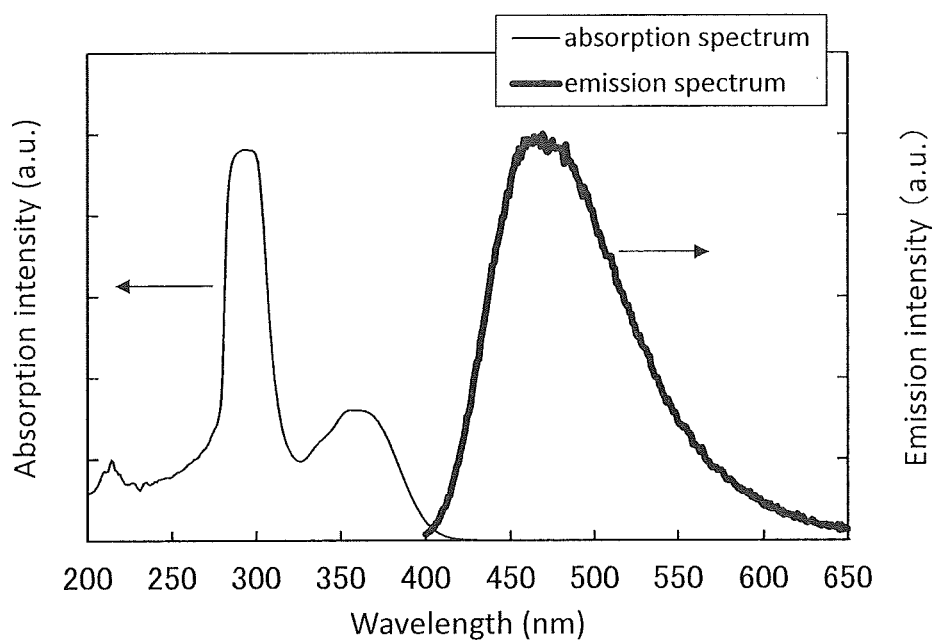
FIG. 45 is a graph showing absorption and emission spectra of a compound of Example.
Figure 46:
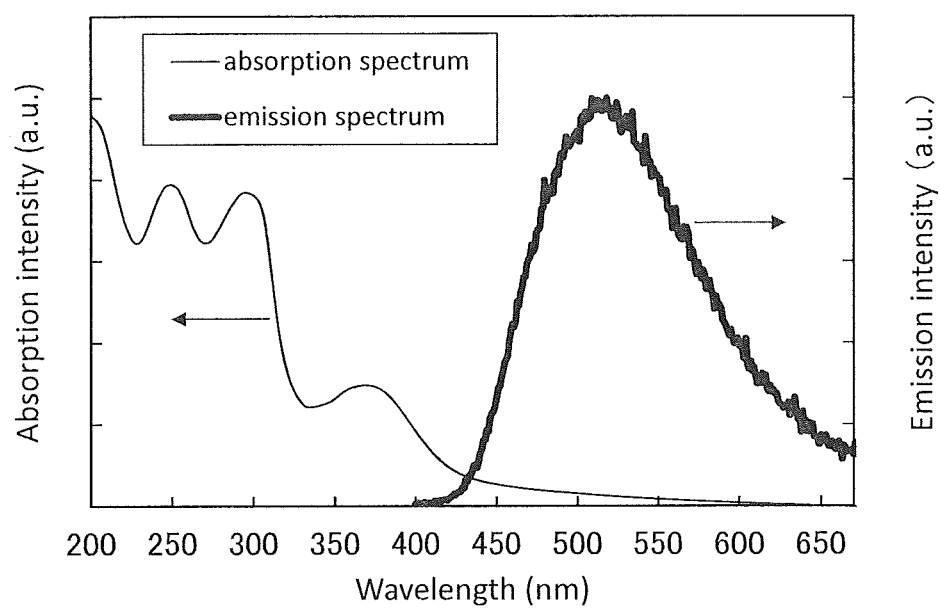
FIG. 46 is a graph showing absorption and emission spectra of a compound of Example.

Absorption and emission spectra of 4PCCzBfpm in a toluene solution of 4PCCzBfpm are shown in FIG. 45, and absorption and emission spectra of a thin film of 4PCCzBfpm are shown in FIG. 46.

The absorption and emission spectra of 4PCCzBfpm in the toluene solution and the thin film of 4PCCzBfpm were measured as in Example 1.

The maximum absorption wavelength of 4PCCzBfpm in the toluene solution was around 357 nm, and the maximum emission wavelength thereof was around 469 nm (an excitation wavelength of 358 nm). Furthermore, the maximum absorption wavelength of the thin film was around 369 nm, and the maximum emission wavelength thereof was around 515 nm (an excitation wavelength of 350 nm).

The ionization potential of the thin film of 4PCCzBfpm was measured in the air with a photoelectron spectrometer (AC-3, produced by Riken Keiki, Co., Ltd.). The obtained value of the ionization potential was converted into a negative value, and the HOMO level of 4PCCzBfpm was −5.77 eV. From the data of the absorption spectrum of the thin film in FIG. 46, the absorption edge of 4PCCzBfpm, which was obtained from Tauc plot with an assumption of direct transition, was 2.98 eV. Thus, the optical energy gap of 4PCCzBfpm in the solid state was estimated at 2.98 eV; from the values of the HOMO level obtained above and this energy gap, the LUMO level of 4PCCzBfpm can be estimated at −2.79 eV. This reveals that 4PCCzBfpm in the solid state has an energy gap as wide as 2.98 eV.

The electrochemical characteristics (oxidation reaction characteristics and reduction reaction characteristics) of 4PCCzBfpm were measured by cyclic voltammetry (CV) measurement. The measurement method was similar to that used in Example 1.

The CV measurement results reveal that the oxidation potential of 4PCCzBfpm is 0.76 V and the reduction potential is −2.10 V. In addition, the HOMO level and LUMO level of 4PCCzBfpm, which are calculated from the CV measurement results, are −5.70 eV and −2.84 eV, respectively. Thus, 4PCCzBfpm is found to have a low LUMO level and a relatively high HOMO level.

Example 3

Figure 47:
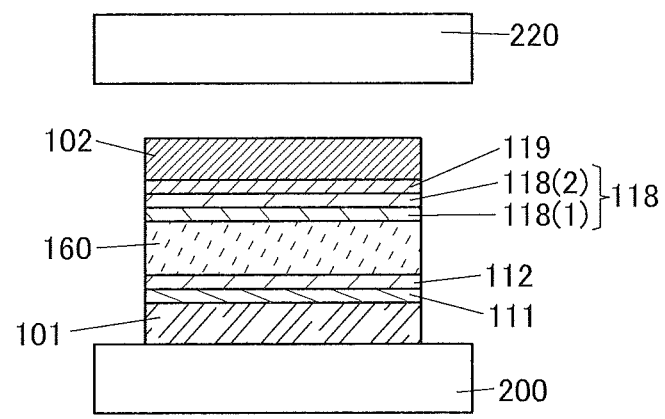
FIG. 47 is a schematic cross-sectional view illustrating a light-emitting element of Example.

In this example, fabrication examples of light-emitting elements each including the compound of one embodiment of the present invention and characteristics of the light-emitting elements are described. FIG. 47 is a schematic cross-sectional view of the light-emitting elements fabricated in this example, and Table 1 shows details of the element structures. In addition, structures and abbreviations of compounds used are given below. Note that the above examples can be referred to for other compounds.

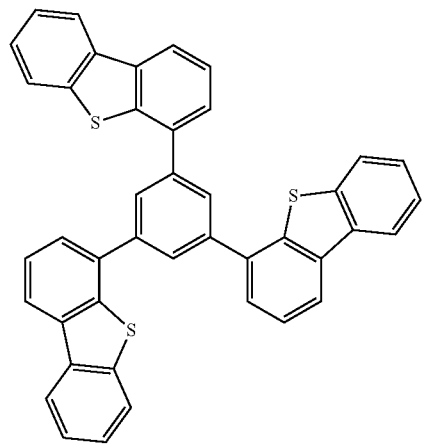

DBT3P-II

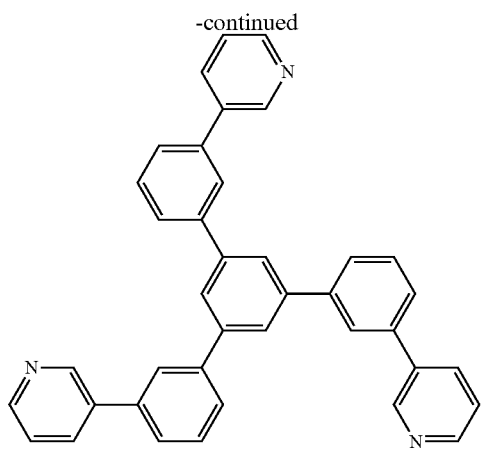

TmPyPB

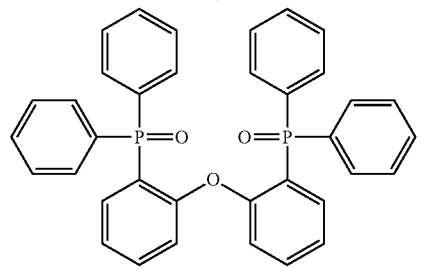

DPEPO

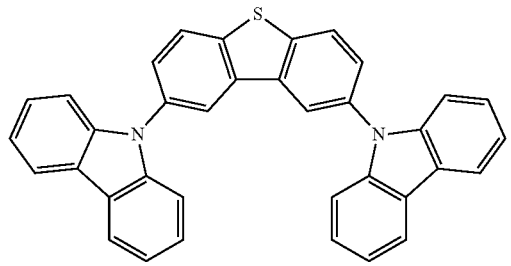

Cz2DBT

TABLE 1

| | Layer | Reference numeral | Film thickness (nm) | Material | Weight ratio |
|---|---|---|---|---|---|
| Light-emitting element 1 | Electrode | 102 | 200 | Al | — |
| | Electron-injection layer | 119 | 1 | LiF | — |
| | Electron-transport layer | 118(2) | 40 | TmPyPB | — |
| | | 118(1) | 5 | DPEPO | — |
| | Light-emitting layer | 160 | 15 | DPEPO:4PCCzPBfpm | 0.85:0.15 |
| | Hole-transport layer | 112 | 20 | Cz2DBT | — |
| | Hole-injection layer | 111 | 20 | DBT3P-II:MoO$_3$ | 1:0.5 |
| | Electrode | 101 | 70 | ITSO | — |
| Light-emitting element 2 | Electrode | 102 | 200 | Al | — |
| | Electron-injection layer | 119 | 1 | LiF | — |
| | Electron-transport layer | 118(2) | 40 | TmPyPB | — |
| | | 118(1) | 5 | DPEPO | — |
| | Light-emitting layer | 160 | 15 | DPEPO:4PCCzBfpm | 0.85:0.15 |
| | Hole-transport layer | 112 | 20 | Cz2DBT | — |
| | Hole-injection layer | 111 | 20 | DBT3P-II:MoO$_3$ | 1:0.5 |
| | Electrode | 101 | 70 | ITSO | — |

<Fabrication of Light-Emitting Elements>
<<Fabrication of Light-Emitting Element 1>>

As the electrode 101, an ITSO film was formed to a thickness of 70 nm over the substrate 200. The electrode area of the electrode 101 was set to 4 mm$^2$ (2 mm×2 mm).

As the hole-injection layer 111, 4,4',4"-(benzene-1,3,5-triyl)tri(dibenzothiophene) (abbreviation: DBT3P-II) and molybdenum oxide (MoO$_3$) were deposited by co-evaporation to a thickness of 20 nm over the electrode 101 such that the weight ratio of DBT3P-II to MoO$_3$ was 1:0.5.

As the hole-transport layer 112, 2,8-di(9H-carbazol-9-yl)-dibenzothiophene (abbreviation: Cz2DBT) was deposited by evaporation to a thickness of 20 nm over the hole-injection layer 111.

As the light-emitting layer 160, bis[2-(diphenylphosphino)phenyl]etheroxide (abbreviation: DPEPO) and 4-[4-(9'-phenyl-3,3'-bi-9H-carbazol-9-yl)phenyl]benzofuro[3,2-d]pyrimidine (abbreviation: 4PCCzPBfpm) were deposited over the hole-transport layer 112 by co-evaporation to a thickness of 15 nm such that the weight ratio of DPEPO to 4PCCzPBfpm was 0.85:0.15. Note that in the light-emitting layer 160, DPEPO corresponds to the host material and 4PCCzPBfpm corresponds to the light-emitting material.

As the electron-transport layer 118, DPEPO and 1,3,5-tris[3-(3-pyridyl)-phenyl]benzene (abbreviation: TmPyPB) were successively deposited by evaporation to thicknesses of 5 nm and 40 nm, respectively, over the light-emitting layer 160. Then, as the electron-injection layer 119, lithium fluoride (LiF) was deposited over the electron-transport layer 118 by evaporation to a thickness of 1 nm. Note that DPEPO in the electron-transport layer 118 also has a function as an exciton-blocking layer, i.e., prevents excitons generated in the light-emitting layer 160 from diffusing to the electrode 102 side.

As the electrode 102, aluminum (Al) was deposited over the electron-injection layer 119 to a thickness of 200 nm.

Next, in a glove box containing a nitrogen atmosphere, the light-emitting element 1 was sealed by fixing the substrate 220 to the substrate 200 over which the organic material was deposited using a sealant for an organic EL device. Specifically, after the sealant was applied to surround the organic material over the substrate 200 and the substrate 200 was bonded to the substrate 220, irradiation with ultraviolet light having a wavelength of 365 nm at 6 J/cm$^2$ and heat treatment at 80° C. for one hour were performed. Through the above steps, the light-emitting element 1 was obtained.

<<Fabrication of Light-Emitting Element 2>>

The light-emitting element 2 was fabricated through the same steps as those for the light-emitting element 1 except for the step of forming the light-emitting layer 160.

As the light-emitting layer 160 of the light-emitting element 2, DPEPO and 4-(9'-phenyl-3,3'-bi-9H-carbazol-9-yl)benzofuro[3,2-d]pyrimidine (abbreviation: 4PCCzBfpm) were deposited by co-evaporation to a thickness of 15 nm such that the weight ratio of DPEPO to 4PCCzBfpm was 0.85:0.15. Note that in the light-emitting layer 160, DPEPO corresponds to the host material and 4PCCzBfpm corresponds to the light-emitting material.

<Characteristics of Light-Emitting Elements>

Next, characteristics of the fabricated light-emitting elements 1 and 2 were measured. Luminances and CIE chromaticities were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 48:
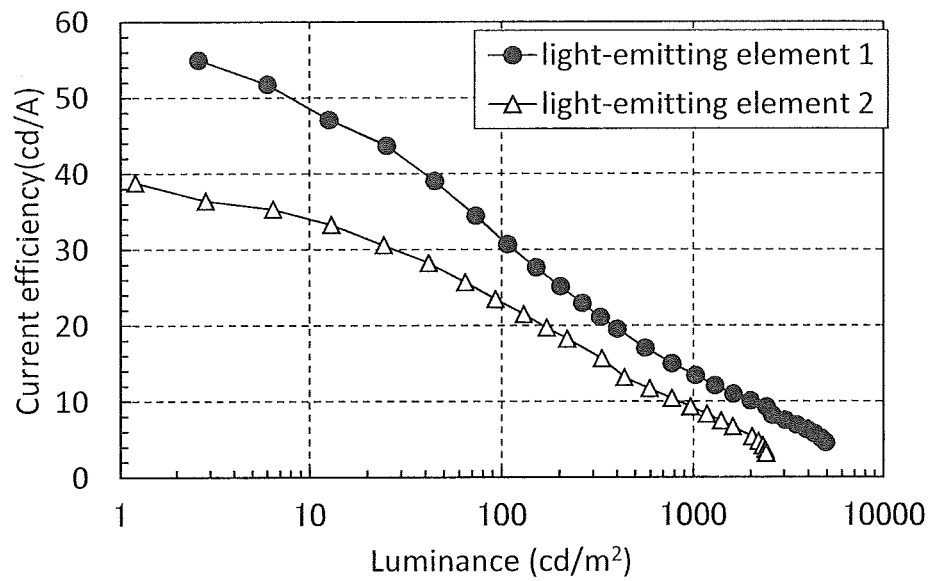
FIG. 48 is a graph showing current efficiency-luminance characteristics of light-emitting elements of Example.
Figure 49:
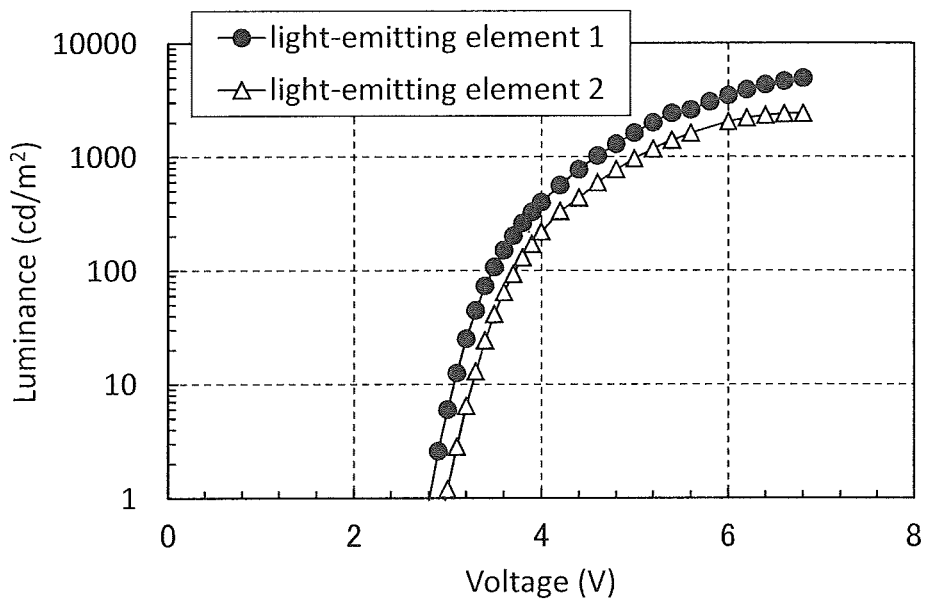
FIG. 49 is a graph showing luminance-voltage characteristics of light-emitting elements of Example.
Figure 50:
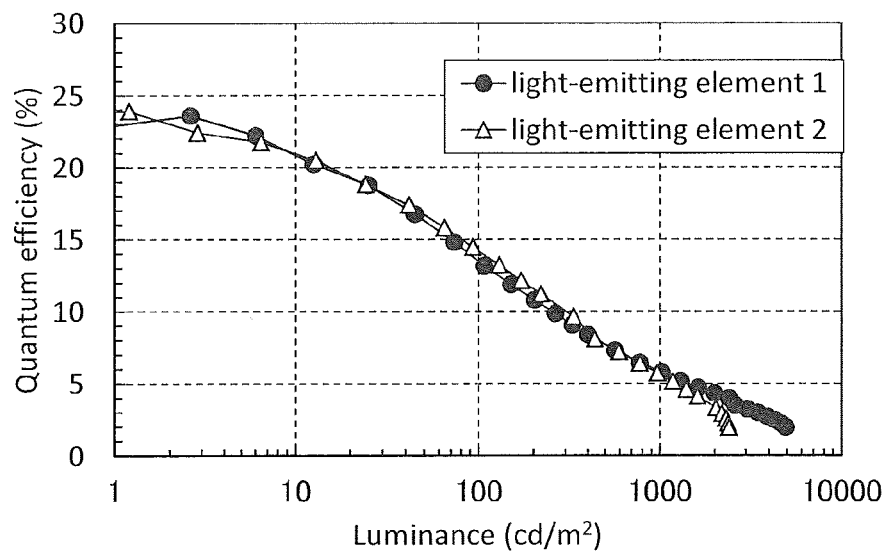
FIG. 50 is a graph showing external quantum efficiency-luminance characteristics of light-emitting elements of Example.

FIG. 48 shows current efficiency-luminance characteristics of the light-emitting elements 1 and 2; FIG. 49 shows luminance-voltage characteristics thereof; and FIG. 50 shows external quantum efficiency-luminance characteristics thereof. The measurements of the light-emitting elements were performed at room temperature (in an atmosphere kept at 23° C.).

Table 2 shows element characteristics of the light-emitting elements 1 and 2 at around 100 cd/m$^2$.

TABLE 2

|  | Voltage (V) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- |
| Light-emitting element 1 | 3.5 | 0.35 | (0.21, 0.43) | 110 | 31 | 28 | 13 |
| Light-emitting element 2 | 3.7 | 0.40 | (0.17, 0.26) | 93 | 23 | 20 | 14 |

Figure 51:
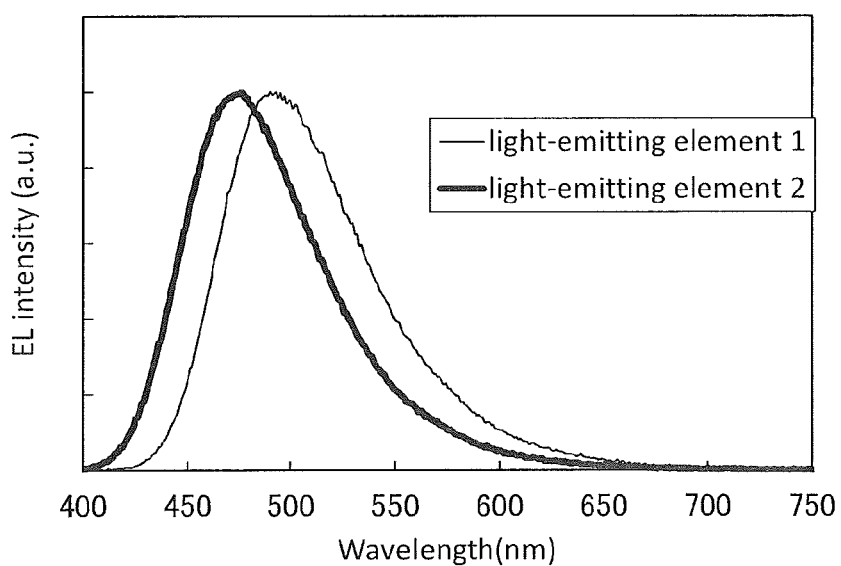
FIG. 51 is a graph showing electroluminescence spectra of light-emitting elements of Example.

FIG. 51 shows electroluminescence spectra when a current at a current density of 2.5 mA/cm$^2$ was supplied to the light-emitting elements 1 and 2.

From FIG. 48 to FIG. 51 and Table 2, it is found that each of the light-emitting elements 1 and 2 has high current efficiency and high external quantum efficiency. The maximum values of the external quantum efficiencies of the light-emitting elements 1 and 2 are 23.6% and 23.9%, respectively, which are extremely excellent values.

As shown in FIG. 51, the light-emitting elements 1 and 2 emit blue light having electroluminescence spectra with peaks at wavelengths of 490 nm and 476 nm, respectively, and with full widths at half maximum of 79 nm and 76 nm, respectively. In particular, the light-emitting element 2 is preferred in that the color purity of the blue light emitted by the light-emitting element 2 is higher than that of the light emitted by the light-emitting element 1.

The light-emitting elements 1 and 2 were driven at a low voltage of 4 V or less at around 100 cd/m$^2$ and thus exhibited high power efficiency.

Since the probability of formation of singlet excitons which are generated by recombination of carriers (holes and electrons) injected from a pair of electrodes is 25%, when the light extraction efficiency to the outside is 25%, the external quantum efficiency is at most 6.25%. The external quantum efficiency of each of the light-emitting elements 1 and 2 is higher than 6.25%. The reason for the high external quantum efficiency of each of the light-emitting elements 1 and 2 is that light originating from singlet excitons generated by reverse intersystem crossing from triplet excitons can be obtained as well as light originating from singlet excitons generated by recombination of carriers injected from the pair of electrodes.

<Transient Fluorescent Characteristics of Light-Emitting Materials>

To confirm the above results, transient fluorescent characteristics of 4PCCzPBfpm and 4PCCzBfpm, which are compounds of embodiments of the present invention, were examined by time-resolved emission measurements.

The time-resolved emission measurements were performed on a thin-film sample in which DPEPO and 4PCCzPBfpm were deposited by co-evaporation over a quartz substrate to a thickness of 50 nm such that the weight ratio of DPEPO to 4PCCzPBfpm was 0.8:0.2 and a thin-film sample in which DPEPO and 4PCCzBfpm were deposited by co-evaporation over a quartz substrate to a thickness of 50 nm such that the weight ratio of DPEPO to 4PCCzBfpm was 0.8:0.2.

A picosecond fluorescence lifetime measurement system (manufactured by Hamamatsu Photonics K.K.) was used for the measurements. In these measurements, the thin film was irradiated with pulsed laser, and emission of the thin film which was attenuated from the laser irradiation underwent a time-resolved measurement using a streak camera to measure the lifetime of fluorescent emission of the thin film. A nitrogen gas laser with a wavelength of 337 nm was used as the pulsed laser. The thin film was irradiated with pulsed laser with a pulse width of 500 ps at a repetition rate of 10 Hz. By integrating data obtained by the repeated measurements, data with a high S/N ratio was obtained. The measurements were performed at room temperature (in an atmosphere kept at 23° C.).

Figure 52A:
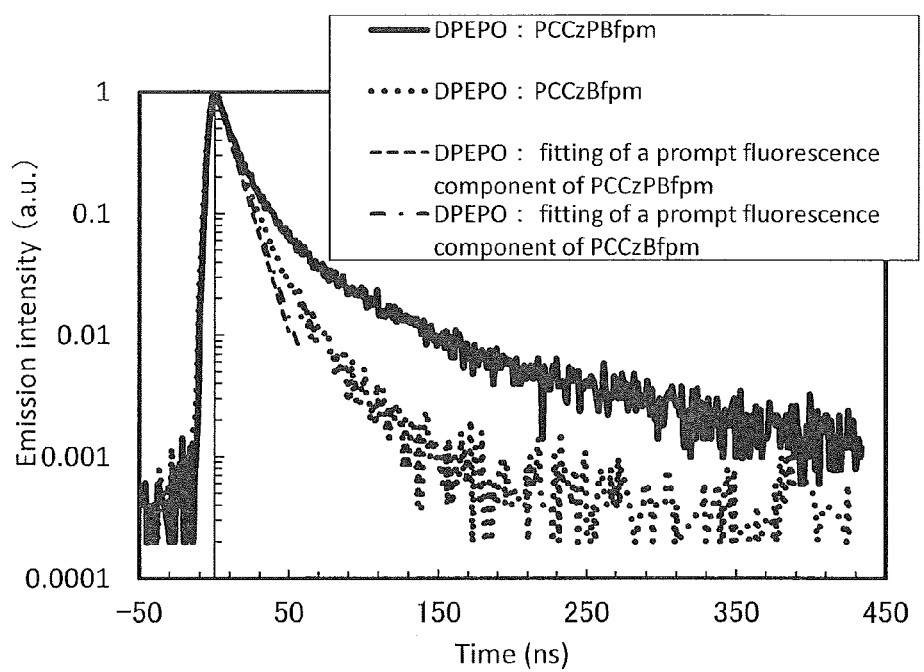
FIGS. 52A and 52B are graphs showing transient fluorescence characteristics of thin films of Example.
Figure 52B:
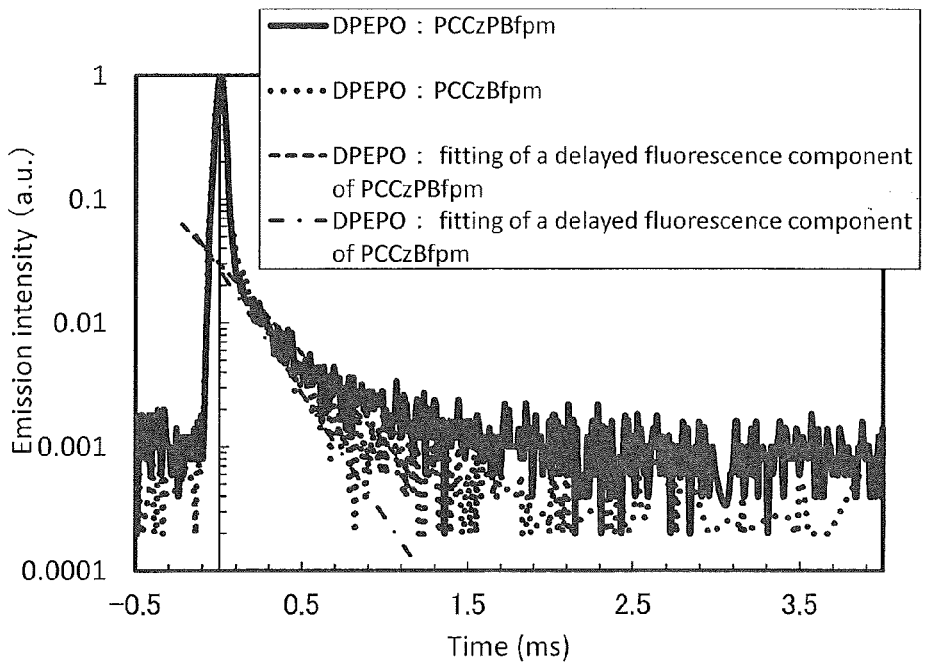

FIGS. 52A and 52B show the transient fluorescent characteristics of 4PCCzPBfpm and 4PCCzBfpm obtained by the measurements. FIG. 52A shows measurement results of emission components having a short emission lifetime, and FIG. 52B shows measurement results of emission components having a long emission lifetime.

The attenuation curves shown in FIGS. 52A and 52B were fitted with Formula 4.

[Formula 4]

$$L = \sum_{n=1} A_n \exp\left(-\frac{t}{a_n}\right) \quad (4)$$

In Formula 4, L and t represent normalized emission intensity and elapsed time, respectively. The fitting results of the attenuation curves show that light emitted by the thin-film samples of 4PCCzPBfpm and 4PCCzBfpm contains a plurality of emission components having different fluorescence lifetimes. The emission component of the thin-film sample of 4PCCzPBfpm is found to include at least a prompt fluorescence component having a fluorescence lifetime of 11.0 ns and a delayed fluorescence component having the longest lifetime of 301 μs. The emission component of the thin-film sample of 4PCCzBfpm is found to include at least a prompt fluorescence component having a prompt fluorescence lifetime of 11.7 ns and a delayed fluorescence component having the longest lifetime of 217 μs. Thus, 4PCCzPBfpm and 4PCCzBfpm are thermally activated delayed fluorescent materials exhibiting delayed fluorescence at room temperature.

Thus, the reason why the light-emitting elements 1 and 2 exhibit significantly excellent light-emitting characteristics with an external quantum efficiency exceeding 23% at a maximum is that 4PCCzPBfpm and 4PCCzBfpm have a function of converting triplet excitation energy into singlet excitation energy by reverse intersystem crossing.

<Measurements of S1 Level and T1 Level>

In order that reverse intersystem crossing leading to thermally activated delayed fluorescence be efficiently caused, the energy difference between the S1 level and the T1 level is preferably greater than 0 eV and less than or equal to 0.3 eV, further preferably greater than 0 eV and less than or equal to 0.2 eV. Calculations were performed to measure the S1 levels and the T1 levels of 4PCCzPBfpm and 4PCCzBfpm, which are compounds of embodiments of the present invention.

Figure 53:
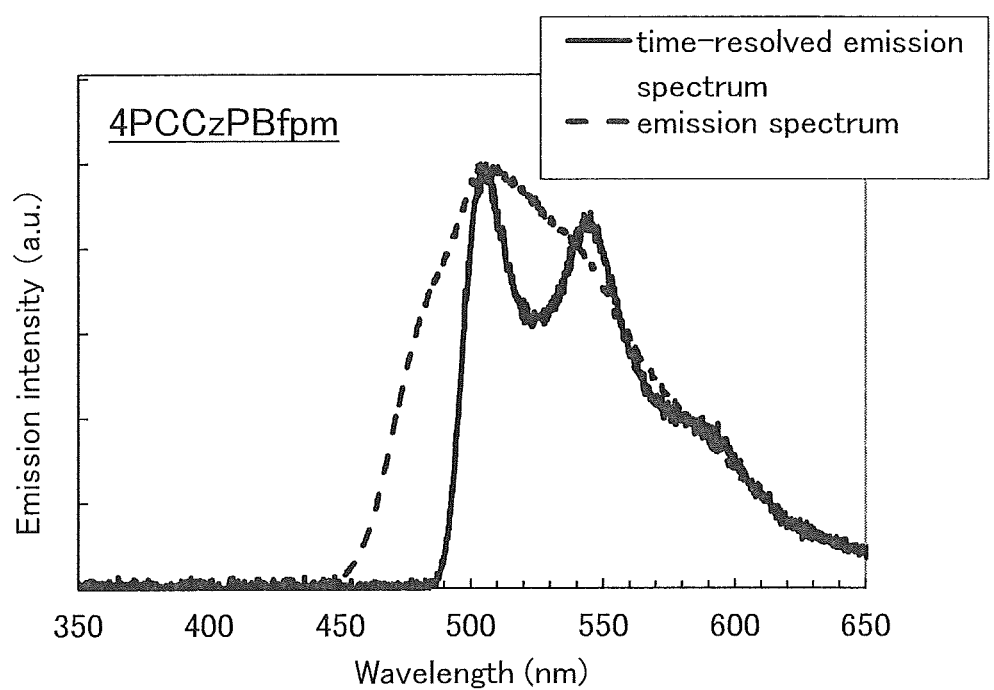
FIG. 53 is a graph showing emission spectra of a compound of Example.
Figure 54:
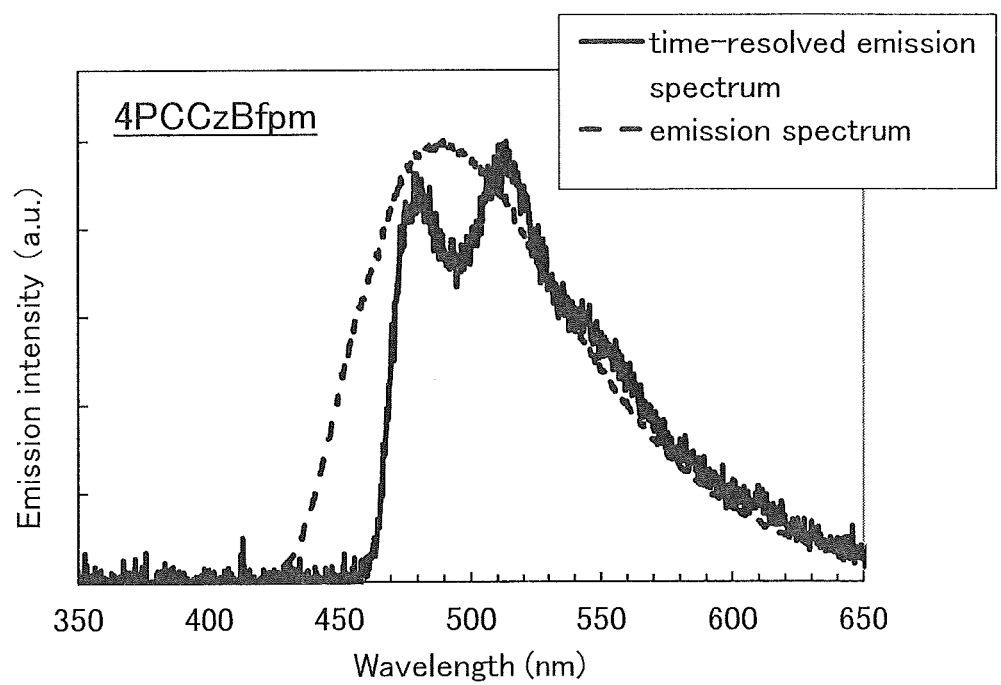
FIG. 54 is a graph showing emission spectra of a compound of Example.

Emission spectra of 4PCCzPBfpm and 4PCCzBfpm were measured so that the S1 levels and T1 levels thereof were measured. FIG. 53 shows measurement results of the emission spectrum of 4PCCzPBfpm, and FIG. 54 shows measurement results of the emission spectrum of 4PCCzBfpm.

The emission spectra were measured with a PL microscope, LabRAM HR-PL, produced by HORIBA, Ltd., a He—Cd laser (325 nm) as excitation light, and a CCD detector, at a measurement temperature of 10 K. For the measurements, a thin film as a sample was formed over a quartz substrate to a thickness of 50 nm and another quartz substrate was attached to the deposition surface in a nitrogen atmosphere.

In the measurement method of the emission spectra, in addition to the measurement of a normal emission spectrum, the measurement of a time-resolved emission spectrum in which light emission with a long lifetime is focused on was also performed. Since in this measurement method of the emission spectra, the measurement temperature was set at a low temperature (10K), in the measurement of the normal emission spectrum, in addition to fluorescence, which is the main emission component, phosphorescence was observed. Furthermore, in the measurement of the time-resolved emission spectrum in which light emission with a long lifetime is focused on, phosphorescence was mainly observed.

The measurement results of the emission spectra show that, in the emission spectrum of 4PCCzPBfpm, peaks (including shoulders) of the fluorescence component and the phosphorescence component on the shortest wavelength side were at 480 nm and 505 nm, respectively. In the emission spectrum of 4PCCzBfpm, peaks (including shoulders) of the fluorescence component and the phosphorescence component on the shortest wavelength side were at 455 nm and 480 nm, respectively.

Thus, the S1 level and the T1 level of 4PCCzPBfpm, which are calculated from the wavelengths of the peaks (including shoulders), are 2.58 eV and 2.46 eV, respectively, and therefore the energy difference between the S1 level and the T1 level is 0.12 eV. The S1 level and the T1 level of 4PCCzBfpm are 2.72 eV and 2.58 eV, respectively, and therefore the energy difference between the S1 level and the T1 level is 0.14 eV.

As can be seen from the measurement results of the emission spectra, in the emission spectrum of 4PCCzPBfpm, the rising portions of the fluorescence component and the phosphorescence component on the shorter wavelength side are at 458 nm and 491 nm, respectively. Furthermore, in the emission spectrum of 4PCCzBfpm, the rising portions of the fluorescence component and the phosphorescence component on the shorter wavelength side are at 435 nm and 464 nm, respectively. Note that the wavelength of the rising portion on the shorter wavelength side in an emission spectrum is a wavelength at the intersection of the horizontal axis and a tangent to the spectrum at a point where the slope of the tangent has a maximum value.

The S1 level and the T1 level of 4PCCzPBfpm, which are thus calculated from the wavelengths of the rising portions, are 2.71 eV and 2.53 eV, respectively, and therefore the energy difference between the S1 level and the T1 level is 0.18 eV. The S1 level and the T1 level of 4PCCzBfpm, which are calculated from the wavelengths of the rising portions, are 2.85 eV and 2.67 eV, respectively, and therefore the energy difference between the S1 level and the T1 level is 0.18 eV.

As described above, the energy difference between the S1 level and the T1 level of each of 4PCCzPBfpm and 4PCCzBfpm, which is calculated from the wavelengths of the peaks (including shoulders) and the rising portions on the shorter wavelength side in the emission spectra, is greater than 0 eV and less than or equal to 0.2 eV, which is extremely small. Therefore, 4PCCzPBfpm and 4PCCzBfpm each have a function of converting triplet excitation energy into singlet excitation energy by reverse intersystem crossing and a function of exhibiting thermally activated delayed fluorescence.

Furthermore, 4PCCzPBfpm and 4PCCzBfpm were found suitable for a light-emitting element that emits high energy light such as blue light with a relatively high T1 level. Although compounds exhibiting thermally activated delayed fluorescence are known as effective in forming high-efficiency light-emitting elements, almost no compounds efficiently emit blue light at present. Also at this point, the compounds of embodiments of the present invention are extremely effective in foiming light-emitting elements.

As described above, by using a compound of one embodiment of the present invention, a light-emitting element having excellent element characteristics with high emission efficiency can be fabricated. A light-emitting element with low drive voltage and reduced power consumption can be fabricated. A light-emitting element that emits blue light with high emission efficiency can be fabricated.

The structures described in this example can be used in an appropriate combination with any of the structures described in the other examples and embodiments.

Example 4

In this example, a fabrication example of a light-emitting element including a compound of one embodiment of the present invention and characteristics of the light-emitting element are described. A schematic cross-sectional view of the light-emitting element fabricated in this example is the same as FIG. 47. Table 3 shows details of the element structure. In addition, structures and abbreviations of compounds used are given below. Note that the above examples are referred to for other compounds.

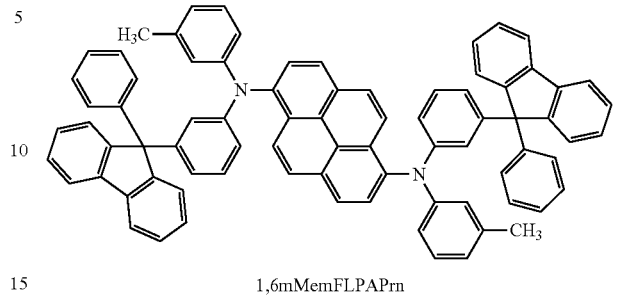

1,6mMemFLPAPrn

TABLE 3

|  | Layer | Reference numeral | Film thickness (nm) | Material | Weight ratio |
|---|---|---|---|---|---|
| Light-emitting element 3 | Electrode | 102 | 200 | Al | — |
|  | Electron-injection layer | 119 | 1 | LiF | — |
|  | Electron-transport layer | 118(2) | 40 | TmPyPB | — |
|  |  | 118(1) | 5 | DPEPO | — |
|  | Light-emitting layer | 160 | 15 | DPEPO:4PCCzBfpm:1,6mMemFLPAPrn | 0.7:0.3:0.01 |
|  | Hole-transport layer | 112 | 20 | Cz2DBT | — |
|  | Hole-injection layer | 111 | 20 | DBT3P-II:MoO$_3$ | 1:0.5 |
|  | Electrode | 101 | 70 | ITSO | — |

<Fabrication of Light-Emitting Element 3>

As the electrode 101, an ITSO film was formed to a thickness of 70 nm over the substrate 200. The electrode area of the electrode 101 was set to 4 mm$^2$ (2 mm×2 mm).

As the hole-injection layer 111, DBT3P-II and MoO$_3$ were deposited by co-evaporation to a thickness of 20 nm over the electrode 101 such that the weight ratio of DBT3P-II to MoO$_3$ was 1:0.5.

As the hole-transport layer 112, Cz2DBT was deposited by evaporation to a thickness of 20 nm over the hole-injection layer 111.

As the light-emitting layer 160, DPEPO, 4PCCzBfpm, and N,N'-bis(3-methylphenyl)-N,N'-bis[3-(9-phenyl-9H-fluoren-9-yl)phenyl]pyrene-1,6-dia mine (abbreviation: 1,6mMemFLPAPm) were deposited over the hole-transport layer 112 by co-evaporation to a thickness of 15 nm such that the weight ratio of DPEPO to 4PCCzBfpm and 1,6mMemFLPAPrn was 0.7:0.3:0.01. Note that in the light-emitting layer 160, DPEPO corresponds to the host material and 1,6mMemFLPAPm corresponds to the guest material.

As the electron-transport layer 118, DPEPO and TmPyPB were successively deposited by evaporation to thicknesses of 5 nm and 40 nm, respectively, over the light-emitting layer 160. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Figure 55:
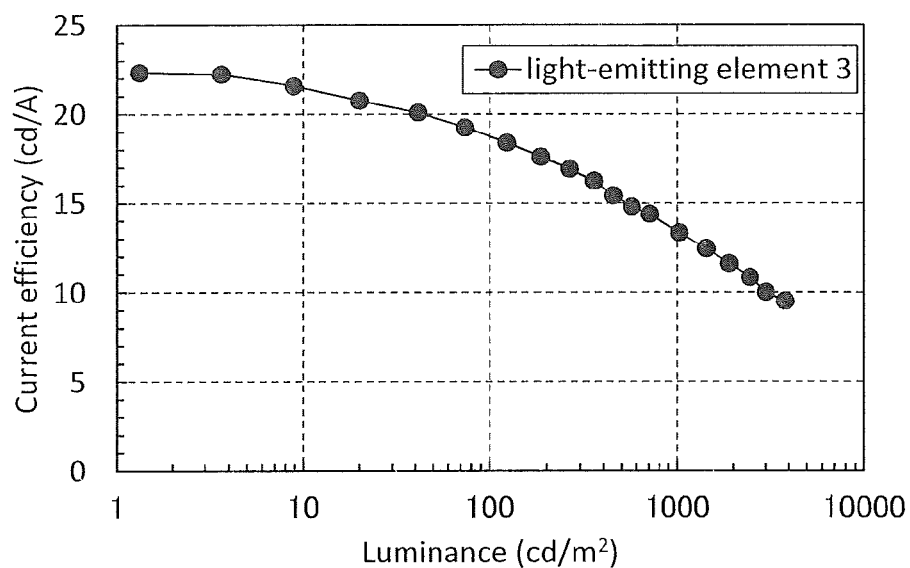
FIG. 55 is a graph showing current efficiency-luminance characteristics of a light-emitting element of Example.
Figure 56:
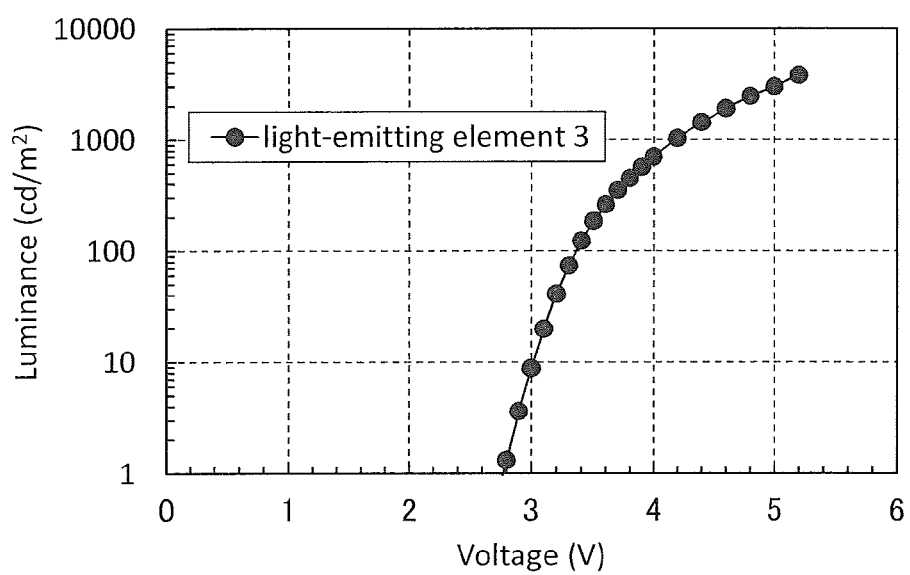
FIG. 56 is a graph showing luminance-voltage characteristics of a light-emitting element of Example.
Figure 57:
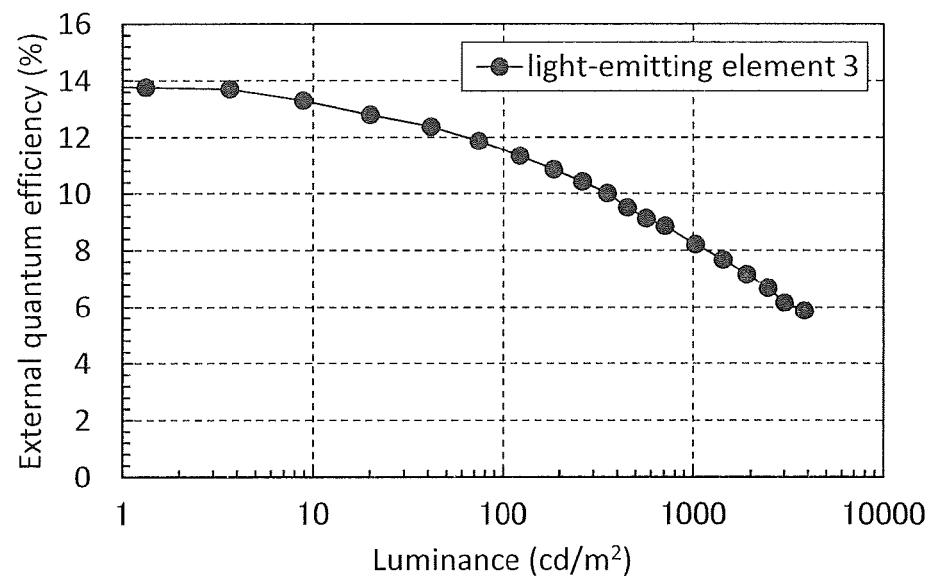
FIG. 57 is a graph showing external quantum efficiency-luminance characteristics of a light-emitting element of Example.

Next, in a glove box containing a nitrogen atmosphere, the light-emitting element 3 was sealed by fixing the substrate 220 to the substrate 200 over which the organic material was deposited using a sealant for an organic EL device. The sealing method is the same as that used for the light-emitting element 1. Through the above steps, the light-emitting element 3 was obtained.
<Characteristics of Light-Emitting Element 3>
FIG. 55 shows current efficiency-luminance characteristics of the light-emitting element 3; FIG. 56 shows luminance-voltage characteristics thereof; and FIG. 57 shows external quantum efficiency-luminance characteristics thereof. The measurements of the light-emitting element were performed at room temperature (in an atmosphere kept at 23° C.). The measurement methods were the same as those used in Example 3.

Table 4 shows element characteristics of the light-emitting element 3 at around 100 cd/m².

TABLE 4

| | Voltage (V) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|
| Light-emitting element 3 | 3.4 | 0.67 | (0.16, 0.26) | 120 | 18 | 17 | 11 |

Figure 58:
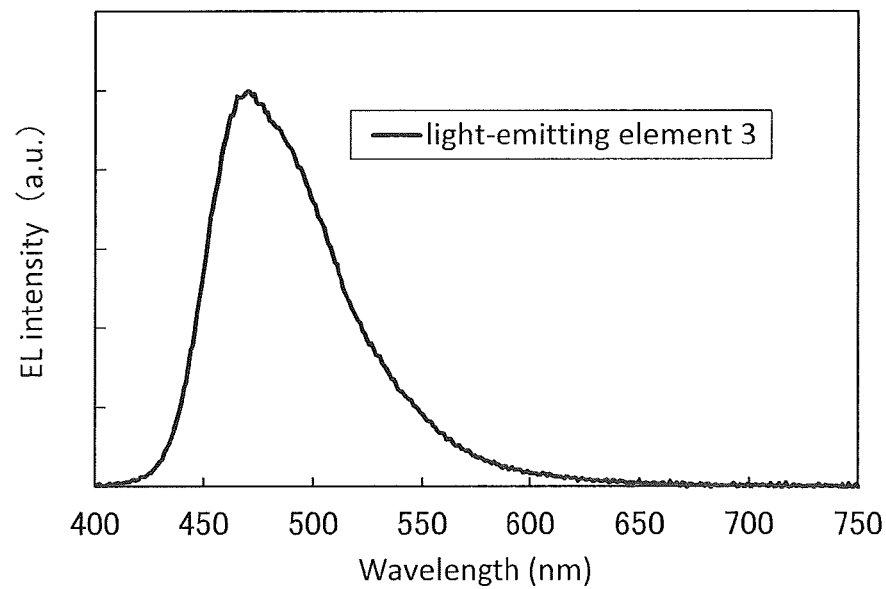
FIG. 58 is a graph showing an electroluminescence spectrum of a light-emitting element of Example.

FIG. 58 shows electroluminescence spectrum when a current at a current density of 2.5 mA/cm² was supplied to the light-emitting element 3.

From FIG. 55 to FIG. 58 and Table 4, it is found that each of the light-emitting element 3 has high current efficiency and high external quantum efficiency. The maximum value of the external quantum efficiency of the light-emitting element 3 is 13.8%, which is an excellent value. In addition, a fall (roll-off) in the emission efficiency of the light-emitting element 3 is small even on the high luminance side, which is excellent.

As shown in FIG. 58, the light-emitting element 3 emits high-purity blue light having an electroluminescence spectrum with a peak at a wavelength of 470 nm and a full width at half maximum of 65 nm. The obtained emission spectrum has a small half-width and a short peak wavelength suitable for blue light emission, which reveals that the light is emitted from 1,6mMemFLPAPm as the guest material.

The light-emitting element 3 was driven at a low voltage of 3.4 V at around 100 cd/m² and thus exhibited high power efficiency.

As described in the above example, 4PCCzBfpm has a function of converting triplet excitation energy into singlet excitation energy by reverse intersystem crossing. Thus, the light-emitting element 3 including 4PCCzBfpm and 1,6mMemFLPAPm as the guest material can efficiently provide blue light which is emitted from 1,6mMemFLPAPm and originates from singlet excitons generated from triplet excitons through reverse intersystem crossing in 4PCCzBfpm in addition to singlet excitons generated by recombination of carriers.

As described above, by using a compound of one embodiment of the present invention and a guest material, a light-emitting element having excellent element characteristics with a small roll-off and high emission efficiency can be fabricated. A light-emitting element with low drive voltage and reduced power consumption can be fabricated. A light-emitting element that emits blue light with high color purity and high emission efficiency can be fabricated.

The structures described in this example can be used in an appropriate combination with any of the structures described in the other examples and embodiments.

Example 5

In this example, a fabrication example of a light-emitting element including a compound of one embodiment of the present invention and characteristics of the light-emitting element are described. A schematic cross-sectional view of the light-emitting element fabricated in this example is the same as FIG. 47. Table 5 shows details of the element structure. In addition, structures and abbreviations of compounds used are given below. Note that the above examples are referred to for other compounds.

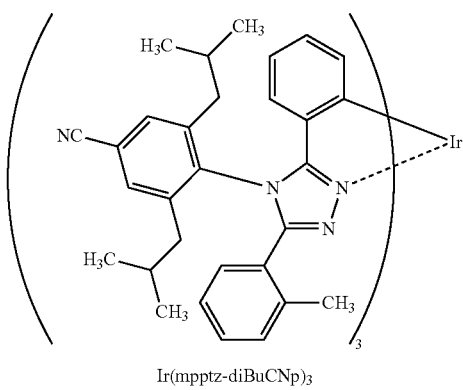

Ir(mpptz-diBuCNp)₃

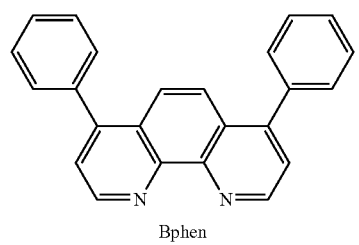

Bphen

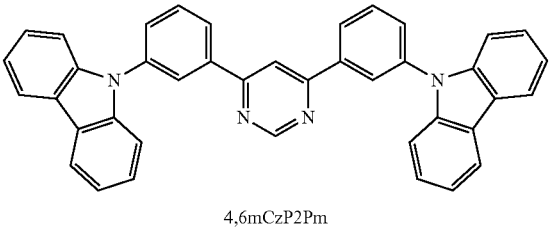

4,6mCzP2Pm

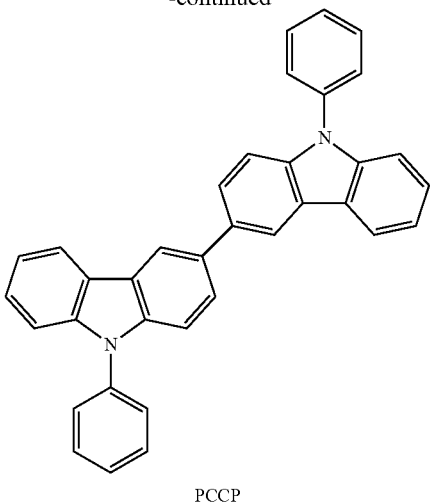

PCCP viation: Ir(mpptz-diBuCNp)$_3$) were deposited over the hole-transport layer 112 by co-evaporation to a thickness of 40 nm such that the weight ratio of 4PCCzBfpm to Ir(mpptz-diBuCNp)$_3$ was 1:0.06. Note that in the light-emitting layer 160, Ir(mpptz-diBuCNp)$_3$ corresponds to the guest material.

As the electron-transport layer 118, 4,6-bis[3-(9H-carbazol-9-yl)phenyl]pyrimidine (abbreviation: 4,6mCzP2Pm) and bathophenanthroline (abbreviation: BPhen) were successively deposited by evaporation to thicknesses of 10 nm and 15 nm, respectively, over the light-emitting layer 160. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the light-emitting element 4 was sealed by fixing the substrate 220 to the substrate 200 over which the organic material was deposited using a sealant for an organic EL device. The sealing method is the same as that used for the light-emitting element 1. Through the above steps, the light-emitting element 4 was obtained.

TABLE 5

| | Layer | Reference numeral | Film thickness (nm) | Material | Weight ratio |
|---|---|---|---|---|---|
| Light-emitting element 4 | Electrode | 102 | 200 | Al | — |
| | Electron-injection layer | 119 | 1 | LiF | — |
| | Electron-transport layer | 118(2) | 15 | BPhen | — |
| | | 118(1) | 10 | 4,6mCzP2Pm | — |
| | Light-emitting layer | 160 | 40 | 4PCCzBfpm:Ir(mpptz-diBuCNp)$_3$ | 1:0.06 |
| | Hole-transport layer | 112 | 20 | PCCP | — |
| | Hole-injection layer | 111 | 15 | DBT3P-II:MoO$_3$ | 1:0.5 |
| | Electrode | 101 | 70 | ITSO | — |

<Fabrication of Light-Emitting Element 4>

As the electrode 101, an ITSO film was formed to a thickness of 70 nm over the substrate 200. The electrode area of the electrode 101 was set to 4 mm$^2$ (2 mm×2 mm).

As the hole-injection layer 111, DBT3P-II and MoO$_3$ were deposited by co-evaporation to a thickness of 15 nm over the electrode 101 such that the weight ratio of DBT3P-II to MoO$_3$ was 1:0.5.

As the hole-transport layer 112, 3,3'-bis(9-phenyl-9H-carbazole) (abbreviation: PCCP) was deposited by evaporation to a thickness of 20 nm over the hole-injection layer 111.

As the light-emitting layer 160, 4PCCzBfpm and tris{2-[4-(4-cyano-2,6-diisobutylphenyl)-5-(2-methylphenyl)-4H-1,2,4-triazol-3-yl-κN$^2$]phenyl-κC}iridium(III) (abbre- <Characteristics of Light-Emitting Element 4>

Figure 59:
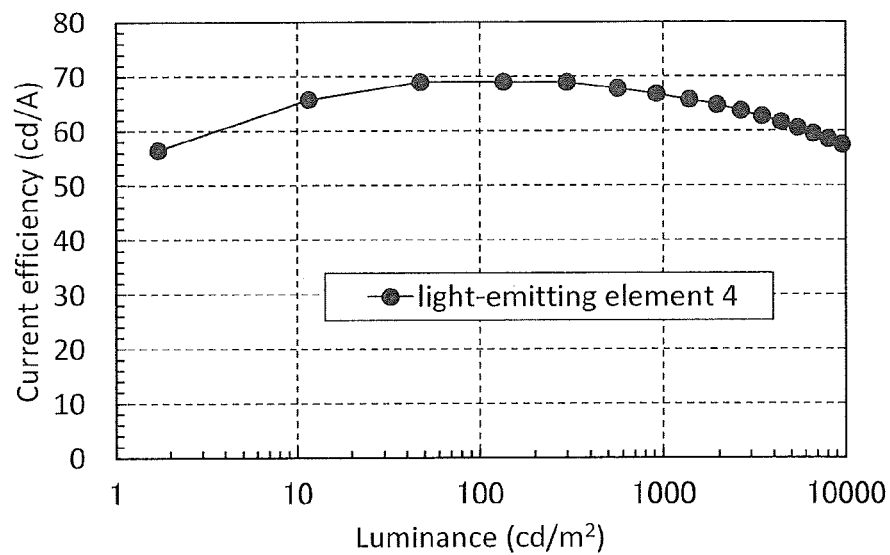
FIG. 59 is a graph showing current efficiency-luminance characteristics of a light-emitting element of Example.
Figure 60:
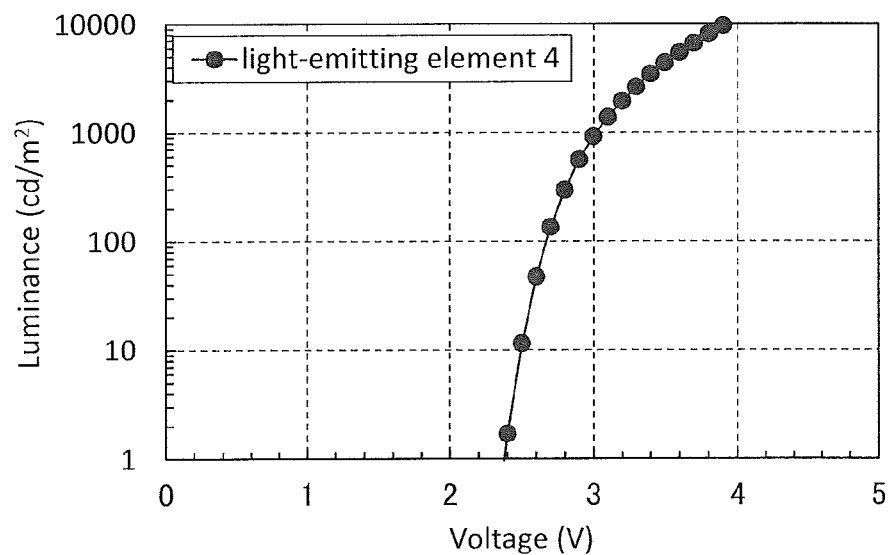
FIG. 60 is a graph showing luminance-voltage characteristics of a light-emitting element of Example.
Figure 61:
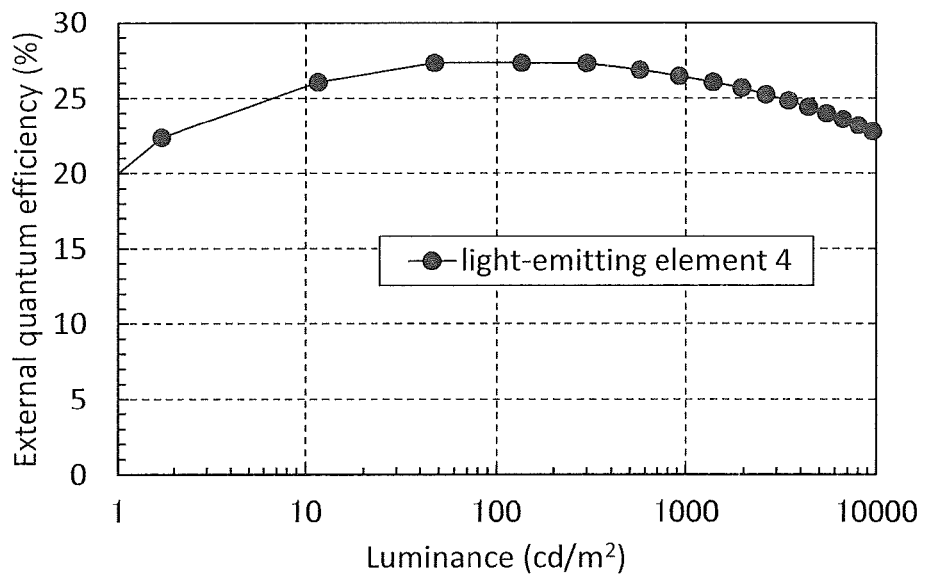
FIG. 61 is a graph showing external quantum efficiency-luminance characteristics of a light-emitting element of Example.

FIG. 59 shows current efficiency-luminance characteristics of the light-emitting element 4; FIG. 60 shows luminance-voltage characteristics thereof; and FIG. 61 shows external quantum efficiency-luminance characteristics thereof. The measurements of the light-emitting element were performed at room temperature (in an atmosphere kept at 23° C.). The measurement methods were the same as those used in Example 3.

Table 6 shows element characteristics of the light-emitting element 4 at around 1000 cd/m$^2$.

TABLE 6

| | Voltage (V) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 4 | 3.00 | 1.38 | (0.196, 0.495) | 923 | 66.8 | 70.0 | 26.5 |

Figure 62:
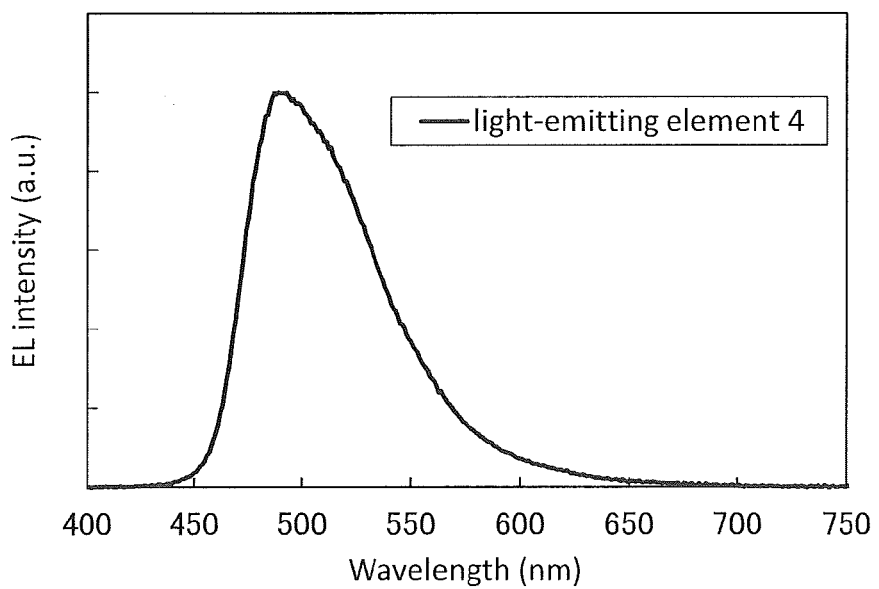
FIG. 62 is a graph showing an electroluminescence spectrum of a light-emitting element of Example.

FIG. 62 shows electroluminescence spectrum when a current at a current density of 2.5 mA/cm$^2$ was supplied to the light-emitting element 4.

From FIG. 59 to FIG. 62 and Table 6, it is found that each of the light-emitting element 4 has extremely high current efficiency and high external quantum efficiency. The maximum value of the external quantum efficiency of the light-emitting element 4 is 27.3%, which is an excellent value. In addition, a fall (roll-off) in the emission efficiency of the light-emitting element 4 is small even on the high luminance side, which is excellent.

As shown in FIG. 62, the light-emitting element 4 emits blue light having an electroluminescence spectrum with a peak at a wavelength of 489 nm and a full width at half maximum of 68 nm. The obtained electroluminescence spectrum reveals that light is emitted from Ir(mpptz-diBuCNp)$_3$ as the guest material.

The light-emitting element 4 was driven at an extremely low voltage of 3.0 V at around 1000 cd/m$^2$ and thus exhibited high power efficiency.

As described in the above example, the energy difference between the S1 level and the T1 level of 4PCCzBfpm is small and a singlet excited state can be formed with energy close to the energy of the triplet excited state. Accordingly, an energy difference between the energy of the singlet excited state of 4PCCzBfpm and the energy of the triplet excited state of Ir(mpptz-diBuCNp)$_3$ can be reduced. Thus, the light-emitting element 4 can be driven at a low voltage.

As described above in Example 3, the wavelength (480 nm) of the peak of the phosphorescence component on the shortest wavelength side in the emission spectrum of 4PCCzBfpm is shorter than the wavelength (489 nm) of the peak in the electroluminescence spectrum of the light-emitting element 4. Furthermore, since 4PCCzBfpm has a high T1 level, it is found suitable for a light-emitting element including a phosphorescent material that emits blue light as a guest material.

As described above, by using a compound of one embodiment of the present invention and a guest material, a light-emitting element having excellent element characteristics with significantly high emission efficiency can be fabricated. Furthermore, a light-emitting element with low drive voltage and reduced power consumption can be fabricated. Furthermore, a light-emitting element that emits blue light with high emission efficiency can be fabricated.

The structures described in this example can be used in an appropriate combination with any of the structures described in the other examples and embodiments.

Example 6

In this example, a method of synthesizing one of the compounds that are described in Embodiment 1 and represented by General Formula (G0), 4-[3-(9'-phenyl-3,3'-bi-9H-carbazol-9-yl)phenyl]benzofuro[3,2-d]pyrimidine (abbreviation: 4mPCCzPBfpm) (Structural Formula (101)), and characteristics of the compound are described.

Synthesis Example 3

Step 1: Synthesis of 9-(3-Bromophenyl)-9'-Phenyl-3,3'-Bi-9H-carbazole

First, 6.0 g (15 mmol) of 9-phenyl-3,3'-bi-9H-carbazole, 8.3 g (29 mmol) of 3-bromoiodobenzene, 6.2 g (29 mmol) of potassium carbonate, 1.5 g (24 mmol) of ethylenediamine (abbreviation: EDA), and 2.5 g (13 mmol) of copper iodide were put in a three-neck flask equipped with a reflux pipe, and the air in the flask was replaced with nitrogen. To this mixture was added 100 mL of toluene, and the mixture was heated at 120° C. for 47 hours under a nitrogen stream. Water was added to the obtained reaction liquid, and the reaction liquid was subjected to extraction with ethyl acetate. The obtained solution of the extract was washed with saturated brine. Magnesium sulfate was added and filtration was performed. The solvent of the obtained filtrate was distilled off. Purification was conducted by silica gel column chromatography using a 1:3 toluene-hexane mixed solvent as the developing solvent to give 4.5 g of the desired substance (as a yellow solid in a yield of 54%). The synthesis scheme of Step 1 is shown in the following equation (A-3).

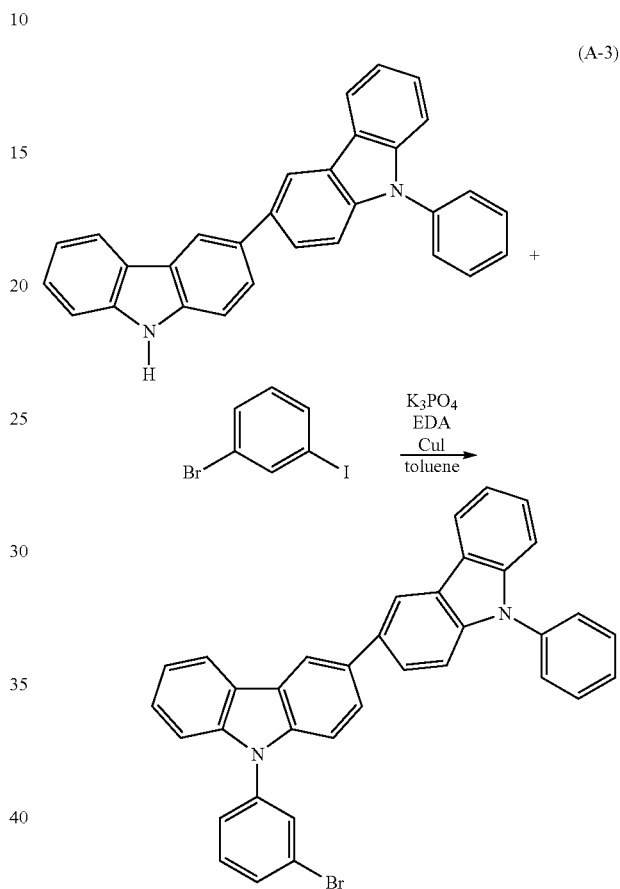

Step 2: Synthesis of 9-[3-(4,4,5,5-tetramethyl-1,3,2-dioxaborolan-2-yl)phenyl]-9'-phenyl-3,3'-bi-9H-carbazole Next, 2.8 g (5.0 mmol) of 9-(3-bromophenyl)-9"-phenyl-3,3"-bi-9H-carbazole synthesized in Step 1 described above, 1.4 g (5.5 mmol) of bis(pinacolato)diboron, and 1.5 g (15 mmol) of potassium acetate were put in a three-neck flask, and the air in the flask was replaced with nitrogen. Then, 50 mL of dimethyl sulfoxide (abbreviation: DMSO) and 0.12 g (0.15 mmol) of [1,1"-bis(diphenylphosphino)ferrocene]palladium(II) dichloride were added to the mixture, and the mixture was heated and stirred at 110° C. for 37 hours. The obtained reaction mixture was subjected to extraction with ethyl acetate. The obtained solution of the extract was washed with saturated brine. Magnesium sulfate was added and filtration was performed. The solvent of the obtained filtrate was distilled off. Purification was conducted by neutral silica gel column chromatography using, as the developing solvent, only toluene obtained by gradually increasing the ratio of toluene to hexane from 1:3 in a mixed solvent. Thus, 1.7 g of the desired substance was obtained (as a yellow solid in a yield of 54%). The synthesis scheme of Step 2 is shown in the following equation (B-3).

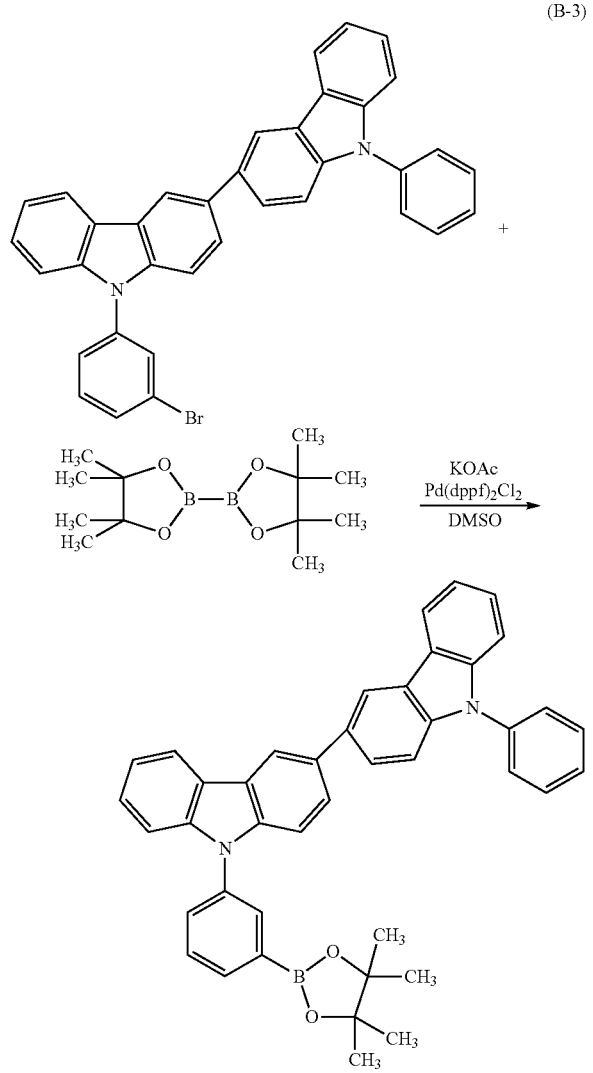

Step 3: Synthesis of 4mPCCzPBfpm

Next, 0.52 g (2.6 mmol) of 4-chloro[1]benzofuro[3,2-d]pyrimidine, 1.7 g (2.8 mmol) of 9-[3-(4,4,5,5-tetramethyl-1,3,2-dioxaborolan-2-yl)phenyl]-9'-phenyl-3,3'-bi-9H-carbazole synthesized in the above synthesis method in Step 2, 1.5 mL of a 2M aqueous solution of potassium carbonate, 13 mL of toluene, and 1 mL of ethanol were put in a three-neck flask equipped with a reflux pipe, and the air in the flask was replaced with nitrogen. To this mixture was added 0.24 g (0.21 mmol) of tetrakis(triphenylphosphine)palladium(0), and the mixture was heated and stirred at 100° C. for 41 hours. The obtained reaction substance was filtered, and washing with water and ethanol was performed. The obtained residue was dissolved in hot toluene, and the mixture was filtered through a filter aid in which Celite, aluminum oxide, and Celite were filled in this order. The solvent of the obtained filtrate was distilled off, and purification was conducted using a mixed solvent of toluene and hexane to give 1.0 g of 4mPCCzPBfpm which was the desired substance (as a yellow solid in a yield of 62%). Then, 1.0 g of the yellow solid was purified by a train sublimation method. In the purification by sublimation, the yellow solid was heated at 300° C. under a pressure of 2.7 Pa with argon gas at a flow rate of 5 mL/min. After the purification by sublimation, 0.9 g of a yellow solid of the desired substance was obtained at a collection rate of 87%. The synthesis scheme of Step 3 is shown in the following equation (C-3).

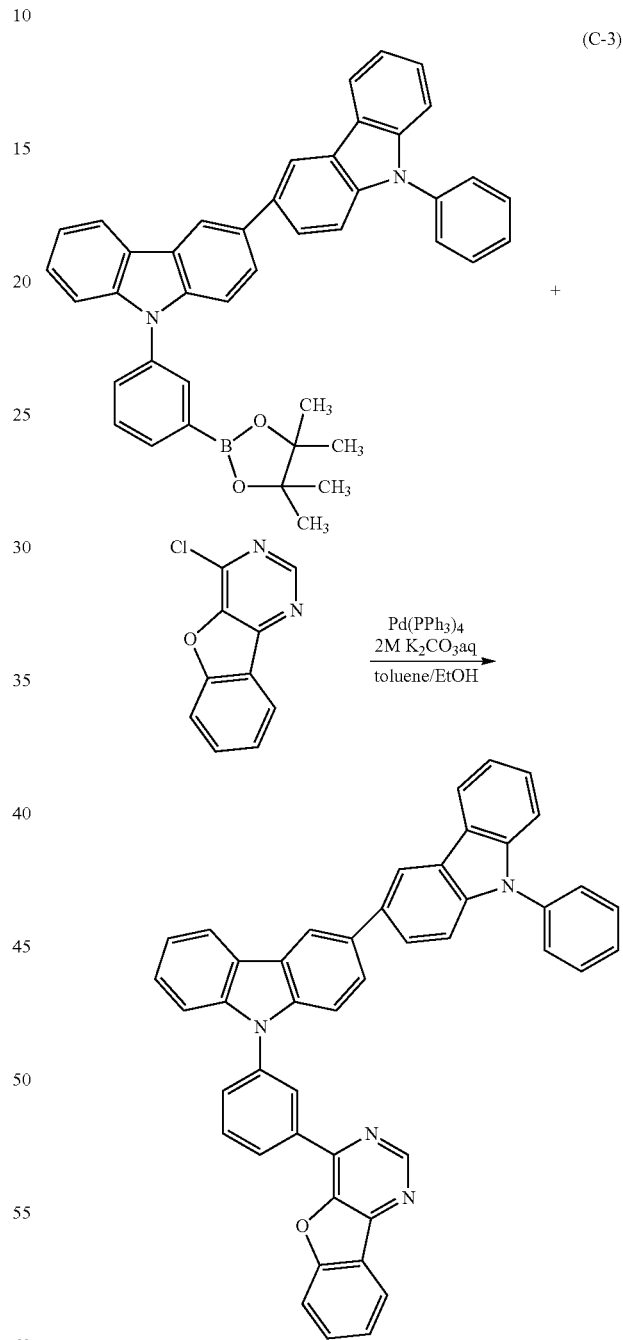

Figure 63:
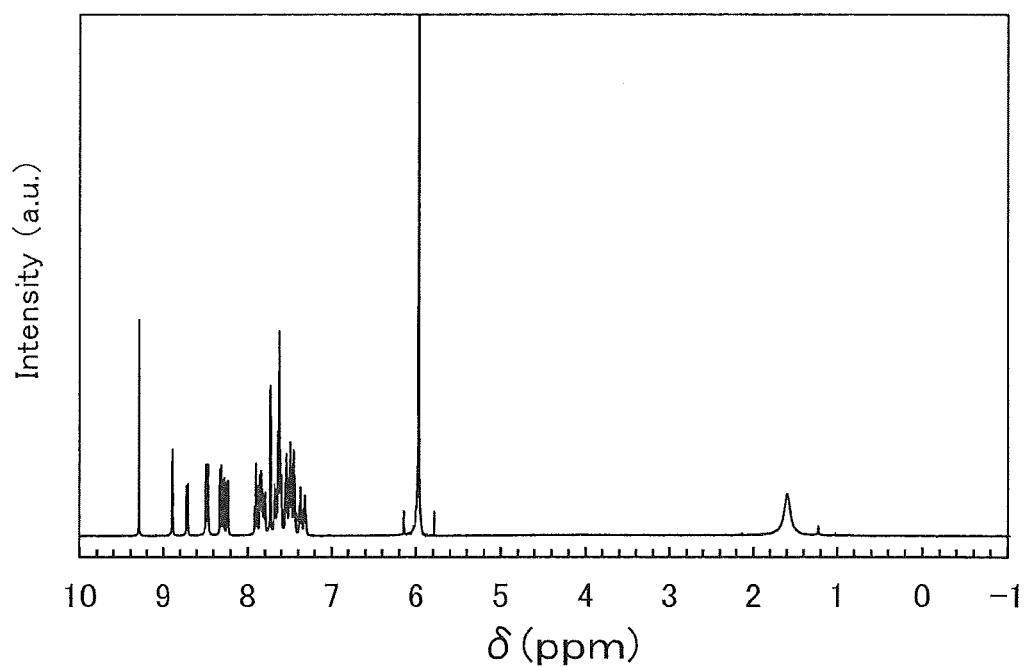
FIG. 63 is an NMR chart of a compound of Example.

Measurement results obtained by nuclear magnetic resonance ($^1$H-NMR) spectroscopy of the yellow solid obtained in Step 3 described above are shown below. The $^1$H-NMR chart is shown in FIG. 63. These results reveal that 4mPCCzPBfpm, which is one embodiment of the present invention, was obtained in Synthesis Example 3.

¹H-NMR. δ(TCE-d2): 7.31-7.34 (t, 1H), 7.36-7.39 (t, 1H), 7.43-7.56 (m, 6H), 7.60-7.69 (m, 6H), 7.74 (ds, 2H), 7.90-7.86 (m, 3H), 7.89-7.92 (t, 1H), 8.24 (d, 1H), 8.28 (d, 1H), 8.32 (d, 1H), 8.47 (d, 2H), 8.71 (d, 1H), 8.89 (s, 1H), 9.29 (s, 1H).

<Characteristics of 4mPCCzPBfpm>

Next, mass spectrometry (MS) analysis of 4mPCCzPBfpm which was obtained was carried out by liquid chromatography mass spectrometry (abbreviation: LC/MS analysis).

In the LC/MS analysis, liquid chromatography (LC) separation was carried out with ACQUITY UPLC (manufactured by Waters Corporation), and mass spectrometry (MS) analysis was carried out with Xevo G2 Tof MS (manufactured by Waters Corporation). As a column for the LC separation, ACQUITY UPLC BEH C8 (2.1×100 mm, 1.7 μm) was used and the column temperature was set to 40° C. Acetonitrile was used for Mobile Phase A and a 0.1% formic acid aqueous solution was used for Mobile Phase B. A sample was prepared in such a manner that 4mPCCzPBfpm was dissolved in chloroform at a given concentration and the solution was diluted with acetonitrile. The injection amount was set to 5.0 μL.

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. A component with m/z of 653.23 which underwent the ionization under the above-described conditions was collided with an argon gas in a collision cell to dissociate into product ions. Energy (collision energy) for the collision with argon was set to 70 eV. The measurement mass range was set to m/z=100 to 1200. The detection results of the dissociated product ions by time-of-flight (TOF) MS are shown in FIG. 64.

Figure 64:
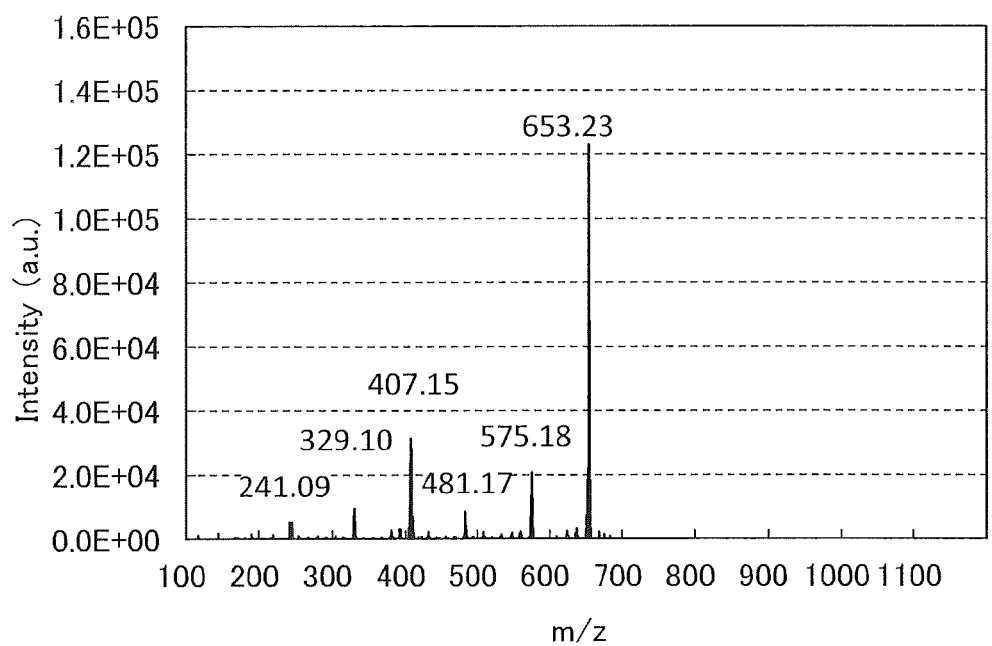
FIG. 64 is a graph showing an MS spectrum of a compound of Example.

FIG. 64 shows that product ions of 4mPCCzPBfpm are mainly detected around m/z=575, 481, 407, 329, and 241. The results in FIG. 64 show characteristics derived from 4mPCCzPBfpm and can thus be regarded as important data for identifying 4mPCCzPBfpm contained in a mixture.

The product ion around m/z=575 is presumed to be a cation in the state where a phenyl group is dissociated from 4mPCCzPBfpm. The product ion around m/z=481 is presumed to be a cation in the state where a benzofuropyrimidine group is dissociated from 4mPCCzPBfpm. The product ion around m/z=407 is presumed to be a cation in the state where a phenyl group is further dissociated from the above cation. The product ion around m/z=329 is presumed to be a cation in the state where a phenyl group is further dissociated from the above cation. The product ion around m/z=241 is presumed to be a cation generated due to dissociation of aniline by further cleavage of a carbazole ring. These data suggest that 4mPCCzPBfpm includes diphenylbicarbazole.

Figure 65:
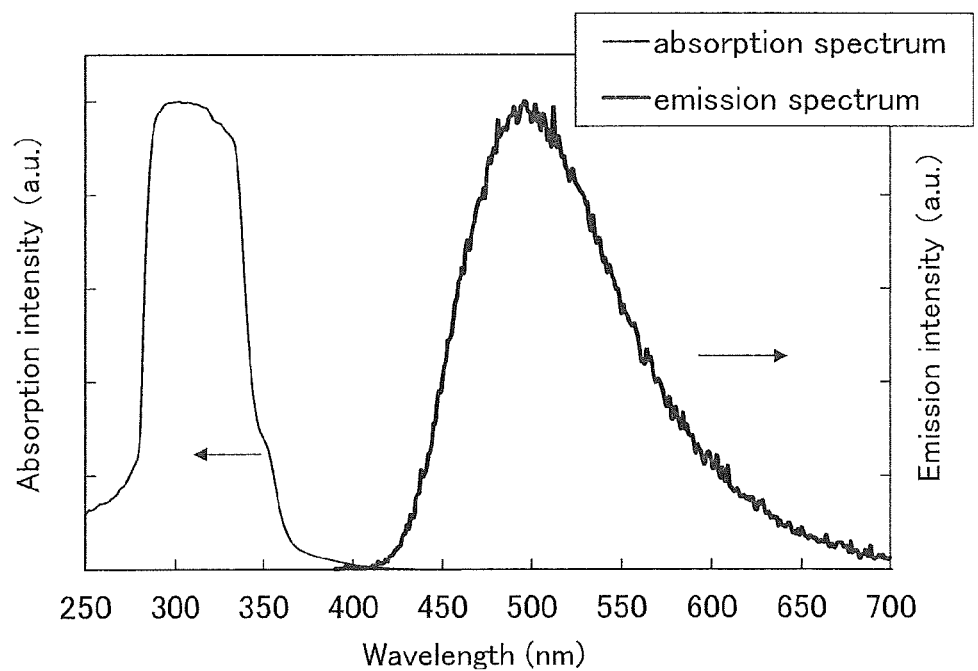
FIG. 65 is a graph showing absorption and emission spectra of a compound of Example.
Figure 66:
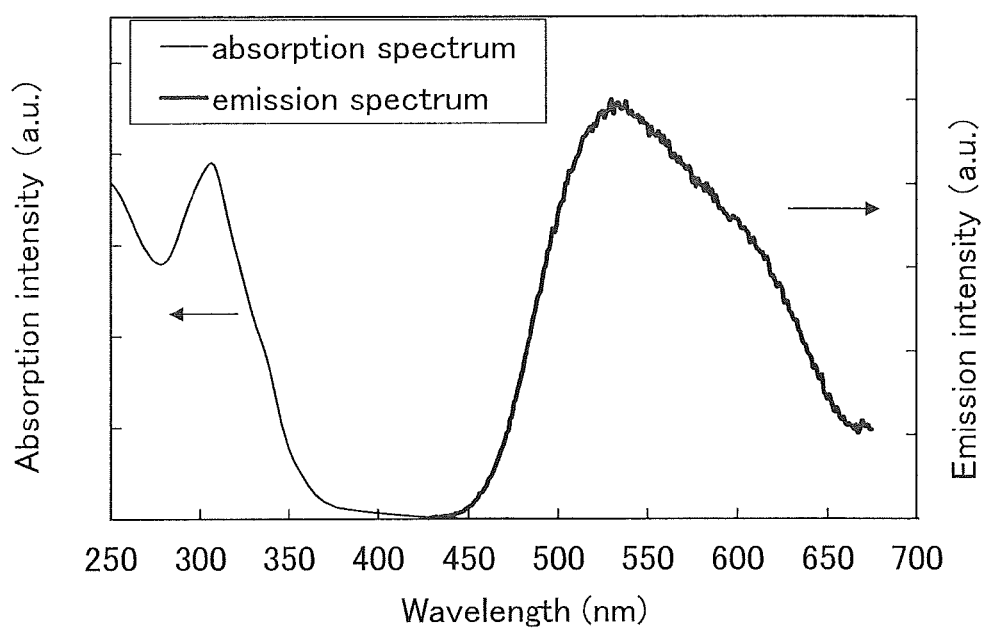
FIG. 66 is a graph showing absorption and emission spectra of a compound of Example.

Absorption and emission spectra of 4mPCCzPBfpm in a toluene solution of 4mPCCzPBfpm are shown in FIG. 65, and absorption and emission spectra of a thin film of 4mPCCzPBfpm are shown in FIG. 66.

The absorption and emission spectra of 4mPCCzPBfpm in the toluene solution and the thin film of 4mPCCzPBfpm were measured as in Example 1.

The absorption wavelength of 4mPCCzPBfpm in the toluene solution has shoulder peaks at around 350 nm and around 380 nm, and the maximum emission wavelength thereof was around 496 nm (an excitation wavelength of 355 nm). Furthermore, the maximum absorption wavelength of the thin film was around 310 nm, and the maximum emission wavelength thereof was around 533 nm (an excitation wavelength of 359 nm).

The ionization potential of the thin film of 4mPCCzPBfpm was measured in the air with a photoelectron spectrometer (AC-3, produced by Riken Keiki, Co., Ltd.). The obtained value of the ionization potential was converted into a negative value, and the HOMO level of 4mPCCzPBfpm was −5.74 eV. From the data of the absorption spectrum of the thin film in FIG. 66, the absorption edge of 4mPCCzPBfpm, which was obtained from Tauc plot with an assumption of direct transition, was 2.97 eV. Thus, the optical energy gap of 4mPCCzPBfpm in the solid state was estimated at 2.97 eV; from the values of the HOMO level obtained above and this energy gap, the LUMO level of 4mPCCzPBfpm can be estimated at −2.77 eV. This reveals that 4mPCCzPBfpm in the solid state has an energy gap as wide as 2.97 eV.

The electrochemical characteristics (oxidation reaction characteristics and reduction reaction characteristics) of 4mPCCzPBfpm were measured by cyclic voltammetry (CV) measurement. The measurement method was similar to that used in Example 1.

The CV measurement results reveal that the oxidation potential of 4mPCCzPBfpm is 0.68 V and the reduction potential is −1.92 V. In addition, the HOMO level and LUMO level of 4mPCCzPBfpm, which are calculated from the CV measurement results, are −5.62 eV and −3.02 eV, respectively. Thus, 4mPCCzPBfpm is found to have a low LUMO level and a relatively high HOMO level.

Example 7

In this example, a method of synthesizing one of the compounds that are described in Embodiment 1 and represented by General Formula (G0), 4-[3-(9″-phenyl-2,3′-bi-9H-carbazol-9-yl)phenyl]benzofuro[3,2-d]pyrimidine (abbreviation: 4mPCCzPBfpm-02) (Structural Formula (103)), and characteristics of the compound are described.

Synthesis Example 4

Step 1: Synthesis of 9-(3-bromophenyl)-9′-phenyl-2,3′-bi-9H-carbazole

First, 5.0 g (12 mmol) of 9-phenyl-2,3′-bi-9H-carbazole, 4.3 g (18 mmol) of 3-bromoiodobenzene, and 3.9 g (18 mmol) of tripotassium phosphate were put in a three-neck flask equipped with a reflux pipe, and the air in the flask was replaced with nitrogen. To this mixture were added 100 mL of dioxane, 0.21 g (1.8 mmol) of trans-N,N′-dimethylcyclohexane-1,2-diamine, and 0.18 g (0.92 mmol) of copper iodide, and the mixture was heated and stirred at 120° C. for 32 hours under a nitrogen stream to be reacted. The obtained reaction mixture was subjected to extraction with toluene. The obtained solution of the extract was washed with saturated brine. Then, magnesium sulfate was added and filtration was performed. The solvent of the obtained filtrate was distilled off and purification was conducted by silica gel column chromatography using a 1:2 toluene-hexane mixed solvent obtained by gradually changing the ratio of toluene to hexane from 1:4 as the developing solvent. Thus, 4.9 g of the desired substance was obtained (as a yellow solid in a yield of 70%). The synthesis scheme of Step 1 is shown in the following equation (A-4).

(A-4)

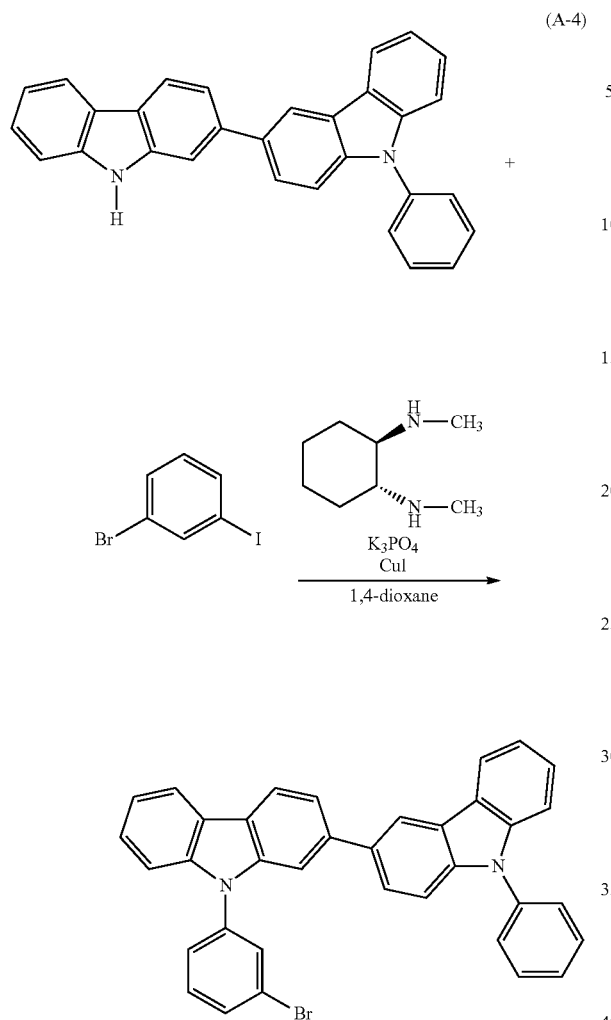

(B-4)

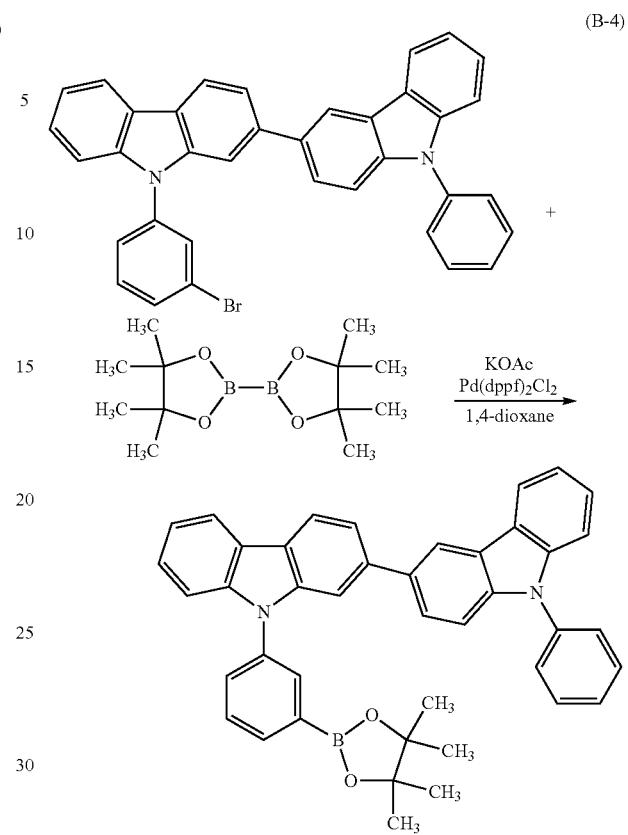

Step 3: Synthesis of 4mPCCzPBfpm-02

Next, 0.72 g (3.5 mmol) of 4-chloro[1]benzofuro[3,2-d]pyrimidine, 2.6 g (4.2 mmol) of 9-[3-(4,4,5,5-tetramethyl-1,3,2-dioxaborolan-2-yl)phenyl]-9'-phenyl-2,3'-bi-9H-carbazole, which was synthesized by the above synthesis method in Step 2, 2 mL of a 2M aqueous solution of potassium carbonate, 18 mL of toluene, and 2 mL of ethanol were put in a three-neck flask equipped with a reflux pipe, and the air in the flask was replaced with nitrogen. To this mixture were added 16 mg (0.071 mmol) of palladium(II) acetate and 43 mg (0.14 mmol) of tris(2-methylphenyl)phosphine (abbreviation: P(o-tolyl)$_3$), and the mixture was heated and stirred at 90° C. for 28 hours. The obtained reaction mixture was filtered and the residue was washed with water and ethanol. The obtained residue was dissolved in hot toluene and filtered through a filter aid in which Celite, silica gel, and Celite were filled in this order. The solvent of the obtained filtrate was distilled off and recrystallization was carried out with a mixed solvent of toluene and ethanol; thus, 1.7 g of 4mPCCzPBfpm-02, which was the desired substance, was obtained (as a yellow solid in a yield of 72%). Then, 1.7 g of the yellow solid was purified by a train sublimation method. In the purification by sublimation, the yellow solid was heated at 290° C. under a pressure of 2.8 Pa with argon gas at a flow rate of 5 mL/min. After the purification by sublimation, 1.1 g of a yellowish white solid of the desired substance was obtained at a collection rate of 64%. The synthesis scheme of Step 3 is shown in the following equation (C-4).

Step 2: Synthesis of 9-[3-(4,4,5,5-tetramethyl-1,3,2-dioxaborolan-2-yl)phenyl]-9'-phenyl-2,3'-bi-9H-carbazole Next, 4.8 g (8.5 mmol) of 9-(3-bromophenyl)-9'-phenyl-2,3'-bi-9H-carbazole, which was synthesized in Step 1 described above, 2.8 g (11 mmol) of bis(pinacolato)diboron, and 2.5 g (26 mmol) of potassium acetate were put in a three-neck flask, and the air in the flask was replaced with nitrogen. To this mixture were added 90 mL of 1,4-dioxane and 0.35 g (0.43 mmol) of [1,1'-bis(diphenylphosphino)ferrocene]palladium(II) dichloride, and the mixture was heated and stirred at 100° C. for 2.5 hours. The obtained reaction mixture was subjected to extraction with toluene. The obtained solution of the extract was washed with saturated brine. Then, magnesium sulfate was added and filtration was performed. The solvent of the obtained filtrate was distilled off and purification was conducted by neutral silica gel column chromatography using a 1:2 toluene-hexane mixed solvent as the developing solvent; thus, 2.6 g of the desired substance was obtained (as a yellow solid in a yield of 48%). The synthesis scheme of Step 2 is shown in the following equation (B-4).

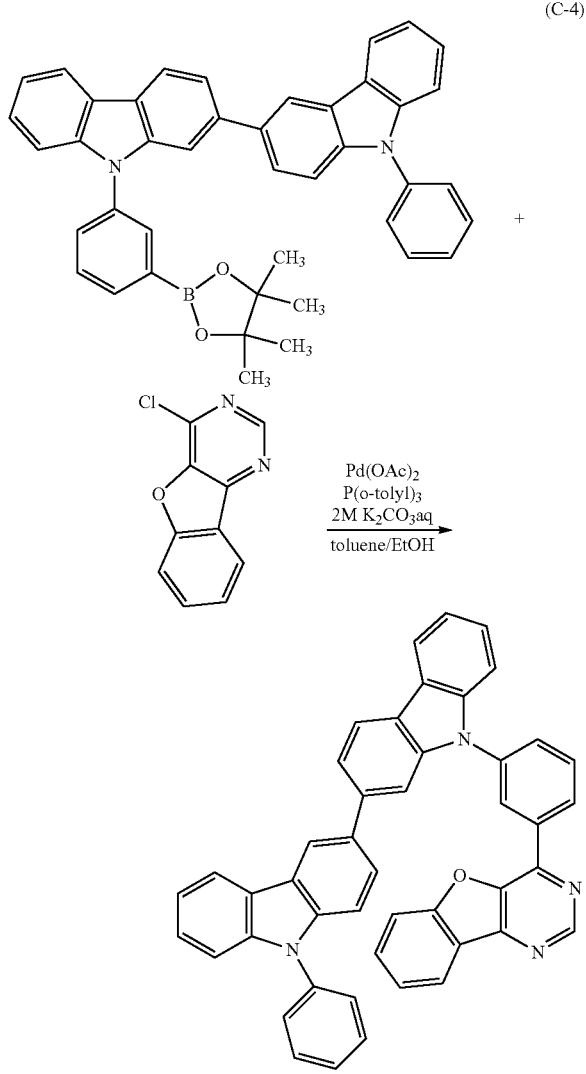

(C-4)

Figure 67:
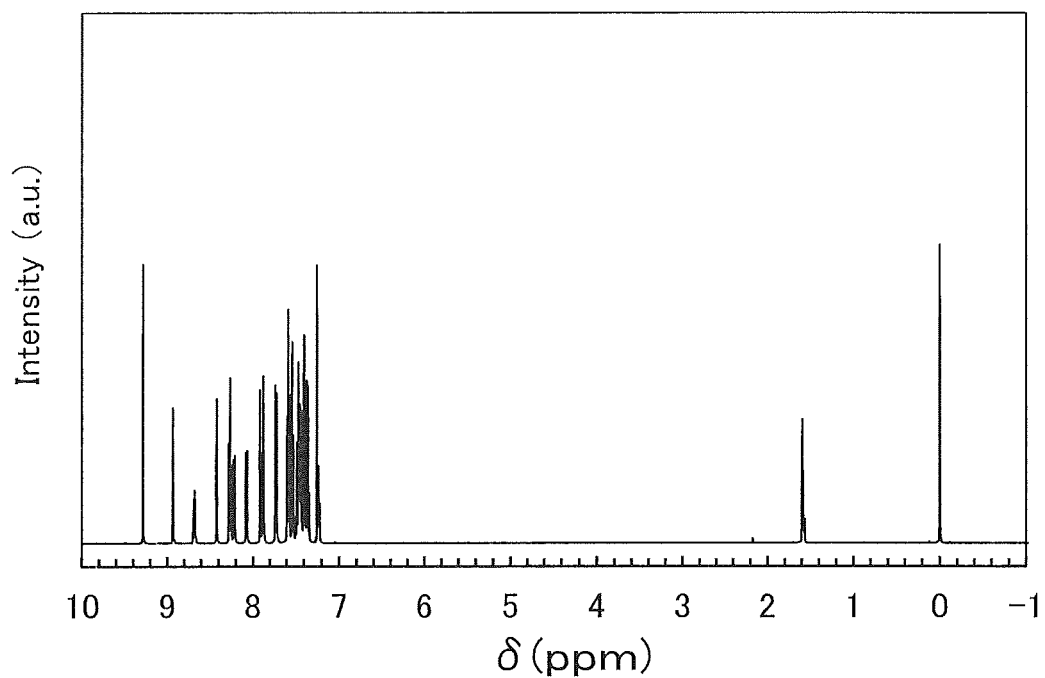
FIG. 67 is an NMR chart of a compound of Example.

Measurement results obtained by nuclear magnetic resonance ($^1$H-NMR) spectroscopy of the yellowish white solid obtained in Step 3 described above are shown below. The $^1$H-NMR chart is shown in FIG. 67. These results reveal that 4mPCCzPBfpm-02, which is one embodiment of the present invention, was obtained in Synthesis Example 4.

$^1$H-NMR δ(CDCl3): 7.21-7.25 (m, 1H), 7.34-7.50 (m, 9H), 7.53 (d, 2H), 7.57-7.60 (t, 3H), 7.73 (d, 2H), 7.88-7.92 (m, 3H), 8.08 (d, 1H), 8.22 (d, 1H), 8.25-8.28 (t, 2H), 8.42 (ds, 1H), 8.68 (ms, 1H), 8.93 (s, 1H), 9.29 (s, 1H).

<Characteristics of 4mPCCzPBfpm-02>

Next, mass spectrometry (MS) analysis of 4mPCCzPB-fpm-02 which was obtained was carried out by liquid chromatography mass spectrometry (abbreviation: LC/MS analysis).

In the LC/MS analysis, liquid chromatography (LC) separation was carried out with ACQUITY UPLC (manufactured by Waters Corporation), and mass spectrometry (MS) analysis was carried out with Xevo G2 Tof MS (manufactured by Waters Corporation). As a column for the LC separation, ACQUITY UPLC BEH C8 (2.1×100 mm, 1.7 μm) was used and the column temperature was set to 40° C. Acetonitrile was used for Mobile Phase A and a 0.1% formic acid aqueous solution was used for Mobile Phase B. A sample was prepared in such a manner that 4mPCCzPBfpm-02 was dissolved in toluene at a given concentration and the solution was diluted with acetonitrile. The injection amount was set to 5.0 μL.

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. A component with m/z of 653.23 which underwent the ionization under the above-described conditions was collided with an argon gas in a collision cell to dissociate into product ions. Energy (collision energy) for the collision with argon was set to 70 eV. The measurement mass range was set to m/z=100 to 1200. The detection results of the dissociated product ions by time-of-flight (TOF) MS are shown in FIG. 68.

Figure 68:
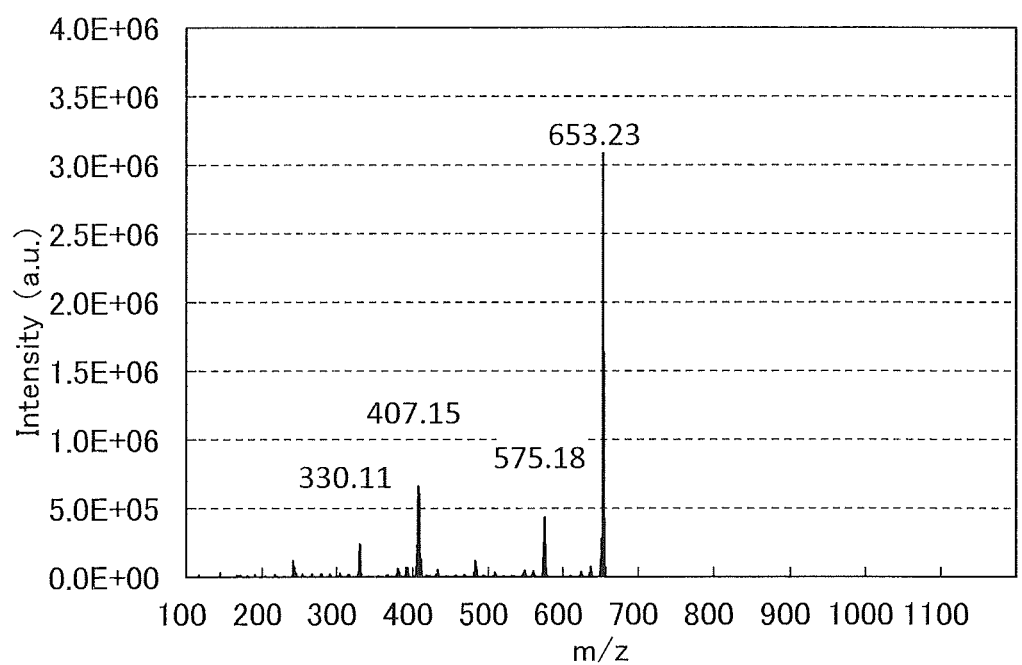
FIG. 68 is a graph showing an MS spectrum of a compound of Example.

FIG. 68 shows that product ions of 4mPCCzPBfpm-02 are mainly detected around m/z=575, 407, and 330. The results in FIG. 68 show characteristics derived from 4mPC-CzPBfpm-02 and can thus be regarded as important data for identifying 4mPCCzPBfpm-02 contained in a mixture.

The product ion around m/z=575 is presumed to be a cation in the state where a phenyl group is dissociated from 4mPCCzPBfpm-02. The product ion around m/z=407 is presumed to be a cation in the state where a phenyl group and benzofuropyrimidine are dissociated from 4mPCCzPB-fpm-02. The product ion around m/z=330 is presumed to be a cation in the state where a phenyl group is further dissociated from the above cation. These data suggest that 4mPCCzPBfpm-02 includes diphenylbicarbazole.

Figure 69:
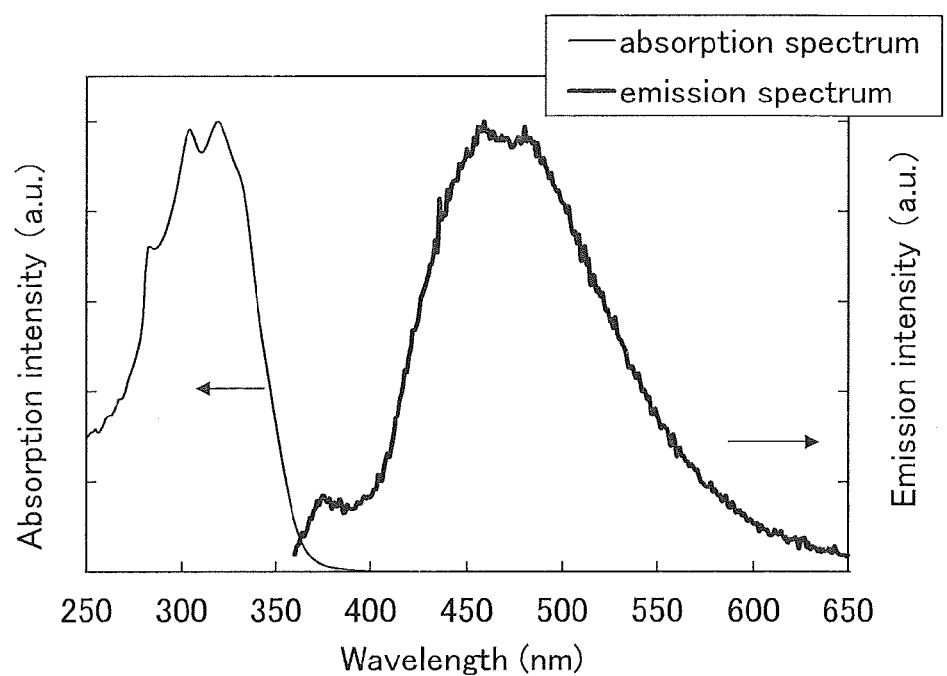
FIG. 69 is a graph showing absorption and emission spectra of a compound of Example.
Figure 70:
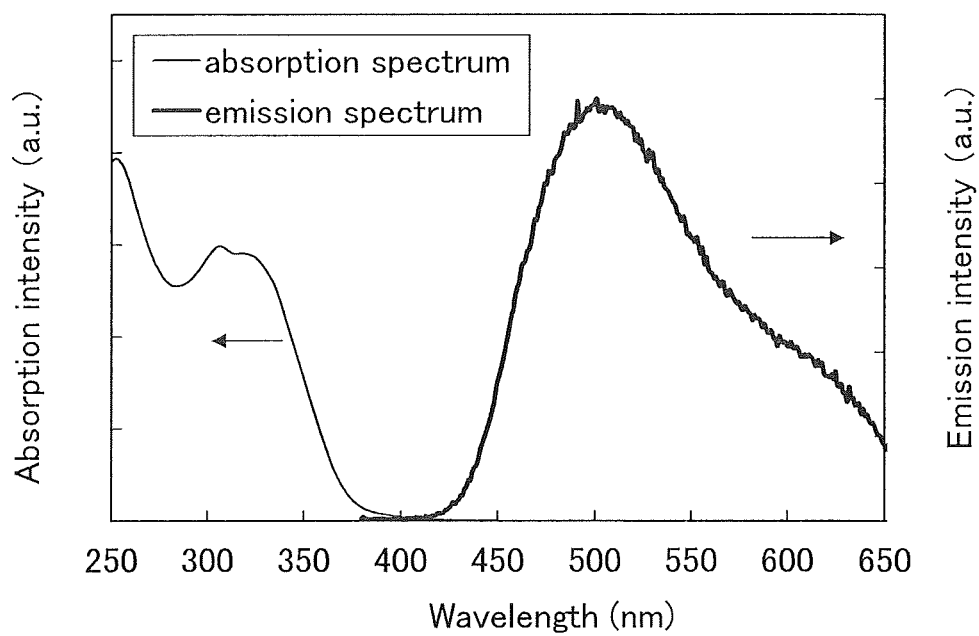
FIG. 70 is a graph showing absorption and emission spectra of a compound of Example.

Absorption and emission spectra of 4mPCCzPBfpm-02 in a toluene solution of 4mPCCzPBfpm-02 are shown in FIG. 69, and absorption and emission spectra of a thin film of 4mPCCzPBfpm-02 are shown in FIG. 70.

The absorption and emission spectra of 4mPCCzPBfpm-02 in the toluene solution and the thin film of 4mPCCzPB-fpm-02 were measured as in Example 1.

The maximum absorption wavelengths of 4mPCCzPB-fpm-02 in the toluene solution were around 305 nm and 325 nm, and the maximum emission wavelength thereof was around 459 nm (an excitation wavelength of 343 nm). Furthermore, the maximum absorption wavelengths of the thin film were around 310 nm and 325 nm, and the maximum emission wavelength thereof was around 500 nm (an excitation wavelength of 360 nm).

The ionization potential of the thin film of 4mPCCzPB-fpm-02 was measured in the air with a photoelectron spectrometer (AC-3, produced by Aiken Keiki, Co., Ltd.). The obtained value of the ionization potential was converted into a negative value, and the HOMO level of 4mPCCzPBfpm-02 was −5.86 eV. From the data of the absorption spectrum of the thin film in FIG. 70, the absorption edge of 4mPC-CzPBfpm-02, which was obtained from Tauc plot with an assumption of direct transition, was 3.43 eV. Thus, the optical energy gap of 4naPCCzPBfpm-02 in the solid state was estimated at 3.43 eV; from the values of the HOMO level obtained above and this energy gap, the LUMO level of 4mPCCzPBfpm-02 can be estimated at −2.43 eV. This reveals that 4mPCCzPBfpm-02 in the solid state has an energy gap as wide as 3.43 eV.

The electrochemical characteristics (oxidation reaction characteristics and reduction reaction characteristics) of 4mPCCzPBfpm-02 were measured by cyclic voltammetry (CV) measurement. The measurement method was similar to that used in Example 1.

The CV measurement results reveal that the oxidation potential of 4mPCCzPBfpm-02 is 0.74 V and the reduction potential is −1.92 V. In addition, the HOMO level and LUMO level of 4mPCCzPBfpm-02, which are calculated from the CV measurement results, are −5.68 eV and −3.02 eV, respectively. Thus, 4mPCCzPBfpm-02 is found to have a low LUMO level and a relatively high HOMO level.

Example 8

In this example, a method of synthesizing one of the compounds that are described in Embodiment 1 and represented by General Formula (G0), 4-(9'-phenyl-2,3'-bi-9H-carbazol-9-yl)benzofuro[3,2-d]pyrimidine (abbreviation: 4PCCzBfpm-02) (Structural Formula (134)), and characteristics of the compound are described.

Synthesis Example 5

Synthesis of 4PCCzBfpm-02

First, 0.24 g (6.0 mmol) of sodium hydride (60%) was added into a three-neck flask in which the air was replaced with nitrogen, and 20 mL of N,N-dimethylformamide (abbreviation: DMF) was dripped thereto while the sodium hydride was stirred. The flask was cooled to 0° C., and a mixed solution of 1.8 g (4.4 mmol) of 9'-phenyl-2,3'-bi-9H-carbazole and 20 mL of DMF was dripped to the mixture and stirring was performed at room temperature for 30 minutes. After the stirring, the container was cooled to 0° C. A mixed solution of 0.82 g (4.0 mmol) of 4-chloro[1]benzofuro[3,2-d]pyrimidine and 20 mL of DMF was added, and stirring was performed at room temperature for 20 hours to be reacted. The obtained reaction solution was added to ice water, and toluene was further added. The mixed solution was subjected to extraction with toluene. The solution of the extract was washed with saturated brine. Then, magnesium sulfate was added and filtration was performed. The solvent of the obtained filtrate was distilled off and purification was conducted by silica gel column chromatography using toluene as the developing solvent. Moreover, recrystallization was carried out with a mixed solvent of toluene and ethanol; thus, 1.6 g of 4PCCzBfpm-02, which was the desired substance, was obtained (as a yellowish white solid in a yield of 65%). The synthetic scheme of this step is shown in the following equation (A-5).

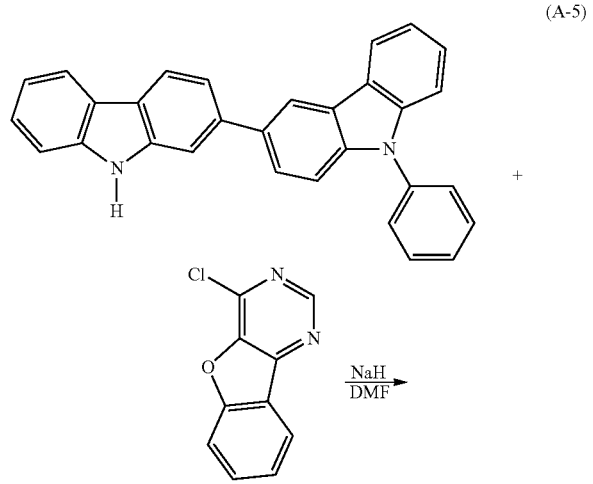

(A-5)

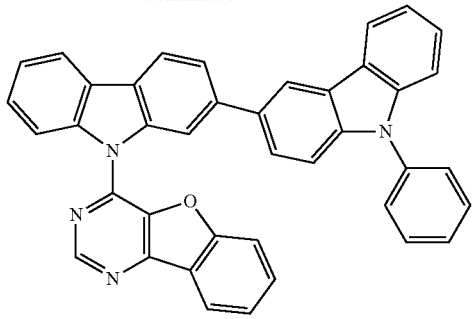

Then, 2.6 g of the yellowish white solid of 4PCCzBfpm-02, which was synthesized by the above synthesis method, was purified by a train sublimation method. In the purification by sublimation, the yellowish white solid was heated at 290° C. under a pressure of 2.5 Pa with a flow rate of argon gas of 10 mL/min. After the purification by sublimation, 2.1 g of a yellowish white solid of the desired substance was obtained at a collection rate of 81%.

Figure 71:
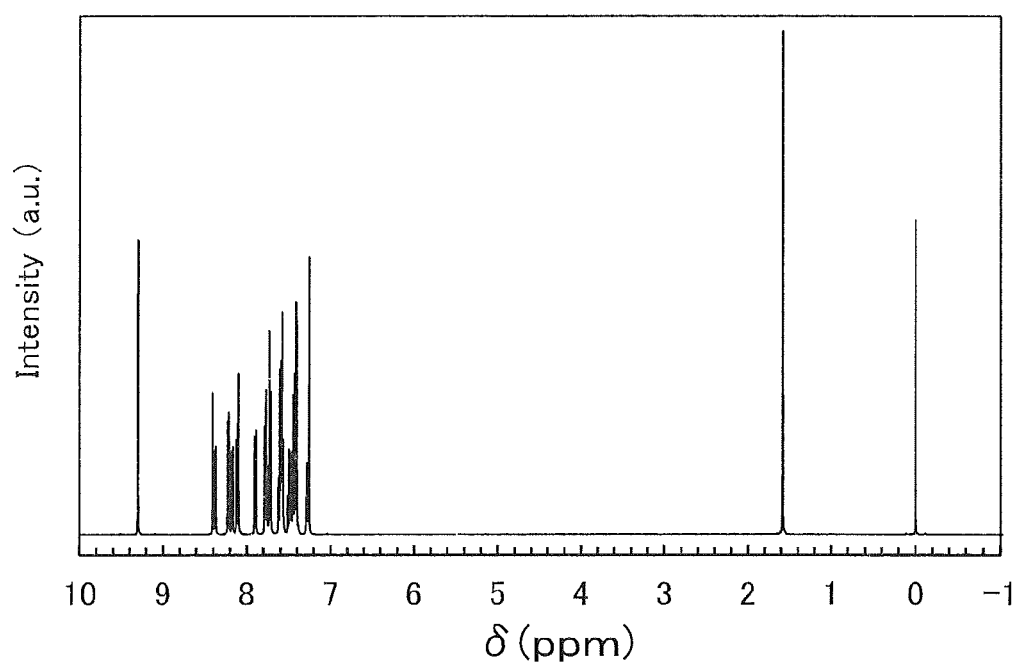
FIG. 71 is an NMR chart of a compound of Example.

Measurement results obtained by nuclear magnetic resonance ($^1$H-NMR) spectroscopy of the yellowish white solid obtained in the above step described above are shown below. The $^1$H-NMR chart is shown in FIG. 71. These results reveal that 4PCCzBfpm-02, which is one embodiment of the present invention, was obtained in Synthesis Example 5.

$^1$H-NMR δ (CDCl3): 7.26-7.30 (m, 1H), 7.41-7.51 (m, 6H), 7.57-7.63 (m, 5H), 7.72-7.79 (m, 4H), 7.90 (d, 1H), 8.10-8.12 (m, 2H), 8.17 (d, 1H), 8.22 (d, 1H), 8.37 (d, 1H), 8.41 (ds, 1H), 9.30 (s, 1H).

<Characteristics of 4PCCzBfpm-02>

Next, mass spectrometry (MS) analysis of 4PCCzBfpm-02 which was obtained was carried out by liquid chromatography mass spectrometry (abbreviation: LC/MS analysis).

In the LC/MS analysis, liquid chromatography (LC) separation was carried out with ACQUITY UPLC (manufactured by Waters Corporation), and mass spectrometry (MS) analysis was carried out with Xevo G2 Tof MS (manufactured by Waters Corporation). As a column for the LC separation, ACQUITY UPLC BEH C8 (2.1×100 mm, 1.7 μm) was used and the column temperature was set to 40° C. Acetonitrile was used for Mobile Phase A and a 0.1% formic acid aqueous solution was used for Mobile Phase B. A sample was prepared in such a manner that 4PCCzBfpm-02 was dissolved in toluene at a given concentration and the solution was diluted with acetonitrile. The injection amount was set to 5.0 μL.

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. A component with m/z of 577.20 which underwent the ionization under the above-described conditions was collided with an argon gas in a collision cell to dissociate into product ions. Energy (collision energy) for the collision with argon was set to 50 eV. The measurement mass range was set to m/z=100 to 1200. The detection results of the dissociated product ions by time-of-flight (TOF) MS are shown in FIG. 72.

Figure 72:
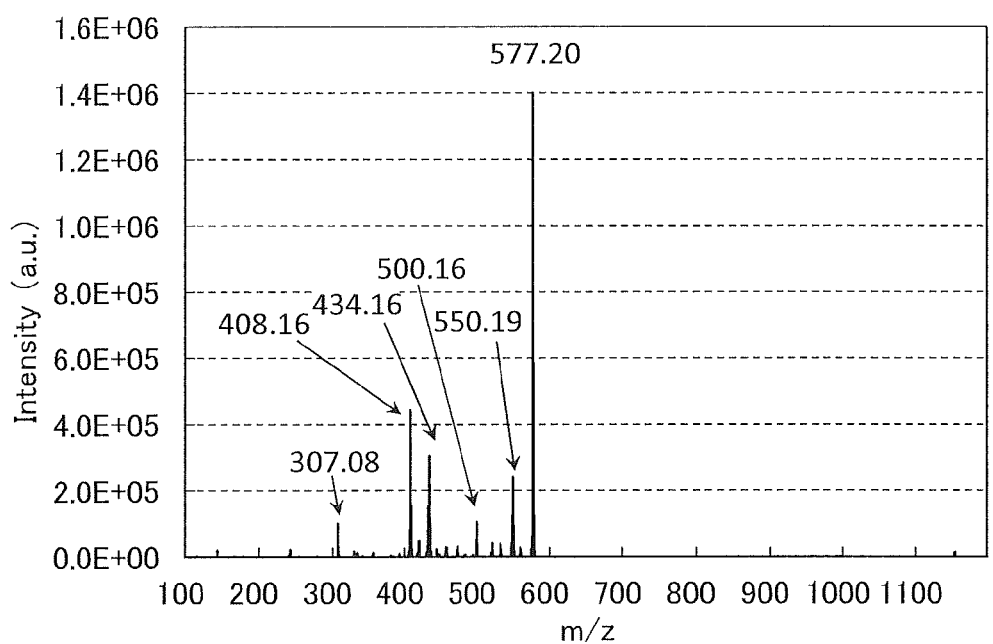
FIG. 72 is a graph showing an MS spectrum of a compound of Example.

FIG. 72 shows that product ions of 4PCCzBfpm-02 are mainly detected around m/z=550, 434, 408, and 307. The results in FIG. 72 show characteristics derived from 4PCCzBfpm-02 and can thus be regarded as important data for identifying 4PCCzBfpm-02 contained in a mixture.

The product ion around m/z=550 is presumed to be a cation generated due to dissociation of nitrile by cleavage of a pyrimidine ring in 4PCCzBfpm-02. The product ion around m/z=434 is presumed to be a cation generated due to dissociation of a benzofuranyl group by further cleavage. These data suggest that 4PCCzBfpm-02 includes a benzofuropyrimidyl group. The product ion around m/z=408 is presumed to be a cation in the state where a benzofuropyrimidyl group is dissociated from 4PCCzBfpm-02, which suggests that 4PCCzBfm-02 includes phenylbicarbazole.

Figure 73:
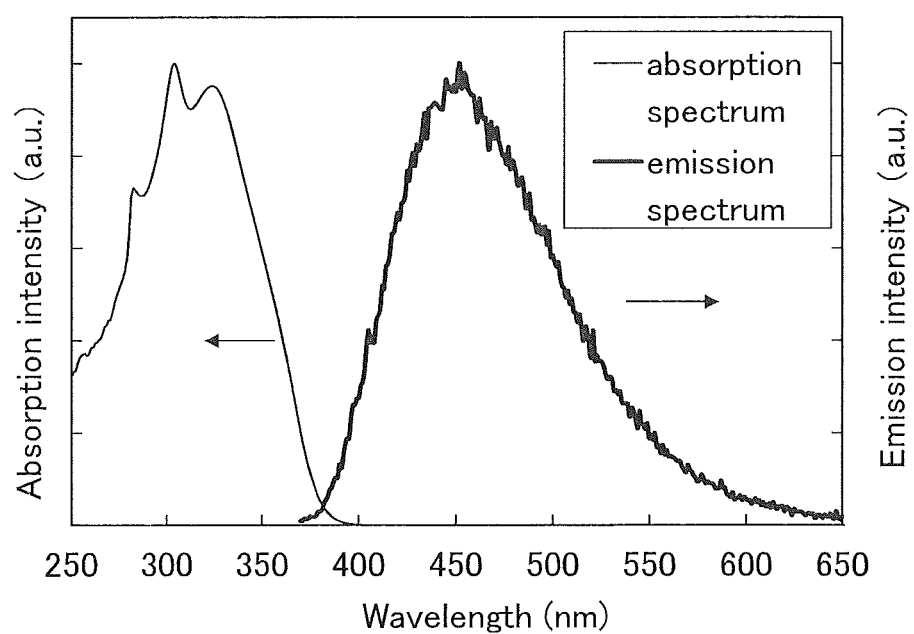
FIG. 73 is a graph showing absorption and emission spectra of a compound of Example.
Figure 74:
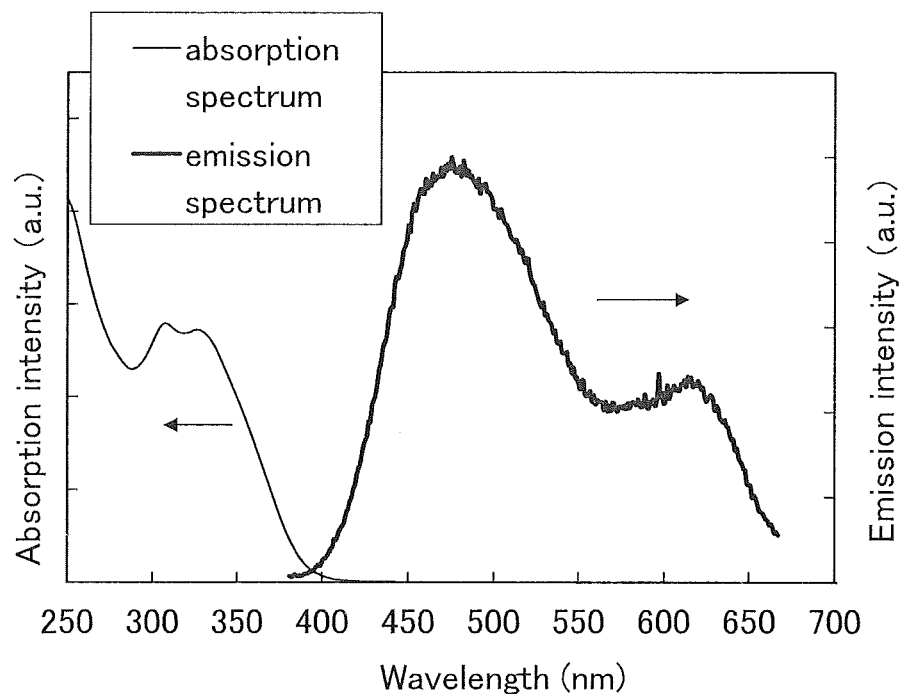
FIG. 74 is a graph showing absorption and emission spectra of a compound of Example.

Absorption and emission spectra of 4PCCzBfpm-02 in a toluene solution of 4PCCzBfpm-02 are shown in FIG. 73, and absorption and emission spectra of a thin film of 4PCCzBfpm-02 are shown in FIG. 74.

The absorption and emission spectra of 4PCCzBfpm-02 in the toluene solution and the thin film of 4PCCzBfpm-02 were measured as in Example 1.

The maximum absorption wavelengths of 4PCCzBfpm-02 in the toluene solution were around 305 nm and 325 nm, and the maximum emission wavelength thereof was around 452 nm (an excitation wavelength of 354 nm). Furthermore, the maximum absorption wavelengths of the thin film were around 310 nm and 330 nm, and the maximum emission wavelength thereof was around 475 nm (an excitation wavelength of 360 nm).

The ionization potential of the thin film of 4PCCzBfpm-02 was measured in the air with a photoelectron spectrometer (AC-3, produced by Riken Keiki, Co., Ltd.). The obtained value of the ionization potential was converted into a negative value, and the HOMO level of 4PCCzBfpm-02 was −5.78 eV. From the data of the absorption spectrum of the thin film in FIG. 74, the absorption edge of 4PCCzBfpm-02, which was obtained from Tauc plot with an assumption of direct transition, was 3.32 eV. Thus, the optical energy gap of 4PCCzBfpm-02 in the solid state was estimated at 3.32 eV; from the values of the HOMO level obtained above and this energy gap, the LUMO level of 4PCCzBfpm-02 can be estimated at −2.46 eV. This reveals that 4PCCzBfpm-02 in the solid state has an energy gap as wide as 3.32 eV.

The electrochemical characteristics (oxidation reaction characteristics and reduction reaction characteristics) of 4PCCzBfpm-02 were measured by cyclic voltammetry (CV) measurement. The measurement method was similar to that used in Example 1.

The CV measurement results reveal that the oxidation potential of 4PCCzBfpm-02 is 0.82 V and the reduction potential is −2.10 V. In addition, the HOMO level and LUMO level of 4PCCzBfpm-02, which are calculated from the CV measurement results, are −5.76 eV and −2.84 eV, respectively. Thus, 4PCCzBfpm-02 is found to have a low LUMO level and a relatively high HOMO level.

Example 9

In this example, fabrication examples of light-emitting elements each including the compound of one embodiment of the present invention and characteristics of the light-emitting elements are described. A schematic cross-sectional view of the light-emitting elements fabricated in this example is the same as FIG. 47. Table 7 shows details of the element structure. In addition, structures and abbreviations of compounds used are given below. Note that the above examples are referred to for other compounds.

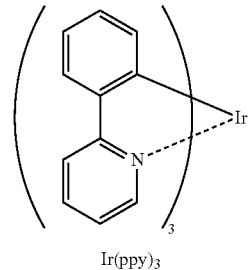

Ir(ppy)$_3$

TABLE 7

| | Layer | Reference numeral | Film thickness (nm) | Material | Weight ratio |
|---|---|---|---|---|---|
| Light-emitting element 5 | Electrode | 102 | 200 | Al | — |
| | Electron-injection layer | 119 | 1 | LiF | — |
| | Electron-transport layer | 118(2) | 10 | BPhen | — |
| | | 118(1) | 20 | 4mPCCzPBfpm | — |
| | Light-emitting layer | 160(2) | 20 | 4mPCCzPBfpm:PCCP:Ir(ppy)$_3$ | 0.8:0.2:0.05 |
| | Hole-transport layer | 160(1) | 20 | 4mPCCzPBfpm:PCCP:Ir(ppy)$_3$ | 0.5:0.5:0.05 |
| | Hole-injection layer | 112 | 20 | PCCP | — |
| | Electrode | 111 | 60 | DBT3P-II:MoO$_3$ | 1:0.5 |
| Light-emitting element 6 | Electrode | 101 | 70 | ITSO | — |
| | Electron-injection layer | 102 | 200 | Al | — |
| | | 119 | 1 | LiF | — |
| | Electron-transport layer | 118(2) | 10 | BPhen | — |
| | Light-emitting layer | 118(1) | 20 | 4mPCCzPBfpm-02 | — |
| | Hole-transport layer | 160(2) | 20 | 4mPCCzPBfpm-02:PCCP:Ir(ppy)$_3$ | 0.8:0.2:0.05 |
| | Hole-injection layer | 160(1) | 20 | 4mPCCzPBfpm-02:PCCP:Ir(ppy)$_3$ | 0.5:0.5:0.05 |
| | Electrode | 112 | 20 | PCCP | — |

TABLE 7-continued

| Layer | | Reference numeral | Film thickness (nm) | Material | Weight ratio |
|---|---|---|---|---|---|
| Light-emitting element 7 | Electrode | 111 | 60 | DBT3P-II:MoO$_3$ | 1:0.5 |
| | Electron-injection layer | 101 | 70 | ITSO | — |
| | Electron-transport layer | 102 | 200 | Al | — |
| | | 119 | 1 | LiF | — |
| | Light-emitting layer | 118(2) | 10 | BPhen | — |
| | Hole-transport layer | 118(1) | 20 | 4PCCzBfpm-02 | — |
| | Hole-injection layer | 160(2) | 20 | 4PCCzBfpm-02:PCCP:Ir(ppy)$_3$ | 0.8:0.2:0.05 |
| | Electrode | 160(1) | 20 | 4PCCzBfpm-02:PCCP:Ir(ppy)$_3$ | 0.5:0.5:0.05 |

<Fabrication of Light-Emitting Elements>
<<Fabrication of Light-Emitting Element 5>>

As the electrode 101, an ITSO film was formed to a thickness of 70 nm over the substrate 200. The electrode area of the electrode 101 was set to 4 mm$^2$ (2 mm×2 mm).

As the hole-injection layer 111, DBT3P-II and MoO$_3$ were deposited by co-evaporation to a thickness of 60 nm over the electrode 101 such that the weight ratio of DBT3P-II to MoO$_3$ was 1:0.5.

As the hole-transport layer 112, PCCP was deposited by evaporation to a thickness of 20 nm over the hole-injection layer 111.

As the light-emitting layer 160, 4mPCCzPBfpm, PCCP, and Ir(ppy)$_3$ were deposited over the hole-transport layer 112 by co-evaporation to a thickness of 20 nm such that the weight ratio of 4mPCCzPBfpm to PCCP and Ir(ppy)$_3$ was 0.5:0.5:0.05. They were further deposited by co-evaporation to a thickness of 20 nm such that the weight ratio of 4mPCCzPBfpm to PCCP and Ir(ppy)$_3$ was 0.8:0.2:0.05. Note that in the light-emitting layer 160, Ir(ppy)$_3$ corresponds to the guest material that emits phosphorescence.

As the electron-transport layer 118, 4mPCCzPBfpm and BPhen were successively deposited by evaporation to thicknesses of 10 nm and 15 nm, respectively, over the light-emitting layer 160. Then, as the electron-injection layer 119, LiF was deposited over the electron-transport layer 118 by evaporation to a thickness of 1 nm.

As the electrode 102, aluminum (Al) was deposited over the electron-injection layer 119 to a thickness of 200 nm.

Next, in a glove box containing a nitrogen atmosphere, the light-emitting element 5 was sealed by fixing the substrate 220 to the substrate 200 over which the organic material was deposited using a sealant for an organic EL device. The sealing method is the same as that used for the light-emitting element 1. Through the above steps, the light-emitting element 5 was obtained.

<<Fabrication of Light-Emitting Element 6 and 7>>

The light-emitting element 6 was fabricated through the same steps as those for the light-emitting element 5 except for the step of forming the light-emitting layer 160.

As the light-emitting layer 160 of the light-emitting element 6, 4mPCCzPBfpm-02, PCCP, and Ir(ppy)$_3$ were deposited by co-evaporation to a thickness of 20 nm such that the weight ratio of 4mPCCzPBfpm-02 to PCCP and Ir(ppy)$_3$ was 0.5:0.5:0.05. They were further deposited by co-evaporation to a thickness of 20 nm such that the weight ratio of 4mPCCzPBfpm-02 to PCCP and Ir(ppy)$_3$ was 0.8:0.2:0.05. As the electron-transport layer 118, 4mPCCzPB-fpm-02 and BPhen were successively deposited by evaporation to thicknesses of 10 nm and 15 nm, respectively, over the light-emitting layer 160.

As the light-emitting layer 160 of the light-emitting element 7, 4PCCzBfpm-02, PCCP, and Ir(ppy)$_3$ were deposited by co-evaporation to a thickness of 20 nm such that the weight ratio of 4PCCzBfpm-02 to PCCP and Ir(ppy)$_3$ was 0.5:0.5:0.05. They were further deposited by co-evaporation to a thickness of 20 nm such that the weight ratio of 4PCCzBfpm-02 to PCCP and Ir(ppy)$_3$ was 0.8:0.2:0.05. As the electron-transport layer 118, 4PCCzBfpm-02 and BPhen were successively deposited by evaporation to thicknesses of 10 nm and 15 nm, respectively, over the light-emitting layer 160.

<Characteristics of Light-Emitting Elements>

Figure 75:
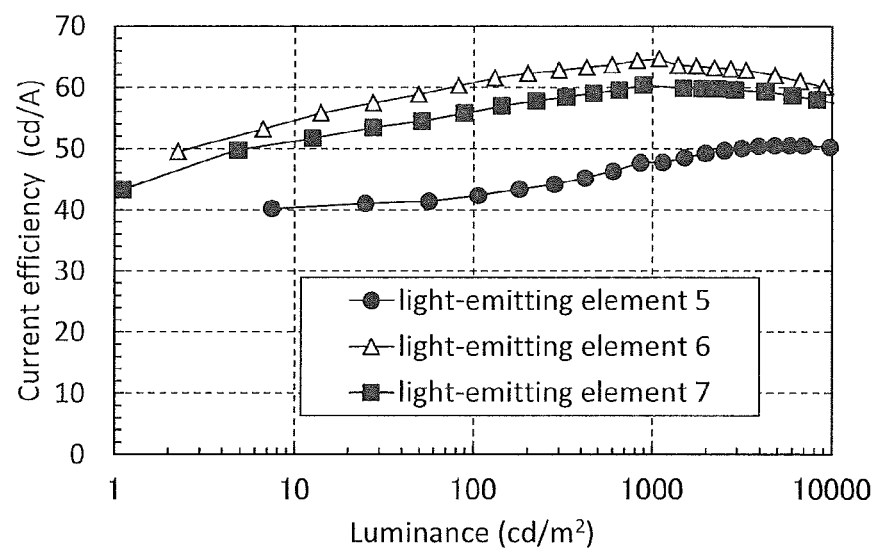
FIG. 75 is a graph showing current efficiency-luminance characteristics of light-emitting elements of Example.
Figure 76:
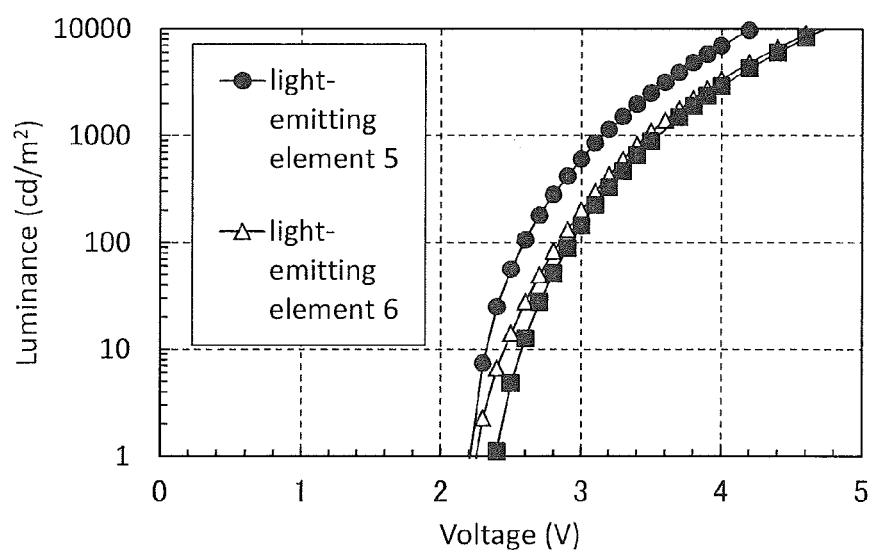
FIG. 76 is a graph showing luminance-voltage characteristics of light-emitting elements of Example.
Figure 77:
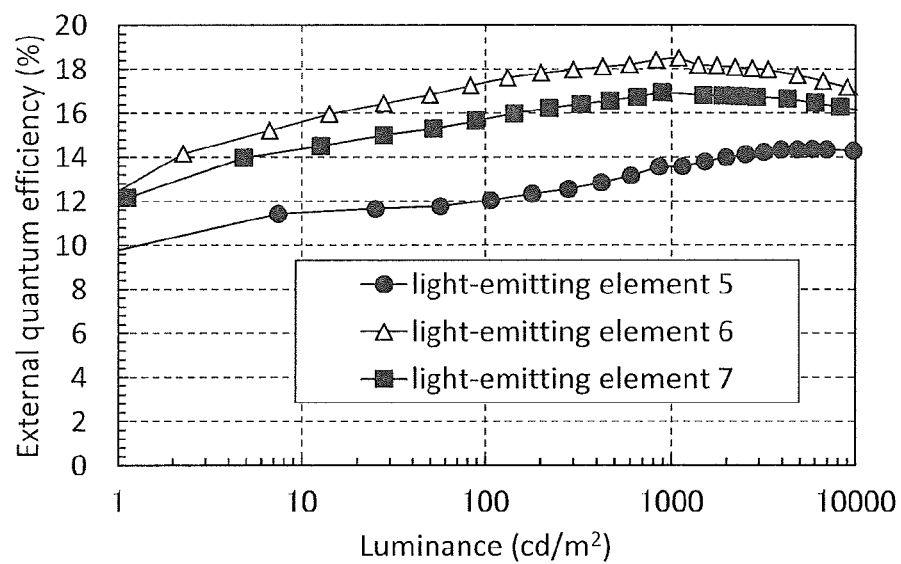
FIG. 77 is a graph showing external quantum efficiency-luminance characteristics of light-emitting elements of Example.
Figure 78:
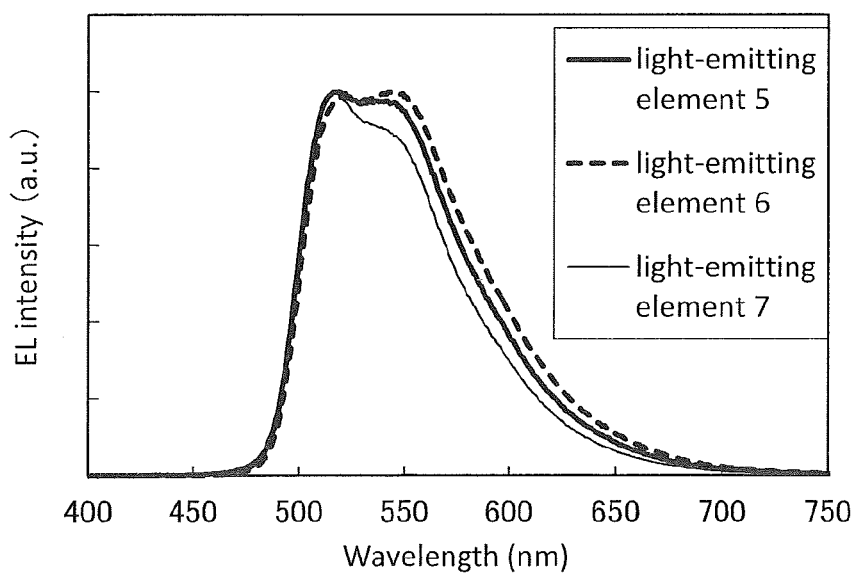
FIG. 78 is a graph showing electroluminescence spectra of light-emitting elements of Example.

FIG. 75 shows current efficiency-luminance characteristics of the light-emitting elements 5 to 7; FIG. 76 shows luminance-voltage characteristics thereof; and FIG. 77 shows external quantum efficiency-luminance characteristics thereof. The measurements of the light-emitting elements 5 to 7 were performed at room temperature (in an atmosphere kept at 23° C.). FIG. 78 shows electroluminescence spectra when a current at a current density of 2.5 mA/cm$^2$ was supplied to each of the light-emitting elements 5 to 7. The measurement methods were the same as those used in Example 3.

Table 8 shows element characteristics of the light-emitting elements 5 to 7 at around 1000 cd/m$^2$.

TABLE 8

| | Voltage (V) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 5 | 3.1 | 1.80 | (0.35, 0.61) | 860 | 48 | 48 | 14 |
| Light-emitting element 6 | 3.5 | 1.69 | (0.36, 0.60) | 1090 | 65 | 58 | 19 |

TABLE 8-continued

|  | Voltage (V) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 7 | 3.5 | 1.47 | (0.33, 0.62) | 890 | 60 | 54 | 17 |

From FIG. 75 to FIG. 77 and Table 8, it is found that each of the light-emitting elements 5 to 7 has high current efficiency and high external quantum efficiency. The maximum vales of the external quantum efficiencies of the light-emitting elements 5 to 7 are 14.4%, 18.5%, and 16.9%, respectively, which are excellent values. In addition, a fall (roll-off) in the emission efficiency of each of the light-emitting elements 5 to 7 is small even on the high luminance side, which is excellent.

As shown in FIG. 78, the light-emitting elements 5 to 7 emit green light having electroluminescence spectra with peaks at wavelengths of 519 nm, 544 nm, and 516 nm, respectively, and full widths at half maximum of 87 nm, 79 nm, and 93 nm, respectively. The obtained electroluminescence spectrum reveals that light is emitted from Ir(ppy)$_3$ as the guest material.

The light-emitting elements 5, 6, and 7 were driven at low voltages of 3.1 V, 3.5 V, and 3.5 V, respectively, at around 1000 cd/m$^2$ and thus exhibited excellent power efficiency.

<Measurements of S1 Level and T1 Level>

Figure 79:
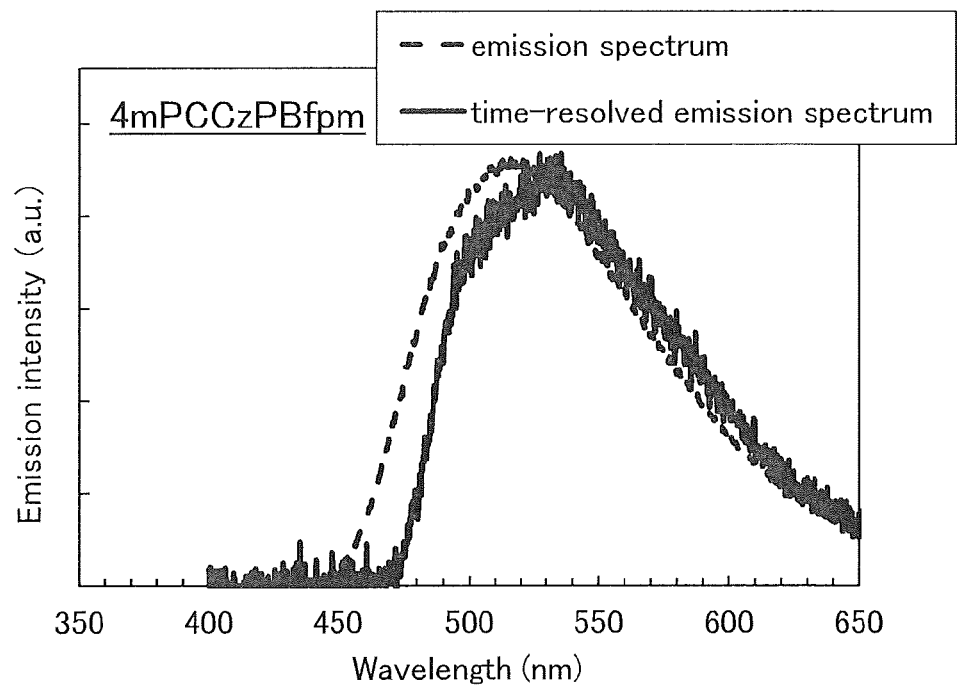
FIG. 79 is a graph showing emission spectra of a compound of Example.
Figure 80:
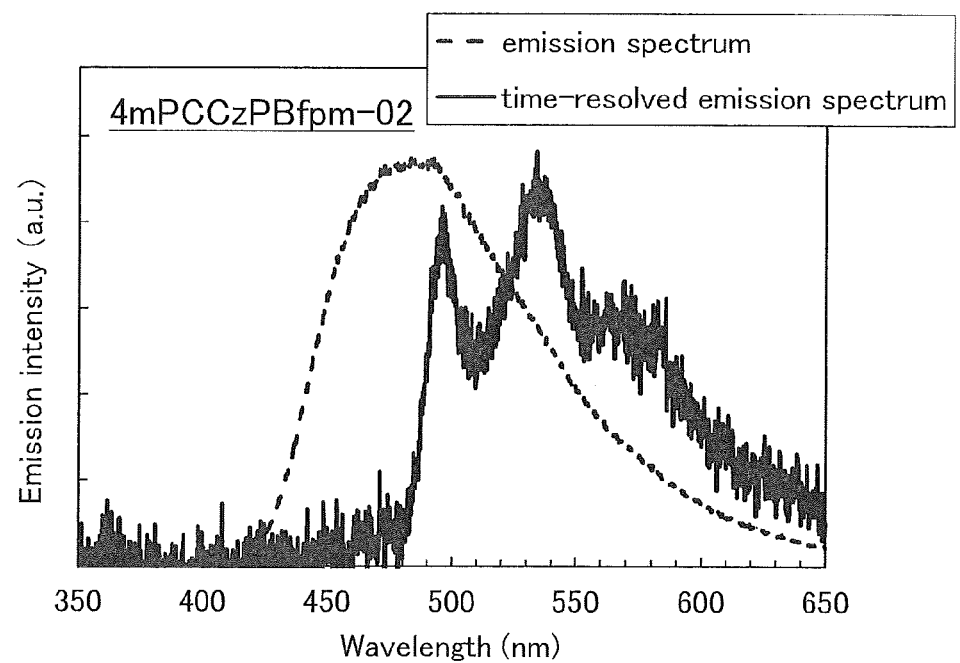
FIG. 80 is a graph showing emission spectra of a compound of Example.
Figure 81:
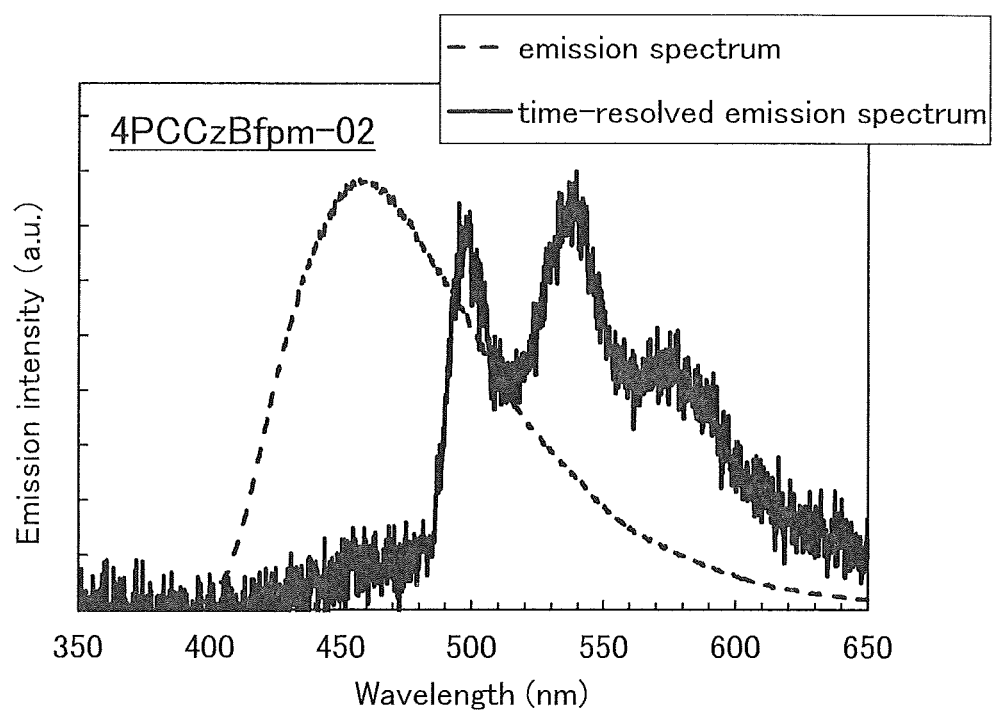
FIG. 81 is a graph showing emission spectra of a compound of Example.

Calculations were performed to measure the S1 levels and the T1 levels of 4mPCCzPBfpm, 4mPCCzPBfpm-02, and 4PCCzBfpm-02, which are compounds of embodiments of the present invention and were each used as the host material of the light-emitting layer 160. The measurement methods were the same as those used in Example 3. FIG. 79 shows measurement results of an emission spectrum of 4mPCCzPBfpm, FIG. 80 shows measurement results of an emission spectrum of 4mPCCzPBfpm-02, and FIG. 81 shows measurement results of an emission spectrum of 4PCCzBfpm-02.

The measurement results of the emission spectra show that, in the emission spectrum of 4mPCCzPBfpm, peaks (including shoulders) of the fluorescence component and the phosphorescence component on the shortest wavelength side were at 488 nm and 496 nm, respectively. In the emission spectrum of 4mPCCzPBfpm-02, peaks (including shoulders) of the fluorescence component and the phosphorescence component on the shortest wavelength side were at 470 nm and 496 nm, respectively. In the emission spectrum of 4PCCzBfpm-02, peaks (including shoulders) of the fluorescence component and the phosphorescence component on the shortest wavelength side were at 458 nm and 495 nm, respectively.

Thus, the S1 level and the T1 level of 4mPCCzPBfpm, which are calculated from the wavelengths of the peaks (including shoulders), are 2.54 eV and 2.50 eV, respectively, and therefore the energy difference between the S1 level and the T1 level is 0.04 eV. The S1 level and the T1 level of 4mPCCzPBfpm-02 are 2.64 eV and 2.50 eV, respectively, and therefore the energy difference between the S1 level and the T1 level is 0.14 eV. In addition, the S1 level and the T1 level of 4PCCzBfpm-02 are 2.71 eV and 2.51 eV, respectively, and therefore the energy difference between the S1 level and the T1 level is 0.20 eV.

As described above, the energy difference between the S1 level and the T1 level of each of 4mPCCzPBfpm, 4mPCCzPBfpm-02, and 4PCCzBfpm-02 is greater than 0 eV and less than or equal to 0.2 eV, which is extremely small.

Therefore, a singlet excited state can be formed with energy close to the energy of the triplet excited state. Accordingly, an energy difference between the energy of the singlet excited state of the host material (4mPCCzPBfpm, 4mPCCzPBfpm-02, or 4PCCzBfpm-02) and the energy of the triplet excited state of Ir(ppy)$_3$ can be reduced. Thus, each of the light-emitting elements 5 to 7 can be driven at a low voltage.

Thus, each of the wavelengths of the peaks of the phosphorescence components on the shortest wavelength sides in the emission spectra of 4mPCCzPBfpm, 4mPCCzPBfpm-02, and 4PCCzBfpm-02 is shorter than each of the wavelengths of the peaks in the electroluminescence spectra of the light-emitting elements 5 to 7. Furthermore, since 4mPCCzPBfpm, 4mPCCzPBfpm-02, and 4PCCzBfpm-02 each have a high T1 level, they are each suitable for a light-emitting element including a phosphorescent material that emits green light as a guest material.

As described above, by using a compound of one embodiment of the present invention and a guest material, a light-emitting element with high emission efficiency can be fabricated. Furthermore, a light-emitting element with low drive voltage and reduced power consumption can be fabricated.

The structures described in this example can be used in an appropriate combination with any of the structures described in the other examples and embodiments.

Reference Example 1

In this reference example, a method for synthesizing tris{2-[4-(4-cyano-2,6-diisobutylphenyl)-5-(2-methylphenyl)-4H-1,2,4-triazol-3-yl-κN$^2$]phenyl-κC}iridium(III) (abbreviation: Ir(mpptz-diBuCNp)$_3$), which is the organometallic complex used as the guest material in Example 5, is described.

Synthesis Example 6

Step 1: Synthesis of 4-amino-3,5-diisobutylbenzonitrile

Into a 1000 mL three-neck flask were put 9.4 g (50 mmol) of 4-amino-3,5-dichlorobenzonitrile, 26 g (253 mmol) of isobutylboronic acid, 54 g (253 mmol) of tripotassium phosphate, 2.0 g (4.8 mmol) of 2-dicyclohexylphosphino-2',6'-dimethoxybiphenyl (S-phos), and 500 mL of toluene. The air in the flask was replaced with nitrogen, and this mixture was degassed while being stirred under reduced pressure. After the degassing, 0.88 g (0.96 mmol) of tris(dibenzylideneacetone)palladium(0) was added, and the mixture was stirred at 130° C. under a nitrogen stream for 8 hours to be reacted. Toluene was added to the reaction solution, and the solution was filtered through a filter aid in which Celite, aluminum oxide, and Celite were stacked in this order. The obtained filtrate was concentrated to give an oily substance. The obtained oily substance was purified by silica column chromatography. Toluene was used as the developing solvent. The obtained fraction was concentrated to give 10 g of a yellow oily substance in a yield of %. The obtained yellow oily substance was identified as 4-amino-3,5-diisobutylbenzonitrile by nuclear magnetic resonance (NMR) spectroscopy. The synthesis scheme of Step 1 is shown in the following equation (a-1).

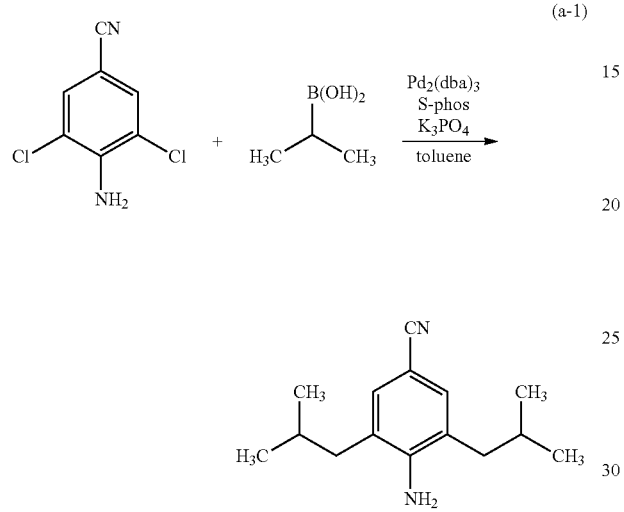

Step 2: Synthesis of Hmpptz-diBuCNp

Into a 300 mL three-neck flask were put 11 g (48 mmol) of 4-amino-3,5-diisobutylbenzonitrile synthesized in Step 1, 4.7 g (16 mmol) of N-(2-methylphenyl)chloromethylidene-N'-phenylchloromethylidenehydrazine, and 40 mL of N,N-dimethylaniline, and the mixture was stirred at 160° C. under a nitrogen stream for 7 hours to be reacted. After the reaction, the reaction solution was added to 300 mL of 1M hydrochloric acid and stirring was performed for 3 hours. Ethyl acetate was added to this mixture, an organic layer and an aqueous layer were separated, and the aqueous layer was subjected to extraction with ethyl acetate. The organic layer and the obtained solution of the extract were combined, and washed with a saturated aqueous solution of sodium hydrogen carbonate and then with saturated brine, and anhydrous magnesium sulfate was added to the organic layer for drying. The obtained mixture was subjected to gravity filtration, and the filtrate was concentrated to give an oily substance. The obtained oily substance was purified by silica column chromatography. As the developing solvent, a 5:1 hexane-ethyl acetate mixed solvent was used. The obtained fraction was concentrated to give a solid. Hexane was added to the obtained solid, and the mixture was irradiated with ultrasonic waves and then subjected to suction filtration to give 2.0 g of a white solid in a yield of 28%. The obtained white solid was identified as 4-(4-cyano-2,6-diisobutylphenyl)-3-(2-methylphenyl)-5-phenyl-4H-1,2,4-triazole (abbreviation: Hmpptz-diBuCNp) by nuclear magnetic resonance (NMR) spectroscopy. The synthesis scheme of Step 2 is shown in the following equation (b-1).

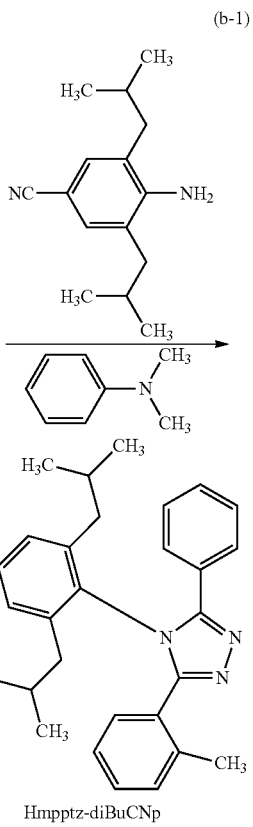

Step 3: Synthesis of Ir(mpptz-diBuCNp)$_3$

Into a reaction container equipped with a three-way cock were put 2.0 g (4.5 mmol) of Hmpptz-diBuCNp synthesized in Step 2 and 0.44 g (0.89 mmol) of tris(acetylacetonato)iridium(III), and the mixture was stirred at 250° C. under an argon stream for 43 hours to be reacted. The obtained reaction mixture was added to dichloromethane, and an insoluble matter was removed. The obtained filtrate was concentrated to give a solid. The obtained solid was purified by silica column chromatography. As the developing solvent, dichloromethane was used. The obtained fraction was concentrated to give a solid. The obtained solid was recrystallized from ethyl acetate/hexane, so that 0.32 g of a yellow solid was obtained in a yield of 23%. Then 0.31 g of the obtained yellow solid was purified by a train sublimation method. The purification by sublimation was performed by heating at 310° C. under a pressure of 2.6 Pa with argon gas at a flow rate of 5.0 mL/min for 19 hours. After the purification by sublimation, 0.26 g of a yellow solid was obtained at a collection rate of 84%. The synthesis scheme of Step 3 is shown in the following equation (c-1).

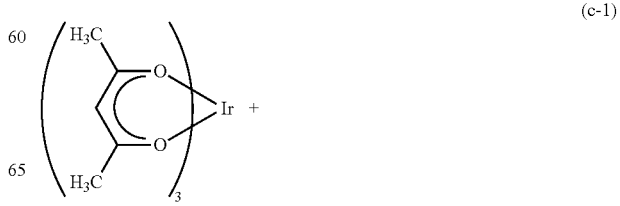

-continued

Hmpptz-diBuCNp

Ir(mpptz-diBuCNp)₃

The protons (¹H) of the yellow solid that was obtained above in Step 3 were measured by nuclear magnetic resonance (NMR) spectroscopy.

¹H-NMR δ(CDCl₃): 0.33 (d, 18H), 0.92 (d, 18H), 1.51-1.58 (m, 3H), 1.80-1.88 (m, 6H), 2.10-2.15 (in, 6H), 2.26-2.30 (m, 3H), 2.55 (s, 9H), 6.12 (d, 3H), 6.52 (t, 3H), 6.56 (d, 3H), 6.72 (t, 3H), 6.83 (t, 3H), 6.97 (d, 3H), 7.16 (t, 3H), 7.23 (d, 3H), 7.38 (s, 3H), 7.55 (s, 3H).

Reference Example 2

In this reference example, organometallic complexes that are phosphorescent materials suitable for a light-emitting element of one embodiment of the present invention are described. The structures and abbreviations of the organometallic complexes described in this reference example are shown below.

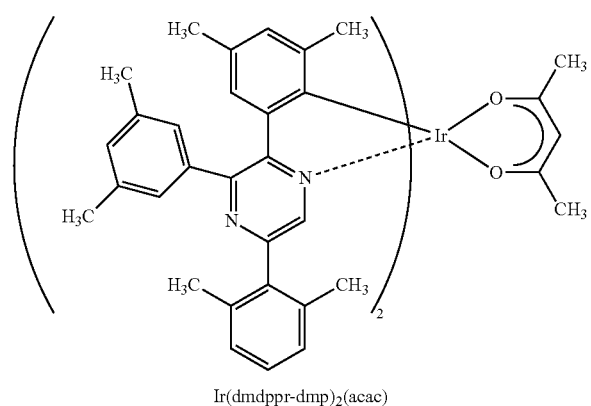

Ir(dmdppr-dmp)₂(acac)

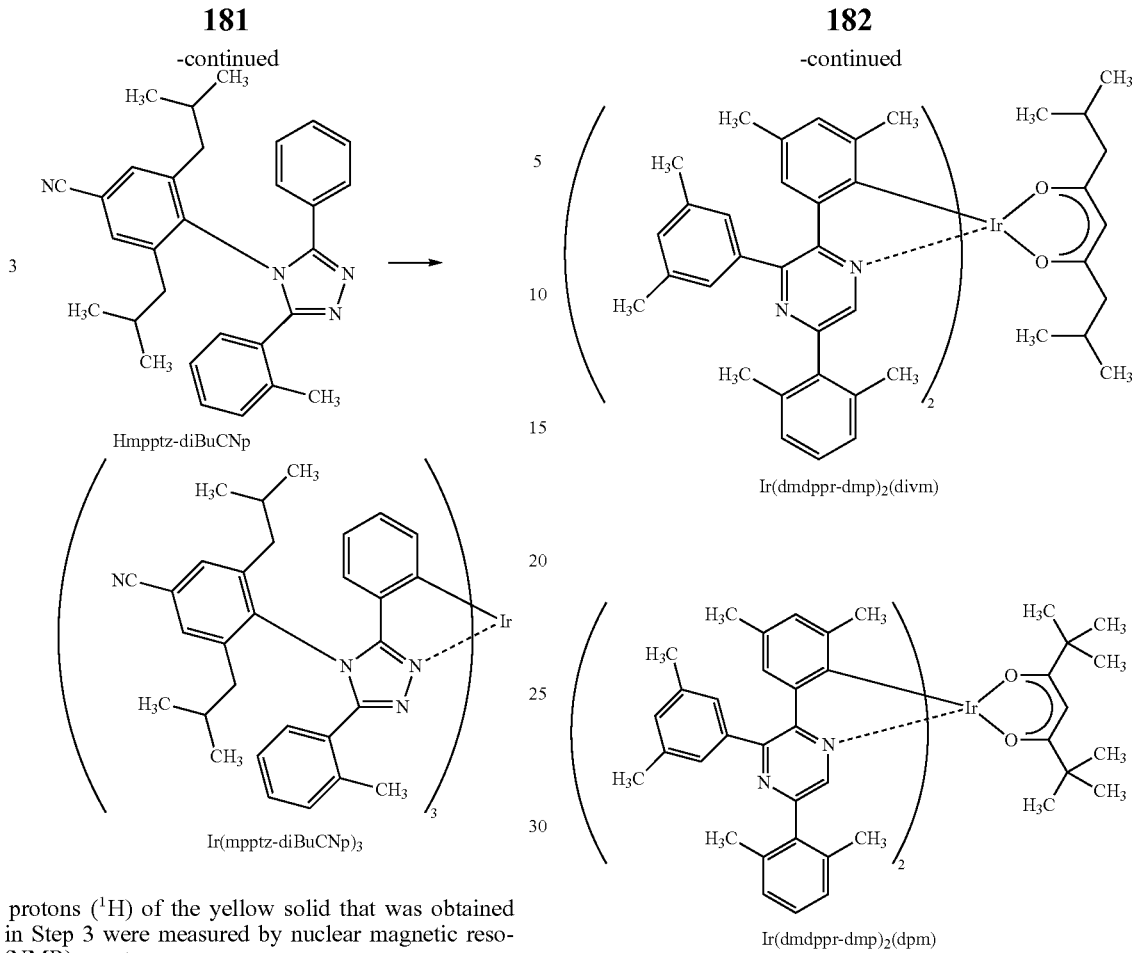

Ir(dmdppr-dmp)₂(divm)

Ir(dmdppr-dmp)₂(dpm)

Thermogravimetry-differential thermal analysis (TG-DTA) was performed on bis{4,6-dimethyl-2-[5-(2,6-dimethylphenyl)-3-(3,5-dimethylphenyl)-2-pyrazinyl-κN]phenyl-κC}(2,4-pentanedionato-K²O,O')iridium(III) (abbreviation: Ir(dmdppr-dmp)₂(acac)), bis{4,6-dimethyl-2-[5-(2,6-dimethylphenyl)-3-(3,5-dimethylphenyl)-2-pyrazinyl-κN]phenyl-κC}(2,8-dimethyl-4,6-nonanedionato-κ²O,O)iridium (III) (abbreviation: Ir(dmdppr-dmp)₂(divm)), and bis {2-[5-(2,6-dimethylphenyl)-3-(3,5-dimethylphenyl)-2-pyrazinyl-κN]-4,6-dimethylphenyl-κC}(2,2,6,6-tetramethyl-3,5-heptanedionato-κ²O,O')iridium(III) (abbreviation: Ir(dmdppr-dmp)₂(dpm)) to measure the thermophysical properties thereof. The measurements were conducted with a high vacuum differential type differential thermal balance (TG/DTA 2410SA, manufactured by Bruker AXS K.K.).

Under conditions of atmospheric pressure, a low vacuum (10 Pa), and a high vacuum (1×10⁻³ Pa), the temperature rising rate was set to 10° C./min, and the weight loss percentage was measured when the temperature was increased. At atmospheric pressure, the measurements were performed under a nitrogen stream (with a flow rate of 200 mL/min). The decomposition temperature at atmospheric pressure, the sublimation temperature under a low vacuum, and the sublimation temperature under a high vacuum were each the temperature at which the weight was reduced by 5%. The results of the TG-DTA measurements are shown in FIGS. 82A to 82C and Table 9.

TABLE 9

| | Decomposition temperature (° C.) at atmospheric pressure | Sublimation temperature (° C.) under low vacuum | Sublimation temperature (° C.) under high vacuum |
|---|---|---|---|
| Ir(dmdppr-dmp)$_2$(acac) | 371 | 267 | 250 |
| Ir(dmdppr-dmp)$_2$(divm) | 361 | 241 | 240 |
| Ir(dmdppr-dmp)$_2$(dpm) | 360 | 240 | 205 |

Figure 82A:
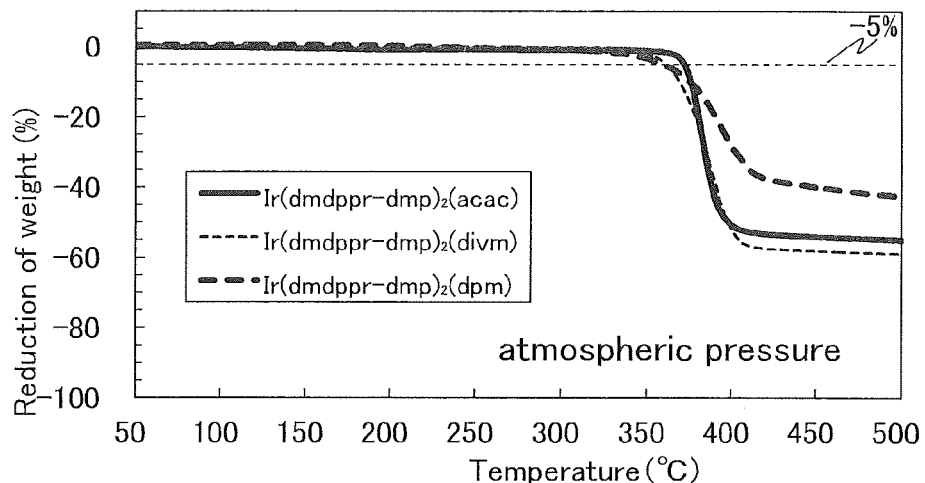
FIGS. 82A to 82C are graphs showing thermophysical properties of organometallic complexes of Reference Example.
Figure 82B:
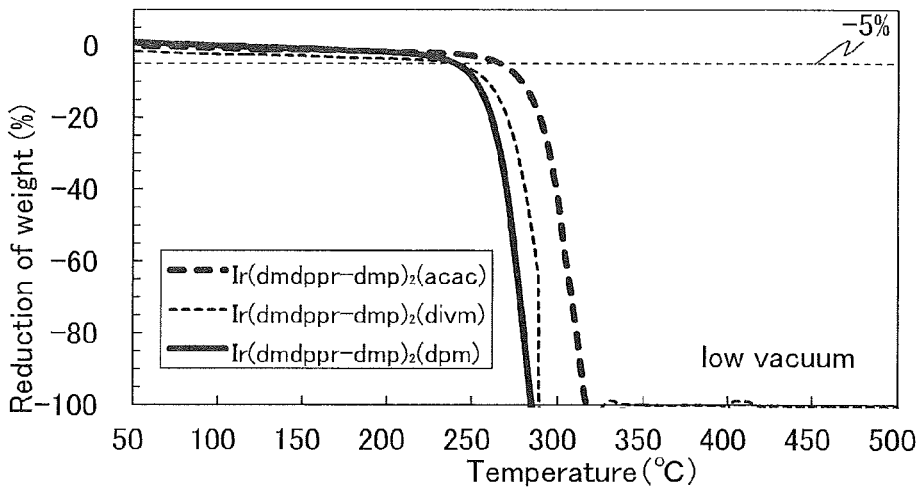
Figure 82C:
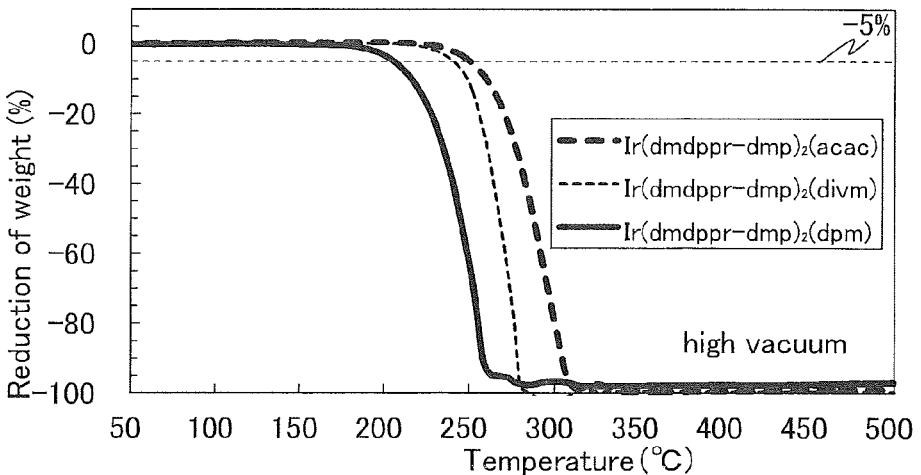

The results in FIG. 82A and Table 9 show that the decomposition temperatures of Ir(dmdppr-dmp)$_2$(acac), Ir(dmdppr-dmp)$_2$(divm), and Ir(dmdppr-dmp)$_2$(dpm) are 371° C., 361° C., and 350° C., respectively. Each organometallic complex has high heat resistance.

The results in FIGS. 82B and 82C and Table 9 show that the sublimation temperatures of each organometallic complex under a low vacuum and a high vacuum are lower than the decomposition temperature by 100° C. or more, and therefore the organometallic complexes can be sublimed without being decomposed. In particular, Ir(dmdppr-dmp)$_2$(divm) and Ir(dmdppr-dmp)$_2$(dpm) have a low sublimation temperature and thus have an excellent sublimation property.

As described above, the above organometallic complexes each have high heat resistance and an excellent sublimation property, which suggests suitability for a vacuum evaporation method and for a light-emitting element of one embodiment of the present invention.

REFERENCE NUMERALS

100: EL layer, 101: electrode, 101a: conductive layer, 101b: conductive layer, 101c: conductive layer, 102: electrode, 103: electrode, 103a: conductive layer, 103b: conductive layer, 104: electrode, 104a: conductive layer, 104b: conductive layer, 106: light-emitting unit, 108: light-emitting unit, 110: light-emitting unit, 111: hole-injection layer, 112: hole-transport layer, 113: electron-transport layer, 114: electron-injection layer, 115: charge generation layer, 116: hole-injection layer, 117: hole-transport layer, 118: electron-transport layer, 119: electron-injection layer, 120: light-emitting layer, 121: host material, 122: guest material, 123B: light-emitting layer, 123G: light-emitting layer, 123R: light-emitting layer, 130: light-emitting layer, 131: material, 132: host material, 133: guest material, 134: guest material, 135: light-emitting layer, 140: light-emitting layer, 141: host material, 141_1: organic compound, 141_2: organic compound, 142: guest material, 145: partition wall, 150: light-emitting layer, 152: light-emitting element, 160: light-emitting layer, 170: light-emitting layer, 190: light-emitting layer, 190a: light-emitting layer, 190b: light-emitting layer, 200: substrate, 220: substrate, 221B: region, 221G: region, 221R: region, 222B: region, 222G: region, 222R: region, 223: light-blocking layer, 224B: optical element, 224G: optical element, 224R: optical element, 250: light-emitting element, 252: light-emitting element, 260a: light-emitting element, 260b: light-emitting element, 262a: light-emitting element, 262b: light-emitting element, 300: organic semiconductor element, 301: source electrode, 301_1: wiring, 301_5: wiring, 301_6: wiring, 301_7: wiring, 302: drain electrode, 302_1: wiring, 302_2: wiring, 303: gate electrode, 303_1: transistor, 303_6: transistor, 303_7: transistor, 304: capacitor, 304_1: capacitor, 304_2: capacitor, 305: light-emitting element, 306_1: wiring, 306_3: wiring, 307_1: wiring, 307_3: wiring, 308_1: transistor, 3086: transistor, 309_1: transistor, 309_2: transistor, 311_1: wiring, 311_3: wiring, 312_1: wiring, 312_2: wiring, 330: active layer, 600: display device, 601: signal line driver circuit portion, 602: pixel portion, 603: scan line driver circuit portion, 604: sealing substrate, 605: sealant, 607: region, 607a: sealing layer, 607b: sealing layer, 607c: sealing layer, 608: wiring, 609: FPC, 610: element substrate, 611: transistor, 612: transistor, 613: lower electrode, 614: partition wall, 616: EL layer, 617: upper electrode, 618: light-emitting element, 621: optical element, 622: light-blocking layer, 623: transistor, 624: transistor, 801: pixel circuit, 802: pixel portion, 804: driver circuit portion, 804a: scan line driver circuit, 804b: signal line driver circuit, 806: protective circuit, 807: terminal portion, 852: transistor, 854: transistor, 862: capacitor, 872: light-emitting element, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: lower electrode, 1024G: lower electrode, 1024R: lower electrode, 1024Y: lower electrode, 1025: partition wall, 1026: upper electrode, 1028: EL layer, 1028B: light-emitting layer, 1028G: light-emitting layer, 1028R: light-emitting layer, 1028Y: light-emitting layer, 1029: sealing layer, 1031: sealing substrate, 1032: sealant, 1033: base material, 1034B: coloring layer, 1034G: coloring layer, 1034R: coloring layer, 1034Y: coloring layer, 1035: light-blocking layer, 1036: overcoat layer, 1037: interlayer insulating film, 1040: pixel portion, 1041: driver circuit portion, 1042: peripheral portion, 2000: touch panel, 2001: touch panel, 2501: display device, 2502R: pixel, 2502t: transistor, 2503c: capacitor, 2503g: scan line driver circuit, 2503s: signal line driver circuit, 2503t: transistor, 2509: FPC, 2510: substrate, 2510a: insulating layer, 2510b: flexible substrate, 2510c: adhesive layer, 2511: wiring, 2519: terminal, 2521: insulating layer, 2528: partition wall, 2550R: light-emitting element, 2560: sealing layer, 2567BM: light-blocking layer, 2567p: anti-reflective layer, 2567R: coloring layer, 2570: substrate, 2570a: insulating layer, 2570b: flexible substrate, 2570c: adhesive layer, 2580R: light-emitting module, 2590: substrate, 2591: electrode, 2592: electrode, 2593: insulating layer, 2594: wiring, 2595: touch sensor, 2597: adhesive layer, 2598: wiring, 2599: connection layer, 2601: pulse voltage output circuit, 2602: current sensing circuit, 2603: capacitor, 2611: transistor, 2612: transistor, 2613: transistor, 2621: electrode, 2622: electrode, 3000: light-emitting device, 3001: substrate, 3003: substrate, 3005: light-emitting element, 3007: sealing region, 3009: sealing region, 3011: region, 3013: region, 3014: region, 3015: substrate, 3016: substrate, 3018: desiccant, 3500: multifunction terminal, 3502: housing, 3504: display portion, 3506: camera, 3508: lighting, 3600: light, 3602: housing, 3608: lighting, 3610: speaker, 7101: housing, 7102: housing, 7103: display portion, 7104: display portion, 7105: microphone, 7106: speaker, 7107: operation key, 7108: stylus, 7121: housing, 7122: display portion, 7123: keyboard, 7124: pointing device, 7200: head mounted display, 7201: mounting portion, 7202: lens, 7203: main body, 7204: display portion, 7205: cable, 7206: battery, 7300: camera, 7301: housing, 7302: display portion, 7303: operation button, 7304: shutter button, 7305: connection portion, 7306: lens, 7400: finder, 7401: housing, 7402: display portion, 7403: button, 7701: housing, 7702: housing, 7703: display portion, 7704: operation key, 7705: lens, 7706: connection portion, 8000: display module, 8001: upper cover, 8002: lower cover, 8003: FPC, 8004: touch sensor, 8005: FPC, 8006: display device, 8009: frame, 8010: printed board, 8011: battery, 8501: lighting device, 8502: lighting device, 8503: lighting device, 8504: lighting device, 9000: housing, 9001: display portion, 9003: speaker, 9005: operation key, 9006: connection terminal, 9007: sensor, 9008: microphone, 9050: operation button, 9051: information, 9052: information, 9053: information, 9054: information, 9055: hinge, 9100: portable information terminal, 9101: portable information terminal, 9102: portable information terminal, 9200: portable information terminal, 9201: portable information terminal, 9300:

The invention claimed is:

1. A compound represented by General Formula (G1):

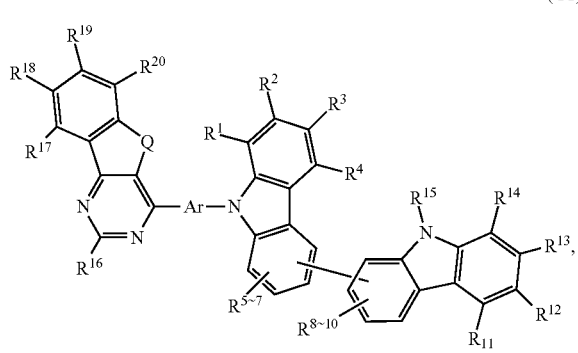

(G1)

wherein:
Q represents oxygen or sulfur;
each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms;
Ar represents a substituted or unsubstituted meta-phenylene group; and
the bicarbazole skeleton is a 2,3'-bi-9H-carbazole skeleton.

2. A compound represented by General Formula (G3):

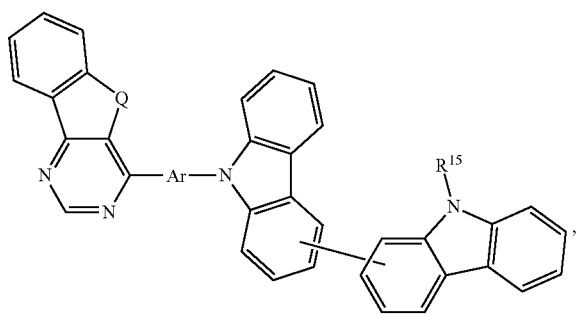

(G3)

wherein:
Q represents oxygen or sulfur;
$R^{15}$ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms;
Ar represents a substituted or unsubstituted meta-phenylene group; and
the bicarbazole skeleton is a 2,3'-bi-9H-carbazole skeleton.

3. A light-emitting element comprising the compound according to claim 1.

4. The light-emitting element according to claim 3, being configured to emit light comprising delayed fluorescence.

5. The light-emitting element according to claim 3, further comprising a phosphorescent material.

6. The light-emitting element according to claim 3, being configured to emit blue light.

7. A display device comprising the light-emitting element according to claim 3,
wherein the display device comprises at least one of a color filter and a transistor.

8. An electronic device comprising the display device according to claim 7,
wherein the electronic device comprises at least one of a housing and a touch sensor.

9. A lighting device comprising the light-emitting element according to claim 3,
wherein the lighting device comprises at least one of a housing and a touch sensor.

10. The compound according to claim 2, wherein the compound is represented by the following formula:

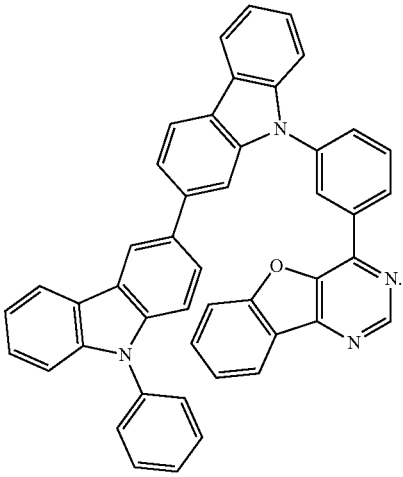 [SMILES: c1ccc(-n2c3ccccc3c3cc(-c4ccc5c6ccccc6n(-c6cccc(-c7ncnc8c7oc7ccccc78)c6)c5c4)ccc32)cc1]

11. A compound represented by General Formula (G1):

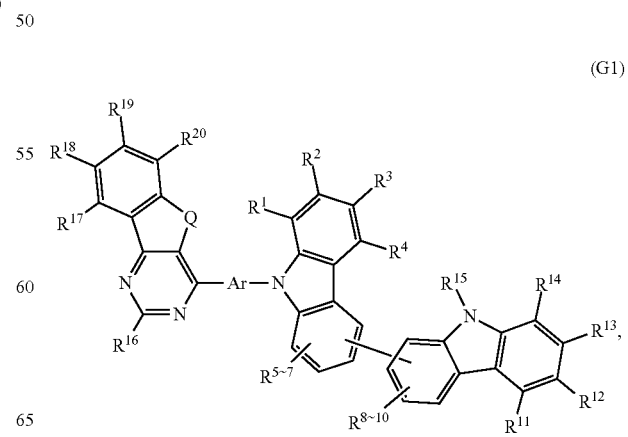

(G1)

wherein:

Q represents oxygen or sulfur;

each of $R^1$ to $R^{20}$ independently represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms;

Ar represents an arylene group represented by any of Structure Formulae (Ar-1) to (Ar-27):

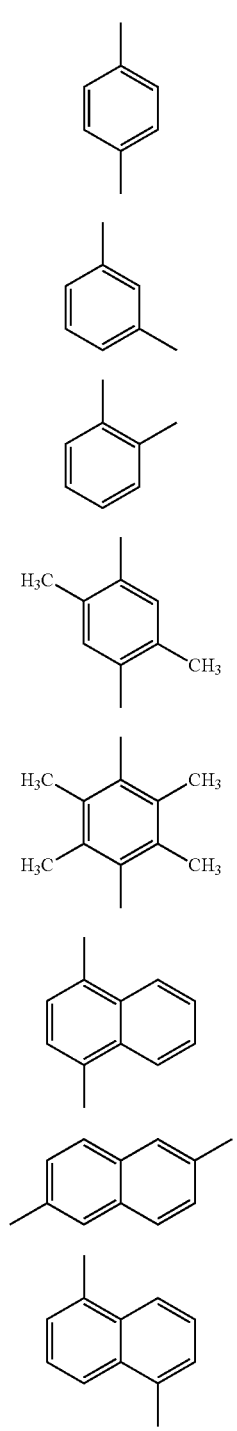

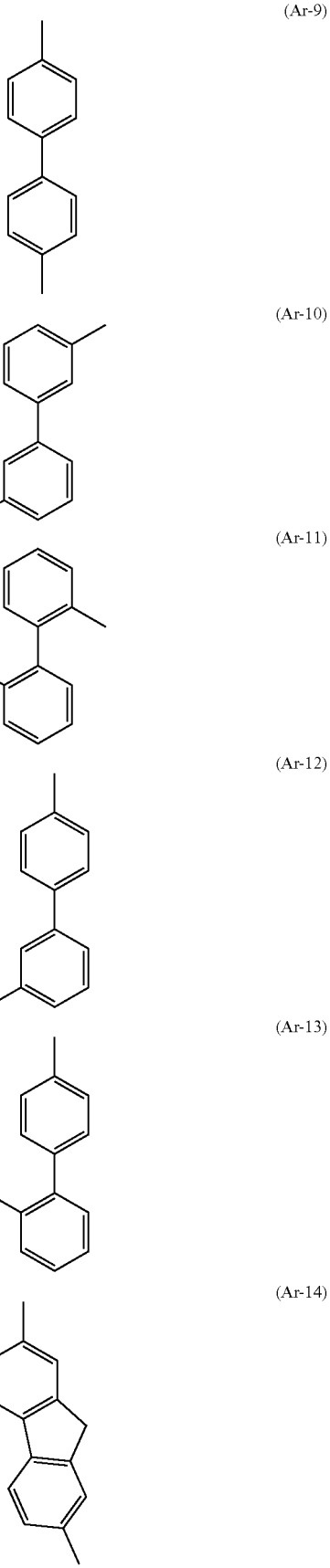

(Ar-15) 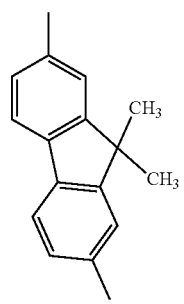
(Ar-16) 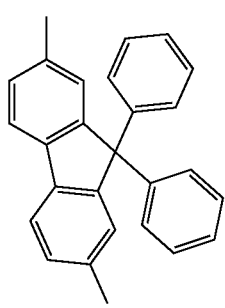
(Ar-17) 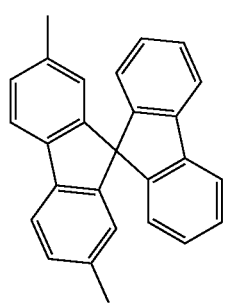
(Ar-18) 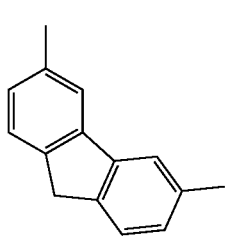
(Ar-19) 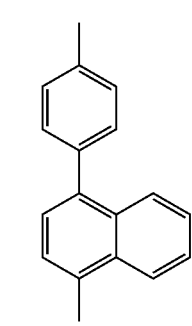
(Ar-20) 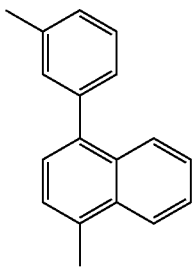
(Ar-21) 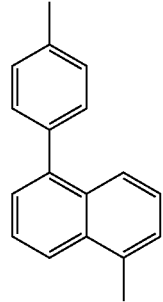
(Ar-22) 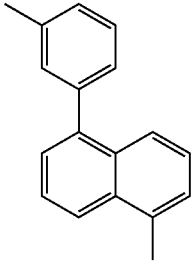
(Ar-23) 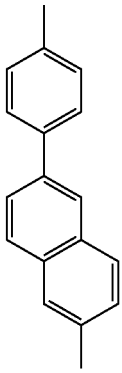
(Ar-24) 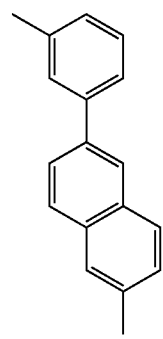

-continued

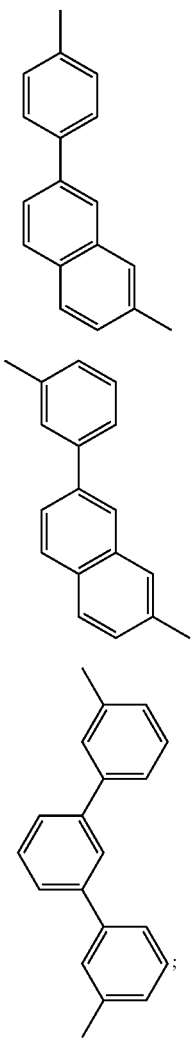

(Ar-25)

(Ar-26)

(Ar-27)

and the bicarbazole skeleton is a 2,3'-bi-9H-carbazole skeleton.

12. A compound represented by General Formula (G3):

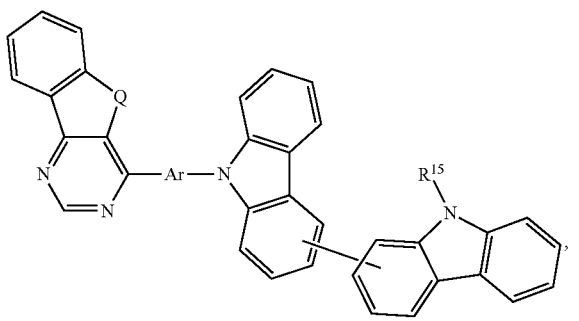

(G3)

wherein:
Q represents oxygen or sulfur;
R¹⁵ represents any of hydrogen, a substituted or unsubstituted alkyl group having 1 to 6 carbon atoms, a substituted or unsubstituted cycloalkyl group having 3 to 7 carbon atoms, and a substituted or unsubstituted aryl group having 6 to 13 carbon atoms;

Ar represents an arylene group represented by any of Structure Formulae (Ar-1) to (Ar-27):

(Ar-1)

(Ar-2)

(Ar-3)

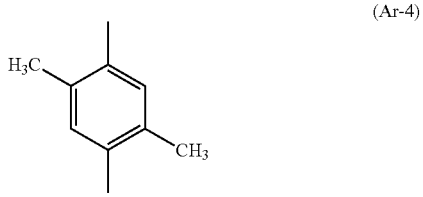

(Ar-4)

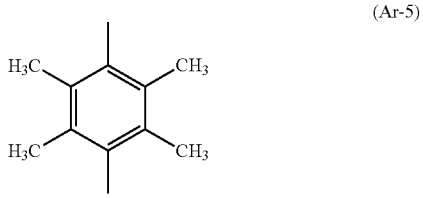

(Ar-5)

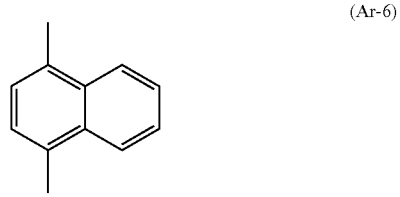

(Ar-6)

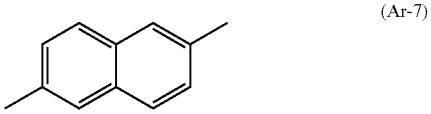

(Ar-7)

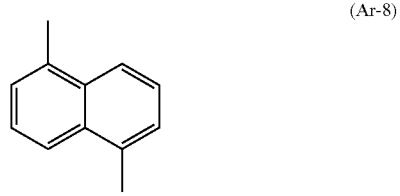

(Ar-8)

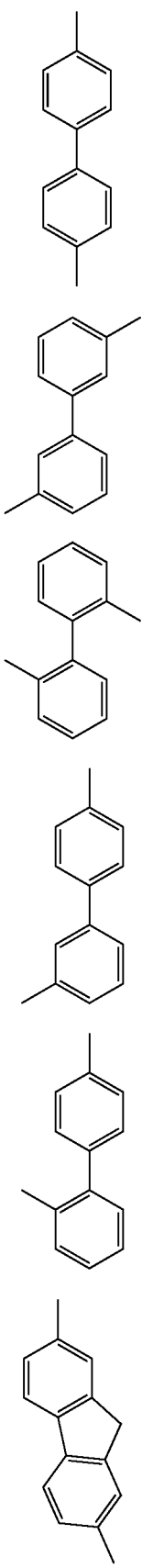
(Ar-9)
(Ar-10)
(Ar-11)
(Ar-12)
(Ar-13)
(Ar-14)
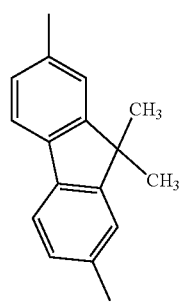
(Ar-15)
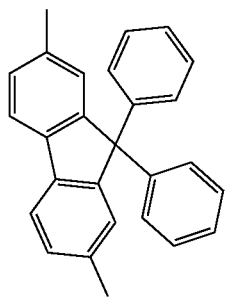
(Ar-16)
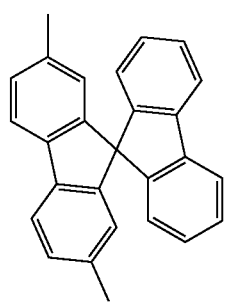
(Ar-17)
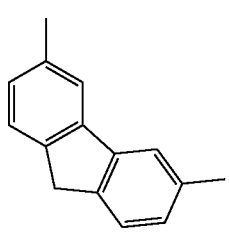
(Ar-18)
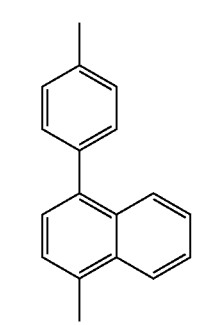
(Ar-19)

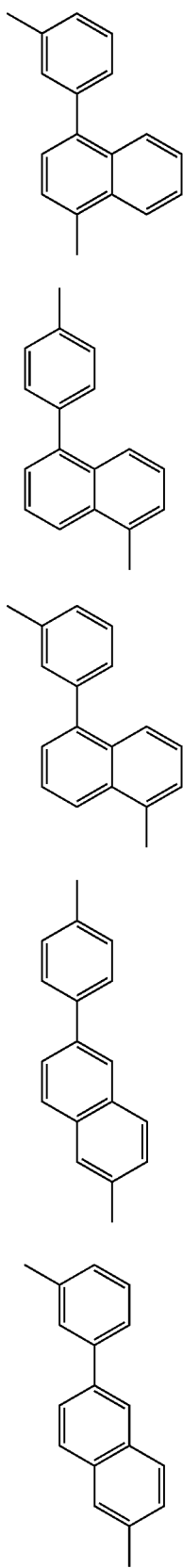

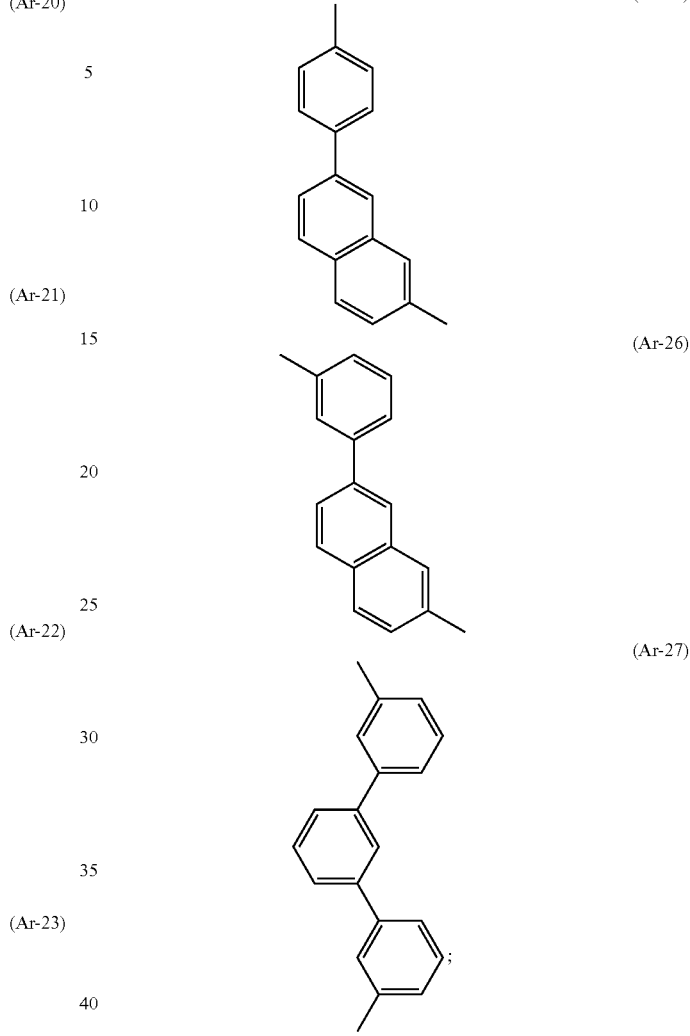

and the bicarbazole skeleton is a 2,3'-bi-9H-carbazole skeleton.

13. A light-emitting element comprising the compound according to claim 11.

14. The light-emitting element according to claim 13, being configured to emit light comprising delayed fluorescence.

15. The light-emitting element according to claim 13, further comprising a phosphorescent material.

16. The light-emitting element according to claim 13, being configured to emit blue light.

17. A display device comprising the light-emitting element according to claim 13,
wherein the display device comprises at least one of a color filter and a transistor.

18. An electronic device comprising the display device according to claim 17,
wherein the electronic device comprises at least one of a housing and a touch sensor.

19. A lighting device comprising the light-emitting element according to claim 13,
wherein the lighting device comprises at least one of a housing and a touch sensor.

* * * * *